(12) United States Patent
Cumming et al.

(10) Patent No.: US 10,414,774 B2
(45) Date of Patent: Sep. 17, 2019

(54) COMPOUND USEFUL FOR ALTERING THE LEVELS OF BILE ACIDS FOR THE TREATMENT OF DIABETES AND CARDIOMETABOLC DISEASE

(71) Applicants: Merck Sharp & Dohme Corp., Rahway, NJ (US); Jared N. Cumming, Garwood, NJ (US); Kevin D. Dykstra, West Milford, NJ (US); Alan Hruza, Hackettstown, NJ (US); Derun Li, Brighton, MA (US); Hong Liu, Hillsborough, NJ (US); Haiqun Tang, Belle Mead, NJ (US); Brandon M. Taoka, Hoboken, NJ (US); Andreas Verras, New York, NY (US); Shawn P. Walsh, Bridgewater, NJ (US); Wen-Lian Wu, Green Brook, NJ (US)

(72) Inventors: Jared N. Cumming, Garwood, NJ (US); Kevin D. Dykstra, West Milford, NJ (US); Alan Hruza, Hackettstown, NJ (US); Derun Li, Brighton, MA (US); Hong Liu, Hillsborough, NJ (US); Haiqun Tang, Belle Mead, NJ (US); Brandon M. Taoka, Hoboken, NJ (US); Andreas Verras, New York, NY (US); Shawn P. Walsh, Bridgewater, NJ (US); Wen-Lian Wu, Green Brook, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/324,596

(22) PCT Filed: Aug. 10, 2017

(86) PCT No.: PCT/US2017/046186
§ 371 (c)(1),
(2) Date: Feb. 11, 2019

(87) PCT Pub. No.: WO2018/034918
PCT Pub. Date: Feb. 22, 2018

(65) Prior Publication Data
US 2019/0218223 A1  Jul. 18, 2019

Related U.S. Application Data

(60) Provisional application No. 62/374,964, filed on Aug. 15, 2016.

(51) Int. Cl.
C07D 487/04 (2006.01)
C07D 519/00 (2006.01)
A61P 3/10 (2006.01)
C07D 498/04 (2006.01)
C07D 513/04 (2006.01)
C07D 471/04 (2006.01)

(52) U.S. Cl.
CPC .............. *C07D 487/04* (2013.01); *A61P 3/10* (2018.01); *C07D 471/04* (2013.01);
(Continued)

(58) Field of Classification Search
CPC .................................................... C07D 519/00
See application file for complete search history.

(56) References Cited

U.S. PATENT DOCUMENTS 7,173,036 B2  2/2007  Sircar et al.
7,220,856 B2 *  5/2007  Dunning .............. C07D 215/46
  540/484

(Continued)

FOREIGN PATENT DOCUMENTS

WO  WO-2006053024 A2 *  5/2006  .......... C07D 221/20
WO  WO2009001128 A1  12/2008

(Continued)

OTHER PUBLICATIONS

Hawkins, Jia Li et al., Cholic Acid Mediates Negative Feedback Regulation of Bile Acid Snthesis in Mice, The Journal of Clinical Investigation, 2002, No. 8, pp. 1191-1200, 110.

(Continued)

*Primary Examiner* — Alexander R Pagano
(74) *Attorney, Agent, or Firm* — Janet E. Fair; Catherine D. Fitch

(57) ABSTRACT

Described herein are compounds of Formula (I) or a pharmaceutically acceptable salt thereof. The compounds of Formula I act as Cyp8b1 inhibitors and can be useful in preventing, treating or acting as a remedial agent for diabetes and cardiovascular disease.

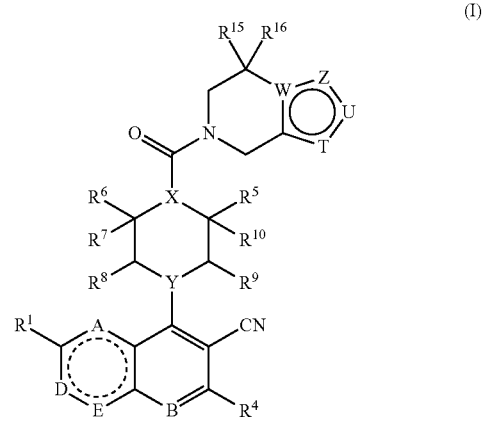

18 Claims, No Drawings

(52) U.S. Cl.
CPC ......... *C07D 498/04* (2013.01); *C07D 513/04* (2013.01); *C07D 519/00* (2013.01)

(56) References Cited

U.S. PATENT DOCUMENTS

| | | | |
|---|---|---|---|
| 2007/0004763 | A1 | 1/2007 | Baindur et al. |
| 2007/0259880 | A1 | 11/2007 | Sakashita et al. |
| 2009/0306048 | A1* | 12/2009 | Kilburn ................ C07D 211/62 514/216 |
| 2012/0157436 | A1 | 6/2012 | Dean et al. |
| 2013/0012485 | A1 | 1/2013 | Baschlin et al. |
| 2013/0296237 | A1 | 11/2013 | Kastan et al. |

FOREIGN PATENT DOCUMENTS

| | | | | |
|---|---|---|---|---|
| WO | WO2012009649 | A1 | | 1/2012 |
| WO | WO2018034917 | A1 | | 2/2018 |
| WO | WO2018034918 | A1 | | 2/2018 |
| WO | WO-2018034971 | A1 * | 2/2018 | ......... H04L 12/4641 |

OTHER PUBLICATIONS

Kaur, Achint et al., Loss of Cyp8b1 Improves Glucose Homeostasis by Increasing GLP-1, Diabetes Journal, 2014, 1168-1179, 64.

Murphy, Charlotte et al., Cholic Acid as Key Regulator of Cholesterol Synthesis, Intestinal Absorption and Hepatic Storage in Mice, Biochimica et Biophysica Acta, 2005, 167-175, 1735.

Slatis, Katharina et al., Abolished Synthesis of Cholic Acid Reduces Atherosclerotic Development in Apolipoprotein E Knockout Mice, Journal of Lipid Research, 2010, 3289-3298, 51.

Staels, Bart et al., Bile Acids and Metabolic Regulation: Mechanisms and Clinical Responses to Bile Acid Sequestration, Diabetes Care, 2009, Supplement 2, S237-S245, 32.

Wang, Jin et al., Critical Role of Cholic Acid for Development of Hypercholesterolemia and Gallstones in Diabetic Mice, Biochemical and Biophysical Research Communications, 2006, 1382-1388, 342.

* cited by examiner

COMPOUND USEFUL FOR ALTERING THE LEVELS OF BILE ACIDS FOR THE TREATMENT OF DIABETES AND CARDIOMETABOLC DISEASE

CROSS-REFERENCE TO RELATED APPLICATIONS

This application is a U.S. National Phase application under 35 U.S.C. § 371 of PCT Application No. PCT/US2017/046186, filed Aug. 10, 2017, which published as WO2018/034913 A1 on Feb. 22, 2018, and claims priority under 35 U.S.C. § 365(b) from U.S. provisional patent application No. 62/374,964, filed Aug. 15, 2016.

TECHNICAL FIELD

The present invention is directed to compounds useful for altering the levels of bile acids for the treatment of diabetes and cardiometabolic disease. Specifically, the compounds inhibit cytochrome P450, family 8, subfamily B, polypeptide 1 (hereinafter also referred to as "Cyp8b1"), and can be useful in preventing, treating or acting as a remedial agent for diabetes mellitus and cardiometabolic disease.

BACKGROUND

Bile acids are amphiphilic molecules synthesized from cholesterol in the liver. They are physiological detergents that maintain cholesterol homeostasis (Staels B, Fonseca V. A., *Bile acids and metabolic regulation: mechanisms and clinical responses to bile acid sequestration*, Diabetes Care. 2009 November; 32 Suppl 2:S237-45.). Bile acid synthesis is a multi-step process consisting of two distinct pathways, the classical and the alternate. The classical pathway accounts for the majority of bile acids produced. Hydrophobic cholic acid (CA) is the major resulting bile acid and cytochrome P450, family 8, subfamily B, polypeptide 1 (Cyp8b1) plays a critical role in its production. Inhibition of Cyp8b1 reduces the amount of cholic acid in the overall bile acid pool which causes an increase in the amount of alternative bile acids to make up for the deficiency. In humans, the other major bile acid is chenodeoxycholic acid (CDCA) and the amount of CDCA is increased upon inhibition of Cyp8b1. This has been demonstrated in a mouse model.

Mice with targeted disruption of Cyp8b1 (Cyp8b1-/-) fail to produce CA. (Li-Hawkins J, Gåfvels M, Olin M, Lund E G, Andersson U, Schuster G, et al, *Cholic acid mediates negative feedback regulation of bile acid synthesis in mice*. J. Clin. Invest. 377 2002 October; 110(8): 1191-200). The fraction of the bile acid pool that would have been occupied by CA is predominantly replaced by hydrophilic bile acid species, α- and β-muricholates, in Cyp8b1-/- mice (since CDCA is converted into muricholic acid (MCA) in rodent livers, the main bile acids found in rodents are CA/MCA instead of CA/CDCA in humans). The resulting increase in hydrophilic bile acid species leads to a reduction in both intestinal absorption and hepatic accumulation of cholesterol (Murphy C, Parini P, Wang J, Björkhem I, Eggertsen G, Gåfvels M, *Cholic acid as key regulator of cholesterol synthesis, intestinal absorption and hepatic storage in mice*, Biochim. Biophys. Acta. 2005 Aug. 15; 1735(3):167-75). Cyp8b1-/-×ApoE-/- mice show reduced atherosclerotic plaques, owing to decreased levels of apolipoprotein B (ApoB)-containing lipoproteins in the plasma, reduced hepatic cholesteryl esters and enhanced bile acid synthesis (Slätis K, Gåfvels M, Kannisto K, Ovchinnikova O, Paulsson-Berne G, Parini P, et al., *Abolished synthesis of cholic acid reduces atherosclerotic development in apolipoprotein E knockout mice*, J. Lipid Res. 2010 November; 51(11): 3289-98). Furthermore, cholesterol fed Alloxan induced type 1 diabetic Cyp8b1-/- mice are protected against hypercholesterolemia and gall stones (Wang J, Gåfvels M, Rudling M, Murphy C, Björkhem I, Einarsson C, et al., *Critical role of cholic acid for development of hypercholesterolemia and gallstones in diabetic mice*, Biochem. Biophys. Res. Commun. 2006 Apr. 21; 342(4):1382-8). These findings suggest that the absence of Cyp8b1 may be beneficial in cases of metabolic syndrome.

Also, it has been found that absence of Cyp8b1 results in improved glucose tolerance, insulin sensitivity and β-cell function, mediated by absence of CA in Cyp8b1-/- mice (Achint Kaurl, Jay V. Patankar, Willeke de Haan1, Piers Ruddle1, Nadeeja Wijesekara1, Albert K. Groen, C. Bruce Verchere, Roshni R. Singaraja and Michael R. Hayden, *Loss of Cyp8b1 improves glucose homeostasis by increasing GLP-1*, Diabetes, Published online before print Oct. 22, 2014, doi: 10.2337/db14-0716). The absence of biliary CA results in reduced intestinal fat absorption and leads to increased free fatty acids reaching the ileal L-cells. Increased free fatty acids reaching the ileal L-cells, causes the ileal L-cells to increase secretion of the incretin hormone glucagon like peptide-1 (GLP-1). GLP-1 in turn increases the biosynthesis and secretion of insulin from β-cells, leading to the improved glucose tolerance observed in the Cyp8b1-/- mice.

Thus, inhibition of Cyp8b1 causes a decrease in cholic acid (CA) levels and an increase in chenodeoxycholic acid (CDCA) levels. Altering the CA/CDCA ratio plays an important role in cholesterol absorption and homeostasis. As such, there is a need for Cyp8b1 inhibitors that are useful in treating cardiometabolic diseases associated with elevated LDL, such as atherosclerosis, fatty liver and nonalcoholic steatohepatitis (NASH). Also, there is a need for Cyp8b1 inhibitors that are useful for treating noninsulin-dependent diabetes (NIDDM), hyperglycemia, and other symptoms associated with NIDDM.

SUMMARY

A compound of Formula I:

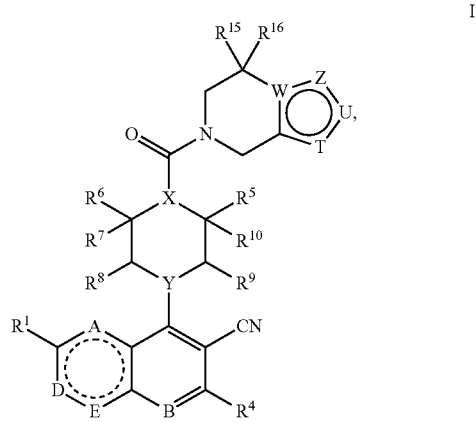

wherein A, B, D, E, T, U, W, X, Y, Z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are described below.

The compounds described herein are Cyp8b1 inhibitors, which can be useful in the prevention, treatment or amelioration of cardiometabolic diseases associated with elevated LDL, such as atherosclerosis, fatty liver and nonalcoholic steatohepatitis (NASH), and noninsulin-dependent diabetes (NIDDM), hyperglycemia, and other symptoms associated with NIDDM.

DETAILED DESCRIPTION

Compounds

Described herein are compounds of Formula I:

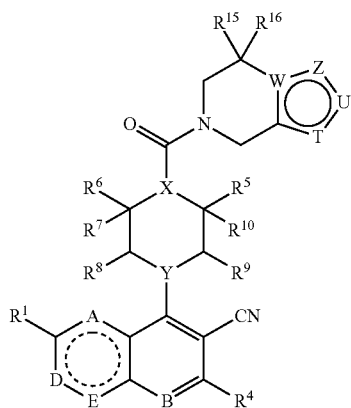

or a pharmaceutically acceptable salt thereof, wherein the dashed lines in Formula I indicate the possibility of aromaticity or no aromaticity in the ring depending on the substitution of the ring and wherein:

A is N or $CR^{17}$;
B is N or NO;
D is N, $NR^{12}$ or $CR^2$;
E is N or $CR^3$;
T is N, $NR^{12}$ or $CR^{12}$, wherein T is not $CR^{12}$ when W is C and Z is $CR^{14}$ and U is $CR^{13}$;
U is N, NH or $CR^{13}$, wherein U is not $CR^{13}$ when W is C and T is $CR^{12}$ and Z is $CR^{14}$;
Z is N, NH, S, O or $CR^{14}$, wherein Z is not $CR^{14}$ when W is C and T is $CR^{12}$ and U is $CR^{13}$;
W is N or C, wherein W is not C when T is $CR^{12}$ and U is $CR^{13}$ and Z is $CR^{14}$;
X is N or $CR^{11}$;
Y is N or CH;
$R^1$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, $COOC_1$-$C_6$alkyl, $COOC_1$-$C_6$alkyl$C_3$-$C_6$cycloalkyl, phenyl and oxazole;
$R^2$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, $COOC_1$-$C_6$alkyl, $COOC_1$-$C_6$alkyl$C_3$-$C_6$cycloalkyl, phenyl and oxazole;
$R^3$ is selected from the group consisting of hydrogen, halogen, CN, OH, $C_1$-$C_6$alkylOH, $C_1$-$C_6$alkoxy, $C_1$-$C_6$alkyl, $C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, $COOC_1$-$C_6$alkyl, $COOC_1$-$C_6$alkyl$C_3$-$C_6$cycloalkyl, phenyl and oxazole;
$R^4$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, $COOC_1$-$C_6$alkyl, $COOC_1$-$C_6$alkyl$C_3$-$C_6$cycloalkyl, phenyl and oxazole;
$R^5$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^{10}$ forms a $C_3$-$C_6$cycloalkyl;
$R^6$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^7$ forms a $C_3$-$C_6$cycloalkyl, or when taken with $R^{11}$ forms a $C_3$-$C_6$cycloalkyl;
$R^7$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^6$ forms a $C_3$-$C_6$cycloalkyl;
$R^8$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl;
$R^9$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl;
$R^{10}$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^5$ forms a $C_3$-$C_6$cycloalkyl;
$R^{11}$ is selected from the group consisting of hydrogen, halogen, OH, $C_1$-$C_6$alkyl, and halo$C_1$-$C_6$alkyl or when taken with $R^6$ forms a $C_3$-$C_6$cycloalkyl;
$R^{12}$ is selected from the group consisting of hydrogen, halogen, OH, $C_1$-$C_6$alkyl, $C_3$-$C_6$cycloalkyl, $COOC_1$-$C_6$alkyl$C_3$-$C_6$cycloalkyl, and halo$C_1$-$C_6$alkyl;
$R^{13}$ is selected from the group consisting of hydrogen, halogen, OH, $C_1$-$C_6$alkyl, $C_3$-$C_6$cycloalkyl and halo$C_1$-$C_6$alkyl;
$R^{14}$ is selected from the group consisting of hydrogen, halogen, OH, $C_1$-$C_6$alkyl, $C_3$-$C_6$cycloalkyl and halo$C_1$-$C_6$alkyl;
$R^{15}$ is selected from the group consisting of hydrogen, halogen, OH, $C_1$-$C_6$alkyl, and halo$C_1$-$C_6$alkyl;
$R^{16}$ is selected from the group consisting of hydrogen, halogen, OH, $C_1$-$C_6$alkyl, and halo$C_1$-$C_6$alkyl; and
$R^{17}$ is selected from the group consisting of hydrogen, halogen, $C_1$-$C_6$alkyl, $C_1$-$C_6$alkoxy, and halo$C_1$-$C_6$alkyl.

In certain embodiments, also described herein are compounds of Formula I:

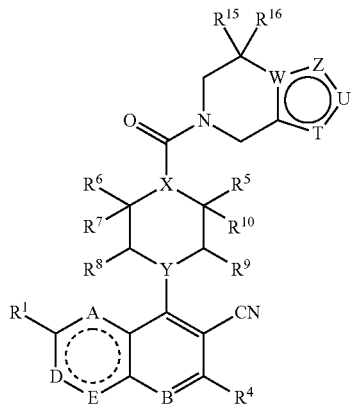

or a pharmaceutically acceptable salt thereof, wherein:
A is N or CR$^{17}$;
B is N or NO;
D is N or CR$^2$;
E is N or CR$^3$;
T is N, NR$^{12}$ or CR$^{12}$, wherein T is not CR$^{12}$ when W is C and Z is CR$^{14}$ and U is CR$^{13}$;
U is N or CR$^{13}$, wherein U is not CR$^{13}$ when W is C and T is CR$^{12}$ and Z is CR$^{14}$;
Z is N, S, O or CR$^{14}$, wherein Z is not CR$^{14}$ when W is C and T is CR$^{12}$ and U is CR$^{13}$;
W is N or C, wherein W is not C when T is CR$^{12}$ and U is CR$^{13}$ and Z is CR$^{14}$;
X is N or CR$^{11}$;
Y is N or CH;
R$^1$ is selected from the group consisting of hydrogen, halogen, CN, OH, C$_1$-C$_6$alkylOH, C$_1$-C$_6$alkoxy, C$_1$-C$_6$alkylC$_1$-C$_6$alkoxy, haloC$_1$-C$_6$alkoxy, C$_3$-C$_6$cycloalkylC$_1$-C$_6$alkoxy, C$_1$-C$_6$alkyl, haloC$_1$-C$_6$alkyl, C$_3$-C$_6$cycloalkyl, C$_2$-C$_6$alkenyl, COOC$_1$-C$_6$alkyl, COOC$_1$-C$_6$alkylC$_3$-C$_6$cycloalkyl, phenyl and oxazole;
R$^2$ is selected from the group consisting of hydrogen, halogen, CN, OH, C$_1$-C$_6$alkylOH, C$_1$-C$_6$alkoxy, C$_1$-C$_6$alkylC$_1$-C$_6$alkoxy, haloC$_1$-C$_6$alkoxy, C$_3$-C$_6$cycloalkylC$_1$-C$_6$alkoxy, C$_1$-C$_6$alkyl, haloC$_1$-C$_6$alkyl, C$_3$-C$_6$cycloalkyl, C$_2$-C$_6$alkenyl, COOC$_1$-C$_6$alkyl, COOC$_1$-C$_6$alkylC$_3$-C$_6$cycloalkyl, phenyl and oxazole;
R$^3$ is selected from the group consisting of hydrogen, halogen, CN, OH, C$_1$-C$_6$alkylOH, C$_1$-C$_6$alkoxy, C$_1$-C$_6$alkylC$_1$-C$_6$alkoxy, haloC$_1$-C$_6$alkoxy, C$_3$-C$_6$cycloalkylC$_1$-C$_6$alkoxy, C$_1$-C$_6$alkyl, haloC$_1$-C$_6$alkyl, C$_3$-C$_6$cycloalkyl, C$_2$-C$_6$alkenyl, COOC$_1$-C$_6$alkyl, COOC$_1$-C$_6$alkylC$_3$-C$_6$cycloalkyl, phenyl and oxazole;
R$^4$ is selected from the group consisting of hydrogen, halogen, CN, OH, C$_1$-C$_6$alkylOH, C$_1$-C$_6$alkoxy, C$_1$-C$_6$alkylC$_1$-C$_6$alkoxy, haloC$_1$-C$_6$alkoxy, C$_3$-C$_6$cycloalkylC$_1$-C$_6$alkoxy, C$_1$-C$_6$alkyl, haloC$_1$-C$_6$alkyl, C$_3$-C$_6$cycloalkyl, C$_2$-C$_6$alkenyl, COOC$_1$-C$_6$alkyl, COOC$_1$-C$_6$alkylC$_3$-C$_6$cycloalkyl, phenyl and oxazole;
R$^5$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with R$^{10}$ forms a C$_3$-C$_6$cycloalkyl;
R$^6$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with R$^7$ forms a C$_3$-C$_6$cycloalkyl, or when taken with R$^{11}$ forms a C$_3$-C$_6$cycloalkyl;
R$^7$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with R$^6$ forms a C$_3$-C$_6$cycloalkyl;
R$^8$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl;
R$^9$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl;
R$^{10}$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with R$^5$ forms a C$_3$-C$_6$cycloalkyl;
R$^{11}$ is selected from the group consisting of hydrogen, halogen, OH, C$_1$-C$_6$alkyl, and haloC$_1$-C$_6$alkyl or when taken with R$^6$ forms a C$_3$-C$_6$cycloalkyl;
R$^{12}$ is selected from the group consisting of hydrogen, halogen, OH, C$_1$-C$_6$alkyl, C$_3$-C$_6$cycloalkyl and haloC$_1$-C$_6$alkyl;
R$^{13}$ is selected from the group consisting of hydrogen, halogen, OH, C$_1$-C$_6$alkyl, C$_3$-C$_6$cycloalkyl and haloC$_1$-C$_6$alkyl;
R$^{14}$ is selected from the group consisting of hydrogen, halogen, OH, C$_1$-C$_6$alkyl, C$_3$-C$_6$cycloalkyl and haloC$_1$-C$_6$alkyl;
R$^{15}$ is selected from the group consisting of hydrogen, halogen, OH, C$_1$-C$_6$alkyl, and haloC$_1$-C$_6$alkyl;
R$^{16}$ is selected from the group consisting of hydrogen, halogen, OH, C$_1$-C$_6$alkyl, and haloC$_1$-C$_6$alkyl and; and
R$^{17}$ is selected from the group consisting of hydrogen, halogen, C$_1$-C$_6$alkyl, C$_1$-C$_6$alkoxy, and haloC$_1$-C$_6$alkyl.

With regard to the compounds described herein, A is N or CR$^{17}$. In certain embodiments, A is N. In other embodiments, A is CR$^{17}$.

With regard to the compounds described herein, B is N or NO. In certain embodiments, B is N. In other embodiments, B is NO.

With regard to the compounds described herein, D is N, NR$^{12}$, or CR$^2$. In certain embodiments, D is N. In other embodiments, D is NR$^{12}$. In other embodiments, D is CR$^2$.

With regard to the compounds described herein, E is N or CR$^3$. In certain embodiments, E is N. In other embodiments, E is CR$^3$.

With regard to the compounds described herein, T is N, NR$^{12}$ or CR$^{12}$. In certain embodiments, T is N. In certain embodiments, T is NR$^{12}$. In other embodiments, T is CR$^{12}$. In certain embodiments, T is not CR$^{12}$ when W is C and Z is CR$^{14}$ and U is CR$^{13}$.

With regard to the compounds described herein, U is N, NH, or CR$^{13}$. In certain embodiments, U is N. In other embodiments, U is NH. In other embodiments, U is CR$^{13}$. In certain embodiments, U is not CR$^{13}$ when W is C and T is CR$^{12}$ and Z is CR$^{14}$.

With regard to the compounds described herein, Z is N, NH, S, O or CR$^{14}$. In certain embodiments, Z is N. In yet other embodiments, Z is NH. In other embodiments, Z is S. In yet other embodiments, Z is O. In still other embodiments, Z is CR$^{14}$. In certain embodiments, Z is not CR$^{14}$ when W is C and T is CR$^{12}$ and U is CR$^{13}$.

With regard to the compounds described herein, W is N or C. In certain embodiments, W is N. In other embodiments, W is C. In certain embodiments, W is not C when T is $CR^{12}$ and U is $CR^{13}$ and Z is $CR^{14}$.

With regard to the compounds described herein, X is N or $CR^{11}$. In certain embodiments, X is N. In other embodiments, X is $CR^{11}$.

With regard to the compounds described herein, Y is N or $CR^{11}$. In certain embodiments, Y is N. In other embodiments, Y is $CR^{11}$.

With regard to the compounds described herein, $R^1$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COO$C_1$-$C_6$alkyl, COO$C_1$-$C_6$alkyl$C_3$-$C_6$cycloalkyl, phenyl and oxazole.

In certain embodiments, $R^1$ is hydrogen. In certain embodiments, $R^1$ is halogen. Suitable halogens include, but are not limited to, fluorine, chlorine, bromine and iodine. In certain embodiments, $R^1$ is CN. In certain embodiments, $R^1$ is OH. In certain embodiments, $R^1$ is $C_1$-$C_6$alkylOH. Suitable $C_1$-$C_6$alkylOHs include, but are not limited to, methanol, propanol, ethanol and butanol.

In certain embodiments, $R^1$ is $C_1$-$C_6$alkoxy. Suitable $C_1$-$C_6$alkoxys include but are not limited to, methoxy and ethoxy. In certain embodiments, $R^1$ is halo$C_1$-$C_6$alkoxy. Suitable halo$C_1$-$C_6$alkoxys include, but are not limited to, trifluoromethoxy. In certain embodiments, $R^1$ is $C_1$-$C_6$alkyl$C_1$-$C_6$alkoxy. Suitable $C_1$-$C_6$alkyl$C_1$-$C_6$alkoxys include, but are not limited to, methylpropoxy. In certain embodiments, $R^1$ is $C_3$-$C_6$cycloalkyl$C_1$-$C_6$alkoxy. Suitable $C_3$-$C_6$cycloalkyl$C_1$-$C_6$alkoxys include, but are not limited to, cyclopropylmethoxy. In certain embodiments, $R^1$ is $C_1$-$C_6$alkyl. Suitable $C_1$-$C_6$alkyls include but are not limited to, methyl, ethyl and isopropyl. In certain embodiments, $R^1$ is halo$C_1$-$C_6$alkyl. Suitable halo$C_1$-$C_6$alkyls include, but are not limited to, trifluoromethyl and difluoroethyl. In certain embodiments, $R^1$ is $C_3$-$C_6$cycloalkyl. Suitable $C_3$-$C_6$cycloalkyls include, but are not limited to, cyclopropyl, cyclobutyl, cyclopentyl and cyclohexyl. In certain embodiments, $R^1$ is $C_2$-$C_6$alkenyl. Suitable $C_2$-$C_6$alkenyls include but are not limited to, vinyl.

In certain embodiments, $R^1$ is COO$C_1$-$C_6$alkyl. Suitable COO$C_1$-$C_6$alkyls include, but are not limited to, methoxycarbonyl, ethoxycarbonyl, propoxycarbonyl and butoxycarbonyl. In certain embodiments, $R^1$ is COO$C_1$-$C_6$alkyl$C_3$-$C_6$cycloalkyl.

In certain embodiments, $R^1$ is phenyl. In certain embodiments, $R^1$ is oxazole.

With regard to the compounds described herein, $R^2$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COO$C_1$-$C_6$alkyl, COO$C_1$-$C_6$alkyl$C_3$-$C_6$cycloalkyl, phenyl and oxazole.

In certain embodiments, $R^2$ is hydrogen. In certain embodiments, $R^2$ is halogen. Suitable halogens include, but are not limited to, fluorine, chlorine, bromine and iodine. In certain an embodiment, R2 is CN. In certain embodiments, $R^2$ is OH. In certain embodiments, $R^2$ is $C_1$-$C_6$alkylOH. Suitable $C_1$-$C_6$alkylOHs include, but are not limited to, methanol, propanol, ethanol and butanol.

In certain embodiments, $R^2$ is $C_1$-$C_6$alkoxy. Suitable $C_1$-$C_6$alkoxys include but are not limited to, methoxy and ethoxy. In certain embodiments, $R^2$ is halo$C_1$-$C_6$alkoxy. Suitable halo$C_1$-$C_6$alkoxys include, but are not limited to, trifluoromethoxy. In certain embodiments, $R^2$ is $C_1$-$C_6$alkyl$C_1$-$C_6$alkoxy. Suitable $C_1$-$C_6$alkyl$C_1$-$C_6$alkoxys include, but are not limited to, methylpropoxy. In certain embodiments, $R^2$ is $C_3$-$C_6$cycloalkyl$C_1$-$C_6$alkoxy. Suitable $C_3$-$C_6$cycloalkyl$C_1$-$C_6$alkoxys include, but are not limited to, cyclopropylmethoxy. In certain embodiments, $R^2$ is $C_1$-$C_6$alkyl. Suitable $C_1$-$C_6$alkyls include but are not limited to, methyl, ethyl and isopropyl. In certain embodiments, $R^2$ is halo$C_1$-$C_6$alkyl. Suitable halo$C_1$-$C_6$alkyls include, but are not limited to, trifluoromethyl and difluoroethyl. In certain embodiments, $R^2$ is $C_3$-$C_6$cycloalkyl. Suitable $C_3$-$C_6$cycloalkyls include, but are not limited to, cyclopropyl, cyclobutyl, cyclopentyl and cyclohexyl. In certain embodiments, $R^2$ is $C_2$-$C_6$alkenyl. Suitable $C_2$-$C_6$alkenyls include but are not limited to, vinyl.

In certain embodiments, $R^2$ is COO$C_1$-$C_6$alkyl. Suitable COO$C_1$-$C_6$alkyls include, but are not limited to, methoxycarbonyl, ethoxycarbonyl, propoxycarbonyl and butoxycarbonyl. In certain embodiments, $R^2$ is COO$C_1$-$C_6$alkyl$C_3$-$C_6$cycloalkyl.

In certain embodiments, $R^2$ is phenyl. In certain embodiments, $R^2$ is oxazole.

With regard to the compounds described herein, $R^3$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COO$C_1$-$C_6$alkyl, COO$C_1$-$C_6$alkyl$C_3$-$C_6$cycloalkyl, phenyl and oxazole.

In certain embodiments, $R^3$ is hydrogen. In certain embodiments, $R^3$ is halogen. Suitable halogens include, but are not limited to, fluorine, chlorine, bromine and iodine. In certain embodiments, $R^3$ is CN. In certain embodiments, $R^3$ is OH. In certain embodiments, $R^3$ is $C_1$-$C_6$alkylOH. Suitable $C_1$-$C_6$alkylOHs include, but are not limited to, methanol, propanol, ethanol and butanol.

In certain embodiments, $R^3$ is $C_1$-$C_6$alkoxy. Suitable $C_1$-$C_6$alkoxys include but are not limited to, methoxy and ethoxy. In certain embodiments, $R^3$ is halo$C_1$-$C_6$alkoxy. Suitable halo$C_1$-$C_6$alkoxys include, but are not limited to, trifluoromethoxy. In certain embodiments, $R^3$ is $C_1$-$C_6$alkyl$C_1$-$C_6$alkoxy. Suitable $C_1$-$C_6$alkyl$C_1$-$C_6$alkoxys include, but are not limited to, methylpropoxy. In certain embodiments, $R^3$ is $C_3$-$C_6$cycloalkyl$C_1$-$C_6$alkoxy. Suitable $C_3$-$C_6$cycloalkyl$C_1$-$C_6$alkoxys include, but are not limited to, cyclopropylmethoxy. In certain embodiments, $R^3$ is $C_1$-$C_6$alkyl. Suitable $C_1$-$C_6$alkyls include but are not limited to, methyl, ethyl and isopropyl. In certain embodiments, $R^3$ is halo$C_1$-$C_6$alkyl. Suitable halo$C_1$-$C_6$alkyls include, but are not limited to, trifluoromethyl and difluoroethyl. In certain embodiments, $R^3$ is $C_3$-$C_6$cycloalkyl. Suitable $C_3$-$C_6$cycloalkyls include, but are not limited to, cyclopropyl, cyclobutyl, cyclopentyl and cyclohexyl. In certain embodiments, $R^3$ is $C_2$-$C_6$alkenyl. Suitable $C_2$-$C_6$alkenyls include but are not limited to, vinyl.

In certain embodiments, $R^3$ is COO$C_1$-$C_6$alkyl. Suitable COO$C_1$-$C_6$alkyls include, but are not limited to, methoxycarbonyl, ethoxycarbonyl, propoxycarbonyl and butoxycarbonyl. In certain embodiments, $R^3$ is COO$C_1$-$C_6$alkyl$C_3$-$C_6$cycloalkyl.

In certain embodiments, $R^3$ is phenyl. In certain embodiments, $R^3$ is oxazole.

With regard to the compounds described herein, $R^4$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, COO$C_1$-$C_6$alkyl, COO$C_1$-$C_6$alkyl$C_3$-$C_6$cycloalkyl, phenyl and oxazole.

In certain embodiments, $R^4$ is hydrogen. In certain embodiments, $R^4$ is halogen. Suitable halogens include, but are not limited to, fluorine, chlorine, bromine and iodine. In certain embodiments, $R^4$ is CN. In certain embodiments, $R^4$ is OH. In certain embodiments, $R^4$ is $C_1$-$C_6$alkylOH. Suitable $C_1$-$C_6$alkylOHs include, but are not limited to, methanol, propanol, ethanol and butanol.

In certain embodiments, $R^4$ is $C_1$-$C_6$alkoxy. Suitable $C_1$-$C_6$alkoxys include but are not limited to, methoxy and ethoxy. In certain embodiments, $R^4$ is halo$C_1$-$C_6$alkoxy. Suitable halo$C_1$-$C_6$alkoxys include, but are not limited to, trifluoromethoxy. In certain embodiments, $R^4$ is $C_1$-$C_6$alkyl$C_1$-$C_6$alkoxy. Suitable $C_1$-$C_6$alkyl$C_1$-$C_6$alkoxys include, but are not limited to, methylpropoxy. In certain embodiments, $R^4$ is $C_3$-$C_6$cycloalkyl$C_1$-$C_6$alkoxy. Suitable $C_3$-$C_6$cycloalkyl$C_1$-$C_6$alkoxys include, but are not limited to, cyclopropylmethoxy. In certain embodiments, $R^4$ is $C_1$-$C_6$alkyl. Suitable $C_1$-$C_6$alkyls include but are not limited to, methyl, ethyl and isopropyl. In certain embodiments, $R^4$ is halo$C_1$-$C_6$alkyl. Suitable halo$C_1$-$C_6$alkyls include, but are not limited to, trifluoromethyl and difluoroethyl. In certain embodiments, $R^4$ is $C_3$-$C_6$cycloalkyl. Suitable $C_3$-$C_6$cycloalkyls include, but are not limited to, cyclopropyl, cyclobutyl, cyclopentyl and cyclohexyl. In certain embodiments, $R^4$ is $C_2$-$C_6$alkenyl. Suitable $C_2$-$C_6$alkenyls include but are not limited to, vinyl.

In certain embodiments, $R^4$ is COO$C_1$-$C_6$alkyl. Suitable COO$C_1$-$C_6$alkyls include, but are not limited to, methoxycarbonyl, ethoxycarbonyl, propoxycarbonyl and butoxycarbonyl. In certain embodiments, $R^4$ is COO$C_1$-$C_6$alkyl$C_3$-$C_6$cycloalkyl.

In certain embodiments, $R^4$ is phenyl. In certain embodiments, $R^4$ is oxazole.

With regard to the compounds described herein, $R^5$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^{10}$, and the carbon to which $R^{10}$ and $R^5$ are attached, forms a $C_3$-$C_6$cycloalkyl.

In certain embodiments, $R^5$ is hydrogen. In certain embodiments, $R^5$ is halogen. Suitable halogens include, but are not limited to, fluorine, chlorine, bromine and iodine. In certain embodiments, $R^5$ is $C_1$-$C_6$alkyl. Suitable $C_1$-$C_6$alkyls include but are not limited to, methyl, ethyl and isopropyl. In certain embodiments, $R^5$ is $C_3$-$C_6$cycloalkyl. Suitable $C_3$-$C_6$cycloalkyls include, but are not limited to, cyclopropyl and cyclobutyl. In certain embodiments, $R^5$ is $C_1$-$C_6$alkoxy. Suitable $C_1$-$C_6$alkoxys include but are not limited to, methoxy and ethoxy. In certain embodiments, $R^5$ is halo$C_1$-$C_6$alkyl. Suitable halo$C_1$-$C_6$alkyls include but are not limited to, trifluoromethyl.

In certain embodiments, $R^5$ forms a $C_3$-$C_6$cycloalkyl with $R^{10}$ and the carbon in which $R^5$ and $R^{10}$ are attached. Suitable $C_3$-$C_6$cycloalkyls include, but are not limited to, cyclopropyl and cyclobutyl.

With regard to the compounds described herein, $R^6$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^7$, and the carbon to which $R^6$ and $R^7$ are attached, forms a $C_3$-$C_6$cycloalkyl or when taken with $R^{11}$, and the carbon to which $R^6$ and $R^{11}$ are attached, form a $C_3$-$C_6$cycloalkyl.

In certain embodiments, $R^6$ is hydrogen. In certain embodiments, $R^6$ is halogen. Suitable halogens include, but are not limited to, fluorine, chlorine, bromine and iodine. In certain embodiments, $R^6$ is $C_1$-$C_6$alkyl. Suitable $C_1$-$C_6$alkyls include but are not limited to, methyl, ethyl and isopropyl. In certain embodiments, $R^6$ is $C_3$-$C_6$cycloalkyl. Suitable $C_3$-$C_6$cycloalkyls include, but are not limited to, cyclopropyl and cyclobutyl. In certain embodiments, $R^6$ is $C_1$-$C_6$alkoxy. Suitable $C_1$-$C_6$alkoxys include but are not limited to, methoxy and ethoxy. In certain embodiments, $R^6$ is halo$C_1$-$C_6$alkyl. Suitable halo$C_1$-$C_6$alkyls include but are not limited to, trifluoromethyl.

In certain embodiments, $R^6$ forms a $C_3$-$C_6$cycloalkyl with $R^7$ and the carbon in which $R^6$ and $R^7$ are attached. Suitable $C_3$-$C_6$cycloalkyls include, but are not limited to, cyclopropyl and cyclobutyl.

In certain embodiments, $R^6$ forms a $C_3$-$C_6$cycloalkyl with $R^{11}$ and the carbon in which $R^6$ and $R^{11}$ are attached. Suitable $C_3$-$C_6$cycloalkyls include, but are not limited to, cyclopropyl and cyclobutyl.

With regard to the compounds described herein, $R^7$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^6$, and the carbon to which $R^7$ and $R^6$ are attached, forms a $C_3$-$C_6$cycloalkyl.

In certain embodiments, $R^7$ is hydrogen. In certain embodiments, $R^7$ is halogen. Suitable halogens include, but are not limited to, fluorine, chlorine, bromine and iodine. In certain embodiments, $R^7$ is $C_1$-$C_6$alkyl. Suitable $C_1$-$C_6$alkyls include but are not limited to, methyl, ethyl and isopropyl. In certain embodiments, $R^7$ is $C_3$-$C_6$cycloalkyl. Suitable $C_3$-$C_6$cycloalkyls include, but are not limited to, cyclopropyl and cyclobutyl. In certain embodiments, $R^7$ is $C_1$-$C_6$alkoxy. Suitable $C_1$-$C_6$alkoxys include but are not limited to, methoxy and ethoxy. In certain embodiments, $R^7$ is halo$C_1$-$C_6$alkyl. Suitable halo$C_1$-$C_6$alkyls include but are not limited to, trifluoromethyl.

In certain embodiments, $R^7$ forms a $C_3$-$C_6$cycloalkyl with $R^6$ and the carbon in which $R^7$ and $R^6$ are attached. Suitable $C_3$-$C_6$cycloalkyls include, but are not limited to, cyclopropyl and cyclobutyl.

With regard to the compounds described herein, $R^8$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl.

In certain embodiments, $R^8$ is hydrogen. In certain embodiments, $R^8$ is halogen. Suitable halogens include, but are not limited to, fluorine, chlorine, bromine and iodine. In certain embodiments, $R^8$ is $C_1$-$C_6$alkyl. Suitable $C_1$-$C_6$alkyls include but are not limited to, methyl, ethyl and isopropyl. In certain embodiments, $R^8$ is $C_3$-$C_6$cycloalkyl. Suitable $C_3$-$C_6$cycloalkyls include, but are not limited to, cyclopropyl and cyclobutyl. In certain embodiments, $R^8$ is $C_1$-$C_6$alkoxy. Suitable $C_1$-$C_6$alkoxys include but are not limited to, methoxy and ethoxy. In certain embodiments, $R^8$ is halo$C_1$-$C_6$alkyl. Suitable halo$C_1$-$C_6$alkyls include but are not limited to, trifluoromethyl.

With regard to the compounds described herein, $R^9$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl.

In certain embodiments, $R^9$ is hydrogen. In certain embodiments, $R^9$ is halogen. Suitable halogens include, but are not limited to, fluorine, chlorine, bromine and iodine. In certain embodiments, $R^9$ is $C_1$-$C_6$alkyl. Suitable $C_1$-$C_6$alkyls include but are not limited to, methyl, ethyl and isopropyl. In certain embodiments, $R^9$ is $C_3$-$C_6$cycloalkyl. Suitable $C_3$-$C_6$cycloalkyls include, but are not limited to, cyclopropyl and cyclobutyl. In certain embodiments, $R^9$ is $C_1$-$C_6$alkoxy. Suitable $C_1$-$C_6$alkoxys include but are not limited to, methoxy and ethoxy. In certain embodiments, $R^9$ is haloC$_1$-C$_6$alkyl. Suitable haloC$_1$-C$_6$alkyls include but are not limited to, trifluoromethyl.

With regard to the compounds described herein, $R^{10}$ is selected from the group consisting of hydrogen, halogen, C$_1$-C$_6$alkyl, C$_3$-C$_6$cycloalkyl, C$_1$-C$_6$alkoxy and haloC$_1$-C$_6$alkyl or when taken with $R^5$, and the carbon to which $R^{10}$ and $R^5$ are attached, forms a C$_3$-C$_6$cycloalkyl.

In certain embodiments, $R^{10}$ is hydrogen. In certain embodiments, $R^{10}$ is halogen. Suitable halogens include, but are not limited to, fluorine, chlorine, bromine and iodine. In certain embodiments, $R^{10}$ is C$_1$-C$_6$alkyl. Suitable C$_1$-C$_6$alkyls include but are not limited to, methyl, ethyl and isopropyl. In certain embodiments, $R^{10}$ is C$_3$-C$_6$cycloalkyl. Suitable C$_3$-C$_6$cycloalkyls include, but are not limited to, cyclopropyl and cyclobutyl. In certain embodiments, $R^{10}$ is C$_1$-C$_6$alkoxy. Suitable C$_1$-C$_6$alkoxys include but are not limited to, methoxy and ethoxy. In certain embodiments, $R^{10}$ is haloC$_1$-C$_6$alkyl. Suitable haloC$_1$-C$_6$alkyls include but are not limited to, trifluoromethyl.

In certain embodiments, $R^{10}$ forms a C$_3$-C$_6$cycloalkyl with $R^5$ and the carbon in which $R^{10}$ and $R^5$ are attached. Suitable C$_3$-C$_6$cycloalkyls include, but are not limited to, cyclopropyl and cyclobutyl.

With regard to the compounds described herein, $R^{11}$ is selected from the group consisting of hydrogen, halogen, OH, C$_1$-C$_6$alkyl, and haloC$_1$-C$_6$alkyl or when taken with $R^6$, and the carbon to which $R^{11}$ and $R^6$ are attached, forms a C$_3$-C$_6$cycloalkyl. In certain embodiments, $R^{11}$ is hydrogen. In certain embodiments, $R^{11}$ is halogen. Suitable halogens include, but are not limited to, fluorine, chlorine, bromine and iodine. In certain embodiments, $R^{11}$ is —OH. In certain embodiments, $R^{11}$ is C$_1$-C$_6$alkyl. Suitable C$_1$-C$_6$alkyls include but are not limited to, methyl, ethyl and isopropyl. In certain embodiments, $R^{11}$ is haloC$_1$-C$_6$alkyl. Suitable haloC$_1$-C$_6$alkyls include but are not limited to, trifluoromethyl.

In certain embodiments, $R^{11}$ forms a C$_3$-C$_6$cycloalkyl with $R^6$ and the carbon in which $R^{11}$ and $R^6$ are attached. Suitable C$_3$-C$_6$cycloalkyls include, but are not limited to, cyclopropyl and cyclobutyl.

With regard to the compounds described herein, $R^{12}$ is selected from the group consisting of hydrogen, halogen, OH, C$_1$-C$_6$alkyl, COOC$_1$-C$_6$alkylC$_3$-C$_6$cycloalkyl, C$_3$-C$_6$cycloalkyl and haloC$_1$-C$_6$alkyl. In certain embodiments, $R^{12}$ is hydrogen. In certain embodiments, $R^{12}$ is halogen. Suitable halogens include, but are not limited to, fluorine, chlorine, bromine and iodine. In certain embodiments, $R^{12}$ is —OH. In certain embodiments, $R^{12}$ is C$_1$-C$_6$alkyl. Suitable C$_1$-C$_6$alkyls include but are not limited to, methyl, ethyl and isopropyl. In certain embodiments, $R^{12}$ is COOC$_1$-C$_6$alkylC$_3$-C$_6$cycloalkyl. Suitable COOC$_1$-C$_6$alkylC$_3$-C$_6$cycloalkyls include, but are not limited to, COOmethylcyclopropyl. In certain embodiments, $R^{12}$ is C$_3$-C$_6$cycloalkyl. Suitable C$_3$-C$_6$cycloalkyls include, but are not limited to, cyclopropyl and cyclobutyl. In certain embodiments, $R^{12}$ is haloC$_1$-C$_6$alkyl. Suitable haloC$_1$-C$_6$alkyls include but are not limited to, trifluoromethyl.

With regard to the compounds described herein, $R^{13}$ is selected from the group consisting of hydrogen, halogen, OH, C$_1$-C$_6$alkyl, C$_3$-C$_6$cycloalkyl and haloC$_1$-C$_6$alkyl. In certain embodiments, $R^{13}$ is hydrogen. In certain embodiments, $R^{13}$ is halogen. Suitable halogens include, but are not limited to, fluorine, chlorine, bromine and iodine. In certain embodiments, $R^{13}$ is —OH. In certain embodiments, $R^{13}$ is C$_1$-C$_6$alkyl. Suitable C$_1$-C$_6$alkyls include but are not limited to, methyl, ethyl and isopropyl. In certain embodiments, $R^{13}$ is C$_1$-C$_6$alkyl. Suitable C$_1$-C$_6$alkyls include but are not limited to, methyl, ethyl and isopropyl. In certain embodiments, $R^{13}$ is C$_3$-C$_6$cycloalkyl. Suitable C$_3$-C$_6$cycloalkyls include, but are not limited to, cyclopropyl and cyclobutyl. In certain embodiments, $R^{13}$ is haloC$_1$-C$_6$alkyl. Suitable haloC$_1$-C$_6$alkyls include but are not limited to, trifluoromethyl.

With regard to the compounds described herein, $R^{14}$ is selected from the group consisting of hydrogen, halogen, OH, C$_1$-C$_6$alkyl, C$_3$-C$_6$cycloalkyl and haloC$_1$-C$_6$alkyl. In certain embodiments, $R^{14}$ is hydrogen. In certain embodiments, $R^{14}$ is halogen. Suitable halogens include, but are not limited to, fluorine, chlorine, bromine and iodine. In certain embodiments, $R^{14}$ is —OH. In certain embodiments, $R^{14}$ is C$_1$-C$_6$alkyl. Suitable C$_1$-C$_6$alkyls include but are not limited to, methyl, ethyl and isopropyl. In certain embodiments, $R^{14}$ is C$_3$-C$_6$cycloalkyl. Suitable C$_3$-C$_6$cycloalkyls include, but are not limited to, cyclopropyl and cyclobutyl. In certain embodiments, $R^{14}$ is haloC$_1$-C$_6$alkyl. Suitable haloC$_1$-C$_6$alkyls include but are not limited to, trifluoromethyl.

With regard to the compounds described herein, $R^{15}$ is selected from the group consisting of hydrogen, halogen, OH, C$_1$-C$_6$alkyl, and haloC$_1$-C$_6$alkyl. In certain embodiments, $R^{15}$ is hydrogen. In certain embodiments, $R^{15}$ is halogen. Suitable halogens include, but are not limited to, fluorine, chlorine, bromine and iodine. In certain embodiments, $R^{15}$ is —OH. In certain embodiments, $R^{15}$ is C$_1$-C$_6$alkyl. Suitable C$_1$-C$_6$alkyls include but are not limited to, methyl, ethyl and isopropyl. In certain embodiments, $R^{15}$ is haloC$_1$-C$_6$alkyl. Suitable haloC$_1$-C$_6$alkyls include but are not limited to, trifluoromethyl.

With regard to the compounds described herein, $R^{16}$ is selected from the group consisting of hydrogen, halogen, OH, C$_1$-C$_6$alkyl, and haloC$_1$-C$_6$alkyl. In certain embodiments, $R^{16}$ is hydrogen. In certain embodiments, $R^{16}$ is halogen. Suitable halogens include, but are not limited to, fluorine, chlorine, bromine and iodine. In certain embodiments, $R^{16}$ is —OH. In certain embodiments, $R^{16}$ is C$_1$-C$_6$alkyl. Suitable C$_1$-C$_6$alkyls include but are not limited to, methyl, ethyl and isopropyl. In certain embodiments, $R^{16}$ is haloC$_1$-C$_6$alkyl. Suitable haloC$_1$-C$_6$alkyls include but are not limited to, trifluoromethyl.

With regard to the compounds described herein, $R^{17}$ is selected from the group consisting of hydrogen, halogen, C$_1$-C$_6$alkyl, C$_1$-C$_6$alkoxy, and haloC$_1$-C$_6$alkyl. In certain embodiments, $R^{17}$ is hydrogen. In certain embodiments, $R^{17}$ is halogen. Suitable halogens include, but are not limited to, fluorine, chlorine, bromine and iodine. In certain embodiments, $R^{17}$ is C$_1$-C$_6$alkyl. Suitable C$_1$-C$_6$alkyls include but are not limited to, methyl, ethyl and isopropyl. In certain embodiments, $R^{17}$ is C$_1$-C$_6$alkoxy. Suitable C$_1$-C$_6$alkoxys include but are not limited to, methoxy and ethoxy. In certain embodiments, $R^{17}$ is haloC$_1$-C$_6$alkyl. Suitable haloC$_1$-C$_6$alkyls include but are not limited to, trifluoromethyl.

The dashed lines in Formula I indicate the possibility of aromaticity or no aromaticity in the ring depending on the substitution of the ring.

Also described herein are compounds selected from the group consisting of:
7-chloro-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
8-fluoro-7-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-8-(difluoromethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-bromo-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-hydroxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6,7,8-trifluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7,8-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6,8-difluoro-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-chloro-7-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-chloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-chloro-6,8-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)quinoline-3-carbonitrile;

8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)quinoline-3-carbonitrile;

6-chloro-8-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-methoxy-8-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-bromo-7-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)-1,8-naphthyridine-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethoxy)quinoline-3-carbonitrile;

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-(trifluoromethyl)quinoline-3-carbonitrile;

6,7-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6,8-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-chloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-fluoro-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-bromo-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-1,8-naphthyridine-3-carbonitrile;

6-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-1,7-naphthyridine-3-carbonitrile 6-methoxy-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-1,5-naphthyridine-3-carbonitrile;

7-methoxy-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

5-methoxy-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-(difluoromethoxy)-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(propan-2-yloxy)quinoline-3-carbonitrile;

7-(cyclopropyloxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-ethoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-bromo-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

7-chloro-8-fluoro-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

8-fluoro-7-methoxy-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

7-(trifluoromethyl)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

7-methoxy-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-fluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-methoxy-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-methoxy-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-bromo-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6,8-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6,7-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

5,6-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

2,6-dimethyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-cyclopropyl-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

2-methyl-4-(4-(3-(trifluoromethyl)-5,6,7,8-tetrahydro-[1,2,4]triazolo[4,3-a]pyrazine-7-carbonyl)piperidin-1-yl)-6-vinylquinoline-3-carbonitrile;

6-(difluoromethyl)-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

2,6-dichloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-2-(difluoromethyl)-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-2-(difluoromethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-2-(difluoromethyl)-4-[(3R,4R)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-8-(difluoromethyl)-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

methyl 6-chloro-3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2-carboxylate;

dimethyl 3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2,6-dicarboxylate;

methyl 6-chloro-3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2-carboxylate;

7-(difluoromethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-cyclopropyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(propan-2-yloxy)quinoline-3-carbonitrile;

7-chloro-4-{(3R,4R)-4-[(3-cyclopropyl-5,6-dihydro[1,2,4]triazolo[4,3-a]pyrazin-7(8H)-yl)carbonyl]-3-methylpiperidin-1-yl}-8-fluoroquinoline-3-carbonitrile;

7-chloro-4-{(3S,4S)-4-[(3-cyclopropyl-5,6-dihydro[1,2,4]triazolo[4,3-a]pyrazin-7(8H)-yl)carbonyl]-3-methylpiperidin-1-yl}-8-fluoroquinoline-3-carbonitrile;

7-cyclopropyl-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-(cyclopropylmethoxy)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

7-(2-methylpropoxy)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

4-[(3S,4S)-4-{[3-(difluoromethyl)-5,6-dihydro[1,2,4]triazolo[4,3-a]pyrazin-7(8H)-yl]carbonyl}-3-methylpiperidin-1-yl]-7-methoxyquinoline-3-carbonitrile;

7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 1-oxide;

6-chloro-4-[(3S,4S)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3S,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3R,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3R,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2R,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 6-chloro-4-[(2S,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2R,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2S,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2R,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4[(2S,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3R,4R)-3-ethyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxy quinoline-3-carbonitrile;

6-chloro-4-[(3R,4R)-3-ethyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-ethyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile;

6-chloro-4-[(3S,4S)-3-ethyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3R,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3S,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3R,4R)-3-cyclopropyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile;

6-chloro-4-[(3S,4S)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3S,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-cyclopropyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile;

7-(1,1-difluoroethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-[($^2$H$_3$)methyloxy]-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-((1S,6R)-6-(3-(trifluoromethyl)-5,6,7,8-tetrahydro-[1,2,4]triazolo[4,3-a]pyrazine-7-carbonyl)-3-azabicyclo[4.1.0]heptan-3-yl)quinoline-3-carbonitrile;

6-chloro-4-((1R,6S)-6-(3-(trifluoromethyl)-5,6,7,8-tetrahydro-[1,2,4]triazolo[4,3-a]pyrazine-7-carbonyl)-3-azabicyclo[4.1.0]heptan-3-yl)quinoline-3-carbonitrile;

4-((3S,4S)-4-(5,5-dimethyl-3-(trifluoromethyl)-5,6,7,8-tetrahydro-[1,2,4]triazolo[4,3-a]pyrazine-7-carbonyl)-3-methylpiperidin-1-yl)-8-fluoro-7-methoxyquinoline-3-carbonitrile;

4-((3R,5R)-3,5-dimethyl-4-(3-(trifluoromethyl)-5,6,7,8-tetrahydro-[1,2,4]triazolo[4,3-a]pyrazine-7-carbonyl)piperazin-1-yl)-7-methoxyquinoline-3-carbonitrile;

4-((3S,5R)-3,5-dimethyl-4-(3-(trifluoromethyl)-5,6,7,8-tetrahydro-[1,2,4]triazolo[4,3-a]pyrazine-7-carbonyl)piperazin-1-yl)-7-methoxyquinoline-3-carbonitrile;

7-methoxy-4-{3-methyl-4-[(3-methyl-5,6-dihydro[1,2,4]triazolo[4,3-a]pyrazin-7(8H)-yl)carbonyl]piperidin-1-yl}quinoline-3-carbonitrile;

1-methylcyclopropyl 3-cyano-4-((3S,4S)-4-(3-cyclopropyl-5,6,7,8-tetrahydro-[1,2,4]triazolo[4,3-a]pyrazine-7-carbonyl)-3-methylpiperidin-1-yl)-5,6-dihydro-1,7-naphthyridine-7(8H)-carboxylate;

6-cyclopropyl-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-cyclobutyl-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-(difluoromethyl)-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-(oxazol-2-yl)quinoline-3-carbonitrile;

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-phenylquinoline-3-carbonitrile;

6-chloro-4-[(3S,4S)-4-(3,4-dihydropyrrolo[1,2-a]pyrazin-2(1H)-ylcarbonyl)-3-methylpiperidin-1-yl]-2-methylquinoline-3-carbonitrile;

6-chloro-2-methyl-4-[(3S,4S)-3-methyl-4-{[3-(trifluoromethyl)-2,4,6,7-tetrahydro-5H-pyrazolo[4,3-c]pyridin-5-yl]carbonyl}piperidin-1-yl]quinoline-3-carbonitrile;

6-chloro-2-methyl-4-[(3S,4S)-3-methyl-4-{[3-(trifluoromethyl)-2,4,5,7-tetrahydro-6H-pyrazolo[3,4-c]pyridin-6-yl]carbonyl}piperidin-1-yl]quinoline-3-carbonitrile;

6-chloro-4-[(3S,4S)-4-(6,7-dihydro[1,2,3]triazolo[1,5-a]pyrazin-5(4H)-ylcarbonyl)-3-methylpiperidin-1-yl]-2-methylquinoline-3-carbonitrile;

6-chloro-2-methyl-4-[(3S,4S)-3-methyl-4-(1,4,6,7-tetrahydro-5H-pyrazolo[4,3-c]pyridin-5-ylcarbonyl)piperidin-1-yl]quinoline-3-carbonitrile;

6-chloro-4-[(3S,4S)-4-(6,7-dihydropyrazolo[1,5-a]pyrazin-5(4H)-ylcarbonyl)-3-methylpiperidin-1-yl]-2-methylquinoline-3-carbonitrile;

6-chloro-4-[(3S,4S)-4-(6,7-dihydroisoxazolo[4,5-c]pyridin-5(4H)-ylcarbonyl)-3-methylpiperidin-1-yl]-2-methylquinoline-3-carbonitrile;

6-chloro-2-methyl-4-[(3S,4S)-3-methyl-4-{[2-(trifluoromethyl)-6,7-dihydro[1,3]thiazolo[4,5-c]pyridin-5(4H)-yl]carbonyl}piperidin-1-yl]quinoline-3-carbonitrile; and 6-chloro-2-methyl-4-[(3S,4S)-3-methyl-4-{[2-(trifluoromethyl)-5,6-dihydroimidazo[1,2-a]pyrazin-7(8H)-yl]carbonyl}piperidin-1-yl]quinoline-3-carbonitrile;

7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-(2-methylpropoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-(2,2-difluoroethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-chloro-4-(4-{[2-(trifluoromethyl)-5,6-dihydroimidazo[1,2-a]pyrazin-7(8H)-yl]carbonyl}piperidin-1-yl)quinoline-3-carbonitrile;

6-chloro-4-[4-(5,6-dihydroimidazo[1,5-a]pyrazin-7(8H)-ylcarbonyl)piperidin-1-yl]quinoline-3-carbonitrile;

6-chloro-4-{4-[(3-ethyl-5,6-dihydro[1,2,4]triazolo[4,3-a]pyrazin-7(8H)-yl)carbonyl]piperidin-1-yl}quinoline-3-carbonitrile;

6-chloro-4-{4-[(3-cyclopropyl-1,4,5,7-tetrahydro-6H-pyrazolo[3,4-c]pyridin-6-yl)carbonyl]piperidin-1-yl}quinoline-3-carbonitrile;

6-chloro-4-[4-(1,4,5,7-tetrahydro-6H-pyrazolo[3,4-c]pyridin-6-ylcarbonyl)piperidin-1-yl]quinoline-3-carbonitrile;

6-chloro-4-(4-{[5,5-dimethyl-3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-[4-(5,6-dihydro[1,2,4]triazolo[4,3-a]pyrazin-7(8H)-ylcarbonyl)piperidin-1-yl]quinoline-3-carbonitrile;

6-chloro-4-(4-{[3-(trifluoromethyl)-1,4,5,7-tetrahydro-6H-pyrazolo[3,4-c]pyridin-6-yl]carbonyl}piperidin-1-yl)quinoline-3-carbonitrile;

6-chloro-4-(4-{[5-methyl-3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-(4-{[1-methyl-3-(trifluoromethyl)-1,4,5,7-tetrahydro-6H-pyrazolo[3,4-c]pyridin-6-yl]carbonyl}piperidin-1-yl)quinoline-3-carbonitrile;

6-chloro-4-{4-[(3-ethyl-5,6-dihydroimidazo[1,5-a]pyrazin-7(8H)-yl)carbonyl]piperidin-1-yl}quinoline-3-carbonitrile;

6-chloro-4-(4-{[3-(propan-2-yl)-5,6-dihydroimidazo[1,5-a]pyrazin-7(8H)-yl]carbonyl}piperidin-1-yl)quinoline-3-carbonitrile;

6-chloro-4-(3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-fluoro-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-[3-(trifluoromethyl)-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-(3-methyl-4-{[3-(trifluoromethyl)-5,6-dihydro[1,2,4]triazolo[4,3-a]pyrazin-7(8H)-yl]carbonyl}piperidin-1-yl)-6-(trifluoromethyl)quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-6-(trifluoromethyl)quinoline-3-carbonitrile;

4-[(3R,4R)-3-methyl-4-{[3-(trifluoromethyl)-5,6-dihydro[1,2,4]triazolo[4,3-a]pyrazin-7(8H)-yl]carbonyl}piperidin-1-yl]-6-(trifluoromethyl)quinoline-3-carbonitrile;

6-chloro-4-(4-fluoro-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-(4-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-2-methyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-chloro-3-cyano-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinolone 1-oxide;

6-chloro-4-(4-{[3-(trifluoromethyl)-5,6-dihydro[1,2,4]triazolo[4,3-a]pyrazin-7(8H)-yl]carbonyl}cyclohexyl)quinoline-3-carbonitrile;

6-chloro-2-hydroxy-4-(3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-chloro-2-methoxy-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-(4-{[3-(trifluoromethyl)-5,6-dihydro[1,2,4]triazolo[4,3-a]pyrazin-7(8H)-yl]carbonyl}-4,7-diazaspiro[2.5]oct-7-yl)quinoline-3-carbonitrile;

6-chloro-4-[(3R)-3-methyl-4-{[3-(trifluoromethyl)-5,6-dihydro[1,2,4]triazolo[4,3-a]pyrazin-7(8H)-yl]carbonyl}piperazin-1-yl]quinoline-3-carbonitrile;

6-chloro-4-(4-{[3-(trifluoromethyl)-5,6-dihydro[1,2,4]triazolo[4,3-a]pyrazin-7(8H)-yl]carbonyl}piperazin-1-yl)quinoline-3-carbonitrile;

or a pharmaceutically acceptable salt thereof.

Definitions

The term "halogen" includes a fluorine atom, a chlorine atom, a bromine atom, and an iodine atom.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "$C_1$-$C_6$alkoxy" refers to an alkyl group having 1 to 6 carbons linked to oxygen. Examples include methoxy, ethoxy, butoxy and propoxy.

The term "halo$C_1$-$C_6$alkyl" refers to a $C_1$-$C_6$alkyl with the hydrogen atoms thereof being partially or completely substituted with halogen, examples thereof including fluoromethyl, difluoromethyl, trifluoromethyl, 2-fluoroethyl, 1,2-difluoroethyl, 2,2-difluoroethyl and the like.

The term "halo$C_1$-$C_6$alkoxy" refers to —O$C_1$-$C_6$alkyl as defined above, which is substituted with 1-3 halogen atoms which are identical or different, and specifically includes, for example, a trifluoromethoxy group.

The term "—COO$C_1$-$C_6$alkyl" refers to a —COOH group wherein the —OH is replaced with an alkoxy group as defined above. Examples include methoxycarbonyl, ethoxycarbonyl and butoxycarbonyl.

The term "$C_3$-$C_6$cycloalkyl" encompasses saturated cycloalkyls having 3 to 6 carbons. Examples of cycloalkyls include cyclopropyl, cyclobutyl, cyclopentyl, cyclohexyl, and the like.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The term "patient" refers to a mammalian patient, including human or animal. In certain embodiments, "patient" refers to domesticated animal such as a cat or dog. Preferably, "patient" refers to a human patient, receiving or registered to receive medical treatment.

The compounds of the present invention contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that reference to compounds described herein is meant to include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the Schemes and Examples herein using appropriate isotopically-enriched reagents and/or Intermediates.

Methods of Treatment

Also encompassed by the present invention are methods of treating Cyp8b1-related diseases. The compounds described herein can be effective in preventing or treating various Cyp8b1-related diseases, such as cardiometabolic diseases associated with elevated LDL, such as atherosclerosis, fatty liver and nonalcoholic steatohepatitis (NASH), and noninsulin-dependent diabetes (NIDDM), hyperglycemia, and other symptoms associated with NIDDM. The compounds of the invention can be useful as a preventive or a remedy for noninsulin-dependent diabetes (NIDDM), hyperglycemia, and other symptoms associated with NIDDM.

One aspect of the invention that is of interest relates to a method of treating hyperglycemia, diabetes or insulin resistance in a mammalian patient in need of such treatment which comprises administering to said patient a compound described herein or a pharmaceutically acceptable salt thereof or a pharmaceutical composition comprising the compound or pharmaceutically acceptable salt, in an amount that is effective to treat hyperglycemia, diabetes or insulin resistance.

More particularly, another aspect of the invention that is of interest relates to a method of treating type 2 diabetes in a mammalian patient in need of such treatment comprising administering to the patient a compound described herein or a pharmaceutically acceptable salt thereof or a pharmaceutical composition comprising the compound or pharmaceutically acceptable salt, in an amount that is effective to treat type 2 diabetes.

Yet another aspect of the invention that is of interest relates to a method of treating non-insulin dependent diabetes mellitus in a mammalian patient in need of such treatment comprising administering to the patient a compound described herein or a pharmaceutically acceptable salt thereof or a pharmaceutical composition comprising the compound or pharmaceutically acceptable salt, in an amount that is effective to treat non-insulin dependent diabetes mellitus.

The present invention is also directed to the use of a compound described herein or a pharmaceutically acceptable salt thereof in the manufacture of a medicament for use in treating various CYP8B1-related diseases, such as cardiometabolic diseases associated with elevated LDL, such as atherosclerosis, fatty liver and nonalcoholic steatohepatitis (NASH), and noninsulin-dependent diabetes (NIDDM), hyperglycemia, and other symptoms associated with NIDDM, metabolic diseases such as obesity, diabetes, hormone secretion disorder, hyperlipemia, gout, fatty liver, and the like; circulatory diseases such as angina pectoris, acute/congestive cardiac insufficiency, myocardial infarction, coronary arteriosclerosis, hypertension, nephropathy, electrolyte abnormality, and the like. The compounds described herein are especially useful as a preventive or a remedy for noninsulin-dependent diabetes (NIDDM), hyperglycemia, and other symptoms associated with NIDDM.

For example, the present invention is directed to the use of a compound described herein or a pharmaceutically acceptable salt thereof in the manufacture of a medicament for use in treating noninsulin-dependent diabetes (NIDDM), hyperglycemia, and other symptoms associated with NIDDM.

Additionally, the present invention is directed to the use of a compound described herein or a pharmaceutically acceptable salt thereof in the manufacture of a medicament for use in treating diabetes.

Additionally, the present invention is directed to the use of a compound described herein or a pharmaceutically acceptable salt thereof in the manufacture of a medicament for use in treating fatty liver and nonalcoholic steatohepatitis (NASH).

Pharmaceutical Compositions

Compounds described herein may be administered orally or parenterally. As formulated into a dosage form suitable for administration, the compounds described herein can be used as a pharmaceutical composition for the prevention, treatment, or remedy of the above diseases.

In clinical use of the compounds described herein, usually, the compound is formulated into various preparations together with pharmaceutically acceptable additives according to the dosage form, and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders, suppositories; and liquid preparations such as syrups, elixirs, injections. These may be formulated according to conventional methods known in the field of pharmaceutical preparations. The liquid preparations may also be in such a form that may be dissolved or suspended in water or in any other suitable medium in their use.

Especially for injections, if desired, the preparations may be dissolved or suspended in physiological saline or glucose liquid, and a buffer or a preservative may be optionally added thereto.

The pharmaceutical compositions may contain the compound of the invention in an amount of from 1 to 99.9% by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day. For oral administration, the compositions are preferably provided in the form of tablets or capsules containing from 0.01 mg to 1,000 mg. In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound of described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

Examples of other active ingredients that may be administered in combination with a compound of any of the Formulas described herein or a pharmaceutically acceptable salt thereof and either administered separately or in the same pharmaceutical composition, include, but are not limited to:

(1) dipeptidyl peptidase-IV (DPP-4) inhibitors, such as, sitagliptin (disclosed in U.S. Pat. No. 6,699,871), vildagliptin, saxagliptin, alogliptin, denagliptin, carmegliptin, dutogliptin, melogliptin, linagliptin;

(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), such as those disclosed in WO 02/060388, WO 02/08188, WO 2004/019869, WO 2004/020409, WO 2004/020408, and WO 2004/066963, and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;

(3) insulin or insulin analogs, such as insulin lispro, insulin detemir, insulin glargine, insulin glulisine, and inhalable formulations of each thereof;

(4) leptin and leptin derivatives and agonists;

(5) amylin and amylin analogs, such as pramlintide;

(6) sulfonylurea and non-sulfonylurea insulin secretagogues, such as tolbutamide, glyburide, glipizide, glimepiride, mitiglinide, and meglitinides, such as nateglinide and repaglinide;

(7) α-glucosidase inhibitors (such as acarbose, voglibose and miglitol);

(8) glucagon receptor antagonists, such as those disclosed in WO 98/04528, WO 99/01423, WO 00/39088, and WO 00/69810;

(9) incretin mimetics, such as GLP-1, GLP-1 analogs, derivatives, and mimetics; and GLP-1 receptor agonists, such as exenatide, liraglutide, taspoglutide, AVE0010, CJC-1131, and BIM-51077, including intranasal, transdermal, and once-weekly formulations thereof;

(10) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(11) HDL-raising drugs, such as niacin or a salt thereof and extended-release versions thereof;

(12) antiobesity compounds such as topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $β_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin;

(13) agents intended for use in inflammatory conditions, such as aspirin, non-steroidal anti-inflammatory drugs (NSAIDs), glucocorticoids, and selective cyclooxygenase-2 (COX-2) inhibitors;

(14) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(15) glucokinase activators (GKAs), such as LY2599506;

(16) inhibitors of 11β-hydroxysteroid dehydrogenase type 1, such as those disclosed in U.S. Pat. No. 6,730,690; WO 03/104207; and WO 04/058741;

(17) inhibitors of cholesteryl ester transfer protein (CETP), such as torcetrapib and MK-0859;

(18) inhibitors of fructose 1,6-bisphosphatase, such as those disclosed in U.S. Pat. Nos. 6,054,587; 6,110,903; 6,284,748; 6,399,782; and 6,489,476;

(19) inhibitors of acetyl CoA carboxylase-1 or 2 (ACC1 or ACC2);

(20) AMP-activated Protein Kinase (AMPK) activators;

(21) agonists of the G-protein-coupled receptors: GPR-109, GPR-119, and GPR-40;

(22) SSTR3 antagonists, such as those disclosed in WO 2009/011836;

(23) neuromedin U receptor agonists, such as those disclosed in WO2009/042053, including, but not limited to, neuromedin S (NMS);

(24) inhibitors of stearoyl-coenzyme A delta-9 desaturase (SCD);

(25) GPR-105 antagonists, such as those disclosed in WO 2009/000087;

(26) inhibitors of glucose uptake, such as sodium-glucose transporter (SGLT) inhibitors and its various isoforms, such as SGLT-1; SGLT-2, such as dapagliflozin, canagliflozin, ertugliflozin, empagliflozin, ipragliflozin and remogliflozin; and SGLT-3;

(27) inhibitors of acyl coenzyme A:diacylglycerol acyltransferase 1 and 2 (DGAT-1 and DGAT-2);

(28) inhibitors of fatty acid synthase;

(29) inhibitors of acetyl-CoA carboxylase-1 and 2 (ACC-1 and ACC-2);

(30) inhibitors of acyl coenzyme A:monoacylglycerol acyltransferase 1 and 2 (MGAT-1 and MGAT-2);

(31) agonists of the TGR5 receptor (also known as GPBAR1, BG37, GPCR19, GPR131, and M-BAR); and

(32) bromocriptine mesylate and rapid-release formulations thereof.

In another aspect of the invention, a pharmaceutical composition is disclosed which comprises one or more of the following agents:

(a) a compound described herein or a pharmaceutically acceptable salt thereof;

(b) one or more compounds selected from the group consisting of:
(1) dipeptidyl peptidase-IV (DPP-4) inhibitors;
(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;
(3) sulfonylurea and non-sulfonylurea insulin secretagogues, such as tolbutamide, glyburide, glipizide, glimepiride, mitiglinide, and meglitinides, such as nateglinide and repaglinide;
(4) α-glucosidase inhibitors (such as acarbose, voglibose and miglitol);
(5) glucagon receptor antagonists;
(6) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;
(7) HDL-raising drugs, such as niacin or a salt thereof and extended-release versions thereof;
(8) antiobesity compounds;
(9) agents intended for use in inflammatory conditions, such as aspirin, non-steroidal anti-inflammatory drugs (NSAIDs), glucocorticoids, and selective cyclooxygenase-2 (COX-2) inhibitors;
(10) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;
(11) glucokinase activators (GKAs), such as LY2599506;
(12) inhibitors of 11β-hydroxysteroid dehydrogenase type 1;
(13) inhibitors of cholesteryl ester transfer protein (CETP), such as torcetrapib and anacetrapib;
(14) inhibitors of fructose 1,6-bisphosphatase;
(15) inhibitors of acetyl CoA carboxylase-1 or 2 (ACC1 or ACC2);
(16) AMP-activated Protein Kinase (AMPK) activators;
(17) agonists of the G-protein-coupled receptors: GPR-109, GPR-119, and GPR-40;
(18) SSTR3 antagonists;
(19) neuromedin U receptor agonists, including, but not limited to, neuromedin S (NMS);
(20) inhibitors of stearoyl-coenzyme A delta-9 desaturase (SCD);
(21) GPR-105 antagonists;
(22) inhibitors of glucose uptake, such as sodium-glucose transporter (SGLT) inhibitors and its various isoforms, such as SGLT-1; SGLT-2, such as dapagliflozin, canagliflozin, ertugliflozin, empagliflozin, ipragliflozin and remogliflozin; and SGLT-3;
(23) inhibitors of acyl coenzyme A:diacylglycerol acyltransferase 1 and 2 (DGAT-1 and DGAT-2);
(24) inhibitors of fatty acid synthase;
(25) inhibitors of acetyl-CoA carboxylase-1 and 2 (ACC-1 and ACC-2);
(26) inhibitors of acyl coenzyme A:monoacylglycerol acyltransferase 1 and 2 (MGAT-1 and MGAT-2);
(27) agonists of the TGR5 receptor (also known as GPBAR1, BG37, GPCR19, GPR131, and M-BAR); and
(28) bromocriptine mesylate and rapid-release formulations thereof; and
(c) a pharmaceutically acceptable carrier.

When a compound of the present invention is used contemporaneously with one or more other drugs a specific embodiment hereof pertains to, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, in particular embodiments from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

EXAMPLES

The meanings of the abbreviations in Examples are shown below.
ACN=MeCN=acetonitrile
CELITE=diatomaceous earth
Conc.=concentrated
CuI=Copper(I) iodide
$Cs_2CO_3$=Caesium carbonate
DAST—diethylaminosulfurtrifluoride
DCM=dichloromethane
DEA=diethylamine
DIBALH=diisobutylaluminum hydride
DIEA=DIPEA=N,N-Diisopropylethylamine
DMA=N,N-Dimethylacetamide
DMAP=4-dimethylaminopyridine
DMF=N,N-Dimethylformamide
DMSO=Dimethyl sulfoxide DOWNTHERM A=a eutectic mixture of 26% diphenyl and 74% diphenyl ether
DTBPFPdCl$_2$=[1,1'-Bis(di-tert-butylphosphino)ferrocene]dichloropalladium(II)
ee=enantomertic excess
Et$_2$O=diethyl ether
EtOAc=ethyl acetate
EtOH=ethanol Me=methyl
h=hours
HATU=(1-[Bis(dimethylamino)methylene]-1H-1,2,3-triazolo[4,5-b]pyridinium 3-oxid hexafluorophosphate)
HOAt=1-Hydroxy-7-azabenzotriazole
HCl=hydrochloric acid
HOBt=hydroxybenzotriazole
IPA=isopropyl alcohol
K$_2$CO$_3$=potassium carbonate
K$_3$PO$_4$=Tripotassium phosphate
LCMS=Liquid chromatography-mass spectrometry
LDA=Lithium diisopropylamide
LDH=lactic acid dehydrogenase
LHMDS=LiHMDS=lithium bis(trimethylsilyl)amide
LiOH=lithium hydroxide
mCPBA=meta-Chloroperoxybenzoic acid
min=minutes
MeOH=methanol
MgSO$_4$=magnesium sulfate
MPLC=medium pressure liquid chromatography
NaHCO$_3$=sodium bicarbonate
NaSO$_3$=sodium sulfite
Na$_2$SO$_4$=sodium sulfate
NH$_4$Cl=Ammonium chloride
NH$_4$OH=Ammonium hydroxide
NMP=N-methyl-2-pyrrolidone
PdCl$_2$(dppf)-CH$_2$Cl$_2$=[1,1'-Bis(diphenylphosphino)ferrocene]dichloropalladium(II)
PCl$_5$=Phosphorus pentachloride
P-HPLC or prep-HPLC=preparative high performance liquid chromatography
POCl$_3$=Phosphorus Oxychloride
P-TLC=preparative thin layer chromatography
Py=Pyridine
RT=room temperature
SFC=Supercritical Fluid Chromatography
TEA=triethylamine
TFA=trifluoroacetic acid
THF=tetrahydrofuran
TLC=thin layer chromatography
TMS=Trimethylsilyl
Xantphos=4,5-Bis(diphenylphosphino)-9,9-dimethylxanthene
CDCl$_3$=heavy chloroform
CD$_3$OD=heavy methanol
DMSO=dimethylsulfoxide The meanings of the abbreviations in the nuclear magnetic resonance spectra are shown below:
s=singlet, d=doublet, dd=double doublet, dt=double triplet, ddd=double double doublet, Sept=septet, t=triplet, m=multiplet, br=broad, brs=broad singlet, q=quartet, J=coupling constant and Hz=hertz.

Compounds of this invention can be prepared using the Schemes outlined below. The various starting materials used in the Schemes are commercially available or are readily made by persons skilled in the art.

INTERMEDIATES

Intermediate 1

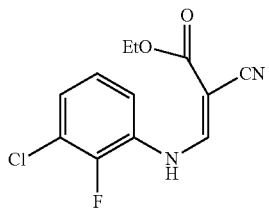 [SMILES: CCOC(=O)/C(C#N)=C\Nc1cccc(Cl)c1F]

(Z)-ethyl 3-((3-chloro-2-fluorophenyl)amino)-2-cyanoacrylate (Z)-ethyl 2-cyano-3-ethoxyacrylate (5.0 g, 29.6 mmol) and 3-chloro-2-fluoroaniline (3.57 ml, 32.5 mmol) were combined in a flask and refluxed in EtOH (29.6 ml) for 15 h. The reaction was cooled to room temperature and a precipitate crashed out. The precipitate was filtered out and washed with EtOH to afford the title compound. MS: 269 (M+1).

Intermediate 2

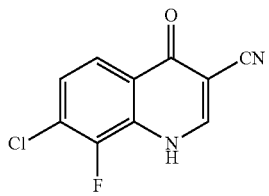 [SMILES: N#Cc1c[nH]c2c(F)c(Cl)ccc2c1=O]

7-chloro-8-fluoro-4-oxo-1,4-dihydroquinoline-3-carbonitrile

To DOWTHERM A (Dow Chemical Company) (22.54 ml) was added (Z)-ethyl 3-((3-chloro-2-fluorophenyl)amino)-2-cyanoacrylate (6.057 g, 22.54 mmol). The mixture was heated to reflux (refluxing seen at about 280-300° C.) using a sand bath. The mixture was refluxed for about 8 h. The reaction was cooled reaction to room temperature and ether was added. The precipitate was washed with ether to give the title compound. MS: 223 (M+1).

Intermediate 3

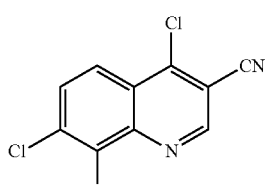

7-chloro-8-fluoro-4-oxo-1,4-dihydroquinoline-3-carbonitrile

To a stirred slurry of 7-chloro-8-fluoro-4-oxo-1,4-dihydroquinoline-3-carbonitrile (3.05 g, 13.70 mmol) in dioxane (68.5 ml) was added POCl₃ (3.83 ml, 41.1 mmol). The reaction was heated to 90° C. for 3 h. The reaction was cooled and poured over ice. The reaction was quenched with aqueous saturated sodium bicarbonate and extracted with EtOAc (3×). The combined organic layers were dried with magnesium sulfate, filtered and concentrated. The residue was purified by column chromatography (0-70% EtOAc in Hex). The combined fractions were concentrated to give the title compound. MS: 241 (M+1).

Intermediates 4-21 in Table 1 were made in a similar way to Intermediate 3, starting with Starting Material A.

TABLE 1

| Intermediate No. | Name | Structure | Starting Material A |
|---|---|---|---|
| 4 | 4-chloro-8-fluoro-7-methoxyquinoline-3-carbonitrile MS: 237 (M + 1). | 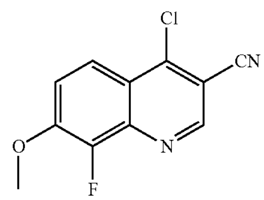 [SMILES: COc1ccc2c(Cl)c(C#N)cnc2c1F] | 2-fluoro-3-methoxy aniline |
| 5 | 4-chloro-7-fluoroquinoline-3-carbonitrile MS: 207 (M + 1) | 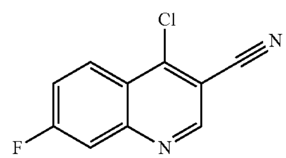 [SMILES: N#Cc1cnc2cc(F)ccc2c1Cl] | 7-fluoro-4-oxo-1,4-dihydroquinoline-3-carbonitrile |
| 6 | 4-chloro-7,8-difluoroquinoline-3-carbonitrile MS: 225 (M + 1) | 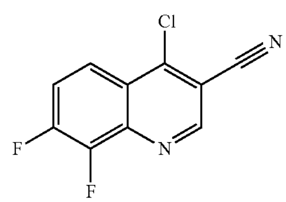 [SMILES: N#Cc1cnc2c(F)c(F)ccc2c1Cl] | 2,3-difluoro aniline |
| 7 | 4-chloro-8-fluoroquinoline-3-carbonitrile MS: 207 (M + 1) | 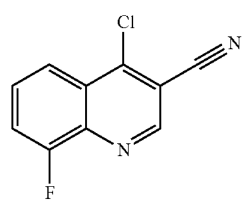 [SMILES: N#Cc1cnc2c(F)cccc2c1Cl] | 2-fluoro aniline |
| 8 | 4,8-dichloro-7-fluoroquinoline-3-carbonitrile MS: 241 (M + 1) | 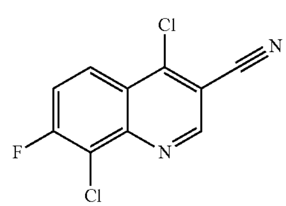 [SMILES: N#Cc1cnc2c(Cl)c(F)ccc2c1Cl] | 2-chloro-3-fluoro aniline |
| 9 | 4,7-dichloro-6,8-difluoroquinoline-3-carbonitrile MS: 259 (M + 1) | 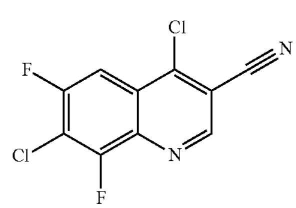 [SMILES: N#Cc1cnc2c(F)c(Cl)c(F)cc2c1Cl] | 3-chloro-2,4-difluoro aniline |

TABLE 1-continued

| Intermediate No. | Name | Structure | Starting Material A |
|---|---|---|---|
| 10 | 4-chloro-8-fluoro-7-(trifluoromethyl)quinoline-3-carbonitrile<br>MS: 275 (M + 1) | 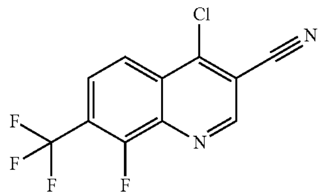 [SMILES: N#Cc1cnc2c(F)c(C(F)(F)F)ccc2c1Cl] | 2-fluoro-3-(trifluoromethyl)aniline |
| 11 | 7-bromo-4-chloro-8-fluoroquinoline-3-carbonitrile<br>MS: 285 (M + 1) | 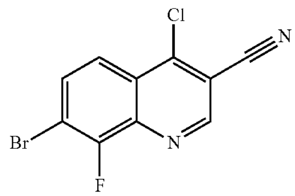 [SMILES: N#Cc1cnc2c(F)c(Br)ccc2c1Cl] | 3-bromo-2-fluoroaniline |
| 12 | 4,6-dichloro-8-methoxyquinoline-3-carbonitrile<br>MS: 253 (M + 1) | 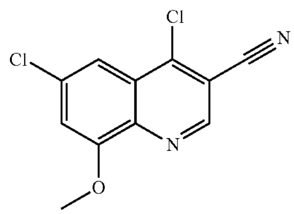 [SMILES: COc1cc(Cl)cc2c(Cl)c(C#N)cnc12] | 4-chloro-2-methoxyaniline |
| 13 | 4-chloro-7-methoxy-8-methylquinoline-3-carbonitrile<br>MS: 233 (M + 1) | 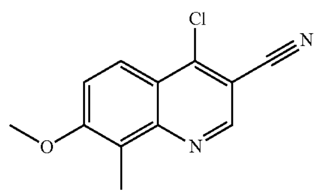 [SMILES: COc1ccc2c(Cl)c(C#N)cnc2c1C] | 3-methoxy-2-methylaniline |
| 14 | 6-bromo-4-chloro-7-methoxyquinoline-3-carbonitrile<br>MS: 299 (M + 1) | 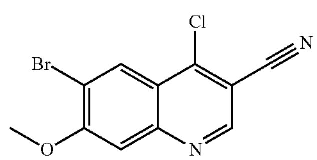 [SMILES: COc1cc2ncc(C#N)c(Cl)c2cc1Br] | -bromo-3-methoxyaniline |
| 15 | 4-chloro-7-(difluoromethoxy)-8-fluoroquinoline-3-carbonitrile<br>MS: 273 (M + 1) | 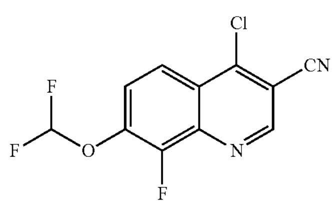 [SMILES: N#Cc1cnc2c(F)c(OC(F)F)ccc2c1Cl] | 3-(difluoromethoxy)-2-fluoroaniline |
| 16 | 4-chloro-8-fluoro-7-isopropoxyquinoline-3-carbonitrile<br>MS: 265 (M + 1) | 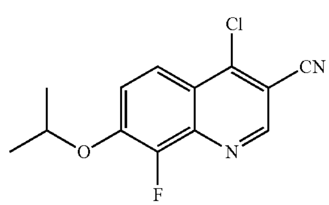 [SMILES: CC(C)Oc1ccc2c(Cl)c(C#N)cnc2c1F] | 2-fluoro-3-isopropoxyaniline |
| 17 | 4-chloro-7-ethoxyquinoline-3-carbonitrile<br>MS: 233 (M + 1) | 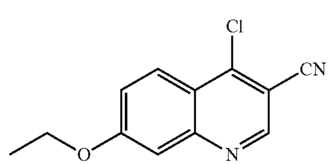 [SMILES: CCOc1ccc2c(Cl)c(C#N)cnc2c1] | 3-ethoxyaniline |

TABLE 1-continued

| Intermediate No. | Name | Structure | Starting Material A |
|---|---|---|---|
| 18 | 4-chloro-7-(difluoromethyl)quinoline-3-carbonitrile<br>MS: 267 (M + 1) | 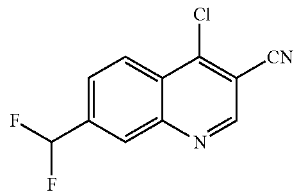 [SMILES: N#Cc1cnc2cc(C(F)F)ccc2c1Cl] | 3-(difluoromethyl)aniline |
| 19 | 4-chloro-7-cyclopropoxyquinoline-3-carbonitrile<br>MS: 245 (M + 1) | 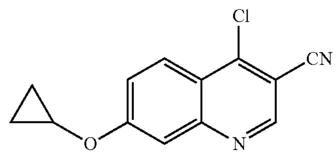 [SMILES: N#Cc1cnc2cc(OC3CC3)ccc2c1Cl] | 3-cyclopropoxyaniline |
| 20 | 4-chloro-7-(trifluoromethyl)-1,8-naphthyridine-3-carbonitrile<br>MS: 258 (M + 1) | 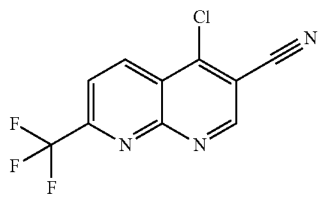 [SMILES: N#Cc1cnc2nc(C(F)(F)F)ccc2c1Cl] | 4-oxo-7-(trifluoromethyl)-1,4-dihydro-1,8-naphthyridine-3-carbonitrile |
| 21 | 4-chloro-7-(trifluoromethoxy)quinoline-3-carbonitrile<br>MS: 273 (M + 1) | 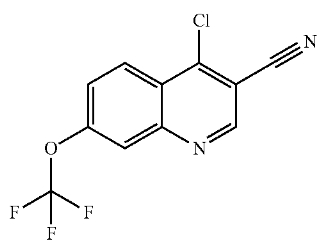 [SMILES: N#Cc1cnc2cc(OC(F)(F)F)ccc2c1Cl] | 4-oxo-7-(trifluoromethoxy)-1,4-dihydroquinoline-3-carbonitrile |

Intermediate 22

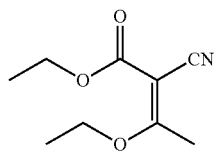

(Z)-ethyl 2-cyano-3-ethoxybut-2-enoate

To a mixture of ethyl cyanoacetate (50 g, 442 mmol) in acetic anhydride (125 mL) was added triethyl orthoacetate (81 mL, 442 mmol) and the mixture heated to reflux at 140° C. for 6 h. The reaction mixture was concentrated to remove the solvent acetic anhydride to give (Z)-ethyl 2-cyano-3-ethoxybut-2-enoate as an oil. MS: 184 (M+1).

Intermediate 23

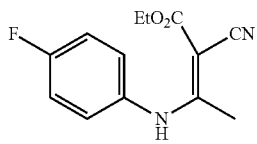 [SMILES: CCOC(=O)/C(C#N)=C(/C)Nc1ccc(F)cc1]

(Z)-ethyl 2-cyano-3-((4-fluorophenyl)amino) but-2-enoate

To a mixture of (Z)-ethyl 2-cyano-3-ethoxybut-2-enoate (15 g, 82 mmol) in EtOH (80 mL) was added 4-fluoroaniline (9.10 g, 82 mmol) and the mixture heated to reflux at 80° C. for 16 h. The reaction mixture was then cooled to 0° C. and the desired solid was crystallized, filtered and washed with EtOH (10 mL) to give (Z)-ethyl 2-cyano-3-((4-fluorophenyl)amino) but-2-enoate. MS: 249 (M+1).

Intermediate 24

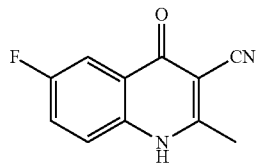

6-fluoro-2-methyl-4-oxo-1,4-dihydroquinoline-3-carbonitrile

A mixture of (Z)-ethyl 2-cyano-3-((4-fluorophenyl)amino)but-2-enoate (3.85 g, 15.51 mmol) in DOWTHERM A (Dow Chemical Company) (14 mL) was heated at 270° C. (using a heating mantle). Solid precipitated out after 20 mins at 270° C. and heated at 270° C. for an additional 70 min. The reaction mixture was cooled to 18° C. and filtered. The desired solid was washed with ether (30 mL) to give 6-fluoro-2-methyl-4-oxo-1,4-dihydroquinoline-3-carbonitrile. $^1$H NMR (400 MHz, DMSO-$d_6$) δ=12.72 (br. s., 1H), 7.73 (d, J=8.4 Hz, 1H), 7.66 (d, J=5.1 Hz, 2H), 2.58 (s, 3H).

Intermediate 25

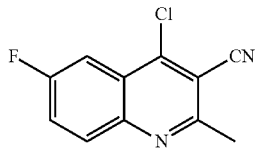

4-chloro-6-fluoro-2-methylquinoline-3-carbonitrile

To a stirred slurry of 6-fluoro-2-methyl-4-oxo-1,4-dihydroquinoline-3-carbonitrile (1.71 g, 8.46 mmol) in dioxane (90 mL) was added $POCl_3$ (2.37 mL, 25.4 mmol). The reaction was heated at 90° C. for 4 h. The reaction was cooled and poured into water (10 mL). The reaction was quenched with saturated sodium bicarbonate (30 mL), extracted with EtOAc (3×50 mL). The combined organic layers were dried over $Na_2SO_4$, filtered and concentrated. The residue was purified by silica gel chromatography (ether:EtOAc=3:1) to give 4-chloro-6-fluoro-2-methylquinoline-3-carbonitrile. MS: 221 (M+1).

Intermediates 26-33 in Table 2 were made in a similar way to Intermediate 25, starting with Starting Material A.

TABLE 2

| Intermediate No. | Name | Structure | Starting Material A |
|---|---|---|---|
| 26 | 4-chloro-2,6-dimethylquinoline-3-carbonitrile<br>MS: 217 (M + 1) | 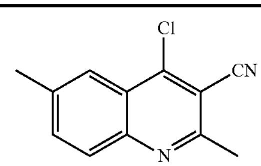 | p-toluidine |
| 27 | 4-chloro-6-methoxy-2-methylquinoline-3-carbonitrile<br>MS: 233 (M + 1) | 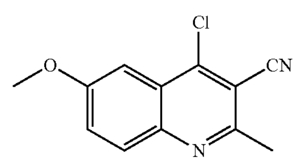 [SMILES: COc1ccc2nc(C)c(C#N)c(Cl)c2c1] | 4-methoxyaniline |
| 28 | 6-bromo-4-chloro-2-methylquinoline-3-carbonitrile<br>$^1$H NMR (400 MHz, Chloroform-d) δ = 8.38 (s, 1H), 7.93 (s, 2H), 2.92 (s, 3H) | 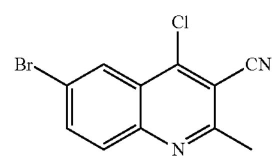 | 4-bromoaniline |
| 29 | 4-chloro-6,8-difluoro-2-methylquinoline-3-carbonitrile<br>MS: 239 (M + 1) | 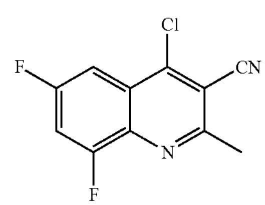 [SMILES: Cc1nc2c(F)cc(F)cc2c(Cl)c1C#N] | 2,4-difluoroaniline |
| 30 | 4-chloro-6,7-difluoro-2-methylquinoline-3-carbonitrile<br>MS: 239 (M + 1) | 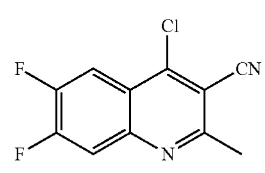 [SMILES: Cc1nc2cc(F)c(F)cc2c(Cl)c1C#N] | 3,4-difluoroaniline |

TABLE 2-continued

| Intermediate No. | Name | Structure | Starting Material A |
|---|---|---|---|
| 31 | 4-chloro-5,6-difluoro-2-methylquinoline-3-carbonitrile MS: 239 (M + 1) | 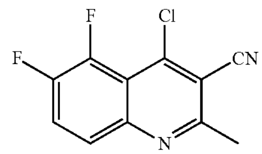 [SMILES: Cc1nc2ccc(F)c(F)c2c(Cl)c1C#N] | 3,4-difluoroaniline |
| 32 | 4-chloro-7-methoxy-2-methylquinoline-3-carbonitrile MS: 233 (M + 1) | 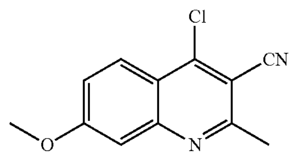 [SMILES: COc1ccc2c(Cl)c(C#N)c(C)nc2c1] | 3-methoxyaniline |
| 33 | 4-chloro-5-methoxy-2-methylquinoline-3-carbonitrile MS: 233 (M + 1) | 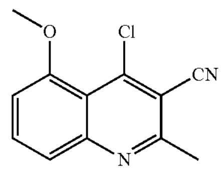 [SMILES: COc1cccc2nc(C)c(C#N)c(Cl)c12] | 3-methoxyaniline |

Intermediate 34

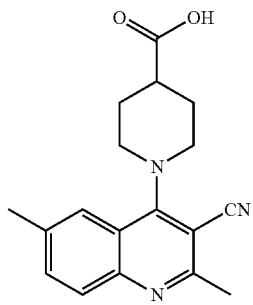 [SMILES: Cc1ccc2nc(C)c(C#N)c(N3CCC(C(=O)O)CC3)c2c1]

1-(3-cyano-2,6-dimethylquinolin-4-yl)piperidine-4-carboxylic Acid

A mixture of 4-chloro-2,6-dimethylquinoline-3-carbonitrile (100 mg, 0.462 mmol), piperidine-4-carboxylic acid (59.6 mg, 0.462 mmol) and DIEA (242 µL, 1.385 mmol) in DMF (2.31 mL) was heated to 70° C. for 15 h. The mixture was poured into water (50 mL), acidified with HCl (aq, 1 N) to pH=4, and extracted with 3:1 chloroform/IPA (50 mL×3). The combined extracts were dried over Na$_2$SO$_4$, filtered and concentrated in vacuo to give crude 1-(3-cyano-2,6-dimethylquinolin-4-yl)piperidine-4-carboxylic acid. MS: 310 (M+1).

Intermediates 35 and 36

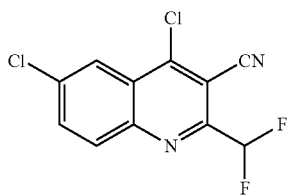

4,6-dichloro-2-(difluoromethyl)quinoline-3-carbonitrile 4,6-dichloro-8-(difluoromethyl)quinoline-3-carbonitrile To a stirred solution of 4,6-dichloroquinoline-3-carbonitrile (1.6 g, 7.17 mmol) and zinc difluoromethanesulfinate (5.72 g, 19.4 mmol) in DCM (28.7 mL) and water (12.3 mL) was added TFA (0.553 mL, 7.17 mmol) and then tert-butyl hydroperoxide (4.97 ml, 35.9 mmol) slowly. The reaction was allowed to stir at room temperature for 15 h. Additional tert-butyl hydroperoxide (4.97 ml, 35.9 mmol) and zinc difluoromethanesulfinate (5.72 g, 19.4 mmol) was added and stirred for 15 h at room temperature. The reaction was quenched with saturated sodium bicarbonate and extracted with EtOAc (3×). The combined organic layers were dried with magnesium sulfate, filtered, concentrated and purified by silica gel chromatography (0-50% EtOAc in Hexane). The combined fractions were concentrated to give 4,6-dichloro-2-(difluoromethyl)quinoline-3-carbonitrile (MS: 272.9 (M+1)) and 4,6-dichloro-8-(difluoromethyl)quinoline-3-carbonitrile (MS: 272.8 (M+1)).

Intermediate 37

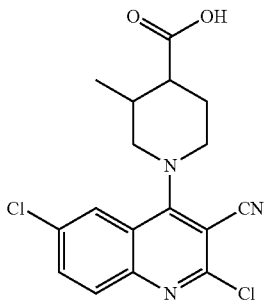 [SMILES: CC1CN(c2c(C#N)c(Cl)nc3ccc(Cl)cc23)CCC1C(=O)O]

1-(2,6-dichloro-3-cyanoquinolin-4-yl)-3-methylpiperidine-4-carboxylic Acid

To a stirred mixture of 2,4,6-trichloroquinoline-3-carbonitrile (4.11 g, 16.0 mmol) and 3-methylpiperidine-4-carboxylic acid hydrochloride (4.30 g, 23.9 mmol) in DMF (53 ml) was added DIPEA (8.36 ml, 47.9 mmol) at room temperature and the resulting mixture was heated at 70° C. for 1 hour. The reaction mixture for concentrated in vacuo and the resulting residue was purified by reverse phase chromatography (0-60% acetonitrile in water). The fractions were combined and concentrated to give the title compound. MS: 364 (M+1).

Intermediate 38

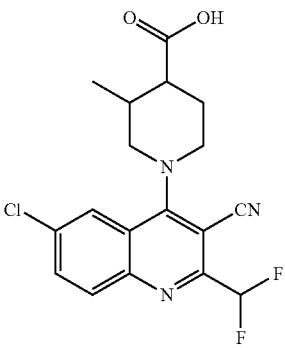 [SMILES: CC1CN(c2c(C#N)c(C(F)F)nc3ccc(Cl)cc23)CCC1C(=O)O]

1-(6-chloro-3-cyano-2-(difluoromethyl)quinolin-4-yl)-3-methylpiperidine-4-carboxylic Acid To a mixture of 1-(tert-butoxycarbonyl)-3-methylpiperidine-4-carboxylic acid (110 mg, 0.45 mmol) in DCM (1.04 mL) was added TFA (0.322 ml, 4.17 mmol). The mixture was stirred 12 h at room temperature, then concentrated and dried under vacuum. 4,6-dichloro-2-(difluoromethyl)quinoline-3-carbonitrile (114 mg, 0.42 mmol) in DMF (1.04 mL) was added to the piperidine residue and the reaction was heated at 70° C. for 3 hour. The reaction mixture was filtered and purified by reverse phase HPLC (10-100% MeCN/Water with 0.05% TFA). The combined fractions were extracted with EtOAc (3×). The combined organic layers were dried with magnesium sulfate, filtered, and concentrated to give the title compound. MS: 380 (M+1).

Intermediate 39

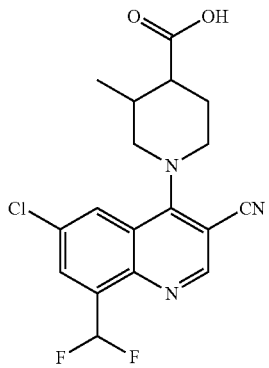 [SMILES: CC1CN(c2c(C#N)cnc3c(C(F)F)cc(Cl)cc23)CCC1C(=O)O]

1-[6-chloro-3-cyano-8-(difluoromethyl)quinolin-4-yl]-3-methylpiperidine-4-carboxylic Acid 1-[6-chloro-3-cyano-8-(difluoromethyl)quinolin-4-yl]-3-methylpiperidine-4-carboxylic acid was made in a similar way to Intermediate 36, starting with 4,6-dichloro-8-(difluoromethyl)quinoline-3-carbonitrile (51 mg, 0.19 mmol) to afford the title compound. MS: 380 (M+1).

Intermediate 40

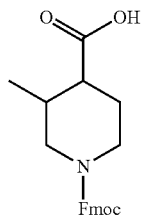

1-[(9H-fluoren-9-ylmethoxy)carbonyl]-3-methylpiperidine-4-carboxylic Acid 1-(tert-butoxycarbonyl)-3-methylpiperidine-4-carboxylic acid (15.0 g, 61.7 mmol) was combined with DCM (308 mL) and TFA (15.90 mL, 206 mmol) and stirred at room temperature for 15 h. The mixture was concentrated and the reaction was diluted with 1,4-dioxane (400 mL). To the reaction mixture was added sodium carbonate (2.1M in water, 294 mL, 617 mmol) and the reaction was placed under an overhead stirrer. To the reaction mixture was added (9H-fluoren-9-yl)methyl carbonochloridate (16.0 g, 61.7 mmol) and the reaction was stirred at room temperature for 15 h. The reaction was diluted with water and extracted with EtOAc (1×). The aqueous layer was then acidified to pH 2 with 1N HCl. EtOAc was added and the aqueous layer was extracted with EtOAc (2×). The residue was purified by column chromatography (0-70% 3:1 EtOAc:EtOH in Hexanes) to afford the title compound. MS: 366 (M+1).

Intermediate 41

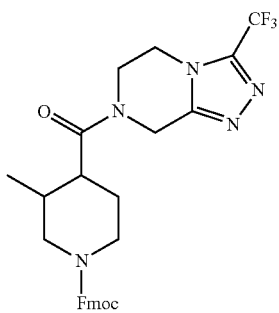

9H-fluoren-9-ylmethyl 3-methyl-4-{[3-(trifluoromethyl)-5,6-dihydro[1,2,4]triazolo[4,3-a]pyrazin-7(8H)-yl]carbonyl}piperidine-1-carboxylate A mixture of HATU (23.1 g, 60.8 mmol), 3-(trifluoromethyl)-5,6,7,8-tetrahydro-[1,2,4]triazolo[4,3-a]pyrazin-7-ium chloride (11.75 g, 51.4 mmol) was 1-(((9H-fluoren-9-yl)methoxy)carbonyl)-3-methylpiperidine-4-carboxylic acid (17.08 g, 46.7 mmol) was flushed with nitrogen three times and anhydrous DMF (160 mL) was added, followed by DIPEA (24.42 mL, 140 mmol). The mixture was stirred at room temperature overnight. To the reaction was added water and the combined fractions were extracted with EtOAc (3×). The combined organic layers were dried with magnesium sulfate, filtered, and concentrated. The residue was purified by silica gel chromatography (0-100% 3:1 EtOAc:EtOH in Hexane). The fractions were combined and concentrated to give an oil. MS: 540 (M+1).

Intermediates 42

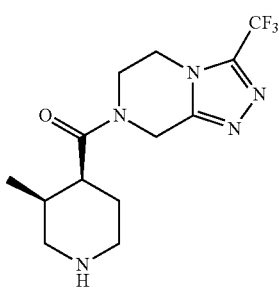 [SMILES: C[C@@H]1CNCC[C@@H]1C(=O)N1CCn2c(nnc2C(F)(F)F)C1]

[(3S,4S)-3-methylpiperidin-4-yl][3-(trifluoromethyl)-5,6-dihydro[1,2,4]triazolo[4,3-a]pyrazin-7(8H)-yl]methanone 9H-fluoren-9-ylmethyl 3-methyl-4-{[3-(trifluoromethyl)-5,6-dihydro[1,2,4]triazolo[4,3-a]pyrazin-7(8H)-yl]carbonyl}piperidine-1-carboxylate (17.29 g, 32.0 mmol) was separated (Column: IC (2×15 cm), injection volume 0.8 mL at 30 mg/mL in 3:1 MeOH:DCM, wavelength 220 nm, 30% MeOH (0.1% NH$_4$OH)/CO$_2$ at 100 bar). The single diastereomers were analyzed at 99% ee before drying down. To major peak 1 was added DCM (156 mL) and MeOH (67 mL). Piperidine (5.51 mL, 55.6 mmol) was added and the reaction was stirred for 15 h at room temperature. The slurry was directly concentrated and purified by silica gel chromatography (0-10% MeOH in DCM w/0.1% NH$_4$OH, then 20% MeOH in DCM w/0.1% NH$_4$OH isocratic). The fractions were combined and concentrated to give the title compound.

Intermediate 43

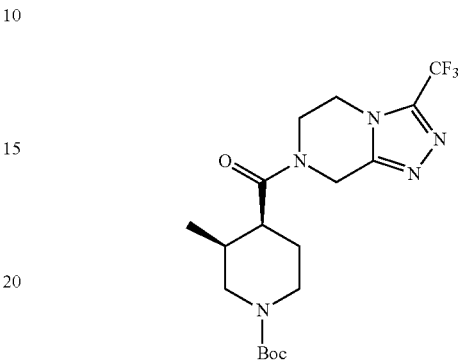

tert-butyl (3S,4S)-3-methyl-4-{[3-(trifluoromethyl)-5,6-dihydro[1,2,4]triazolo[4,3-a]pyrazin-7(8H)-yl]carbonyl}piperidine-1-carboxylate ((3S,4S)-3-methylpiperidin-4-yl)(3-(trifluoromethyl)-5,6-dihydro-[1,2,4]triazolo[4,3-a]pyrazin-7(8H)-yl)methanone (2.25 g, 7.09 mmol) was dissolved in DCM (35.5 mL). Boc-anhydride (2.32 g, 10.6 mmol) was added followed by DIPEA (2.48 mL, 14.2 mmol) and the mixture was left to stir for 8 h. Water was added to the reaction and the combined fractions were extracted with EtOAc 2×. The combined organic layers were dried with magnesium sulfate, filtered, and concentrated. The residue was purified by silica gel chromatography (0-100% 3:1 EtOAc:EtOH in Hex). The fractions were combined and concentrated to give the title compound. MS: 418 (M+1).

Intermediate 44

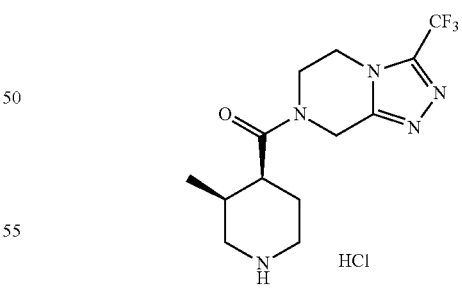

[(3S,4S)-3-methylpiperidin-4-yl][3-(trifluoromethyl)-5,6-dihydro[1,2,4]triazolo[4,3-a]pyrazin-7(8H)-yl]methanone hydrochloride To a mixture of tert-butyl (3S,4S)-3-methyl-4-{[3-(trifluoromethyl)-5,6-dihydro[1,2,4]triazolo[4,3-a]pyrazin-7(8H)-yl]carbonyl}piperidine-1-carboxylate (2.76 g, 6.61 mmol) in DCM (33 mL) was added HCl (1M in dioxane, 8.26 mL, 33.1 mmol). The mixture was stirred for 12 h at room temperature, then was concentrated and dried under vacuum to provide the title compound.

Intermediate 45

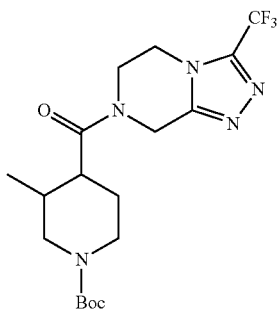 [SMILES: CC1CN(C(=O)OC(C)(C)C)CCC1C(=O)N1CCn2c(nnc2C(F)(F)F)C1]

tert-butyl 3-methyl-4-(3-(trifluoromethyl)-5,6,7,8-tetrahydro-[1,2,4]triazolo[4,3-a]pyrazine-7-carbonyl)piperidine-1-carboxylate To a mixture of 3-(trifluoromethyl)-5,6,7,8-tetrahydro-[1,2,4]triazolo[4,3-a]pyrazine hydrochloride (2.26 g, 9.86 mmol), 1-(tert-butoxycarbonyl)-3-methylpiperidine-4-carboxylic acid (2.4 g, 9.86 mmol), and HATU (6.00 g, 15.78 mmol) in DMF (50 mL) was added DIPEA (6.89 mL, 39.5 mmol) in DMF (50 mL). The mixture was stirred at 25° C. for 23 h. The reaction was quenched with water (100 mL) and extracted with EtOAc (60 mL×4). The combined organic phases were washed with brine (50 mL), dried over Na₂SO₄, filtered and concentrated. The residue was purified by silica gel chromatography (PE:EtOAc=2:1~1:2, added 0.5% NH₄OH) to give tert-butyl 3-methyl-4-(3-(trifluoromethyl)-5,6,7,8-tetrahydro-[1,2,4]triazolo[4,3-a]pyrazine-7-carbonyl)piperidine-1-carboxylate. MS: 418 (M+1).

Intermediates 46a and 46b

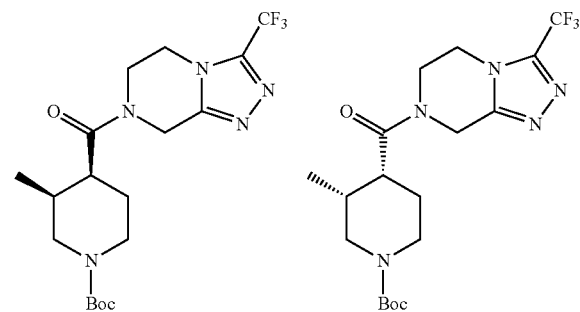 [SMILES: C[C@@H]1CN(C(=O)OC(C)(C)C)CC[C@@H]1C(=O)N1CCn2c(nnc2C(F)(F)F)C1 ; C[C@H]1CN(C(=O)OC(C)(C)C)CC[C@H]1C(=O)N1CCn2c(nnc2C(F)(F)F)C1]

(3S,4S)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate (3R,4R)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate Tert-butyl 3-methyl-4-(3-(trifluoromethyl)-5,6,7,8-tetrahydro-[1,2,4]triazolo[4,3-a]pyrazine-7-carbonyl)piperidine-1-carboxylate (3.6 g, 8.62 mmol) was resolved by supercritical fluid chromatography (Column: Chiralpak AD-3 Mobile phase: A: CO₂ B: Methanol (0.05% DEA); Gradient: from 5% to 40% of B.) to give (3R,4R)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate (peak 2, SFC $t_R$=2.36 min) MS: 418 (M+1) and (3S,4S)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate (peak 3, SFC $t_R$=2.64 min). MS: 418 (M+1).

Intermediate 47

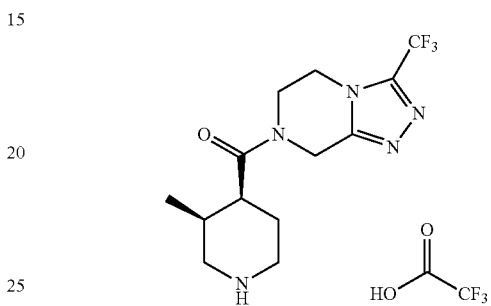

[(3S,4S)-3-methylpiperidin-4-yl][3-(trifluoromethyl)-5,6-dihydro[1,2,4]triazolo[4,3-a]pyrazin-7(8H)-yl]methanone Trifluoroacetate To a mixture of (3S,4S)-tert-butyl 3-methyl-4-(3-(trifluoromethyl)-5,6,7,8-tetrahydro-[1,2,4]triazolo[4,3-a]pyrazine-7-carbonyl)piperidine-1-carboxylate (1.1 g, 2.64 mmol) in DCM (9 mL) was added TFA (3 mL, 38.9 mmol) at 0° C. The reaction mixture was stirred at 25° C. for 2 h. The reaction was concentrated and dried under reduced pressure to provide the title compound. MS: 318 (M+1).

Intermediate 48

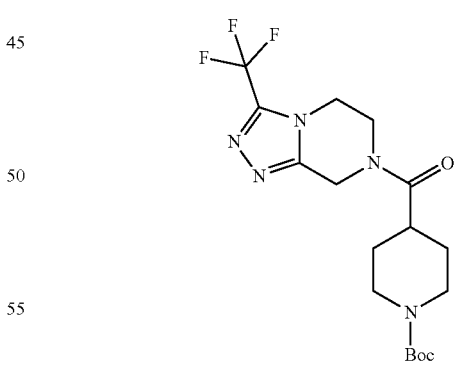

tert-butyl 4-(3-(trifluoromethyl)-5,6,7,8-tetrahydro-[1,2,4]triazolo[4,3-a]pyrazine-7-carbonyl)piperidine-1-carboxylate A mixture of HATU (6.47 g, 17.0 mmol), 3-(trifluoromethyl)-5,6,7,8-tetrahydro-[1,2,4]triazolo[4,3-a]pyrazin-7-ium chloride (3.29 g, 14.4 mmol) and 1-(tert-butoxycarbonyl)piperidine-4-carboxylic acid (3.0 g, 13.1 mmol) was flushed with nitrogen gas three times and anhydrous DMF (26.2 mL) was added, followed by DIPEA (6.84 mL, 39.3 mmol). The mixture was stirred at room temperature overnight. Water was added to the reaction mixture and the combined fractions were extracted 3× with EtOAc. The combined organic layers were dried with magnesium sulfate, filtered, and concentrated. The residue was purified by silica gel chromatography (0-60% 3:1 EtOAc:EtOH in Hexanes). The fractions were combined and concentrated to give the title compound. MS: 404 (M+1).

Intermediate 49

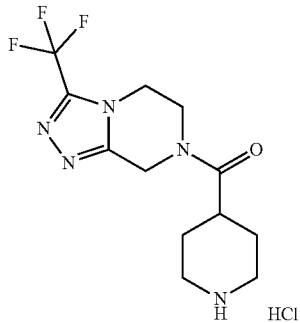 [SMILES: O=C(C1CCNCC1)N1CCn2c(nnc2C(F)(F)F)C1 ; Cl]

piperidin-4-yl[3-(trifluoromethyl)-5,6-dihydro[1,2,4]triazolo[4,3-a]pyrazin-7(8H)-yl]methanone Hydrochloride To a mixture of tert-butyl 4-(3-(trifluoromethyl)-5,6,7,8-tetrahydro-[1,2,4]triazolo[4,3-a]pyrazine-7-carbonyl)piperidine-1-carboxylate (4.56 g, 11.30 mmol) in MeOH (56.5 mL) was added HCl in dioxane (14.13 mL, 56.5 mmol). The mixture was stirred for 12 h at room temperature, then was concentrated and dried under vacuum to provide the title compound.

Intermediate 50

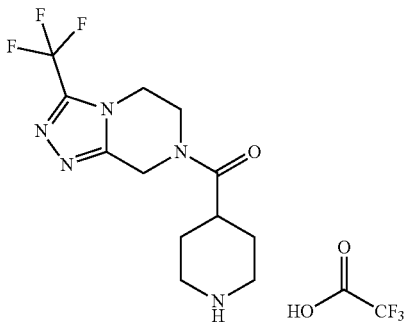 [SMILES: O=C(C1CCNCC1)N1CCn2c(nnc2C(F)(F)F)C1 ; O=C(O)C(F)(F)F]

piperidin-4-yl(3-(trifluoromethyl)-5,6-dihydro-[1,2,4]triazolo[4,3-a]pyrazin-7(8H)-yl)methanone 2,2,2-trifluoroacetate To a mixture of tert-butyl 4-(3-(trifluoromethyl)-5,6,7,8-tetrahydro-[1,2,4]triazolo[4,3-a]pyrazine-7-carbonyl)piperidine-1-carboxylate (500 mg, 1.24 mmol) in DCM (6 mL) was added TFA (2 mL, 26.0 mmol) and stirred at 18° C. for 1.5 h. The reaction was concentrated to give piperidin-4-yl (3-(trifluoromethyl)-5,6-dihydro-[1,2,4]triazolo[4,3-a]pyrazin-7(8H)-yl)methanone 2,2,2-trifluoroacetate. MS: 304 (M+1).

Intermediate 51

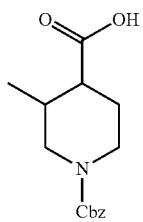 [SMILES: CC1CN(C(=O)OCc2ccccc2)CCC1C(=O)O]

1-[(benzyloxy)carbonyl]-3-methylpiperidine-4-carboxylic Acid 1-(tert-butoxycarbonyl)-3-methylpiperidine-4-carboxylic acid (10.0 g, 41.1 mmol) was combined with DCM (206 mL) and TFA (15.8 mL, 206 mmol) and stirred at room temperature for 15 h. The mixture was concentrated and the reaction diluted with dioxane (200 mL). Added potassium carbonate (56.8 g, 411 mmol) in water (200 mL) followed by benzyl chloroformate (7.04 mL, 49.3 mmol) and stirred at room temperature for 15 h. The reaction was diluted with water and extracted with EtOAc (1×). The aqueous layer was then acidified to pH 2 with 1N HCl. Added EtOAc and extracted (3×). The organic layers were combined and dried with magnesium sulfate, filtered, and concentrated. The residue was purified by silica gel chromatography (0-70% 3:1 EtOAc:EtOH in hexane). The combined fractions were concentrated to give the title compound. MS: 278 (M+1).

Intermediate 52

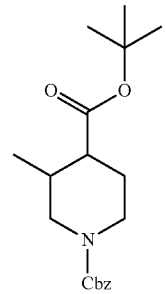 [SMILES: CC1CN(C(=O)OCc2ccccc2)CCC1C(=O)OC(C)(C)C]

1-benzyl 4-tert-butyl 3-methylpiperidine-1,4-dicarboxylate 1-((benzyloxy)carbonyl)-3-methylpiperidine-4-carboxylic acid (9.08 g, 32.7 mmol), tert-butanol (4.70 mL, 49.1 mmol), 1-ethyl-3-(-3-dimethylaminopropyl) carbodiimide hydrochloride (7.53 g, 39.3 mmol), and DMAP (4.00 g, 32.7 mmol) were combined with DCM (164 mL). To the reaction was added TEA (13.7 mL, 98 mmol) and the reaction was stirred at room temperature over the weekend. Additional tert-butanol (4.70 mL, 49.1 mmol), 1-ethyl-3-(-3-dimethylaminopropyl) carbodiimide hydrochloride (7.53 g, 39.3 mmol), and DMAP (4.00 g, 32.7 mmol) was added and the mixture was stirred at room temperature for 15 h. Water was added to the reaction and the combined fractions were extracted with EtOAc (3×). The combined organic layers were dried with magnesium sulfate, filtered, concentrated and purified by silica chromatography (0-50% EtOAc in Hexane). The fractions were combined and concentrated to give the title compound. MS: 334 (M+1).

Intermediates 53a and 53b

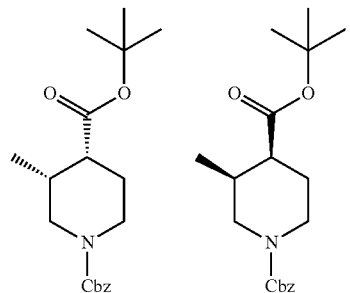 [SMILES: C[C@H]1CN(C(=O)OCc2ccccc2)CC[C@H]1C(=O)OC(C)(C)C ; C[C@@H]1CN(C(=O)OCc2ccccc2)CC[C@@H]1C(=O)OC(C)(C)C]

1-benzyl 4-tert-butyl
(3R,4R)-3-methylpiperidine-1,4-dicarboxylate 1-benzyl 4-tert-butyl
(3S,4S)-3-methylpiperidine-1,4-dicarboxylate 1-benzyl 4-tert-butyl 3-methylpiperidine-1,4-dicarboxylate (4.30 g, 12.9 mmol) was separated into diasteromers be SFC (Column: AD-H (2×25 cm), injection volume 0.5 mL at 17 mg/mL in MeOH, wavelength 210 nm, 30% MeOH/CO₂ at 100 bar). SFC separation afforded 1-benzyl 4-tert-butyl (3R,4R)-3-methylpiperidine-1,4-dicarboxylate (1.47 g, 4.41 mmol) MS: 334 (M+1) (peak 1, SFC $t_R$=1.83 min) and 1-benzyl 4-tert-butyl (3S,4S)-3-methylpiperidine-1,4-dicarboxylate MS: 334 (M+1) (peak 2, SFC $t_R$=2.93 min).

Intermediate 54a

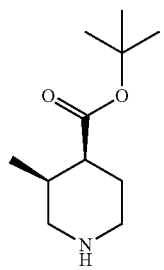

tert-butyl (3S,4S)-3-methylpiperidine-4-carboxylate 1-benzyl 4-tert-butyl (3S,4S)-3-methylpiperidine-1,4-dicarboxylate (1.47 g, 4.41 mmol) was dissolved in EtOAc (88 mL). 10% Pd—C (469 mg, 0.44 mmol) was added. The reaction was run under an atmosphere of hydrogen gas on the Parr shaker for 15 h at room temperature and 50 psi. The reaction was filtered through CELITE, washing the CELITE cake with EtOAc. The filtrate was concentrated to give the title compound. MS: 200 (M+1).

Intermediate 54b

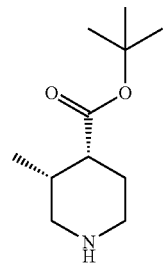

tert-butyl (3R,4R)-3-methylpiperidine-4-carboxylate 1-benzyl 4-tert-butyl (3R,4R)-3-methylpiperidine-1,4-dicarboxylate (75 mg, 0.23 mmol) was dissolved in EtOAc (4.5 mL). 10% Pd—C (24 mg, 0.022 mmol) was added. The reaction was run under an atmosphere of hydrogen gas on the Parr shaker for 15 h at room temperature and 50 psi. The reaction was filtered through CELITE, washing the CELITE cake with EtOAc. The filtrate was concentrated to give the title compound. MS: 200 (M+1).

Intermediate 55

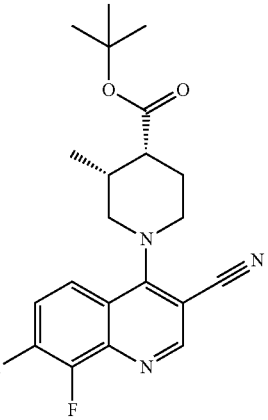

tert-butyl (3R,4R)-1-(7-chloro-3-cyano-8-fluoroquinolin-4-yl)-3-methylpiperidine-4-carboxylate 4,7-dichloro-8-fluoroquinoline-3-carbonitrile (40 mg, 0.17 mmol), tert-butyl (3R,4R)-3-methylpiperidine-4-carboxylate (33 mg, 0.17 mmol), DIPEA (0.087 mL, 0.50 mmol), and DMF (1.66 mL) were combined in a sealed tube. The reaction was heated to 70° C. for 3 h. The reaction mixture was diluted with EtOAc and washed with water 3×. The organic layers were dried with magnesium sulfate, filtered, concentrated and purified by silica gel chromatography (0-40% EtOAc in hexane). The combined fractions were concentrated to give the title compound. MS: 404 (M+1).

Intermediate 56a

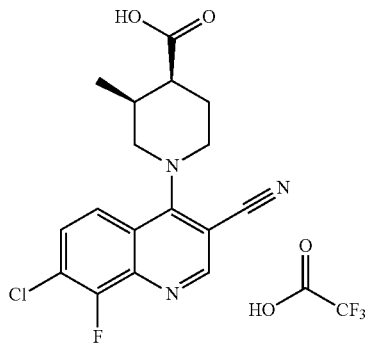 [SMILES: C[C@@H]1CN(c2c(C#N)cnc3c(F)c(Cl)ccc23)CC[C@@H]1C(=O)O ; O=C(O)C(F)(F)F]

(3S,4S)-1-(7-chloro-3-cyano-8-fluoroquinolin-4-yl)-3-methylpiperidine-4-carboxylic (3S,4S)-1-(7-chloro-3-cyano-8-fluoroquinolin-4-yl)-3-methylpiperidine-4-carboxylic acid trifluoroacetate was made in a similar way to Intermediate 56b using tert-butyl (3R,4R)-1-(7-chloro-3-cyano-8-fluoroquinolin-4-yl)-3-methylpiperidine-4-carboxylate. MS: 348 (M+1).

Intermediate 56b

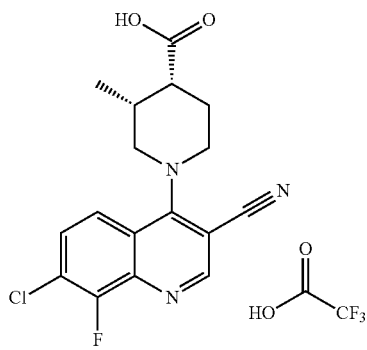 [SMILES: C[C@H]1CN(c2c(C#N)cnc3c(F)c(Cl)ccc23)CC[C@H]1C(=O)O ; O=C(O)C(F)(F)F]

(3R,4R)-1-(7-chloro-3-cyano-8-fluoroquinolin-4-yl)-3-methylpiperidine-4-carboxylic tert-butyl (3R,4R)-1-(7-chloro-3-cyano-8-fluoroquinolin-4-yl)-3-methylpiperidine-4-carboxylate (53 mg, 0.13 mmol) was dissolved in DCM (2.62 ml) and TFA (0.253 mL, 3.28 mmol) was added. The reaction was stirred for 3 h at room temperature. The material was concentrated and dried on the lyophilizer overnight to give the title compound. MS: 348 (M+1).

Intermediate 57

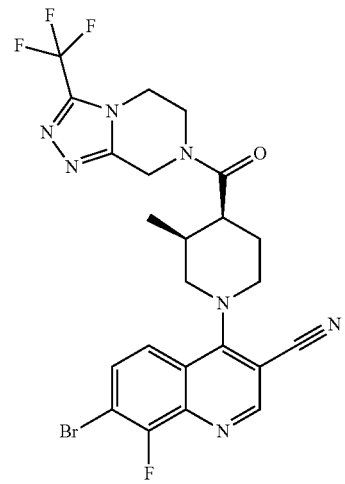 [SMILES: C[C@@H]1CN(c2c(C#N)cnc3c(F)c(Br)ccc23)CC[C@@H]1C(=O)N1CCn2c(nnc2C(F)(F)F)C1]

7-bromo-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 7-bromo-4-chloro-8-fluoroquinoline-3-carbonitrile (200 mg, 0.701 mmol), ((3S,4S)-3-methylpiperidin-4-yl)(3-(trifluoromethyl)-5,6-dihydro-[1,2,4]triazolo[4,3-a]pyrazin-7(8H)-yl)methanone hydrochloride (248 mg, 0.701 mmol), DIPEA (0.367 ml, 2.102 mmol), and DMF (7.01 ml) were combined in a sealed tube. The reaction was heated to 70° C. for 3 h. The reaction mixture was filtered and purified by reverse phase HPLC (10-100% MeCN/Water, with 0.05% TFA). The fractions were combined and neutralized with saturated sodium bicarbonate. The aqueous layer was extracted with EtOAc (3×). The combined organic layers were washed with water (1×), dried with magnesium sulfate, filtered and concentrated to give the title compound. MS: 566 (M+1).

Intermediate 58

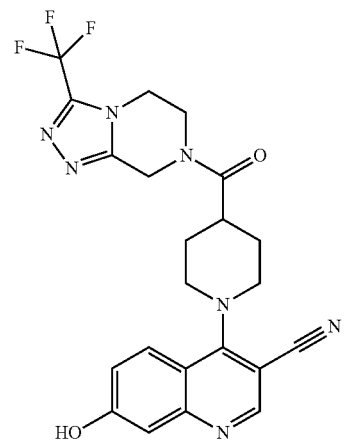 [SMILES: N#Cc1cnc2cc(O)ccc2c1N1CCC(C(=O)N2CCn3c(nnc3C(F)(F)F)C2)CC1]

7-hydroxy-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile 4-chloro-7-hydroxyquinoline-3-carbonitrile (100 mg, 0.49 mmol), piperidin-4-yl(3-(trifluoromethyl)-5,6-dihydro-[1,2,4]triazolo[4,3-a]pyrazin-7(8H)-yl)methanone hydrochloride (166 mg, 0.49 mmol), DIPEA (0.26 mL, 1.47 mmol), and DMF (2.44 mL) were combined in a sealed tube. The reaction was heated to 70° C. for 4 h. The reaction mixture was filtered and purified via reverse phase chromatography (10-100% MeCN/Water, with 0.05% TFA). The combined fractions were neutralized with saturated sodium bicarbonate and extracted 3× with EtOAc. The combined organics were dried with magnesium sulfate, filtered, and concentrated to give the title compound. MS: 472 (M+1).

Intermediate 59

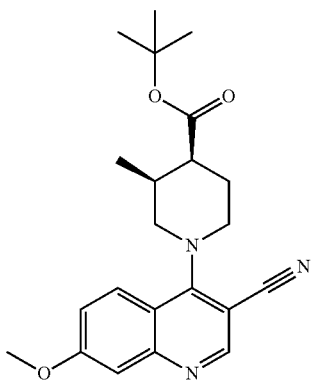 [SMILES: COc1ccc2c(N3CC[C@H](C(=O)OC(C)(C)C)[C@H](C)C3)c(C#N)cnc2c1]

tert-butyl (3S,4S)-1-(3-cyano-7-methoxyquinolin-4-yl)-3-methylpiperidine-4-carboxylate 4-chloro-7-methoxyquinoline-3-carbonitrile (100 mg, 0.46 mmol), (3S,4S)-tert-butyl 3-methylpiperidine-4-carboxylate (91 mg, 0.46 mmol), DIPEA (0.240 mL, 1.372 mmol), and DMF (2.29 mL) were combined in a sealed tube. The reaction was heated to 70° C. for 15 h. The reaction mixture was diluted with EtOAc and washed with water (3×). The organic layers were dried with magnesium sulfate, filtered, concentrated and purified by silica gel chromatography (0-70% 3:1 EtOAc:EtOH in hexane). The combined fractions were concentrated to give the title compound. MS: 382 (M+1).

Intermediate 60

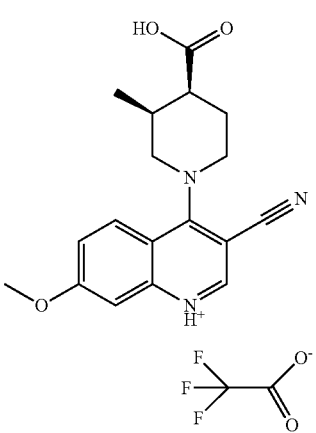 [SMILES: COc1ccc2c(N3CC[C@H](C(=O)O)[C@H](C)C3)c(C#N)c[nH+]c2c1 ; O=C([O-])C(F)(F)F]

(3S,4S)-1-(3-cyano-7-methoxyquinolin-4-yl)-3-methylpiperidine-4-carboxylic Acid tert-butyl (3S,4S)-1-(3-cyano-7-methoxyquinolin-4-yl)-3-methylpiperidine-4-carboxylate (137 mg, 0.36 mmol) was dissolved in DCM (7.18 mL) and TFA (0.553 mL, 7.18 mmol) added. The reaction was stirred at room temperature for 15 h. The reaction was concentrated and dried on the lyophilizer for 15 h to give the title compound. MS: 326 (M+1).

Intermediate 61

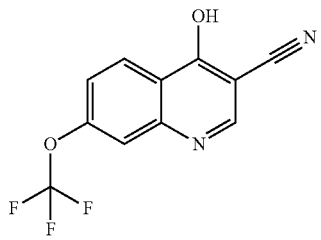 [SMILES: N#Cc1cnc2cc(OC(F)(F)F)ccc2c1O]

4-hydroxy-7-(trifluoromethoxy)quinoline-3-carbonitrile

A dry round bottom flask was charged with 4-hydroxy-7-(trifluoromethoxy)quinoline-3-carboxylic acid (4.33 g, 15.9 mmol), ammonium chloride (1.27 g, 23.8 mmol), EtOAc (52.8 mL), 2,4,6-tripropyl-1,3,5,2,4,6-trioxatriphosphorinane-2,4,6-trioxide (23.14 mL, 39.6 mmol), and triethylamine (6.63 mL, 47.6 mmol) and the mixture was heated to 80° C. over the weekend. The reaction was quenched with saturated sodium bicarbonate and filtered. The aqueous layer was extracted with 3:1 chloroform:isopropanol (3×). The combined organic layers were dried with magnesium sulfate, filtered and concentrated to give the title compound. MS: 255 (M+1).

Intermediate 62a

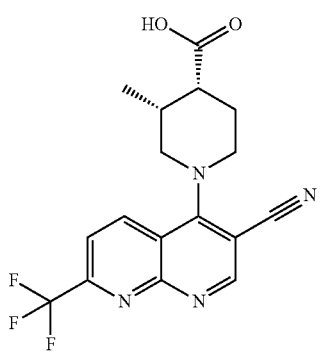 [SMILES: C[C@H]1CN(c2c(C#N)cnc3nc(C(F)(F)F)ccc23)CC[C@H]1C(=O)O]

(3R,4R)-1-[3-cyano-7-(trifluoromethyl)-1,8-naphthyridin-4-yl]-3-methylpiperidine-4-carboxylic Acid 4-chloro-7-(trifluoromethyl)-1,8-naphthyridine-3-carbonitrile (100 mg, 0.39 mmol), (3R,4R)-3-methylpiperidine-4-carboxylic acid hydrochloride (74 mg, 0.41 mmol), DIPEA (0.203 mL, 1.17 mmol), and DMF (3.88 mL) were combined in a sealed tube. The reaction was heated to 70° C. for 3 h. The reaction mixture was filtered and purified by reverse phase HPLC (10-100% MeCN/Water, with 0.05% TFA). The fractions were combined and neutralized with saturated sodium bicarbonate. The aqueous layer was extracted with EtOAc (3×). The organic layers were dried with magnesium sulfate, filtered, and concentrated to give the title compound. MS: 365 (M+1).

Intermediate 62b

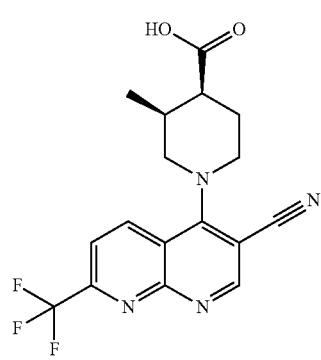 [SMILES: C[C@@H]1CN(c2c(C#N)cnc3nc(C(F)(F)F)ccc23)CC[C@@H]1C(=O)O]

(3S,4S)-1-[3-cyano-7-(trifluoromethyl)-1,8-naphthyridin-4-yl]-3-methylpiperidine-4-carboxylic Acid (3S,4S)-1-[3-cyano-7-(trifluoromethyl)-1,8-naphthyridin-4-yl]-3-methylpiperidine-4-carboxylic acid was made in a similar way to Intermediate 62a, using (3S,4S)-3-methylpiperidine-4-carboxylic acid hydrochloride. MS: 365 (M+1).

Intermediate 63

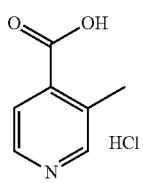

3-methylpyridine-4-carboxylic Acid Hydrochloride

To a solution of methyl 3-methylisonicotinate (90 g, 596 mmol) in MeOH (900 ml) and water (450 ml) was added LiOH (42.8 g, 1786 mmol) and the reaction mixture was stirred for 15 h at room temperature. Then the reaction mixture was adjusted to pH 3-4 with 1N HCl. The mixture was concentrated and purified on a silica gel chromatography (DCM:MeOH 3:1) to afford 3-methylisonicotinic acid. The 3-methylisonicotinic acid was stirred with HCl (4N in dioxane, 173 mL, 693 mmol) for 3 h at room temperature and filtered. The solid was washed with ether and dried to afford the title compound. MS: 138 (M+1).

Intermediate 64a and 64b

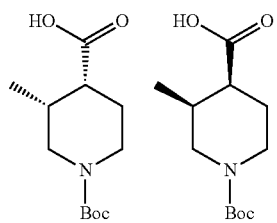

(3R,4R)-1-(tert-butoxycarbonyl)-3-methylpiperidine-4-carboxylic Acid (3S,4S)-1-(tert-butoxycarbonyl)-3-methylpiperidine-4-carboxylic Acid To a solution of 3-methylpyridine-4-carboxylic acid hydrochloride (200 g, 461 mmol) in MeOH (2000 mL) was added rhodium (30 g, 292 mmol). The reaction was flushed with hydrogen gas (10 atm). The reaction mixture was stirred for 5 days at 50° C. The solids were filtered out and the filtrate concentrated in vacuo. The residue was dissolved in water (1000 ml). Then NaOH (46.1 g, 1152 mmol) and Boc$_2$O (151 g, 691 mmol) was added. The mixture was stirred overnight at room temperature. The pH value of the solution was adjusted to 2-3 with 3N HCl and the combined fractions were extracted with EtOAc (800 mL, ×2). The combined organic layer was washed with brine and dried over anhydrous sodium sulfate and concentrated under vacuum. The solid was stirred overnight in EtOAc/n-hexane (1:10, 300 ml) and filtered. The solid was collected to afford racemic 1-(tert-butoxycarbonyl)-3-methylpiperidine-4-carboxylic acid. 1-(tert-butoxycarbonyl)-3-methylpiperidine-4-carboxylic acid (80 g, 329 mmol) was purified by SFC (twice) (Instrument: Thar SFC 350 Column: CHIRALPAK AD-H Mobile phase: % Solvent A: CO$_2$:85% Solvent B: MeOH (0.1% DEA)) to afford (3R,4R)-1-(tert-butoxycarbonyl)-3-methylpiperidine-4-carboxylic acid. MS: 266 (M+Na) (peak 1, SFC $t_R$=0.80 min) and (3S,4S)-1-(tert-butoxycarbonyl)-3-methylpiperidine-4-carboxylic acid. MS: 266 (M+Na) (peak 2, SFC $t_R$=1.14 min).

Intermediate 65a

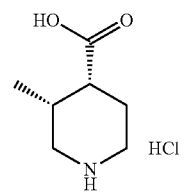

(3R,4R)-3-methylpiperidine-4-carboxylic Acid Hydrochloride (3R,4R)-1-(tert-butoxycarbonyl)-3-methylpiperidine-4-carboxylic acid (100 mg, 0.411 mmol) was dissolved in DCM (2.06 mL). HCl (4M in dioxane, 1.03 mL, 4.11 mmol) was added and the reaction was stirred at room temperature for 15 h. The reaction was concentrated and dried on the lyophilizer to give the title compound.

Intermediate 65b

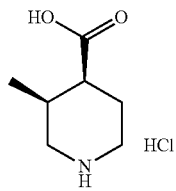

(3S,4S)-3-methylpiperidine-4-carboxylic Acid Hydrochloride (3S,4S)-3-methylpiperidine-4-carboxylic acid hydrochloride was made in a similar way to Intermediate 65a, using (3S,4S)-1-(tert-butoxycarbonyl)-3-methylpiperidine-4-carboxylic acid.

Intermediate 66

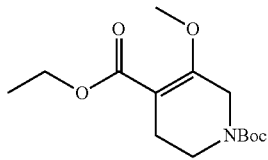 [SMILES: CCOC(=O)C1=C(OC)CN(C(=O)OC(C)(C)C)CC1]

1-(tert-butyl) 4-ethyl 5-methoxy-3,6-dihydropyridine-1,4(2H)-dicarboxylate

To a solution of 1-(tert-butyl) 4-ethyl 3-oxopiperidine-1,4-dicarboxylate (2 g, 7.37 mmol) in THF (20.48 mL) was gradually added NaH (0.451 g, 11.28 mmol). The mixture was stirred at 20° C. for 1 h. To the mixture was added Me$_2$SO$_4$ (1.021 mL, 10.69 mmol) and the mixture was stirred at 60° C. for 3 h. The mixture was poured into water (100 mL), extracted with EtOAc (50 mL×2). The combined extracts were dried over Na$_2$SO$_4$, filtered and concentrated in vacuo. The residue was purified by silica gel chromatography (PE:EtOAc=10:1~5:1) to 1-(tert-butyl) 4-ethyl 5-methoxy-3,6-dihydropyridine-1,4(2H)-dicarboxylate (900 mg, 2.68 mmol). $^1$H NMR (400 MHz, CHLOROFORM-d) δ=4.19 (q, J=8.0 Hz, 2H), 4.14-4.00 (m, 2H), 3.77 (s, 3H), 3.43 (t, J=5.3 Hz, 2H), 2.41 (br. s., 2H), 1.46 (s, 9H), 1.29 (t, J=8.0 Hz, 3H)

Intermediate 66a

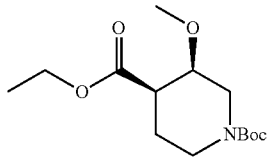 [SMILES: CCOC(=O)[C@@H]1CCN(C(=O)OC(C)(C)C)C[C@@H]1OC]

cis-1-(tert-butyl) 4-ethyl 3-methoxypiperidine-1,4-dicarboxylate

A mixture of 1-(tert-butyl) 4-ethyl 5-methoxy-3,6-dihydropyridine-1,4(2H)-dicarboxylate (0.9 g, 3.15 mmol) and Pd—C (0.336 g, 0.315 mmol) in MeOH (20 mL) was stirred under hydrogen balloon at 20° C. for 1 h. The mixture was filtered, and the filter cake washed with EtOH (30 mL). The filtrate was concentrated in vacuo to give cis-1-(tert-butyl) 4-ethyl 3-methoxypiperidine-1,4-dicarboxylate (810 mg, 2.82 mmol) as an oil. $^1$H NMR (400 MHz, CHLOROFORM-d) δ=4.53-4.29 (m, 1H), 4.25-4.08 (m, 3H), 3.76-3.69 (m, 1H), 3.35 (s, 3H), 2.87-2.58 (m, 2H), 2.51 (td, J=3.4, 12.1 Hz, 1H), 1.98 (dq, J=4.1, 12.7 Hz, 1H), 1.62 (br. s., 1H), 1.45 (s, 9H), 1.26 (t, J=8.0 Hz, 3H)

Intermediate 67

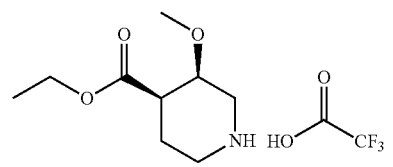

cis-ethyl-3-methoxypiperidine-4-carboxylate 2,2,2-trifluoroacetate

To a solution of cis-1-(tert-butyl) 4-ethyl 3-methoxypiperidine-1,4-dicarboxylate (0.81 g, 2.82 mmol) in DCM (14.09 mL) was added TFA (4.34 mL, 56.4 mmol). The resulting mixture was stirred at 20° C. for 5 h. The mixture was concentrated in vacuo directly to give the title compound. $^1$H NMR (400 MHz, METHANOL-d$_4$) δ=4.29-4.08 (m, 3H), 3.63 (d, J=13.5 Hz, 1H), 3.40 (s, 3H), 3.39-3.34 (m, 1H), 3.09-2.95 (m, 2H), 2.81 (td, J=3.5, 12.5 Hz, 1H), 2.14 (dq, J=4.3, 13.6 Hz, 1H), 2.02-1.96 (m, 1H), 1.28 (t, J=8.0 Hz, 3H)

Intermediate 68

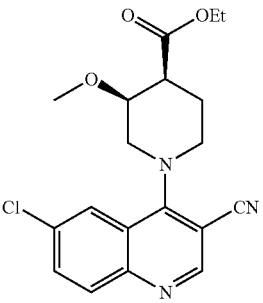 [SMILES: CCOC(=O)[C@H]1CCN(c2c(C#N)cnc3ccc(Cl)cc23)C[C@H]1OC]

cis-ethyl-1-(6-chloro-3-cyanoquinolin-4-yl)-3-methoxypiperidine-4-carboxylate

A mixture of 4,6-dichloroquinoline-3-carbonitrile (200 mg, 0.897 mmol), ethyl 3-methoxypiperidine-4-carboxylate (420 mg, 1.39 mmol) and DIEA (470 μL, 2.69 mmol) in DMF (4.48 mL) was heated to 70° C. for 15 h. The mixture was poured into water (50 mL), and extracted with EtOAc (50 mL×3). The combined extracts were dried over Na$_2$SO$_4$, filtered and concentrated in vacuo. The residue was purified by silica gel chromatography (PE:EtOAc=5:1~3:1) to give the title compound. MS: 374 (M+1).

Intermediate 68a and 68b

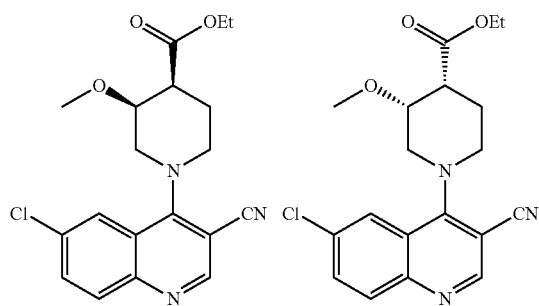

ethyl (3S,4S)-1-(6-chloro-3-cyanoquinolin-4-yl)-3-methoxypiperidine-4-carboxylate ethyl (3R,4R)-1-(6-chloro-3-cyanoquinolin-4-yl)-3-methoxypiperidine-4-carboxylate cis-ethyl-1-(6-chloro-3-cyanoquinolin-4-yl)-3-methoxypiperidine-4-carboxylate (0.29 g, 0.776 mmol) was separated by SFC (Column: Chiralpak AD (250 mm*30 mm, 10 um) Mobile phase: A: CO$_2$ B: methanol (0.05% DEA) Gradient: from 35% to 35% of B in 5.5 min Flow rate: 80 mL/min) to give ethyl (3R,4R)-1-(6-chloro-3-cyanoquinolin-4-yl)-3-methoxypiperidine-4-carboxylate (110 mg, 0.291 mmol) MS: 374 (M+1) (peak 2, SFC t$_R$=4.94 min) and ethyl (3S,4S)-1-(6-chloro-3-cyanoquinolin-4-yl)-3-methoxypiperidine-4-carboxylate (118 mg, 0.294 mmol) MS: 374 (M+1) (peak 1, SFC t$_R$=3.55 min).

Intermediate 69b

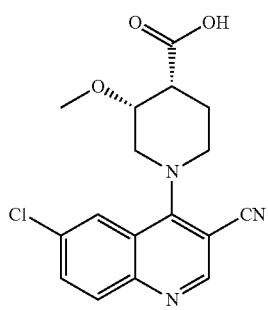 [SMILES: CO[C@H]1CN(c2c(C#N)cnc3ccc(Cl)cc23)CC[C@H]1C(=O)O]

(3R,4R)-1-(6-chloro-3-cyanoquinolin-4-yl)-3-methoxypiperidine-4-carboxylic Acid

To a solution of ethyl (3R,4R)-1-(6-chloro-3-cyanoquinolin-4-yl)-3-methoxypiperidine-4-carboxylate (15 mg, 0.040 mmol) in THF (0.201 mL) was added NaOH (4 M in water, 0.050 mL, 0.201 mmol), and the mixture was stirred at 15° C. for 40 min. Another 10 eq. of aq NaOH (4M in water, 0.500, 2.01 mmol) was added. The mixture was stirred at 15° C. for another 16 h at RT. The mixture was neutralized with 1 N HCl to pH=7 and concentrated in vacuo to give 1-(6-chloro-3-cyanoquinolin-4-yl)-3-methoxypiperidine-4-carboxylic. MS: 346 (M+1).

Intermediate 69a

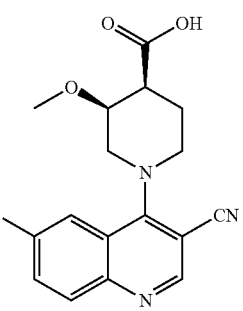

(3S,4S)-1-(6-chloro-3-cyanoquinolin-4-yl)-3-methoxypiperidine-4-carboxylic Acid

To a solution of ethyl (3S,4S)-1-(6-chloro-3-cyanoquinolin-4-yl)-3-methoxypiperidine-4-carboxylate (60 mg, 0.161 mmol) in EtOH/H$_2$O (4:1, 3 mL) was added NaOH (4M in water, 601 μL, 2.407 mmol). The mixture was stirred at 30° C. for 1.5 h. LCMS showed the reaction was complete. The reaction was acidified with 1 M HCl (aq) to pH=6~7. The mixture was concentrated to dryness, to provide the title compound. MS: 346 (M+1).

Intermediate 70

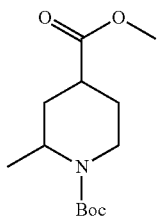

1-(tert-butyl) 4-methyl 2-methylpiperidine-1,4-dicarboxylate

A mixture of di-tert-butyl dicarbonate (8.0 g, 36.7 mmol), methyl 2-methylisonicotinate (2.6 g, 17.20 mmol) and platinum(IV) oxide (260 mg, 1.145 mmol) in MeOH (30 mL) was stirred under hydrogen atmosphere (50 psi) for 5 days at 25° C. The mixture was filtered through CELITE and concentrated. The residue was purified by silica gel chromatography (PE:EtOAc=50:1) to afford 1-tert-butyl 4-methyl 2-methylpiperidine-1,4-dicarboxylate. $^1$H NMR (400 MHz, CDCl$_3$): δ=4.21-4.13 (m, 1H), 3.87-3.78 (m, 1H), 3.70 (s, 3H), 3.17-3.00 (m, 1H), 2.63-2.51 (m, 1H), 2.02-1.82 (m, 3H), 1.73 (tt, J=6.2, 12.8 Hz, 1H), 1.45 (s, 9H), 1.07 (d, J=6.8 Hz, 3H).

Intermediate 71

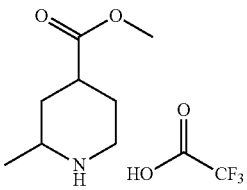

methyl 2-methylpiperidine-4-carboxylate
2,2,2-trifluoroacetate

To a mixture of 1-(tert-butyl) 4-methyl 2-methylpiperidine-1,4-dicarboxylate (800 mg, 3.11 mmol) in DCM (5 mL) was added TFA (2.5 mL, 32.4 mmol). The reaction was stirred at 20° C. for 2.5 h. The reaction was concentrated to give methyl 2-methylpiperidine-4-carboxylate 2,2,2-trifluoroacetate (1.162 g, 3.00 mmol). MS: 158 (M+1).

Intermediates 72a and 72b

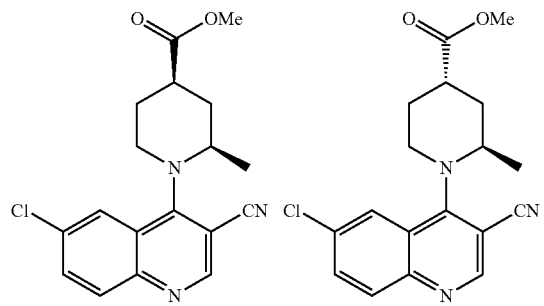

cis-methyl-1-(6-chloro-3-cyanoquinolin-4-yl)-2-methylpiperidine-4-carboxylate trans-methyl-1-(6-chloro-3-cyanoquinolin-4-yl)-2-methylpiperidine-4-carboxylate To a mixture of methyl 2-methylpiperidine-4-carboxylate 2,2,2-trifluoroacetate (688 mg, 1.775 mmol) and DIPEA (1.268 mL, 7.26 mmol) in DMF (3 mL) was added 4,6-dichloroquinoline-3-carbonitrile (360 mg, 1.614 mmol) and the mixture was stirred at 90° C. for 16 h. The reaction was quenched with H$_2$O (20 mL), and the combined fractions were extracted with EtOAc (30 mL×3). The combined organic layers was washed with brine (20 mL), dried over Na$_2$SO$_4$, filtered and concentrated. The residue was purified by silica gel chromatography (PE:EtOAc=15:1~10:1) and further purified by p-HPLC to give cis-methyl 1-(6-chloro-3-cyanoquinolin-4-yl)-2-methylpiperidine-4-carboxylate (342 mg, 0.895 mmol) and trans-methyl 1-(6-chloro-3-cyanoquinolin-4-yl)-2-methylpiperidine-4-carboxylate (144 mg, 0.410 mmol). MS: 344 (M+1).

Intermediate 73a

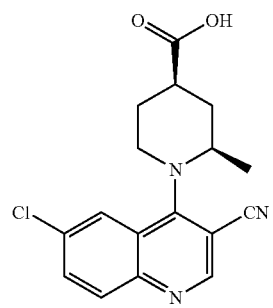 [SMILES: C[C@@H]1C[C@H](C(=O)O)CCN1c1c(C#N)cnc2ccc(Cl)cc12]

cis-1-(6-chloro-3-cyanoquinolin-4-yl)-2-methylpiperidine-4-carboxylic Acid

To a mixture of cis-methyl 1-(6-chloro-3-cyanoquinolin-4-yl)-2-methylpiperidine-4-carboxylate (155 mg, 0.451 mmol) in THF (2 mL) and water (1 mL) was added lithium hydroxide monohydrate (132 mg, 3.16 mmol). The reaction mixture was stirred at 18° C. for 16 h. The reaction was acidified with 6 N HCl to pH<4, concentrated and lyophilized to give cis-1-(6-chloro-3-cyanoquinolin-4-yl)-2-methylpiperidine-4-carboxylic acid. MS: 330 (M+1).

Intermediate 73b

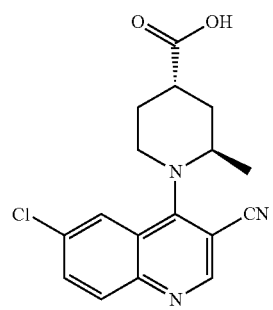 [SMILES: C[C@@H]1C[C@@H](C(=O)O)CCN1c1c(C#N)cnc2ccc(Cl)cc12]

trans-1-(6-chloro-3-cyanoquinolin-4-yl)-2-methylpiperidine-4-carboxylic Acid

To a mixture of trans-methyl 1-(6-chloro-3-cyanoquinolin-4-yl)-2-methylpiperidine-4-carboxylate (140 mg, 0.407 mmol) in THF (2 mL) and water (1 mL) was added lithium hydroxide monohydrate (120 mg, 2.85 mmol). The reaction mixture was stirred at 18° C. for 16 h. The reaction was acidified with 6N HCl to pH<4, concentrated and lyophilized to give trans-1-(6-chloro-3-cyanoquinolin-4-yl)-2-methylpiperidine-4-carboxylic acid as a solid. MS: 330 (M+1).

Intermediate 74

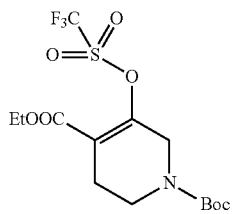 [SMILES: CCOC(=O)C1=C(OS(=O)(=O)C(F)(F)F)CN(C(=O)OC(C)(C)C)CC1]

1-tert-butyl 4-ethyl 5-{[(trifluoromethyl)sulfonyl]oxy}-3,6-dihydropyridine-1,4(2H)-dicarboxylate A solution of 1-tert-butyl 4-ethyl 3-oxopiperidine-1,4-dicarboxylate (5.0 g, 18.43 mmol) and DIEA (4.83 mL, 27.6 mmol) in CH$_2$Cl$_2$ (80 mL) was cooled to −78° C. under a nitrogen atmosphere. Triflic anhydride (Tf$_2$O) (3.74 mL, 22.11 mmol) was added dropwise, and the reaction mixture was stirred at this temperature for 45 min. The mixture was treated with saturated NaHCO$_3$ (50 mL). The organic phase was separated and the aqueous phase was extracted with DCM (2×60 mL). The combined organic layers were dried over Na$_2$SO$_4$, filtered and concentrated to give 1-tert-butyl 4-ethyl 5-{[(trifluoromethyl)sulfonyl]oxy}-3,6-dihydropyridine-1,4(2H)-dicarboxylate. $^1$H NMR (400 MHz, CHLOROFORM-d) δ=4.28 (q, J=7.1 Hz, 2H), 4.10 (br. s., 2H), 3.51 (t, J=5.5 Hz, 2H), 2.58 (br. s., 2H), 1.46 (s, 9H), 1.32 (t, J=7.2 Hz, 3H).

Intermediate 77

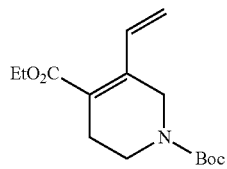

1-tert-butyl 4-ethyl 3-vinyl-5,6-dihydropyridine-1,4(2H)-dicarboxylate

A mixture of 1-tert-butyl 4-ethyl 5-{[(trifluoromethyl)sulfonyl]oxy}-3,6-dihydropyridine-1,4(2H)-dicarboxylate (12.39 g, 18.43 mmol), 4,4,5,5-tetramethyl-2-vinyl-1,3,2-dioxaborolane (3.41 g, 22.12 mmol), Cs$_2$CO$_3$ (12.01 g, 36.9 mmol) and [1,1'-bis(diphenylphosphino)ferrocene]dichloropalladium(II) complex with dichloromethane (1.505 g, 1.843 mmol) in 1,4-dioxane (73.7 mL) and water (18.43 mL) was heated under N$_2$ atmosphere (1 atm) at 80° C. for 4 h. The reaction mixture was cooled to room temperature and poured into water (100 mL). The mixture was extracted with EtOAc (3×80 mL). The combined organic layers were dried with Na$_2$SO$_4$, filtered and concentrated. The residue was purified by column chromatography on silica gel eluting with EtOAc/petroleum ether (1:20) to give 1-tert-butyl 4-ethyl 3-vinyl-5,6-dihydropyridine-1,4(2H)-dicarboxylate. $^1$H NMR (400 MHz, CHLOROFORM-d) δ=7.31-7.20 (m, 1H), 5.40 (br. s., 1H), 5.31-5.21 (m, 1H), 4.28-4.12 (m, 4H), 3.49 (br. s., 2H), 2.49 (br. s., 2H), 1.47 (s, 9H), 1.31 (t, J=7.0 Hz, 3H).

Intermediate 78

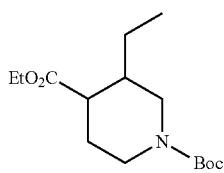

1-tert-butyl 4-ethyl 3-ethylpiperidine-1,4-dicarboxylate

A mixture of 1-tert-butyl 4-ethyl 3-vinyl-5,6-dihydropyridine-1,4(2H)-dicarboxylate (503 mg, 1.788 mmol) and Pd—C (19.03 mg, 0.179 mmol) in MeOH (8 mL) was stirred at 25° C. under H$_2$ atmosphere (15 psi) for 18 h. The mixture was filtered and the filter cake washed with MeOH (8 mL). The filtrate was concentrated to give 1-tert-butyl 4-ethyl 3-ethylpiperidine-1,4-dicarboxylate. MS: 286 (M+1).

Intermediate 79

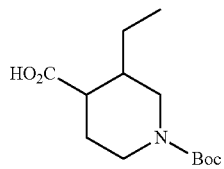 [SMILES: CCC1CN(C(=O)OC(C)(C)C)CCC1C(=O)O]

1-(tert-butoxycarbonyl)-3-ethylpiperidine-4-carboxylic Acid

To a solution of 1-tert-butyl 4-ethyl 3-ethylpiperidine-1,4-dicarboxylate (485 mg, 1.70 mmol) in EtOH (8 mL) was added NaOH (2.124 mL, 8.50 mmol). The mixture was stirred at 25° C. for 16 h. The mixture was heated to 50° C. and stirred for additional 2 h. The mixture was neutralized with concentrated HCl to pH=7. The reaction was concentrated to give 1-(tert-butoxycarbonyl)-3-ethylpiperidine-4-carboxylic acid, which was used directly without purification. MS: 515 (2M+1).

Intermediate 80

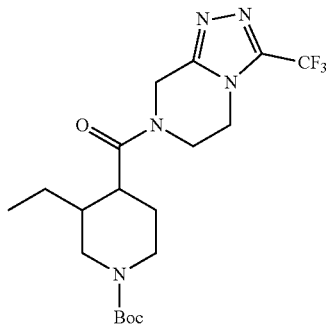 [SMILES: CCC1CN(C(=O)OC(C)(C)C)CCC1C(=O)N1CCn2c(nnc2C(F)(F)F)C1]

tert-butyl 3-ethyl-4-{[3-(trifluoromethyl)-5,6-dihydro[1,2,4]triazolo[4,3-a]pyrazin-7(8H)-yl]carbonyl}piperidine-1-carboxylate DIEA (1.19 mL, 6.80 mmol) was added to a stirred mixture of 1-(tert-butoxycarbonyl)-3-ethylpiperidine-4-carboxylic acid (437 mg, 1.70 mmol), 3-(trifluoromethyl)-5,6,7,8-tetrahydro-[1,2,4]triazolo[4,3-a]pyrazine hydrochloride (427 mg, 1.87 mmol) and HATU (711 mg, 1.87 mmol) in DMF (5663 μL) and the mixture was stirred at 25° C. for 16 h. The reaction mixture was cooled and poured into water (20 mL). The mixture was extracted with EtOAc (3×20 mL). The combined organic layers were dried with $Na_2SO_4$, filtered and concentrated. The residue was purified by column chromatography on silica gel eluting with EtOAc/petroleum ether/$NH_4OH$ (1:1:0.1) to give tert-butyl 3-ethyl-4-(3-(trifluoromethyl)-5,6,7,8-tetrahydro-[1,2,4]triazolo[4,3-a]pyrazine-7-carbonyl)piperidine-1-carboxylate. MS: 432 (2M+1).

Intermediate 80a and 80b

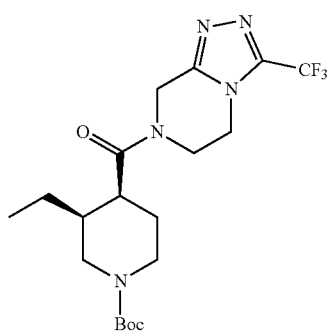

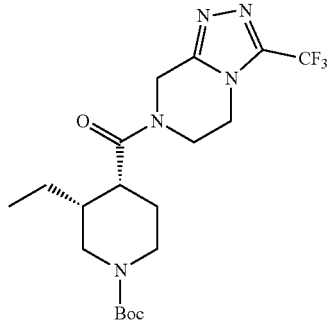

tert-butyl (3S,4S)-3-ethyl-4-{[3-(trifluoromethyl)-5,6-dihydro[1,2,4]triazolo[4,3-a]pyrazin-7(8H)-yl]carbonyl}piperidine-1-carboxylate tert-butyl (3R,4R)-3-ethyl-4-{[3-(trifluoromethyl)-5,6-dihydro[1,2,4]triazolo[4,3-a]pyrazin-7(8H)-yl]carbonyl}piperidine-1-carboxylate Tert-butyl 3-ethyl-4-(3-(trifluoromethyl)-5,6,7,8-tetrahydro-[1,2,4]triazolo[4,3-a]pyrazine-7-carbonyl)piperidine-1-carboxylate (584 mg, 1.354 mmol) was separated. Column: Lux Cellulose-2 150×4.6 mm I.D., 3 μm. Mobile phase: A: $CO_2$ B: IPA (0.05% DEA). Gradient: from 5% to 40% of B in 5.5 min, held at 40% of B for 3 min, then at 5% of B for 1.5 min. Flow rate: 2.5 mL/min Column temperature: 40° C. The SFC separation yielded the titled cis diastereomers (major peak 1 at 4.73 minutes, 208 mg, 0.476 mmol; major peak 2 at 5.35 min, 245 mg, 0.564 mmol). MS: 432 (2M+1).

Intermediate 81b

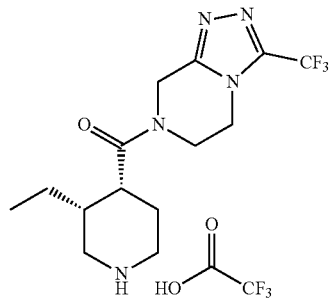

[(3R,4R)-3-ethylpiperidin-4-yl][3-(trifluoromethyl)-5,6-dihydro[1,2,4]triazolo[4,3-a]pyrazin-7(8H)-yl]methanone trifluoroacetate To a solution of tert-butyl (3R,4R)-3-ethyl-4-{[3-(trifluoromethyl)-5,6-dihydro[1,2,4]triazolo[4,3-a]pyrazin-7(8H)-yl]carbonyl}piperidine-1-carboxylate (SFC major peak 1, 208 mg, 0.482 mmol) in DCM (5 mL) was added TFA (0.557 mL, 7.23 mmol) dropwise and the mixture was stirred at 30° C. for 1.5 h. The reaction mixture was concentrated to give [(3R,4R)-3-ethylpiperidin-4-yl][3-(trifluoromethyl)-5,6-dihydro[1,2,4]triazolo[4,3-a]pyrazin-7(8H)-yl]methanone trifluoroacetate. MS: 332 (M+1) $[a]_D^{25}$=−15.39 (MeOH, c=1 mg/mL).

Intermediate 81a

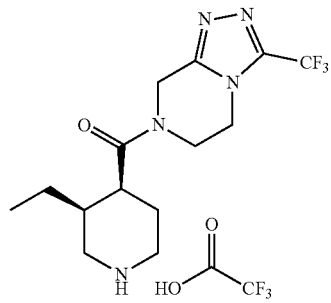

[(3S,4S)-3-ethylpiperidin-4-yl][3-(trifluoromethyl)-5,6-dihydro[1,2,4]triazolo[4,3-a]pyrazin-7(8H)-yl]methanone trifluoroacetate To a solution of tert-butyl (3S,4S)-3-ethyl-4-{[3-(trifluoromethyl)-5,6-dihydro[1,2,4]triazolo[4,3-a]pyrazin-7(8H)-yl]carbonyl}piperidine-1-carboxylate (SFC major peak 2, 245 mg, 0.568 mmol) in DCM (5 mL) was added TFA (0.656 mL, 8.52 mmol) dropwise, and the mixture was stirred at 30° C. for 1.5 h. The reaction mixture was concentrated to give [(3S,4S)-3-ethylpiperidin-4-yl][3-(trifluoromethyl)-5,6-dihydro[1,2,4]triazolo[4,3-a]pyrazin-7

(8H)-yl]methanone trifluoroacetate. MS: 332 (M+1) [M+H⁺]. [a]$_D^{25}$=+19.41 (MeOH, c=1 mg/mL).

Intermediate 82

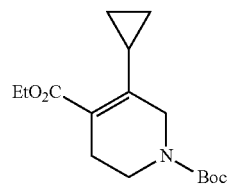

1-(tert-butyl) 4-ethyl 5-cyclopropyl-3,6-dihydropyridine-1,4(2H)-dicarboxylate

A mixture of 1-tert-butyl 4-ethyl 5-{[(trifluoromethyl)sulfonyl]oxy}-3,6-dihydropyridine-1,4(2H)-dicarboxylate (12.39 g, 18.43 mmol), cyclopropylboronic acid (1.900 g, 22.12 mmol), Cs₂CO₃ (12.01 g, 36.9 mmol) and [1,1'-bis(diphenylphosphino)ferrocene]dichloropalladium(II) complex with dichloromethane (1.505 g, 1.843 mmol) in 1,4-dioxane (73.7 mL) and water (18.43 mL) was heated under N₂ atmosphere (1 atm) at 80° C. for 5 h. The reaction mixture was cooled and poured into water (80 mL). The mixture was extracted with EtOAc (3×50 mL). The combined organic layers were dried with Na₂SO₄, filtered and concentrated. The residue was purified by silica gel chromatography (EtOAc:petroleum ether 1:20) to give the title compound. ¹H NMR (400 MHz, CHLOROFORM-d) δ=4.21 (q, J=7.2 Hz, 2H), 3.64 (br. s., 2H), 3.42 (t, J=5.1 Hz, 2H), 2.50 (br. s., 1H), 2.39 (br. s., 2H), 1.44 (s, 9H), 1.29 (t, J=7.2 Hz, 3H), 0.82-0.53 (m, 4H).

Intermediate 83

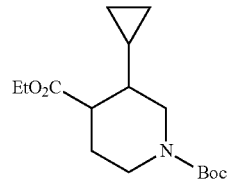

1-(tert-butyl) 4-ethyl 3-cyclopropylpiperidine-1,4-dicarboxylate

A mixture of 1-tert-butyl 4-ethyl 3-cyclopropyl-5,6-dihydropyridine-1,4(2H)-dicarboxylate (500 mg, 1.693 mmol) and Rh/C (87 mg, 0.846 mmol) in MeOH (5 mL) was stirred at 25° C. under H₂ atmosphere (15 psi) for 16 h. The mixture was filtered through CELITE, washed with MeOH (5 mL), and the filtrate was concentrated to give 1-tert-butyl 4-ethyl 3-cyclopropylpiperidine-1,4-dicarboxylate. MS: 298 (M+1)

Intermediate 84

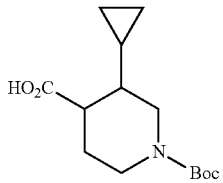 [SMILES: CC(C)(C)OC(=O)N1CCC(C(=O)O)C(C2CC2)C1]

1-(tert-butoxycarbonyl)-3-cyclopropylpiperidine-4-carboxylic Acid

To a solution of 1-tert-butyl 4-ethyl 3-cyclopropylpiperidine-1,4-dicarboxylate (0.503 g, 1.693 mmol) in EtOH (5 mL) was added NaOH (4.23 mL, 16.93 mmol). The mixture was stirred at 25° C. for 16 h. The mixture was heated to 50° C. and stirred for additional 3 h. The mixture was neutralized with conc HCl to pH=7 and concentrated to give 1-(tert-butoxycarbonyl)-3-cyclopropylpiperidine-4-carboxylic acid. MS: 539 (2M+1)

Intermediate 85

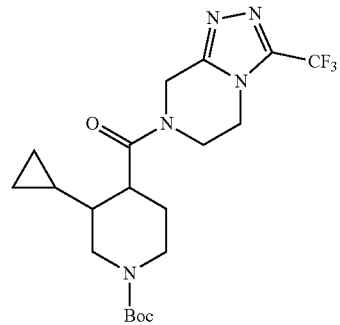 [SMILES: CC(C)(C)OC(=O)N1CCC(C(=O)N2CCn3c(nnc3C(F)(F)F)C2)C(C2CC2)C1]

tert-butyl 3-cyclopropyl-4-(3-(trifluoromethyl)-5,6,7,8-tetrahydro-[1,2,4]triazolo[4,3-a]pyrazine-7-carbonyl)piperidine-1-carboxylate DIEA (1500 μL, 8.59 mmol) was added to a stirred mixture of 1-(tert-butoxycarbonyl)-3-cyclopropylpiperidine-4-carboxylic acid (578 mg, 2.147 mmol), 3-(trifluoromethyl)-5,6,7,8-tetrahydro-[1,2,4]triazolo[4,3-a]pyrazine hydrochloride (540 mg, 2.362 mmol) and HATU (898 mg, 2.362 mmol) in DMF (7.16 mL) and the mixture was stirred at 25° C. for 16 h. The reaction mixture was cooled and poured into water (20 mL). The mixture was extracted with EtOAc (3×20 ml). The combined organic layers were dried with Na₂SO₄, filtered and concentrated. The residue was purified by column chromatography on silica gel eluting with EtOAc/petroleum ether/NH₄OH (1:1:0.1) to give tert-butyl 3-cyclopropyl-4-(3-(trifluoromethyl)-5,6,7,8-tetrahydro-[1,2,4]triazolo[4,3-a]pyrazine-7-carbonyl)piperidine-1-carboxylate. MS: 887.5 (2M+1).

Intermediates 86, 86a and 86b

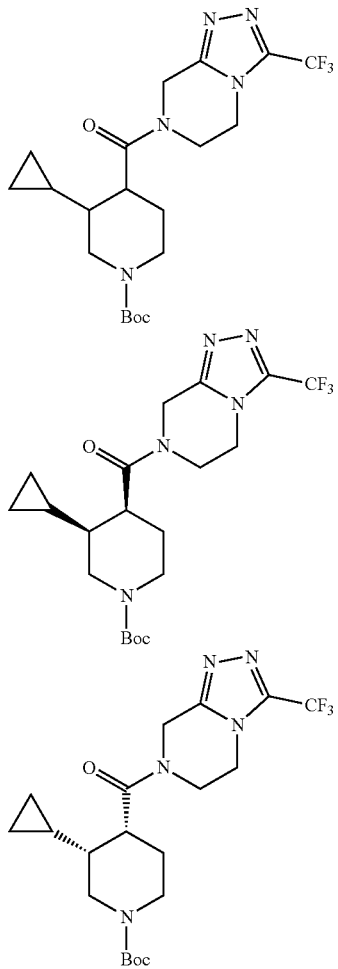

tert-butyl (3S,4S)-3-cyclopropyl-4-{[3-(trifluoromethyl)-5,6-dihydro[1,2,4]triazolo[4,3-a]pyrazin-7(8H)-yl]carbonyl}piperidine-1-carboxylate tert-butyl (3R,4R)-3-cyclopropyl-4-{[3-(trifluoromethyl)-5,6-dihydro[1,2,4]triazolo[4,3-a]pyrazin-7(8H)-yl]carbonyl}piperidine-1-carboxylate trans tert-butyl-3-cyclopropyl-4-{[3-(trifluoromethyl)-5,6-dihydro[1,2,4]triazolo[4,3-a]pyrazin-7(8H)-yl]carbonyl}piperidine-1-carboxylate tert-butyl 3-cyclopropyl-4-(3-(trifluoromethyl)-5,6,7,8-tetrahydro-[1,2,4]triazolo[4,3-a]pyrazine-7-carbonyl)piperidine-1-carboxylate (766 mg, 1.727 mmol) was separated (Column: Pheno Lux Cellulose-2 150×4.6 mm I.D., 5 um, Mobile phase: methanol (0.05% DEA) in carbon dioxide from 5% to 40%, Flow rate: 2.4 mL/min, Wavelength: 220 nm). Separation yielded cis Peak 1 (Rt=5.43 min) (238 mg, 0.534 mmol) which contained about 15% of trans isomer 1; cis Peak 2 (Rt=5.63 min) (212 mg, 0.476 mmol), and trans isomer 2 (Rt=5.94 min) (87 mg, 0.181 mmol). MS: 887.5 (2M+1).

Intermediate 87

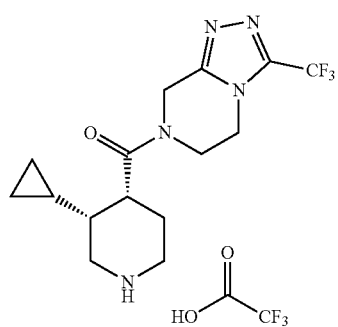 [SMILES: O=C([C@@H]1CCNC[C@@H]1C1CC1)N1CCn2c(nnc2C(F)(F)F)C1 ; O=C(O)C(F)(F)F]

[(3R,4R)-3-cyclopropylpiperidin-4-yl][3-(trifluoromethyl)-5,6-dihydro[1,2,4]triazolo[4,3-a]pyrazin-7(8H)-yl]methanone trifluoroacetate To a solution of tert-butyl (3R,4R)-3-cyclopropyl-4-{[3-(trifluoromethyl)-5,6-dihydro[1,2,4]triazolo[4,3-a]pyrazin-7(8H)-yl]carbonyl}piperidine-1-carboxylate (193 mg, 0.435 mmol) in DCM (5 mL) was added TFA (0.503 mL, 6.53 mmol) dropwise. The mixture was stirred at 30° C. for 3 h. The reaction mixture was concentrated to give the title compound (contaminated with about 15% trans isomer 1 from the previous step). MS: 344 (2M+1). $[a]_D^{25}=-8.046$ (MeOH, c=1 mg/mL).

Intermediate 88

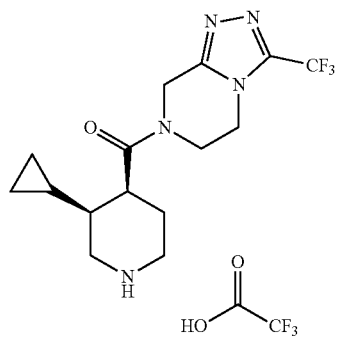 [SMILES: O=C([C@H]1CCNC[C@H]1C1CC1)N1CCn2c(nnc2C(F)(F)F)C1 ; O=C(O)C(F)(F)F]

[(3S,4S)-3-cyclopropylpiperidin-4-yl][3-(trifluoromethyl)-5,6-dihydro[1,2,4]triazolo[4,3-a]pyrazin-7(8H)-yl]methanone Trifluoroacetate To a solution of tert-butyl (3S,4S)-3-cyclopropyl-4-{[3-(trifluoromethyl)-5,6-dihydro[1,2,4]triazolo[4,3-a]pyrazin-7(8H)-yl]carbonyl}piperidine-1-carboxylate (212 mg, 0.478 mmol) in DCM (5 mL) was added TFA (0.552 mL, 7.17 mmol) dropwise, the mixture was stirred at 30° C. for 3 h. The reaction mixture was concentrated to give the title compound. MS: 344 (2M+1). $[a]_D^{25}=5.688$ (MeOH, c=1 mg/mL).

Intermediate 89

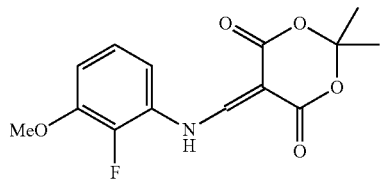 [SMILES: COc1cccc(NC=C2C(=O)OC(C)(C)OC2=O)c1F]

5-{[(2-fluoro-3-methoxyphenyl)amino]methyl-
idene}-2,2-dimethyl-1,3-dioxane-4,6-dione 2,2-dimethyl-1,3-dioxane-4,6-dione (4.58 g, 31.78 mmol) in trimethyl orthoformate (27.3 mL, 245.9 mmol) was refluxed at 100° C. for 1 hr. 2-fluoro-3-methoxyaniline (3.9 g, 27.63 mmol) was then added and refluxing was continued for an additional hour. The reaction was cooled to room temperature and the suspension was filtered. The solid was washed with MeOH (60 mL) and dried under vacuum to yield the title compound. $^1$H NMR H20438-004-04 (400 MHz, CHLOROFORM-d) δ=11.36-11.38 (m, 1H), 8.63-8.60 (m, 1H), 7.26-6.83 (m, 3H), 3.92 (s, 3H), 1.75 (s, 6H).

Intermediates 90a and 90b

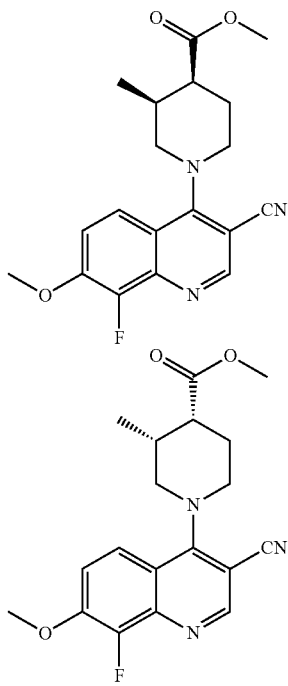

methyl (3S,4S)-1-(3-cyano-8-fluoro-7-methoxyqui-
nolin-4-yl)-3-methylpiperidine-4-carboxylate methyl (3R,4R)-1-(3-cyano-8-fluoro-7-methoxyqui-
nolin-4-yl)-3-methylpiperidine-4-carboxylate To a stirred mixture of methyl 3-methylpiperidine-4-carboxylate hydrochloride (0.82 g, 4.2 mmol) and 4-chloro-8-fluoro-7-methoxyquinoline-3-carbonitrile (1.0 g, 4.2 mmol) in DMF (21 mL) was added DIPEA (2.2 mL, 13 mmol) at room temperature and the resulting mixture was heated at 70° C. for 12 hour. The mixture was diluted with water and EtOAc and the layers were separated. The aqueous was extracted with EtOAc (2×) and the combined organic layers washed with water (2×) and brine, dried (Na2SO4), filtered, and concentrated. MPLC purification (40 g SiO2; 0→50% EtOAc:hexanes) provided the racemic ester. MS: 358 (M+1). The racemic products were further resolved by SFC (Column AD-H (50×250 mm) EtOH (0.24% DIPA)/CO$_2$, 210 nm) to provide methyl (3S,4S)-1-(3-cyano-8-fluoro-7-methoxyquinolin-4-yl)-3-methylpiperidine-4-carboxylate (peak 1, SFC $t_R$=3.0 min) and methyl (3R,4R)-1-(3-cyano-8-fluoro-7-methoxyquinolin-4-yl)-3-methylpiperidine-4-carboxylate (peak 2, SFC $t_R$=4.63 min).

Intermediate 91

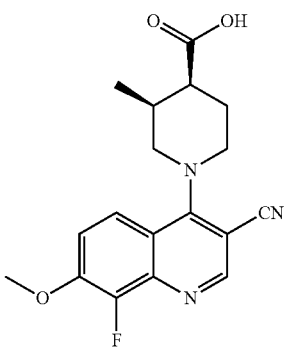 [SMILES: COc1ccc2c(N3CC[C@H](C(=O)O)[C@H](C)C3)c(C#N)cnc2c1F]

(3S,4S)-1-(3-cyano-8-fluoro-7-methoxyquinolin-4-
yl)-3-methylpiperidine-4-carboxylic Acid To a solution of methyl (3S,4S)-1-(3-cyano-8-fluoro-7-methoxyquinolin-4-yl)-3-methylpiperidine-4-carboxylate (0.020 g, 0.056 mmol) in THF (1 mL) was added LiOH (0.14 mL, 0.28 mmol) and the mixture was stirred for 12 h. LC/MS shows complete hydrolysis. The mixture was diluted with water and (3:1) chloroform:IPA and the pH of the aqueous layer was adjusted to pH 4 with 1 N HCl. The aqueous was extracted with (3:1) chloroform:IPA (3×) and the combined organic layers were washed with brine, dried with MgSO$_4$, filtered and concentrated to provide (3S,4S)-1-(3-cyano-8-fluoro-7-methoxyquinolin-4-yl)-3-methylpiperidine-4-carboxylic acid. MS: 344 (M+1).

Intermediate 92

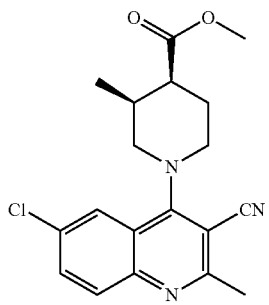 [SMILES: COC(=O)[C@H]1CCN(c2c(C#N)c(C)nc3ccc(Cl)cc23)C[C@H]1C]

methyl (3S,4S)-1-(6-chloro-3-cyano-2-methylquinolin-4-yl)-3-methylpiperidine-4-carboxylate To a stirred mixture of methyl 3-methylpiperidine-4-carboxylate hydrochloride (7.68 g, 39.6 mmol) and 4,6-dichloro-2-methylquinoline-3-carbonitrile (9.4 g, 39.6 mmol) in DMF (198 ml) was added DIPEA (20.77 ml, 119 mmol) at room temperature and the resulting mixture was heated at 70° C. for 12 hour. The mixture was diluted with water and EtOAc and the layers were separated. The aqueous was extracted with EtOAc (2×) and the combined organic layers were washed with water (2×) and brine, dried with Na$_2$SO$_4$, filtered, and concentrated. The residue was purified by silica gel chromatography (0-75% EtOAc: hexanes) to provide a racemic product. The racemic mixture was resolved with SFC (Chiralpak IC, Isopropanol/Hexane/Dichloromethane 45:45:10 with 0.25% Isopropylamine,). Two major peaks were obtained: (3S,4S)-methyl 1-(6-chloro-3-cyano-2-methylquinolin-4-yl)-3-methylpiperidine-4-carboxylate and (3R,4R)-methyl 1-(6-chloro-3-cyano-2-methylquinolin-4-yl)-3-methylpiperidine-4-carboxylate. MS: 358 (M+1).

Intermediate 93

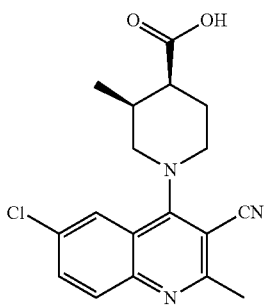 [SMILES: Cc1nc2ccc(Cl)cc2c(N2CC[C@H](C(=O)O)[C@H](C)C2)c1C#N]

(3S,4S)-1-(6-chloro-3-cyano-2-methylquinolin-4-yl)-3-methylpiperidine-4-carboxylic Acid To a solution of methyl (3S,4S)-1-(6-chloro-3-cyano-2-methylquinolin-4-yl)-3-methylpiperidine-4-carboxylate (2.0 g, 5.59 mmol) in THF (28 mL) was added LiOH (2 M in water, 8.38 mL, 16.8 mmol) and the mixture stirred for 12 h. The mixture was diluted with water and (3:1) chloroform:IPA and the pH of the aqueous layer adjusted to ~3-4 with 1 N HCl. The aqueous layer was extracted with (3:1) chloroform:IPA (3×) and the combined organic layers washed with brine, dried with magnesium sulfate, filtered and concentrated to provide (3S,4S)-1-(6-chloro-3-cyano-2-methylquinolin-4-yl)-3-methylpiperidine-4-carboxylic acid.

Intermediate 94

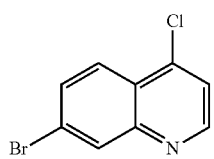

7-bromo-4-chloroquinoline

POCl$_3$ (6.99 mL, 75.0 mmol) was added to a mixture of 7-bromoquinolin-4-ol (5.6 g, 24.99 mmol) in dioxane (50 mL) and the mixture was stirred at 90° C. for 5 h. The mixture was poured into cold water (150 mL) and adjusted to pH~8 with solid Na$_2$CO$_3$. The mixture was extracted with EtOAc (50 mL*3). The organic layers were combined and washed with brine (1×50 mL), dried over Na$_2$SO$_4$, filtered and concentrated. The crude product was purified by silica gel chromatography (PE:EtOAc=30:1) to afford the title compound. MS: 243.9 (M+1).

Intermediate 95

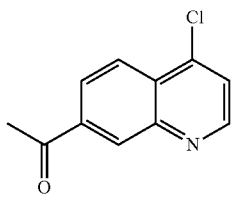

1-(4-chloroquinolin-7-yl)ethan-1-one

A mixture of tributyl(1-ethoxyvinyl)tin (1.392 mL, 4.12 mmol), 7-bromo-4-chloroquinoline (1 g, 4.12 mmol), bis(triphenylphosphine)palladium (II) dichloride (0.289 g, 0.412 mmol) and toluene (10 mL) was purged with N$_2$, then heated to 110° C. under N$_2$ atmosphere for 5 h. The mixture was cooled to room temperature and was used in the next step directly without further purification. A solution of THF/1.0 N HCl (1:1, 10 mL) was added to 4-chloro-7-(1-ethoxyvinyl)quinoline (964 mg, 4.13 mmol) and stirred at 25° C. vigorously for 1 h. Saturated potassium fluoride (aqueous, 30 mL) was added to the mixture and the mixture was stirred at 25° C. for 0.5 h. The mixture was extracted with EtOAc (30 mL×3). The combined organic layers were washed with a saturated aqueous solution of NaCl (10 mL), then dried over Na$_2$SO$_4$, filtered and concentrated. The residue was purified by silica gel chromatography (EtOAc/petroleum ether=1/7) to give the title compound. $^1$H NMR (400 MHz, CDCl$_3$): δ 8.88 (d, J=4.8 Hz, 1H), 8.70 (d, J=1.3 Hz, 1H), 8.35-8.29 (m, 1H), 8.22 (dd, J=1.8, 8.8 Hz, 1H), 7.60 (d, J=4.5 Hz, 1H), 2.78 (s, 3H).

Intermediate 96

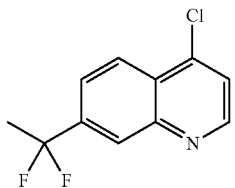

4-chloro-7-(1,1-difluoroethyl)quinoline

A mixture of pyridine hydrofluoride (32.8 mg, 0.331 mmol), 1-(4-chloroquinolin-7-yl)ethan-1-one (680 mg, 3.31 mmol) and BAST (1463 mg, 6.61 mmol) was stirred at 25° C. for 40 h. The mixture was diluted with saturated NaHCO₃ (100 mL) and extracted with EtOAc (30 mL×3). The organic layer was washed with brine (20 mL), dried over Na₂SO₄, filtered and concentrated. The residue was purified by silica gel chromatography (PE:EtOAc=10:1) to afford the title compound. MS: 228.0 (M+1).

Intermediate 97

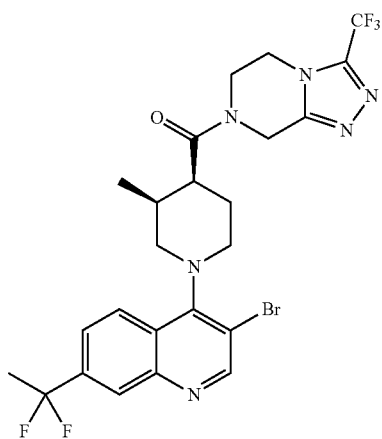 [SMILES: C[C@@H]1CN(c2c(Br)cnc3cc(C(C)(F)F)ccc23)CC[C@@H]1C(=O)N1CCn2c(nnc2C(F)(F)F)C1]

{(3S,4S)-1-[3-bromo-7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone A mixture of {(3S,4S)-1-[7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone (250 mg, 0.246 mmol) and 1-bromopyrrolidine-2,5-dione (43.8 mg, 0.246 mmol) in DCM (3 mL) was stirred at −10° C. for 1 h. The reaction was concentrated and the mixture was purified by p-TLC (DCM:MeOH=20:1) to afford the title compound. ¹H NMR (400 MHz, CDCl₃) δ=8.86 (s, 1H), 8.19 (s, 1H), 7.67 (d, J=8.4 Hz, 1H), 5.22-4.96 (m, 2H), 4.36-4.18 (m, 3H), 4.17-3.96 (m, 2H), 3.46-2.98 (m, 4H), 2.58-2.47 (m, 1H), 2.25-2.19 (m, 1H), 2.02 (t, J=18.2 Hz, 3H), 1.80-1.70 (m, 1H), 1.22-1.04 (m, 3H)

Intermediate 98

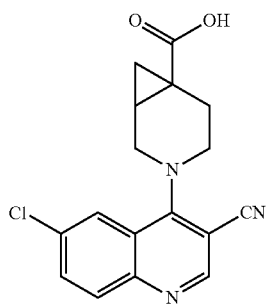 [SMILES: N#Cc1cnc2ccc(Cl)cc2c1N1CCC2(C(=O)O)CC2C1]

3-(6-chloro-3-cyanoquinolin-4-yl)-3-azabicyclo[4.1.0]heptane-6-carboxylic Acid

DIPEA (0.47 mL, 2.7 mmol) was added to a stirred mixture of the methyl 3-azabicyclo[4.1.0]heptane-6-carboxylate hydrochloride (170 mg, 0.90 mmol) and 4,6-dichloroquinoline-3-carbonitrile (200 mg, 0.90 mmol) in DMF (4 mL) at room temperature and the resulting mixture was heated at 70° C. for 12 hour. The mixture was diluted with water and EtOAc and the layers separated. The aqueous layer was extracted with EtOAc (2×) and the combined organic layers were washed with water (2×) and brine, dried (Na₂SO₄), filtered and concentrated to provide methyl 3-(6-chloro-3-cyanoquinolin-4-yl)-3-azabicyclo[4.1.0]heptane-6-carboxylate. MS: 342 (M+1).

LiOH (1.3 ml, 2.6 mmol) was added to a solution of methyl 3-(6-chloro-3-cyanoquinolin-4-yl)-3-azabicyclo[4.1.0]heptane-6-carboxylate (0.30 g, 0.87 mmol) in THF (10 mL) and the mixture stirred for 12 h at room temperature. The mixture was diluted with water and (3:1) CHCl₃:iPrOH and the pH of the aqueous layer adjusted to 4 with 1 N HCl. The aqueous layer was extracted with (3:1) CHCl₃:iPrOH (3×) and the combined organic layers were washed with brine, dried (MgSO₄), filtered and concentrated to provide (1S,6R)-3-(6-chloro-3-cyanoquinolin-4-yl)-3-azabicyclo[4.1.0]heptane-6-carboxylic acid. MS: 328 (M+1).

Intermediate 99

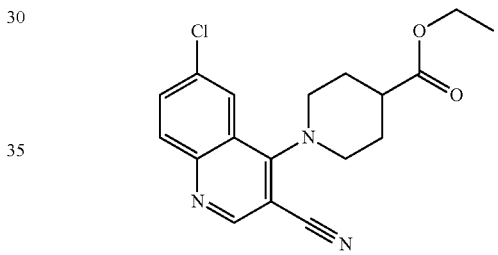

ethyl 1-(6-chloro-3-cyanoquinolin-4-yl)piperidine-4-carboxylate

TEA (3.75 mL, 26.9 mmol) and ethyl piperidine-4-carboxylate (3.70 g, 23.54 mmol) were added to a mixture of 4,6-dichloroquinoline-3-carbonitrile (5 g, 22.42 mmol) in anhydrous DMF (60 ml). The reaction mixture was stirred at room temperature for 1 hour. The reaction mixture was poured into a saturated NaHCO₃ solution (100 mL), and the resulting mixture was stirred for 20 min. The mixture was filtered. The filter cake was washed with brine and dried to afford the title compound. MS: 344 (M+1).

Intermediate 100

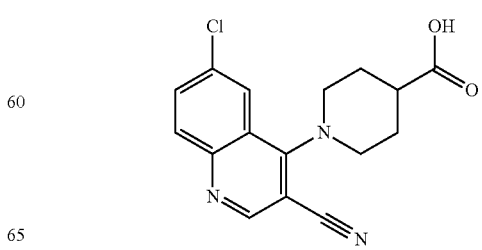

1-(6-chloro-3-cyanoquinolin-4-yl)piperidine-4-carboxylic Acid

Aqueous LiOH solution (1.0 N, 22.69 mL, 22.69 mmol) was added to a solution of ethyl 1-(6-chloro-3-cyanoquinolin-4-yl)piperidine-4-carboxylate (6 g, 17.45 mmol) in THF (100 mL) and MeOH (50 mL). The mixture was stirred at room temperature for 66 hours. The organic solvent was evaporated. The residue was treated with 1N HCl (23 mL) to form a precipitate. The mixture was stirred for 5 min and filtered. The filter cake was rinsed with water and dried to afford the title compound. MS: 316 (M+1).

Intermediate 101

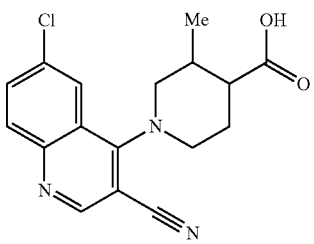 [SMILES: CC1CN(c2c(C#N)cnc3ccc(Cl)cc23)CCC1C(=O)O]

1-(6-chloro-3-cyanoquinolin-4-yl)-3-methylpiperidine-4-carboxylic Acid

To a stirred mixture of 4,6-dichloroquinoline-3-carbonitrile (500 mg, 2.242 mmol) in anhydrous DMF (5.98 mL), triethylamine (1.250 mL, 8.97 mmol) and 3-methylpiperidine-4-carboxylic acid (HCl salt, 443 mg, 2.466 mmol) was added at room temperature. The reaction mixture was stirred overnight. Then the reaction mixture was poured into water (60 mL). The mixture was neutralized with 1 N HCl to pH 7. The mixture was stirred for 20 min and filtered. The filter cake was dried to afford the title compound. MS: 330 (M+1).

Intermediate 102

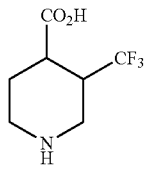 [SMILES: O=C(O)C1CCNCC1C(F)(F)F]

3-(trifluoromethyl)piperidine-4-carboxylic Acid

A mixture of 3-(trifluoromethyl)isonicotinic acid (2.0 g, 10.47 mmol) and platinum (IV) oxide (0.475 g, 2.09 mmol) in HCl in MeOH solution (1.25 M, 8.37 mL) was hydrogenated under hydrogen (50 psi) at room temperature for 16 hours. The reaction mixture was filtered and the filtrate was evaporated to afforded the title compound as HCl salt.

Intermediate 103

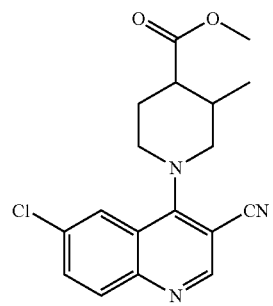 [SMILES: COC(=O)C1CCN(c2c(C#N)cnc3ccc(Cl)cc23)CC1C]

methyl 1-(6-chloro-3-cyanoquinolin-4-yl)-3-methylpiperidine-4-carboxylate

To a solution of 1-(6-chloro-3-cyanoquinolin-4-yl)-3-methylpiperidine-4-carboxylic acid (2.5 g, 7.58 mmol) in DMSO (70 mL) and MeOH (10 mL), TMS-Diazomethane solution (2.0 M in hexanes, 4.55 ml, 9.10 mmol) was added. The mixture was stirred at room temperature for 30 min., then additional TMS-Diazomethane solution (2.0 M in hexanes, 4.55 ml, 9.10 mmol) was added. After 1.5 h, additional TMS-Diazomethane solution (2.0 M in hexanes, 0.4 mL, 0.8 mmol) was added and the mixture was stirred for an additional 5 min. The reaction mixture was added to water and extracted with EtOAc. The organics were washed with water several times, dried over $Na_2SO_4$, filtered and concentrated to afford the title compound. MS: 344 (M+1).

Intermediate 104

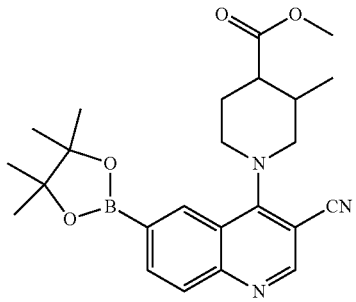

methyl 1-(3-cyano-6-(4,4,5,5-tetramethyl-1,3,2-dioxaborolan-2-yl)quinolin-4-yl)-3-methylpiperidine-4-carboxylate A mixture of potassium acetate (599 mg, 6.11 mmol), methyl 1-(6-chloro-3-cyanoquinolin-4-yl)-3-methylpiperidine-4-carboxylate (700 mg, 2.036 mmol), 4,4,4',4',5,5,5',5'-octamethyl-2,2'-bi(1,3,2-dioxaborolane) (1034 mg, 4.07 mmol), chloro[(tricyclohexylphosphine)-2-(2'-aminobiphenyl)palladium(II) (120 mg, 0.204 mmol) was flushed with $N_2$ three times. Then anhydrous toluene (17 mL) was added. The mixture was bubbled with $N_2$ for 10 min and then stirred at 85° C. overnight. The reaction mixture was cooled to room temperature, filtered and the filter cake was washed by ethyl acetate. The filtrate was evaporated. The residue was purified by silica chromatography (0-100% EtOAc/hexanes) to afford the title product. MS: 436 (M+1).

Intermediate 105

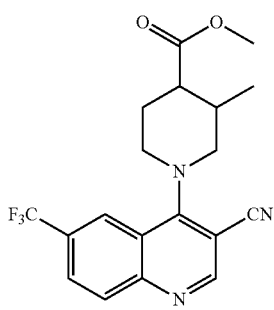 [SMILES: COC(=O)C1CCN(c2c(C#N)cnc3ccc(C(F)(F)F)cc23)CC1C]

methyl 1-(3-cyano-6-(trifluoromethyl)quinolin-4-yl)-3-methylpiperidine-4-carboxylate A 20 ml vial was charged with (1,10-phenanthroline)(trifluoromethyl)copper(I) (172 mg, 0.551 mmol) and potassium fluoride (26.7 mg, 0.459 mmol) in a glove box. Then a solution of methyl 1-(3-cyano-6-(4,4,5,5-tetramethyl-1,3,2-dioxaborolan-2-yl)quinolin-4-yl)-3-methylpiperidine-4-carboxylate (200 mg, 0.459 mmol) in anhydrous DMF (4594 µl) was added. The mixture was bubbled with air using air balloon for 10 mins. Then balloon was removed and the vial was stirred at 50° C. overnight with a 18.5 gauge needle on the septum (open to air). The reaction mixture was cooled to room temperature, diluted with aqueous NH$_4$Cl solution and ethyl acetate. The mixture was stirred for 10 min, filtered. The filtrate was separated. The organic layer was washed with brine, dried over Na$_2$SO$_4$, filtered and evaporated. The residue was purified by silica chromatography (0-100% EtOAc/hexanes) to afford the title product. MS: 378 (M+1).

Intermediate 106 ethyl 4-iodocyclohexanecarboxylate

Iodine (25 g, 98 mmol) in portions at 0° C. was added to a solution of triphenylphosphine (25.9 g, 99 mmol), imidazole (11.86 g, 174 mmol), ethyl 4-hydroxycyclohexanecarboxylate (10 g, 58.1 mmol) in anhydrous DCM (200 mL). The mixture was gradually warm to room temperature and stirred overnight. The mixture was treated with Et$_2$O (300 mL) and aqueous Na$_2$SO$_3$ solution. The organic layer was washed with aqueous Na$_2$SO$_3$ solution and brine, Na$_2$SO$_4$, filtered and evaporated. The residue was dissolved in DCM and treated with ether. White precipitate formed. The mixture was filtered and the filtrate was evaporated. The residue was purified by silica chromatography (0-50% ethyl acetate in hexanes) to afford the title compound. MS: 283 (M+1).

Intermediate 107

(4-(ethoxycarbonyl)cyclohexyl)zinc(II) Iodide

A solution of chlorotrimethylsilane (0.1 ml, 0.920 mmol) and 1,2-dibromoethane (0.071 ml, 0.824 mmol) in DMA (2 mL) was added to a suspension of zinc (0.510 g, 7.80 mmol) dust in anhydrous DMA (4.5 mL) at a rate to maintain the temperature in the range of 45-65° C. The resulting slurry was aged for 15 min, then a solution of ethyl 4-iodocyclohexanecarboxylate (2 g, 7.09 mmol) in DMA (7.5 mL) was added to the mixture described above at a rate to maintain the temperature below 40° C. The resulting mixture was then aged for 30 min at room temperature, then the supernatant was transferred into a flame-dried flask to afford the product as a ca. 0.5 M solution.

Intermediate 108 ethyl 4-(6-chloro-3-cyanoquinolin-4-yl)cyclohexanecarboxylate

A 20 mL vial was charged with CuI (51.2 mg, 0.269 mmol), PdCl$_2$(dppf)-CH$_2$Cl$_2$ adduct (110 mg, 0.134 mmol), 4,6-dichloroquinoline-3-carbonitrile (600 mg, 2.69 mmol) and DMA (3 ml). The resulting mixture was degassed with alternating vacuum/nitrogen purges for three times. Then (4-(ethoxycarbonyl)cyclohexyl)zinc(II) iodide (6.99 ml, ca. 0.5 M solution in DMA, 3.50 mmol) was added. The mixture was degassed one more time and then heated to 80° C. and stirred for 6 hours. The mixture was quenched with aqueous NH$_4$Cl solution and diluted with ethyl acetate (100 mL). The mixture was stirred for 10 min. and then filtered through celite. The organic layer was washed with brine, dried over Na$_2$SO$_4$, filtered and evaporated. The residue was purified by silica chromatography (0-100% EtOAc/hexanes) to afford the title product. MS: 343 (M+1).

Intermediate 110

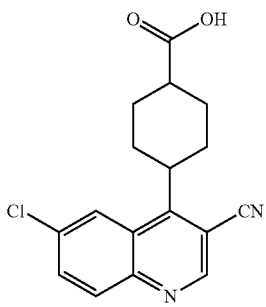 [SMILES: N#Cc1cnc2ccc(Cl)cc2c1C1CCC(C(=O)O)CC1]

4-(6-chloro-3-cyanoquinolin-4-yl)cyclohexanecarboxylic Acid

Aqueous LiOH solution (1.0 N, 1.203 ml, 1.203 mmol) was added to a solution of ethyl 4-(6-chloro-3-cyanoquinolin-4-yl)cyclohexanecarboxylate (250 mg, 0.729 mmol) in THF (3 mL) and MeOH (2 mL). The mixture was stirred overnight at room temperature. The organic solvent was evaporated. The residue was neutralized with 1 N HCl to pH~6. Precipitate formed. The mixture was stirred for 5 min, filtered and rinsed with water. The filter cake was dried to afford the title compound. MS: 315 (M+1).

Intermediate 111

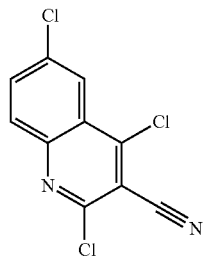 [SMILES: N#Cc1c(Cl)nc2ccc(Cl)cc2c1Cl]

2,4,6-trichloroquinoline-3-carbonitrile

To 6-chloro-4-hydroxy-2-oxo-1,2-dihydroquinoline-3-carbonitrile (18.84 g, 85 mmol), POCl₃ (58.9 g, 384 mmol) and PCl5 (35.6 g, 171 mmol) was added slowly. The reaction mixture was then stirred at 100° C. for 1 h. The reaction mixture was cooled to room temperature and water (500 mL) was added slowly. The resulting mixture was filtered. The filter cake was dried to afford the title compound. MS: 258 (M+1).

Intermediate 112

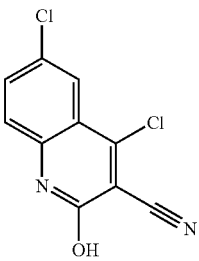 [SMILES: N#Cc1c(O)nc2ccc(Cl)cc2c1Cl]

4,6-dichloro-2-hydroxyquinoline-3-carbonitrile

A mixture of 2,4,6-trichloroquinoline-3-carbonitrile (7.27 g, 28.2 mmol) in TFA (14 mL) and water (3.50 mL) was stirred at 100° C. for one hour. The reaction mixture was then cooled to room temperature and MeOH (2 mL) was added. The mixture was filtered and the filter cake was collected. The filtrate was evaporated and the solid was triturated with MeOH. The solid was combined with the filter cake obtained above and dried to afford the title compound. MS: 238 (M+1).

Intermediate 113

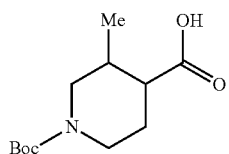

1-(tert-butoxycarbonyl)-3-methylpiperidine-4-carboxylic Acid

Di-tert-butyl dicarbonate (2.67 g, 12.25 mmol) was added to a solution of 3-methylpiperidine-4-carboxylic acid (HCl salt, 2 g, 11.13 mmol), Na₂CO₃ (4.72 g, 44.5 mmol) in THF (20 mL) and water (20.00 mL). The solution was stirred overnight. The solution was concentrated to a third of the volume and and acidified by adding 0.5N HCl. The mixture was filtered and the filtered cake was dried to afford the title compound. MS: 266 (M+23).

Intermediate 114

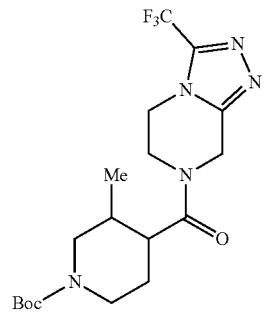 [SMILES: CC1CN(C(=O)OC(C)(C)C)CCC1C(=O)N1CCn2c(nnc2C(F)(F)F)C1]

tert-butyl 3-methyl-4-(3-(trifluoromethyl)-5,6,7,8-tetrahydro-[1,2,4]triazolo[4,3-a]pyrazine-7-carbonyl)piperidine-1-carboxylate A mixture of HATU (1000 mg, 2.63 mmol), HOAT (358 mg, 2.63 mmol), 3-(trifluoromethyl)-5,6,7,8-tetrahydro-[1,2,4]triazolo[4,3-a]pyrazine (HCl salt, 462 mg, 2.023 mmol), 1-(tert-butoxycarbonyl)-3-methylpiperidine-4-carboxylic acid (492 mg, 2.023 mmol) was flushed with N$_2$ three times. Anhydrous DMF (10 mL) was added to the mixture, followed by N-ethyl-N-isopropylpropan-2-amine (784 mg, 6.07 mmol). The mixture was stirred at room temperature overnight. The reaction mixture was poured into NaHCO$_3$ aqueous solution (50 mL), and the resulting mixture was stirred for 1 h. The mixture was filtered and the filter cake was washed with brine, and air-dried to afford the title compound. MS: 418 (M+1).

Intermediate 115

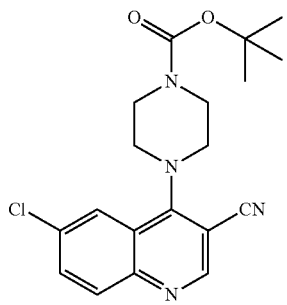 [SMILES: CC(C)(C)OC(=O)N1CCN(c2c(C#N)cnc3ccc(Cl)cc23)CC1]

tert-butyl 4-(6-chloro-3-cyanoquinolin-4-yl)piperazine-1-carboxylate

Tert-butyl piperazine-1-carboxylate (3.51 g, 18.83 mmol) and TEA (3.00 mL, 21.52 mmol) was added to a mixture of 4,6-dichloroquinoline-3-carbonitrile (4 g, 17.93 mmol) in anhydrous DMF (60 mL). The mixture was stirred at room temperature for 1 h. The reaction mixture was poured into 500 mL of water, and the resulting suspension was stirred for 1 h. The mixture was filtered and the filter cake was washed with brine, and dried to afforded the title compound. MS: 373 (M+1).

Intermediate 116

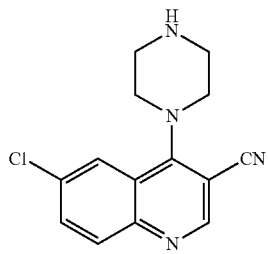 [SMILES: N#Cc1cnc2ccc(Cl)cc2c1N1CCNCC1]

6-chloro-4-(piperazin-1-yl)quinoline-3-carbonitrile

TFA (12.40 ml, 161 mmol) was added to a solution of tert-butyl 4-(6-chloro-3-cyanoquinolin-4-yl)piperazine-1-carboxylate (6 g, 16.09 mmol) in anhydrous DCM (20 mL). The mixture was stirred at room temperature overnight. The mixture was evaporated and the residue was treated with aqueous NaHCO$_3$ solution (150 mL) and DCM (100 mL). The organic layer was separated, dried over Na$_2$SO$_4$ and evaporated to afford the title compound. MS: 273 (M+1).

Intermediate 117

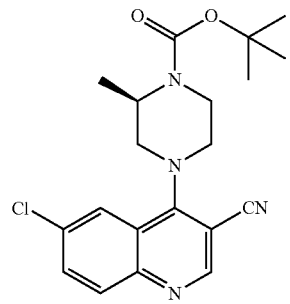 [SMILES: C[C@@H]1CN(c2c(C#N)cnc3ccc(Cl)cc23)CCN1C(=O)OC(C)(C)C]

(R)-tert-butyl 4-(6-chloro-3-cyanoquinolin-4-yl)-2-methylpiperazine-1-carboxylate Triethylamine (0.500 mL, 3.59 mmol) and (R)-tert-butyl 2-methylpiperazine-1-carboxylate (198 mg, 0.986 mmol) was added to a mixture of 4,6-dichloroquinoline-3-carbonitrile (200 mg, 0.897 mmol) in DMF (2.5 mL). The reaction was stirred overnight at room temperature. The reaction was treated with aqueous NaHCO$_3$ solution and stirred for 30 minutes. The resulting solid was filtered off. The filter cake was washed with water and then dried to afford the title compound. MS: 387 (M+1).

Intermediate 118

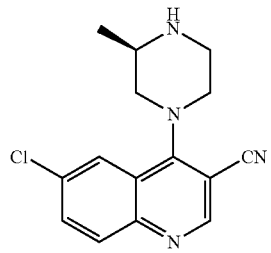 [SMILES: C[C@@H]1CN(c2c(C#N)cnc3ccc(Cl)cc23)CCN1]

(R)-6-chloro-4-(3-methylpiperazin-1-yl)quinoline-3-carbonitrile

Hydrogen chloride dioxane solution (4.0 M, 0.109 mL, 0.434 mmol) was added to a mixture of (R)-tert-butyl 4-(6-chloro-3-cyanoquinolin-4-yl)-2-methylpiperazine-1-carboxylate (168 mg, 0.434 mmol) in DCM (1 mL). The reaction was stirred at room temperature overnight. The reaction was concentrated to dryness. The residue was treated with DCM (1 mL), followed by aqueous sodium hydroxide solution (1.0 M, 0.484 mL, 0.484 mmol). The reaction was stirred at room temperature. The layers were then separated and the DCM layer was dried over Mg₂SO₄, filtered and concentrated to afford the title compound. MS: 287 (M+1).

Intermediate 119

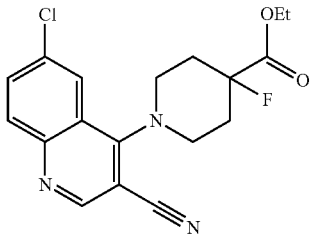 [SMILES: CCOC(=O)C1(F)CCN(c2c(C#N)cnc3ccc(Cl)cc23)CC1]

ethyl 1-(6-chloro-3-cyanoquinolin-4-yl)-4-fluoropiperidine-4-carboxylate 4,6-dichloroquinoline-3-carbonitrile (1.0 g, 4.48 mmol) was dissolved in anhydrous DMF (11.96 mL). TEA (1.437 ml, 10.31 mmol) and ethyl 4-fluoropiperidine-4-carboxylate hydrochloride (1.044 g, 4.93 mmol) was added at room temperature and the reaction stirred for 1 h. The reaction mixture was poured onto saturated NaHCO₃ solution (100 mL), and the resulting mixture was stirred for 20 min. The solution was decanted and the solid washed with water to give the title compound. MS: 362 (M+1).

Intermediate 120

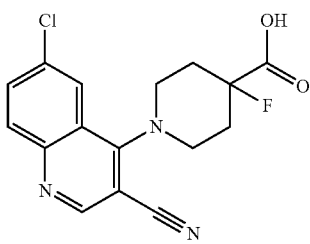 [SMILES: N#Cc1cnc2ccc(Cl)cc2c1N1CCC(F)(C(=O)O)CC1]

1-(6-chloro-3-cyanoquinolin-4-yl)-4-fluoropiperidine-4-carboxylic Acid

Lithium hydroxide (1M, 5.82 ml, 5.82 mmol) aqueous solution was added to a solution of ethyl 1-(6-chloro-3-cyanoquinolin-4-yl)-4-fluoropiperidine-4-carboxylate (1.62 g, 4.48 mmol) in THF (25.9 ml) and MeOH (12.74 ml). The reaction was stirred at room temperature for 15 hours. The organic solvent was evaporated, the residue was treated with 1N HCl (6 mL) until it was pH 7. The precipitate and the mixture was stirred for 5 min, filtered and rinsed with water. The filter cake was dried to give the title compound. MS: 334 (M+1)

Intermediate 121

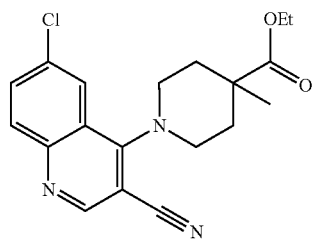 [SMILES: CCOC(=O)C1(C)CCN(c2c(C#N)cnc3ccc(Cl)cc23)CC1]

ethyl 1-(6-chloro-3-cyanoquinolin-4-yl)-4-methylpiperidine-4-carboxylate

Triethylamine (1.250 ml, 8.97 mmol) followed by ethyl 4-methylpiperidine-4-carboxylatehydrochloride (489 mg, 2.354 mmol) was added to dissolved 4,6-dichloroquinoline-3-carbonitrile (500 mg, 2.242 mmol) in DMF (5 ml). The mixture was stirred at room temperature for 30 minutes then poured into 50 mL water and stirred for 1 hour at room temperature. The solids were filtered and dried. MS: 358 (M+1)

Intermediate 122

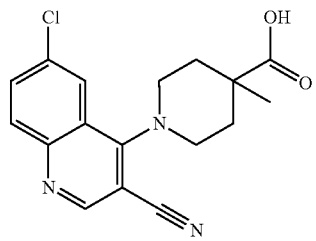

1-(6-chloro-3-cyanoquinolin-4-yl)-4-methylpiperidine-4-carboxylic Acid

LiOH (1M in water, 2.4 mL, 2.4 mmol) was added to ethyl 1-(6-chloro-3-cyanoquinolin-4-yl)-4-methylpiperidine-4-carboxylate (665.9 mg, 1.861 mmol) in THF (8.3 mL) and MeOH (4.1 mL). The mixture was stirred for 15 h at room temperature. The volatile solvents were removed and the solution was neutralized with 1N HCl to pH 7. The solids were filtered and dried to give the title compound. MS: 330 (M+1).

Intermediate 123

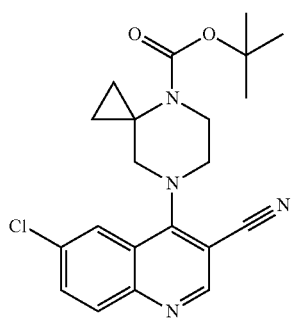 [SMILES: CC(C)(C)OC(=O)N1CCN(c2c(C#N)cnc3ccc(Cl)cc23)CC12CC2]

87 tert-butyl 7-(6-chloro-3-cyanoquinolin-4-yl)-4,7-diazaspiro[2.5]octane-4-carboxylate Tert-butyl 4,7-diazaspiro[2.5]octane-4-carboxylate (209 mg, 0.986 mmol) followed by DMF (2.5 ml) and triethylamine (0.500 ml, 3.59 mmol) were added to a vial containing 4,6-dichloroquinoline-3-carbonitrile (200 mg, 0.897 mmol). The reaction was stirred overning at room temperature for 15 hours. The reaction was treated with $NaHCO_3$ and stirred. The resulting solid was filtered off. The solid was washed with water and then dried to give the title compound. MS: 399 (M+1)

Intermediate 124

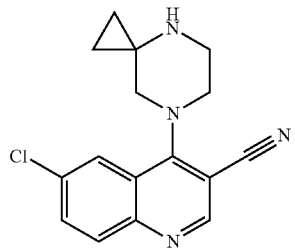 [SMILES: N#Cc1cnc2ccc(Cl)cc2c1N1CCNC2(CC2)C1]

6-chloro-4-(4,7-diazaspiro[2.5]octan-7-yl)quinoline-3-carbonitrile

To a vial containing tert-butyl 7-(6-chloro-3-cyanoquinolin-4-yl)-4,7-diazaspiro[2.5]octane-4-carboxylate (75 mg, 0.188 mmol), DCM (1 ml) and hydrogen chloride (4M in dioxane, 0.047 ml, 0.188 mmol) were added. The reaction was stirred at room temperature for 15 hours. The reaction was concentrated. To the residue, DCM (1 mL) and sodium hydroxide (1M in water, 0.213 ml, 0.213 mmol) were added. The reaction was stirred at room temperature for 3 hours. The layers were then separated and the DCM layer was dried over $MgSO_4$ and concentrated. The residue was. MS: 299 (M+1)

88

EXAMPLES

Example 1

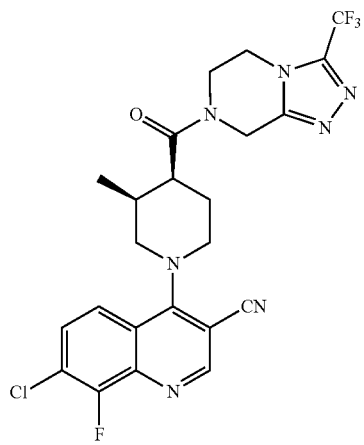 [SMILES: C[C@@H]1CN(c2c(C#N)cnc3c(F)c(Cl)ccc23)CC[C@@H]1C(=O)N1CCn2c(nnc2C(F)(F)F)C1]

7-chloro-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 4,7-dichloro-8-fluoroquinoline-3-carbonitrile (15 mg, 0.062 mmol), ((3S,4S)-3-methylpiperidin-4-yl)(3-(trifluoromethyl)-5,6-dihydro-[1,2,4]triazolo[4,3-a]pyrazin-7(8H)-yl)methanone hydrochloride (22 mg, 0.062 mmol), diisopropylethyl amine (0.033 ml, 0.187 mmol), and DMF (0.622 ml) were combined in a sealed tube. The reaction was heated to 70° C. for 3 h. The reaction mixture was filtered and purified by reverse phase HPLC (10-100% MeCN/Water, with 0.05% TFA). The combined fractions were neutralized with aqueous saturated sodium bicarbonate and extracted with EtOAc (2×). The organic layer was washed with water and dried with magnesium sulfate, filtered, concentrated to give the title compound. MS: 522 (M+1). Human CYP8B1 IC50 (nM) 0.47.

Examples 2-22 were made using a similar synthesis to Example 1 substituting the appropriate reactions and reagents.

TABLE 3

| Example | Structure | Chemical Name | Exact Mass [M + H]+ | Human CYP8B1 IC50 (nM) |
|---|---|---|---|---|
| 2 | 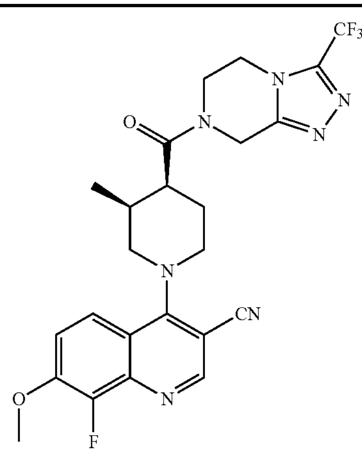 | 8-fluoro-7-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 518 | 0.96 |

TABLE 3-continued

| Example | Structure | Chemical Name | Exact Mass [M + H]+ | Human CYP8B1 IC50 (nM) |
|---|---|---|---|---|
| 3 | 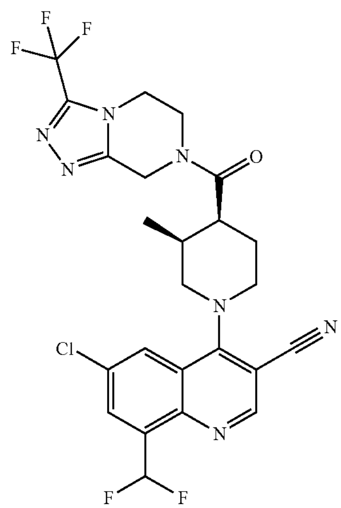 [SMILES: C[C@@H]1CN(c2c(C#N)cnc3c(C(F)F)cc(Cl)cc23)CC[C@@H]1C(=O)N1CCn2c(nnc2C(F)(F)F)C1] | 6-chloro-8-(difluoromethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 554 | 21 |
| 4 | 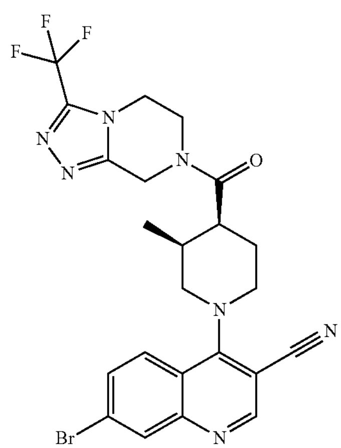 [SMILES: C[C@@H]1CN(c2c(C#N)cnc3cc(Br)ccc23)CC[C@@H]1C(=O)N1CCn2c(nnc2C(F)(F)F)C1] | 7-bromo-4-[(3S,4S)-3-methyl-4-{[3-(trifluoromethyl)-5,6-dihydro[1,2,4]triazolo[4,5-a]pyrazin-7(8H)-yl]carbonyl}piperidin-1-yl]quinoline-3-carbonitrile | 550 | 0.36 |
| 5 | 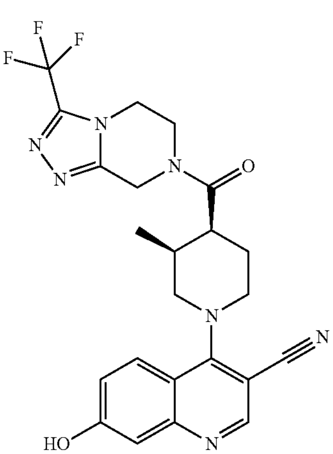 [SMILES: C[C@@H]1CN(c2c(C#N)cnc3cc(O)ccc23)CC[C@@H]1C(=O)N1CCn2c(nnc2C(F)(F)F)C1] | 7-hydroxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 486 | 1.4 |

TABLE 3-continued

| Example | Structure | Chemical Name | Exact Mass [M + H]+ | Human CYP8B1 IC50 (nM) |
|---|---|---|---|---|
| 6 | 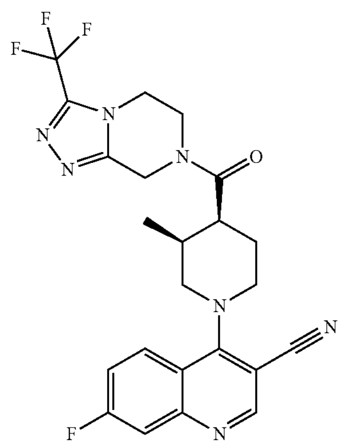 [SMILES: C[C@@H]1CN(c2c(C#N)cnc3cc(F)ccc23)CC[C@@H]1C(=O)N1CCn2c(nnc2C(F)(F)F)C1] | 7-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 488 | 2.1 |
| 7 | 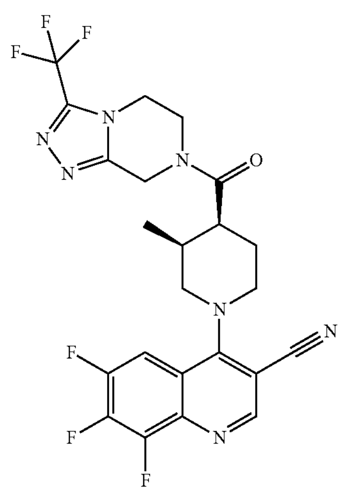 [SMILES: C[C@@H]1CN(c2c(C#N)cnc3c(F)c(F)c(F)cc23)CC[C@@H]1C(=O)N1CCn2c(nnc2C(F)(F)F)C1] | 6,7,8-trifluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 524 | 1.1 |
| 8 | 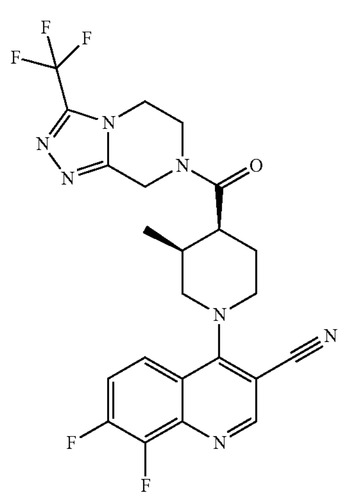 | 7,8-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 506 | 1.3 |

TABLE 3-continued

| Example | Structure | Chemical Name | Exact Mass [M + H]+ | Human CYP8B1 IC50 (nM) |
|---|---|---|---|---|
| 9 | 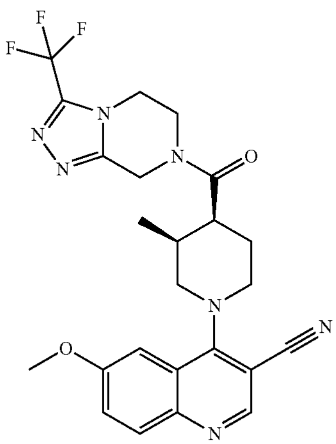 [SMILES: COc1ccc2ncc(C#N)c(N3CC[C@H](C(=O)N4CCn5c(nnc5C(F)(F)F)C4)[C@H](C)C3)c2c1] | 6-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 500 | 0.51 |
| 10 | 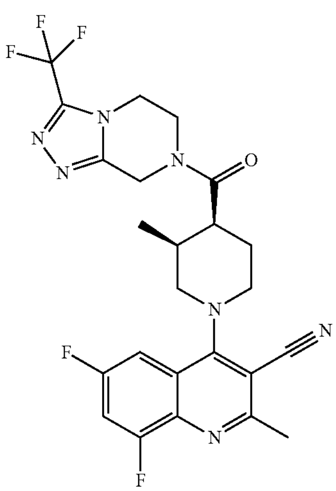 [SMILES: Cc1nc2c(F)cc(F)cc2c(N2CC[C@H](C(=O)N3CCn4c(nnc4C(F)(F)F)C3)[C@H](C)C2)c1C#N] | 6,8-difluoro-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 520 | 2.8 |
| 11 | 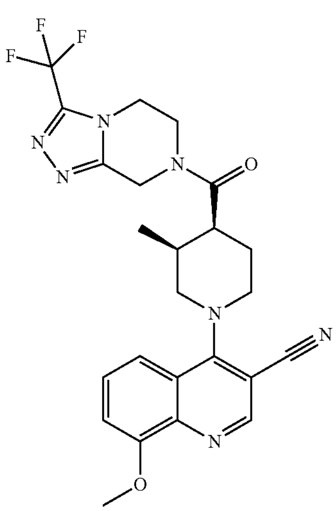 [SMILES: COc1cccc2c(N3CC[C@H](C(=O)N4CCn5c(nnc5C(F)(F)F)C4)[C@H](C)C3)c(C#N)cnc12] | 8-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 500 | 2.5 |

TABLE 3-continued

| Example | Structure | Chemical Name | Exact Mass [M + H]+ | Human CYP8B1 IC50 (nM) |
|---|---|---|---|---|
| 12 | 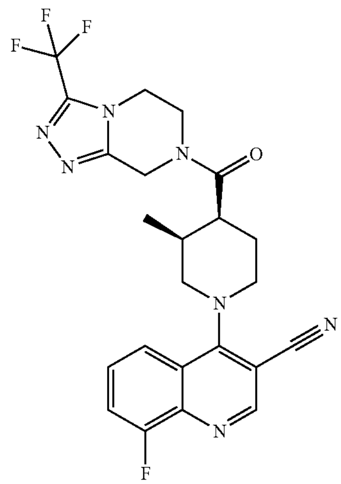 [SMILES: C[C@@H]1CN(c2c(C#N)cnc3c(F)cccc23)CC[C@@H]1C(=O)N1CCn2c(nnc2C(F)(F)F)C1] | 8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 488 | 1.1 |
| 13 | 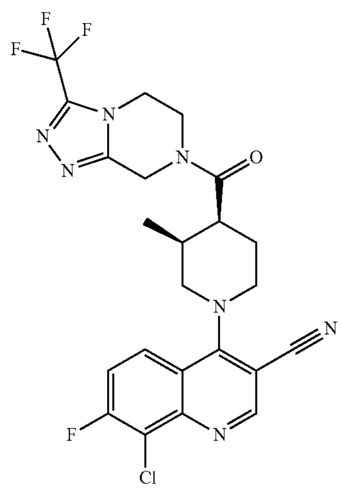 [SMILES: C[C@@H]1CN(c2c(C#N)cnc3c(Cl)c(F)ccc23)CC[C@@H]1C(=O)N1CCn2c(nnc2C(F)(F)F)C1] | 8-chloro-7-fluoro-4-[(3S,4S)-3-methyl-4-{[3-(trifluoromethyl)-5,6-dihdyro[1,2,4]triazolo[4,3-a]pyrazin-7(8H)-yl]carbonyl}piperidin-1-yl]quinoline-3-carbonitrile | 522 | 3.3 |
| 14 | 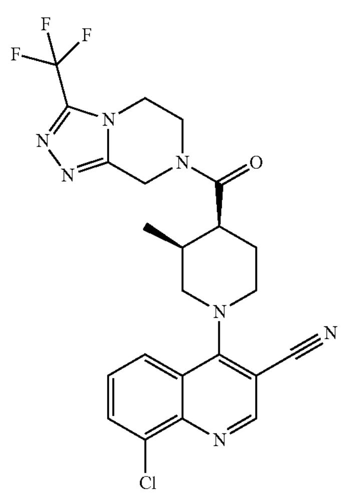 [SMILES: C[C@@H]1CN(c2c(C#N)cnc3c(Cl)cccc23)CC[C@@H]1C(=O)N1CCn2c(nnc2C(F)(F)F)C1] | 8-chloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 504 | 1.7 |

TABLE 3-continued

| Example | Structure | Chemical Name | Exact Mass [M + H]+ | Human CYP8B1 IC50 (nM) |
|---|---|---|---|---|
| 15 | 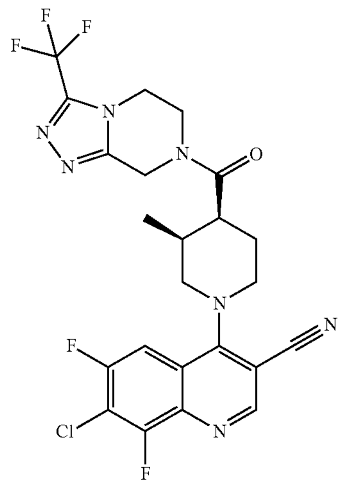 [SMILES: C[C@@H]1CN(c2c(C#N)cnc3c(F)c(Cl)c(F)cc23)CC[C@@H]1C(=O)N1CCn2c(nnc2C(F)(F)F)C1] | 7-chloro-6,8-difluoro-4-[(3S,4S)-3-methyl-4-{[3-(trifluoromethyl)-5,6-dihdyro[1,2,4]triazolo[4,3-a]pyrazin-7(8H)-yl]carobnyl}piperidin-1-yl]quinoline-3-carbonitrile | 540 | 1.0 |
| 16 | 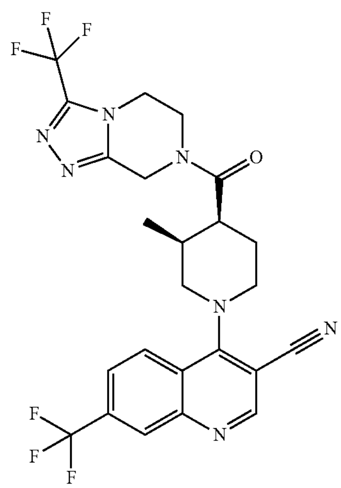 [SMILES: C[C@@H]1CN(c2c(C#N)cnc3cc(C(F)(F)F)ccc23)CC[C@@H]1C(=O)N1CCn2c(nnc2C(F)(F)F)C1] | 4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)quinoline-3-carbonitrile | 538 | 0.38 |
| 17 | 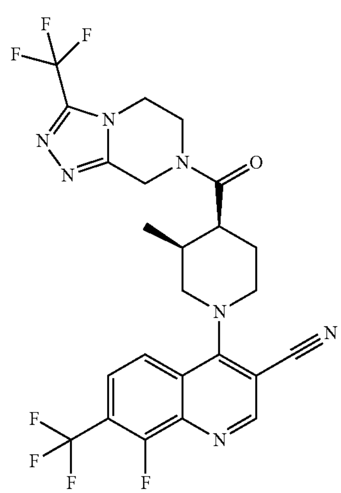 [SMILES: C[C@@H]1CN(c2c(C#N)cnc3c(F)c(C(F)(F)F)ccc23)CC[C@@H]1C(=O)N1CCn2c(nnc2C(F)(F)F)C1] | 8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)quinoline-3-carbonitrile | 556 | 0.36 |

TABLE 3-continued

| Example | Structure | Chemical Name | Exact Mass [M + H]+ | Human CYP8B1 IC50 (nM) |
|---|---|---|---|---|
| 18 | 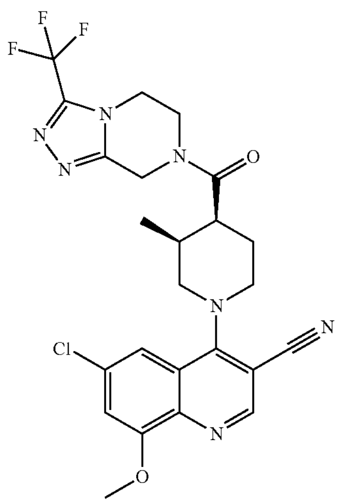 [SMILES: COc1cc(Cl)cc2c(N3CC[C@H](C(=O)N4CCn5c(nnc5C(F)(F)F)C4)[C@H](C)C3)c(C#N)cnc12] | 6-chloro-8-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 534 | 0.53 |
| 19 | 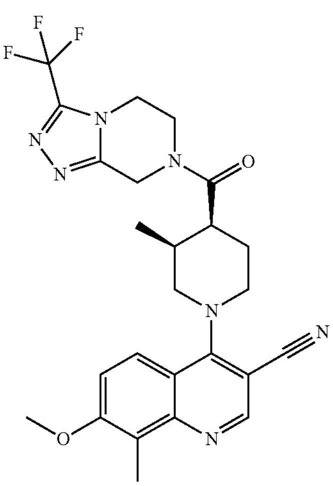 [SMILES: COc1ccc2c(N3CC[C@H](C(=O)N4CCn5c(nnc5C(F)(F)F)C4)[C@H](C)C3)c(C#N)cnc2c1C] | 7-methoxy-8-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 514 | 0.20 |
| 20 | 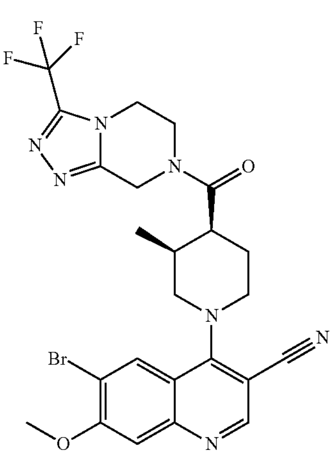 [SMILES: COc1cc2ncc(C#N)c(N3CC[C@H](C(=O)N4CCn5c(nnc5C(F)(F)F)C4)[C@H](C)C3)c2cc1Br] | 6-bromo-7-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 580 | 0.24 |

TABLE 3-continued

| Example | Structure | Chemical Name | Exact Mass [M + H]+ | Human CYP8B1 IC50 (nM) |
|---|---|---|---|---|
| 21 | 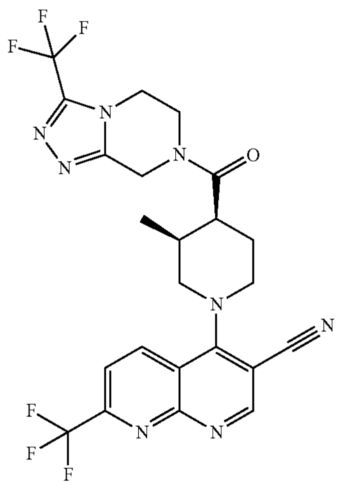 [SMILES: C[C@@H]1CN(c2c(C#N)cnc3nc(C(F)(F)F)ccc23)CC[C@@H]1C(=O)N1CCn2c(nnc2C(F)(F)F)C1] | 4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)-1,8-naphthyridine-3-carbonitrile | 539 | 4.81 |
| 22 | 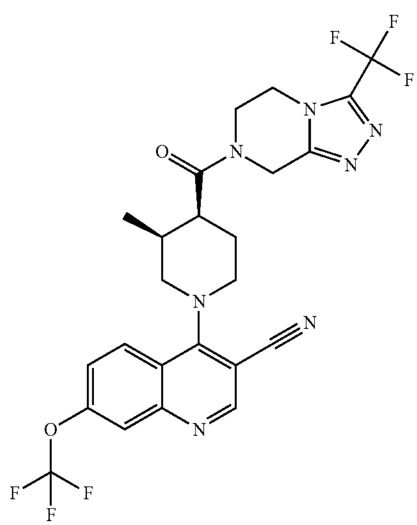 [SMILES: C[C@@H]1CN(c2c(C#N)cnc3cc(OC(F)(F)F)ccc23)CC[C@@H]1C(=O)N1CCn2c(nnc2C(F)(F)F)C1] | 4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethoxy)quinoline-3-carbonitrile | 554 | 0.22 |
| 23 | 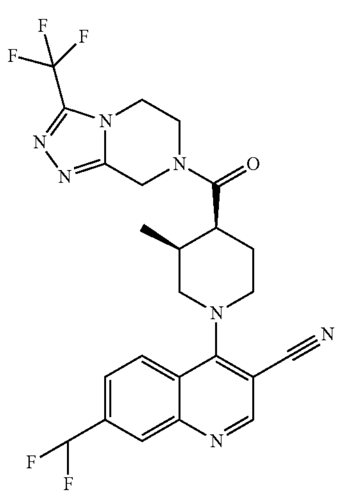 [SMILES: C[C@@H]1CN(c2c(C#N)cnc3cc(C(F)F)ccc23)CC[C@@H]1C(=O)N1CCn2c(nnc2C(F)(F)F)C1] | 7-(difluoromethyl)-4-((3S,4S)-3-methyl-4-(3-(trifluoromethyl)-5,6,7,8-tetrahydro-[1,2,4]trizolo[4,3-a]pyrazine-7-carbonyl)piperidin-1-yl)quinolone-3-carbonitrile | 520 | 0.5 |

Example 24

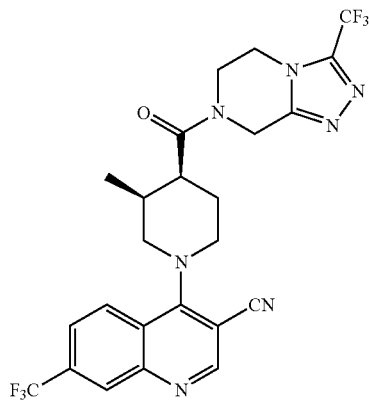 [SMILES: C[C@@H]1CN(c2c(C#N)cnc3cc(C(F)(F)F)ccc23)CC[C@@H]1C(=O)N1CCn2c(nnc2C(F)(F)F)C1]

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-(trifluoromethyl)quinoline-3-carbonitrile 4-chloro-7-(trifluoromethyl)quinoline-3-carbonitrile (5.2 g, 20.26 mmol), ((3S,4S)-3-methylpiperidin-4-yl)(3-(trifluoromethyl)-5,6-dihydro-[1,2,4]triazolo[4,3-a]pyrazin-7(8H)-yl)methanone hydrochloride (6.0 g, 17 mmol), triethylamine (7.09 ml, 50.9 mmol), and DMF (85 ml) were combined and the reaction was heated to 90° C. for 2 h. The reaction mixture was cooled and diluted with water and EtOAc and the aqueous extracted with EtOAc. The combined organic layers were washed with water (2×) and brine, dried with Na2SO4, filtered and concentrated. The residue was purified by MPLC (SiO2; 0→100% (3:1 EtOAc:EtOH):hexanes) to provide 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-(trifluoromethyl)quinoline-3-carbonitrile. MS: 538 (M+1). Human CYP8B1 IC50 (nM) 0.4.

Example 25

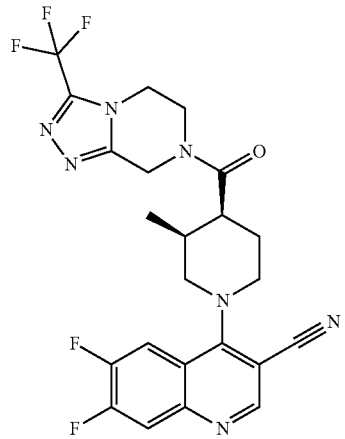 [SMILES: C[C@@H]1CN(c2c(C#N)cnc3cc(F)c(F)cc23)CC[C@@H]1C(=O)N1CCn2c(nnc2C(F)(F)F)C1]

6,7-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 4-chloro-6,7-difluoroquinoline-3-carbonitrile (50 mg, 0.22 mmol), [(3S,4S)-3-methylpiperidin-4-yl][3-(trifluoromethyl)-5,6-dihydro[1,2,4]triazolo[4,3-a]pyrazin-7(8H)-yl]methanone (78 mg, 0.25 mmol), DIPEA (0.117 mL, 0.67 mmol), and DMF (2.23 mL) were combined in a sealed tube. The reaction was heated to 70° C. for 15 h. The reaction mixture was diluted with EtOAc and washed with water 3×. The organic layers were dried with magnesium sulfate, filtered, concentrated and purified by silica gel chromatography (0-70% 3:1 EtOAc:EtOH in hexane). The combined fractions were concentrated to afford the title compound (53 mg, 0.11 mmol). MS: 506 (M+1). Human CYP8B1 IC50 (nM) 0.36.h.

Examples 25-37 were made using a similar synthesis to Example 24 substituting the appropriate reactants and reagents.

TABLE 4

| Example | Structure | Chemical Name | Exact Mass [M + H]+ | Human CYP8B1 IC50 (nM) |
|---|---|---|---|---|
| 26 | 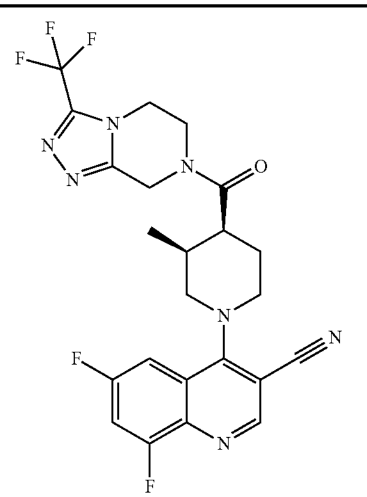 | 6,8-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 506 | 0.49 |

TABLE 4-continued

| Example | Structure | Chemical Name | Exact Mass [M + H]+ | Human CYP8B1 IC50 (nM) |
|---|---|---|---|---|
| 27 | 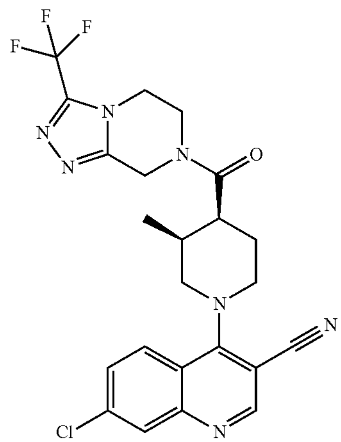 [SMILES: C[C@@H]1CN(c2c(C#N)cnc3cc(Cl)ccc23)CC[C@@H]1C(=O)N1CCn2c(nnc2C(F)(F)F)C1] | 7-chloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 504 | 0.74 |
| 28 | 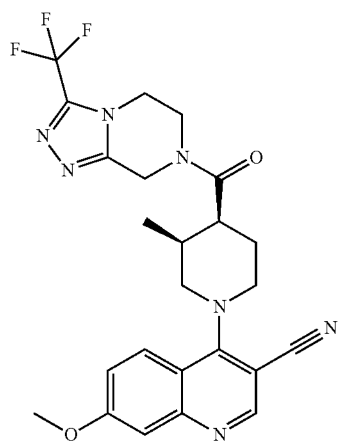 [SMILES: COc1ccc2c(N3CC[C@H](C(=O)N4CCn5c(nnc5C(F)(F)F)C4)[C@H](C)C3)c(C#N)cnc2c1] | 7-methoxy-4-[(3S,4S)-3-methyl-4-{[3-(trifluoromethyl)-5,6-dihdyro[1,2,4]triazolo[4,3-a]pyrazin-7(8H)-yl]carbonyl}piperidin-1-yl]quinoline-3-carbonitrile | 500 | 0.61 |
| 29 | 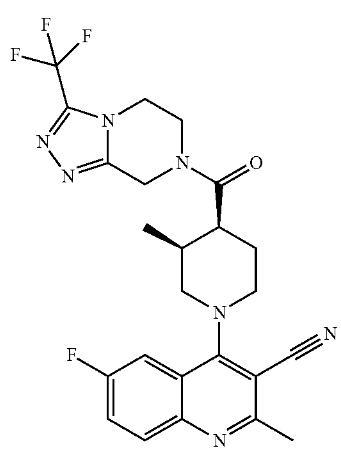 [SMILES: Cc1nc2ccc(F)cc2c(N2CC[C@H](C(=O)N3CCn4c(nnc4C(F)(F)F)C3)[C@H](C)C2)c1C#N] | 6-fluoro-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 502 | 9.4 |

TABLE 4-continued

| Example | Structure | Chemical Name | Exact Mass [M + H]+ | Human CYP8B1 IC50 (nM) |
|---|---|---|---|---|
| 30 | 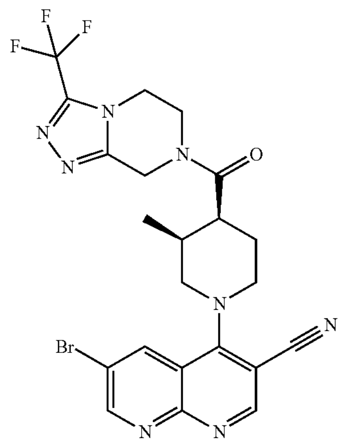 [SMILES: C[C@@H]1CN(c2c(C#N)cnc3ncc(Br)cc23)CC[C@@H]1C(=O)N1CCn2c(nnc2C(F)(F)F)C1] | 6-bromo-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-1,8-naphthyridine-3-carbonitrile | 549 | 30 |
| 31 | 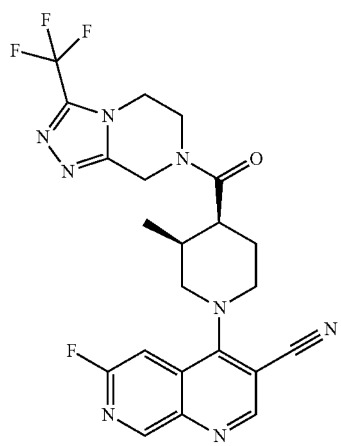 [SMILES: C[C@@H]1CN(c2c(C#N)cnc3cnc(F)cc23)CC[C@@H]1C(=O)N1CCn2c(nnc2C(F)(F)F)C1] | 6-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-1,7-naphthyridine-3-carbonitrile | 489 | 2.6 |
| 32 | 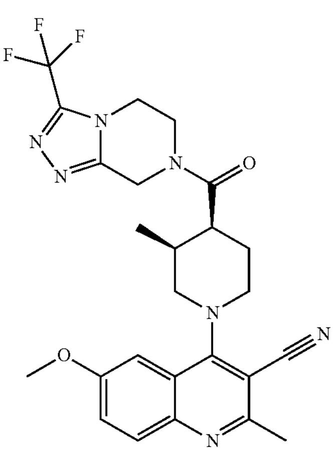 [SMILES: COc1ccc2nc(C)c(C#N)c(N3CC[C@H](C(=O)N4CCn5c(nnc5C(F)(F)F)C4)[C@H](C)C3)c2c1] | 6-methoxy-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 514 | 2.9 |

TABLE 4-continued

| Example | Structure | Chemical Name | Exact Mass [M + H]+ | Human CYP8B1 IC50 (nM) |
|---|---|---|---|---|
| 33 | 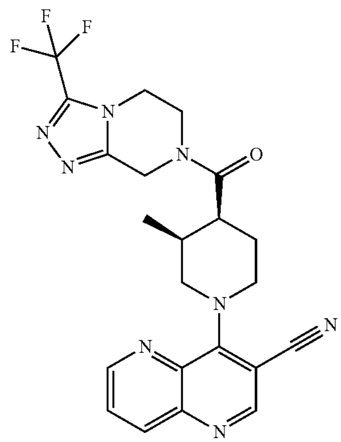 [SMILES: C[C@@H]1CN(c2c(C#N)cnc3cccnc23)CC[C@@H]1C(=O)N1CCn2c(nnc2C(F)(F)F)C1] | 4-[(3S,4S)-3-methyl-4-{[3-(trifluoromethyl)-5,6-dihydro[1,2,4]triazolo[4,3-a]pyrazin-7(8H)-yl]carobnyl}piperidin-1-yl]-1,5-naphthyridine-3-carbonitrile | 471 | 1.3 |
| 34 | 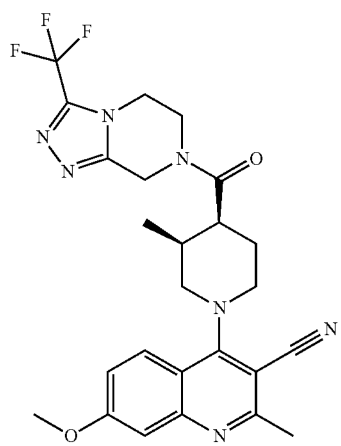 [SMILES: COc1ccc2c(N3CC[C@H](C(=O)N4CCn5c(nnc5C(F)(F)F)C4)[C@H](C)C3)c(C#N)c(C)nc2c1] | 7-methoxy-2-methyl-4-[(3S,4S)-3-methyl-4-{[3-(trifluoromethyl)-5,6-dihdyro[1,2,4]triazolo[4,3-a]pyrazin-7(8H)-yl]carbonyl}piperidin-1-yl]quinoline-3-carbonitrile | 514 | 0.89 |
| 35 | 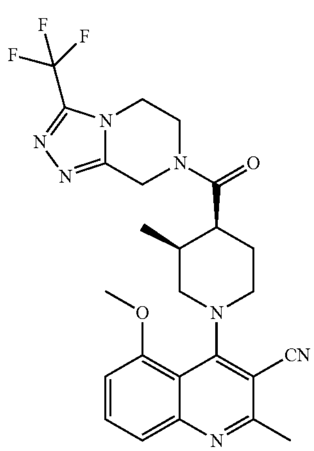 [SMILES: COc1cccc2nc(C)c(C#N)c(N3CC[C@H](C(=O)N4CCn5c(nnc5C(F)(F)F)C4)[C@H](C)C3)c12] | 5-methoxy-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 514 | 1.4 |

TABLE 4-continued

| Example | Structure | Chemical Name | Exact Mass [M + H]+ | Human CYP8B1 IC50 (nM) |
|---|---|---|---|---|
| 36 | 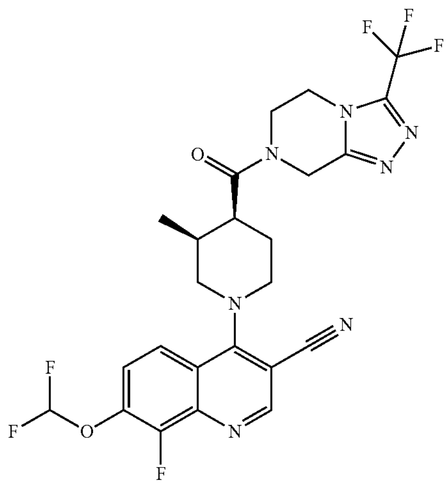 [SMILES: C[C@@H]1CN(c2c(C#N)cnc3c(F)c(OC(F)F)ccc23)CC[C@@H]1C(=O)N1CCn2c(nnc2C(F)(F)F)C1] | 7-(difluoromethoxy)-8-fluoro-4-[(3S,4S)-3-methyl-4-{[3-(trifluoromethyl)-5,6-dihdyro[1,2,4]triazolo[4,3-a]pyrazin-7(8H)-yl]carbonyl}piperidin-1-yl]quinoline-3-carbonitrile | 554 | 0.40 |
| 37 | 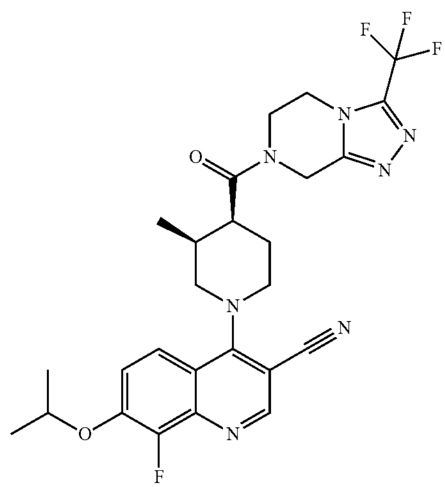 [SMILES: CC(C)Oc1ccc2c(N3CC[C@H](C(=O)N4CCn5c(nnc5C(F)(F)F)C4)[C@H](C)C3)c(C#N)cnc2c1F] | 8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(propan-2-yloxy)quinoline-3-carbonitrile | 546 | 0.54 |
| 38 | 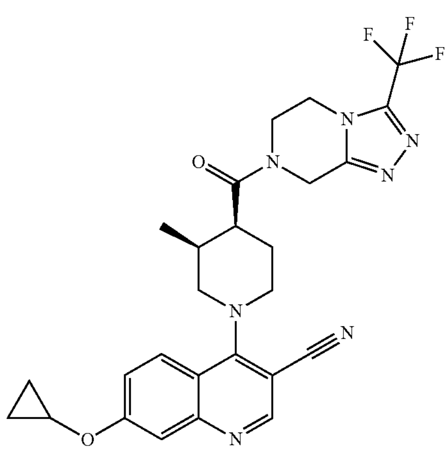 [SMILES: C[C@@H]1CN(c2c(C#N)cnc3cc(OC4CC4)ccc23)CC[C@@H]1C(=O)N1CCn2c(nnc2C(F)(F)F)C1] | 7-(cyclopropyloxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 526 | 0.30 |

Example 39

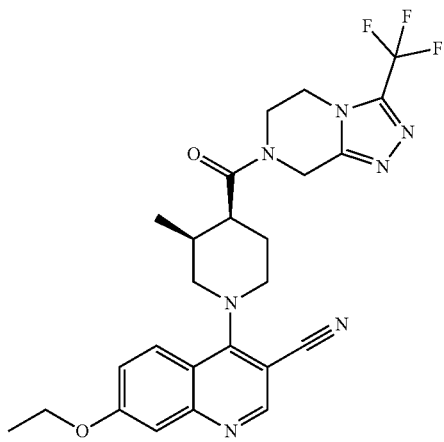 [SMILES: CCOc1ccc2c(N3CC[C@H](C(=O)N4CCn5c(nnc5C(F)(F)F)C4)[C@H](C)C3)c(C#N)cnc2c1]

7-ethoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 4-chloro-7-ethoxyquinoline-3-carbonitrile (200 mg, 0.860 mmol) was added to a mixture of DIPEA (0.751 mL, 4.30 mmol) and [(3S,4S)-3-methylpiperidin-4-yl][3-(trifluoromethyl)-5,6-dihydro[1,2,4]triazolo[4,3-a]pyrazin-7(8H)-yl]methanone trifluoroacetate (604 mg, 1.40 mmol) in DMF (9 mL) and stirred at 25° C. for 16 h. Additional DIPEA (0.25 mL, 1.4 mmol) and [(3S,4S)-3-methylpiperidin-4-yl][3-(trifluoromethyl)-5,6-dihydro[1,2,4]triazolo[4,3-a]pyrazin-7(8H)-yl]methanone trifluoroacetate (150 mg, 0.35 mmol) was added and the reaction was then stirred at 60° C. for 4 h. The reaction was filtered and the filtrate was directly purified by P-HPLC to give 7-ethoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile. MS: 514 (M+1). Human CYP8B1 IC50 (nM) 0.7.

Example 40

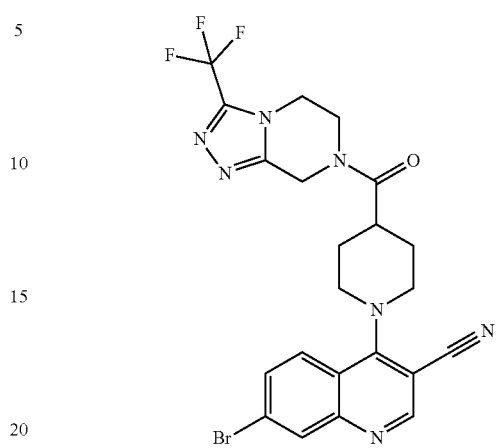

7-bromo-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile 7-bromo-4-chloroquinoline-3-carbonitrile (250 mg, 0.94 mmol), piperidin-4-yl(3-(trifluoromethyl)-5,6-dihydro-[1,2,4]triazolo[4,3-a]pyrazin-7(8H)-yl)methanone hydrochloride (381 mg, 1.12 mmol), DIPEA (0.490 mL, 2.80 mmol), and DMF (4.67 mL) were combined in a sealed tube. The reaction was heated to 90° C. for 15 h. The mixture was diluted with EtOAc and washed with water 3×. The organic layer was dried with magnesium sulfate, filtered, concentrated and purified by silica gel chromatography (0-70% 3:1 EtOAc:EtOH). The combined fractions were concentrated to give the title compound (61 mg, 0.11 mmol). MS: 536 (M+1). Human CYP8B1 IC50 (nM) 12.

Examples 40-43 were made using a similar synthesis to Example 39 substituting the appropriate reactants and reagents.

TABLE 5

| Example | Structure | Chemical Name | Exact Mass [M + H]+ | Human CYP8B1 IC50 (nM) |
|---------|-----------|---------------|---------------------|------------------------|
| 41 | 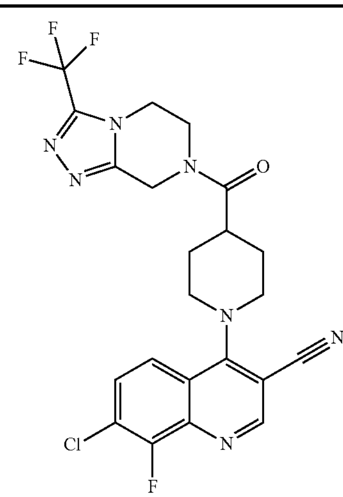 | 7-chloro-8-fluoro-4-(4-{[3-(trifluoromethyl)-5,6-dihdyro[1,2,4]triazolo[4,3-a]pyrazin-7(8H)-yl]carbonyl}piperidin-1-yl)quinoline-3-carbonitrile | 508 | 43 |

TABLE 5-continued

| Example | Structure | Chemical Name | Exact Mass [M + H]+ | Human CYP8B1 IC50 (nM) |
|---------|-----------|---------------|---------------------|------------------------|
| 42 | 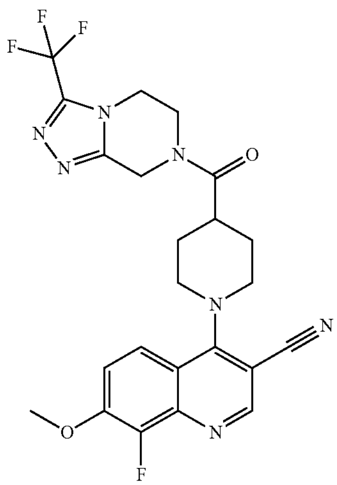 [SMILES: COc1ccc2c(N3CCC(C(=O)N4CCn5c(nnc5C(F)(F)F)C4)CC3)c(C#N)cnc2c1F] | 8-fluoro-7-methoxy-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile | 504 | 49 |
| 43 | 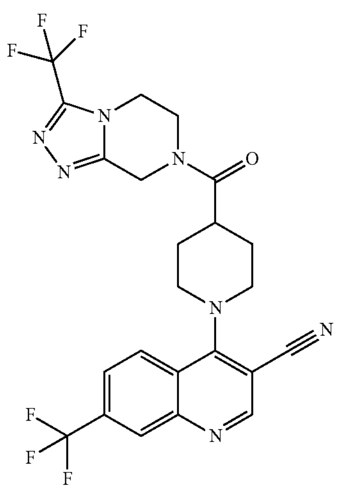 [SMILES: N#Cc1cnc2cc(C(F)(F)F)ccc2c1N1CCC(C(=O)N2CCn3c(nnc3C(F)(F)F)C2)CC1] | 7-(trifluoromethyl)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile | 524 | 6.3 |
| 44 | 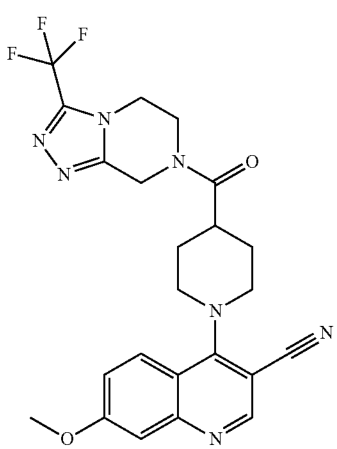 [SMILES: COc1ccc2c(N3CCC(C(=O)N4CCn5c(nnc5C(F)(F)F)C4)CC3)c(C#N)cnc2c1] | 7-methoxy-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile | 486 | 32 |

Example 45

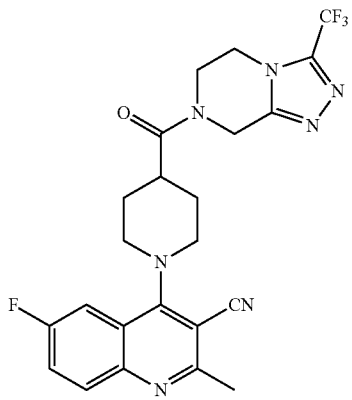 [SMILES: Cc1nc2ccc(F)cc2c(N2CCC(C(=O)N3CCn4c(nnc4C(F)(F)F)C3)CC2)c1C#N]

6-fluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile DIPEA was added to a mixture of 4-chloro-6-fluoro-2-methylquinoline-3-carbonitrile (100 mg, 0.453 mmol) and piperidin-4-yl(3-(trifluoromethyl)-5,6-dihydro-[1,2,4]triazolo[4,3-a]pyrazin-7(8H)-yl) methanone 2,2,2-trifluoroacetate (208 mg, 0.499 mmol) in DMF (3 mL) (0.237 mL, 1.36 mmol) and stirred at 70° C. for 16 h. Water (30 mL) was added to the reaction. The reaction was then extracted with EtOAc (30 mL×3). The combined organic layers were washed with brine (20 mL), dried over $Na_2SO_4$, filtered and concentrated. The residue was purified by prep-HPLC to give 6-fluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile. MS: 488 (M+1). Human CYP8B1 IC50 (nM) 1148.

Examples 45-50 were made using a similar synthesis to Example 44 substituting the appropriate reactants and reagents.

TABLE 6

| Example | Structure | Chemical Name | Exact Mass [M + H]+ | Human CYP8B1 IC50 (nM) |
|---|---|---|---|---|
| 46 | 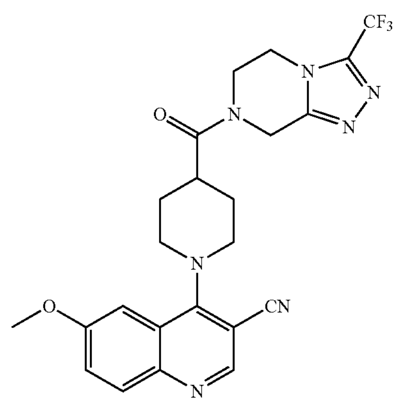 [SMILES: COc1ccc2ncc(C#N)c(N3CCC(C(=O)N4CCn5c(nnc5C(F)(F)F)C4)CC3)c2c1] | 6-methoxy-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile | 486 | 68 |
| 47 | 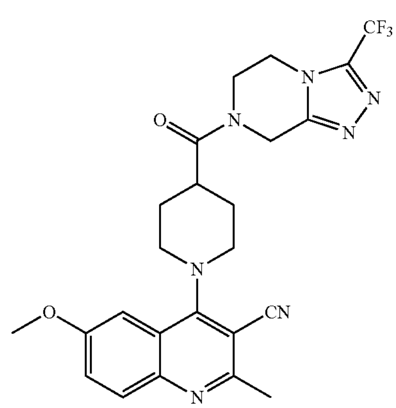 [SMILES: COc1ccc2nc(C)c(C#N)c(N3CCC(C(=O)N4CCn5c(nnc5C(F)(F)F)C4)CC3)c2c1] | 6-methoxy-2-methyl-4-(4-(3-(trifluoromethyl)-5,6,7,8-tetrahydro-[1,2,4]triazolo[4,3-a]pyrazin-7-carbonyl)piperidin-1-yl)quinoline-3-carbonitrile | 500 | 564 |

TABLE 6-continued

| Example | Structure | Chemical Name | Exact Mass [M + H]+ | Human CYP8B1 IC50 (nM) |
|---|---|---|---|---|
| 48 | 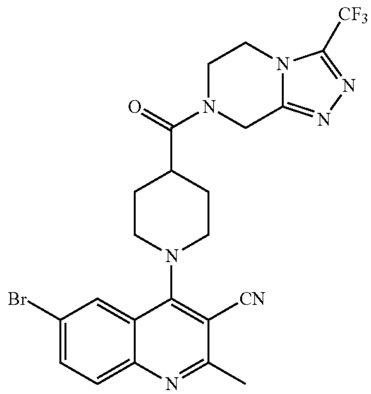 [SMILES: Cc1nc2ccc(Br)cc2c(N2CCC(C(=O)N3CCn4c(nnc4C(F)(F)F)C3)CC2)c1C#N] | 6-bromo-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile | 548 | 109 |
| 49 | 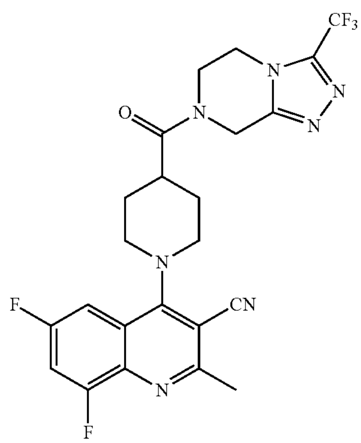 [SMILES: Cc1nc2c(F)cc(F)cc2c(N2CCC(C(=O)N3CCn4c(nnc4C(F)(F)F)C3)CC2)c1C#N] | 6,8-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile | 506 | 1726 |
| 50 | 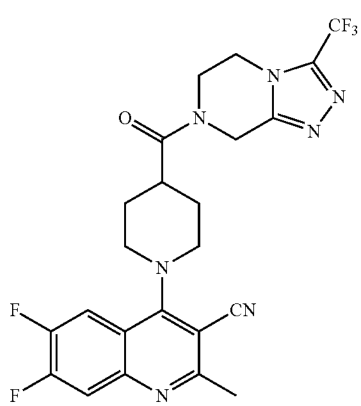 [SMILES: Cc1nc2cc(F)c(F)cc2c(N2CCC(C(=O)N3CCn4c(nnc4C(F)(F)F)C3)CC2)c1C#N] | 6,7-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile | 506 | 2256 |

TABLE 6-continued

| Example | Structure | Chemical Name | Exact Mass [M + H]+ | Human CYP8B1 IC50 (nM) |
|---|---|---|---|---|
| 51 | 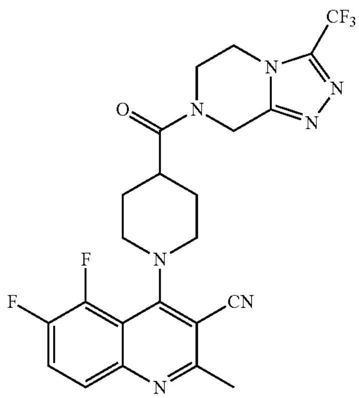 [SMILES: Cc1nc2ccc(F)c(F)c2c(N2CCC(C(=O)N3CCn4c(nnc4C(F)(F)F)C3)CC2)c1C#N] | 5,6-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbontrile | 506 | 774 |

Example 52

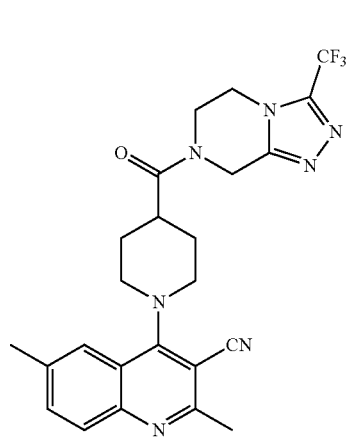 [SMILES: Cc1ccc2nc(C)c(C#N)c(N3CCC(C(=O)N4CCn5c(nnc5C(F)(F)F)C4)CC3)c2c1]

2,6-dimethyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile A mixture of 3-(trifluoromethyl)-5,6,7,8-tetrahydro-[1,2,4]triazolo[4,3-a]pyrazine (107 mg, 0.554 mmol), 1-(3-cyano-2,6-dimethylquinolin-4-yl)piperidine-4-carboxylic acid (143 mg, 0.462 mmol), HATU (351 mg, 0.924 mmol) and DIPEA (0.242 mL, 1.386 mmol) in DMF (2 mL) was stirred at 18° C. for 3 h. Water (30 mL) was added to the reaction. The reaction was then extracted with EtOAc (30 mL×3). The combined organic layers were washed with brine (20 mL), dried over $Na_2SO_4$, filtered and concentrated. The residue was purified by p-HPLC to give 2,6-dimethyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile. MS: 484 (M+1). Human CYP8B1 IC50 (nM) 118.

Example 53

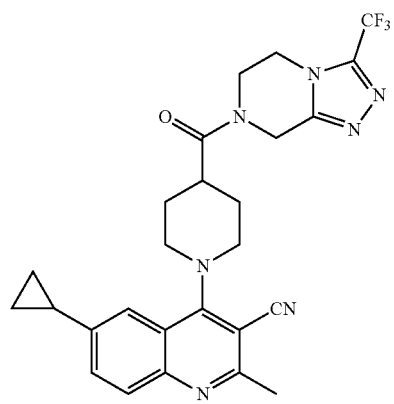 [SMILES: Cc1nc2ccc(C3CC3)cc2c(N2CCC(C(=O)N3CCn4c(nnc4C(F)(F)F)C3)CC2)c1C#N]

6-cyclopropyl-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile A mixture of 6-bromo-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile (100 mg, 0.182 mmol), cyclopropylboronic acid (19 mg, 0.219 mmol), $K_2CO_3$ (75 mg, 0.546 mmol) and Pd(dppf)Cl$_2$—CH$_2$Cl$_2$ (15 mg, 0.018 mmol) in 3 mL of dioxane was heated under $N_2$ atmosphere (1 atm) at 110° C. for 4 h. The reaction mixture was cooled and poured into water (10 mL). The aqueous layer was extracted with EtOAc (3×8 mL). The combined organic layers were dried with $Na_2SO_4$, filtered and concentrated. The residue was purified by prep-HPLC then dried by lyophilization to give 6-cyclopropyl-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile. Human CYP8B1 IC50 (nM) 76.

Example 54

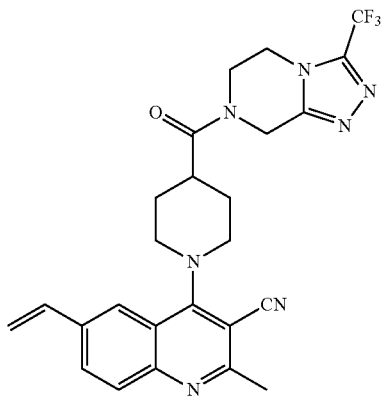 [SMILES: C=Cc1ccc2nc(C)c(C#N)c(N3CCC(C(=O)N4CCn5c(nnc5C(F)(F)F)C4)CC3)c2c1]

2-methyl-4-(4-(3-(trifluoromethyl)-5,6,7,8-tetrahydro-[1,2,4]triazolo[4,3-a]pyrazine-7-carbonyl)piperidin-1-yl)-6-vinylquinoline-3-carbonitrile A mixture of 6-bromo-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile (564 mg, 1.028 mmol), 4,4,5,5-tetramethyl-2-vinyl-1,3,2-dioxaborolane (190 mg, 1.234 mmol), $Cs_2CO_3$ (670 mg, 2.056 mmol) and Pd(dppf)$Cl_2$—$CH_2Cl_2$ (84 mg, 0.103 mmol) in 6 mL of dioxane:$H_2O$ (5:1) was heated under $N_2$ atmosphere (1 atm) at 80° C. for 8 h. The reaction mixture was cooled and poured into water (15 mL). The mixture was extracted with EtOAc (3×8 mL). The combined organic layers were dried with $Na_2SO_4$, filtered and concentrated. The residue was chromatographed on silica gel (EtOAc/petroleum ether=2:1~5:1) to give 2-methyl-4-(4-(3-(trifluoromethyl)-5,6,7,8-tetrahydro[4,3-a]pyrazine-7-carbonyl)piperidin-1-yl)-6-vinylquinoline-3-carbonitrile. MS: 496 (M+1). Human CYP8B1 IC50 (nM) 149.

Example 55

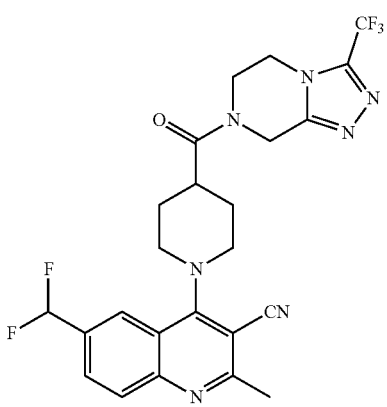 [SMILES: Cc1nc2ccc(C(F)F)cc2c(N2CCC(C(=O)N3CCn4c(nnc4C(F)(F)F)C3)CC2)c1C#N]

6-(difluoromethyl)-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile (Diethylamino)sulfur trifluoride (38 µL, 0.286 mmol) was added to a stirred solution of 6-formyl-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile (95 mg, 0.191 mmol) in DCM (3 mL) at 0° C. under N2 atmosphere. The reaction mixture was allowed to warm to 18° C. and stirred for 3.5 h. The reaction mixture was diluted with DCM (15 mL) and then quenched with saturated $NaHCO_3$ solution (10 mL). The separated aqueous layer was extracted with DCM (3×8 mL). The combined organic layers were dried with $Na_2SO_4$, filtered and concentrated. The residue was purified by prep-HPLC then dried by lyophilization to give 6-(difluoromethyl)-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile. MS: 520 (M+1). Human CYP8B1 IC50 (nM) 78.

Example 56

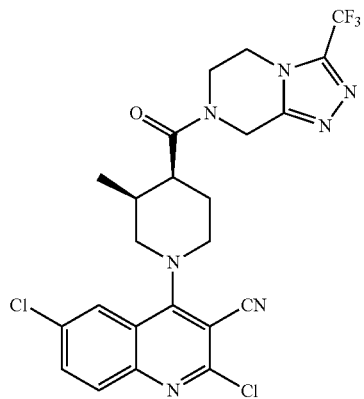 [SMILES: C[C@@H]1CN(c2c(C#N)c(Cl)nc3ccc(Cl)cc23)CC[C@@H]1C(=O)N1CCn2c(nnc2C(F)(F)F)C1]

2,6-dichloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile Step 1: DIPEA (2.88 mL, 16.5 mmol) and 2,4,6-tripropyl-1,3,5,2,4,6-trioxatriphosphorinane-2,4,6-trioxide (6.54 ml, 10.98 mmol) was added to a stirred solution of 1-(2,6-dichloro-3-cyanoquinolin-4-yl)-3-methylpiperidine-4-carboxylic acid (2.00 g, 5.49 mmol) and 3-(trifluoromethyl)-5,6,7,8-tetrahydro-[1,2,4]triazolo[4,3-a]pyrazine hydrochloride (1.51 g, 6.59 mmol) in DMF (27 ml) at 0° C. The resulting mixture was stirred at room temperature for 16 hours. The reaction mixture was diluted with aq. $Na_2CO_3$ and extracted with EtOAc (2×500 mL). The combined organic layers were washed with brine (300 mL), dried over $Na_2SO_4$, filtered and concentrated. The resulting residue was purified by flash column chromatography on silica gel (0-60% ethyl acetate in DCM) to afford 2,6-dichloro-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile. MS: 538 (M+1).

Step 2: 2,6-dichloro-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile (200 mg, 0.37 mmol) was dissolved in an MeOH/MeCN (1:1; 40 mL) mixture until the solution became homogeneous. The solution was submitted for chiral SFC separation (Column: Chiral AD-H 21×250 mm, co-solvent: EtOH, 25% $CO_2$) to separate out the minor diastereomers (peak 1 and 3, SFC $t_R$=2.98 and 4.43 min respectively). The major desired diastereomer (peak 2, SFC $t_R$=3.67 min) had to be re-separated via SFC separation (Column: OD-H 21×250 mm 55% MeOH/$CO_2$) to afford the title compound (peak 2b, SFC $t_R$=2.75 min). MS: 538 (M+1). Human CYP8B1 IC50 (nM) 1.5.

Example 57

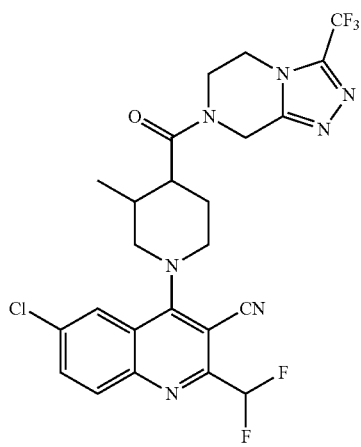 [SMILES: CC1CN(c2c(C#N)c(C(F)F)nc3ccc(Cl)cc23)CCC1C(=O)N1CCn2c(nnc2C(F)(F)F)C1]

6-chloro-2-(difluoromethyl)-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile HATU (131 mg, 0.34 mmol) and DIPEA (0.120 ml, 0.69 mmol) were added to a stirred solution of 1-[6-chloro-3-cyano-2-(difluoromethyl)quinolin-4-yl]-3-methylpiperidine-4-carboxylic acid (87 mg, 0.23 mmol) in DMF (2.3 mL) and 3-(trifluoromethyl)-5,6,7,8-tetrahydro-[1,2,4]triazolo[4,3-a]pyrazine hydrochloride (63 mg, 0.28 mmol) in DMF (2.29 ml) at room temperature. The resulting mixture was stirred at room temperature for 15 hours. The reaction mixture was diluted with EtOAc and washed with water (3×). The organic layers were dried with magnesium sulfate, filtered, concentrated and purified by silica gel chromatography (0-70% 3:1 EtOAc:EtOH in hexane). The combined fractions were concentrated to give the title compound. MS: 554 (M+1). Human CYP8B1 IC50 (nM) 69.

Example 57a and 57b

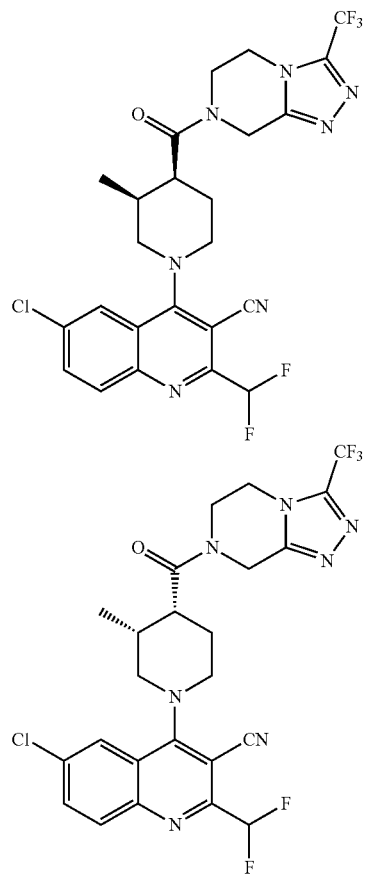

6-chloro-2-(difluoromethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 6-chloro-2-(difluoromethyl)-4-[(3R,4R)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 6-chloro-2-(difluoromethyl)-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile was sent to SFC for diastereomer separation (Column: LUX-4 21×250 mm, injection volume 0.5 mL at 75 mg in 15 mL of 1:1 MeOH:MeCN, wavelength 210 nm, 35% MeOH (0.2% DIPA)/$CO_2$ at 120 bar, 40° C.) to afford 6-chloro-2-(difluoromethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile (MS: 554 (M+1)) (peak 4, SFC $t_R$=7.59 min) Human CYP8B1 IC50 (nM) 41 and 6-chloro-2-(difluoromethyl)-4-[(3R,4R)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile (MS: 554 (M+1)) (peak 3, SFC $t_R$=6.61 min) Human CYP8B1 IC50 (nM) 1494.

The following compounds were made in a similar way to Example 56 substituting the appropriate reactants and reagents.

TABLE 7

| Example | Structure | Chemical Name | Exact Mass [M + H] + 1 | Human CYP8B1 IC50 (nM) |
|---------|-----------|---------------|------------------------|------------------------|
| 58 | 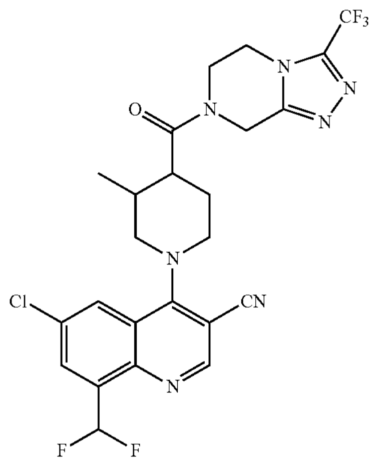 [SMILES: CC1CN(c2c(C#N)cnc3c(C(F)F)cc(Cl)cc23)CCC1C(=O)N1CCn2c(nnc2C(F)(F)F)C1] | 6-chloro-8-(difluoromethyl)-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile | 554 | 4.8 |

Examples 59 and 60 methyl 6-chloro-3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2-carboxylate dimethyl 3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2,6-dicarboxylate

[1,1'-bis(diphenylphosphino)ferrocene]dichloropalladium (II) (17 mg, 0.023 mmol) and TEA (0.064 mL, 0.457 mmol) was added to a solution of 2,6-dichloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (82 mg, 0.15 mmol) in DMF:MeOH (1:1; 3.04 mL). The reaction was set up in a carbonylation tube at 60 psi and stirred for 15 h at 80° C. The reaction was cooled to room temperature and diluted with EtOAc. The organic layer was washed with water 2×. The organic layer was dried with magnesium sulfate, filtered, concentrated and purified by column chromatography (0-50% 3:1 EtOAc:EtOH in hexane). The fractions were combined and concentrated to give methyl 6-chloro-3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2-carboxylate (MS: 562 (M+1)) Human CYP8B1 IC50 (nM) 18 and dimethyl 3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2,6-dicarboxylate (MS: 586 (M+1)). Human CYP8B1 IC50 (nM) 270.

Example 61

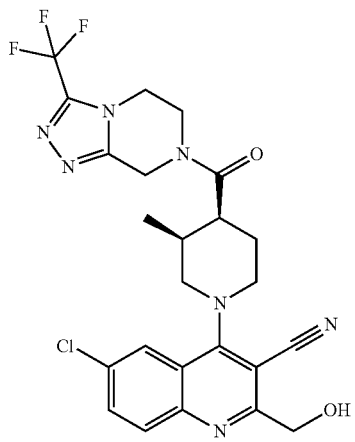 [SMILES: C[C@@H]1CN(c2c(C#N)c(CO)nc3ccc(Cl)cc23)CC[C@@H]1C(=O)N1CCn2c(nnc2C(F)(F)F)C1]

methyl 6-chloro-3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2-carboxylate 6-chloro-2-(hydroxymethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile methyl 6-chloro-3-cyano-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-2-carboxylate (27 mg, 0.048 mmol) was dissolved in THF (1 mL). Lithium borohydride (2M in THF, 0.048 mL, 0.096 mmol) was added and the reaction stirred at room temperature for 2 h. NH$_4$Cl was added and stirred for 10 min. Water was added and the reaction was extracted 3× with EtOAc. The combined organic layers were dried with magnesium sulfate, filtered, concentrated and purified by silica gel chromatography (0-70% 3:1 EtOAc:EtOH in Hexane). The fractions were combined and concentrated. The compound was repurified by silica gel chromatography (0-6% MeOH in DCM). The fractions were combined and concentrated to give the title compound. MS: 534 (M+1). Human CYP8B1 IC50 (nM) 4.5.

Example 62

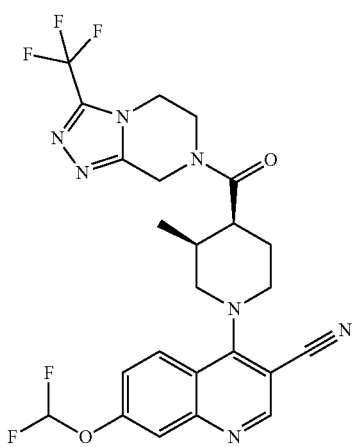 [SMILES: C[C@@H]1CN(c2c(C#N)cnc3cc(OC(F)F)ccc23)CC[C@@H]1C(=O)N1CCn2c(nnc2C(F)(F)F)C1]

7-(difluoromethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 7-hydroxy-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (50 mg, 0.10 mmol), cesium carbonate (50 mg, 0.15 mmol), sodium 2-chloro-2,2-difluoroacetate (24 mg, 0.15 mmol), and DMF (1.03 mL) were combined in a sealed tube. The reaction was heated to 80° C. for 4 h. Additional sodium 2-chloro-2,2-difluoroacetate (16 mg, 0.10 mmol) was added and the reaction continually stirred for 2 h at 80° C. The reaction mixture was cooled to room temperature, diluted with EtOAc and washed with water 3×. The organic layers were dried with magnesium sulfate, filtered, concentrated and purified by silica gel chromatography (0-100% 3:1 EtOAc:EtOH in hexane). The combined fractions were concentrated to give the title compound. MS: 536 (M+1). Human CYP8B1 IC50 (nM) 1.1.

Example 63

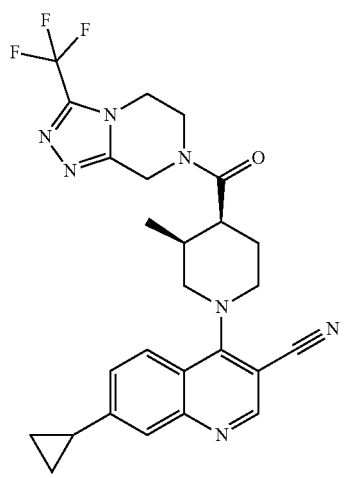 [SMILES: C[C@@H]1CN(c2c(C#N)cnc3cc(C4CC4)ccc23)CC[C@@H]1C(=O)N1CCn2c(nnc2C(F)(F)F)C1]

7-cyclopropyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 7-bromo-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (32 mg, 0.058 mmol) and potassium cyclopropyltrifluoroborate (13 mg, 0.088 mmol), PdCl$_2$(dppf)-CH$_2$Cl$_2$Adduct (4.8 mg, 5.8 µmol), potassium phosphate tribasic (1M in water, 0.18 mL, 0.18 mmol) were added to a sealed tube. Dioxane was added (1.17 ml) and the reaction was purged with nitrogen gas for 5 min. The reaction was heated to 60° C. After 4 h the reaction was cooled to room temperature and more potassium cyclopropyltrifluoroborate (13 mg, 0.088 mmol) and PdCl$_2$(dppf)-CH$_2$Cl$_2$Adduct (4.8 mg, 5.8 µmol) were added. The mixture was purged with nitrogen gas for 5 minutes and heated to 60° C. for 15 h. The reaction mixture was cooled and diluted with water and washed with EtOAc (3×). The organic layers were dried with magnesium sulfate, filtered, concentrated and purified by silica gel chromatography (0-100% 3:1 EtOAc:EtOH in hexane). The combined fractions were concentrated to give the title compound. MS: 510 (M+1). Human CYP8B1 IC50 (nM) 1.1.

Example 64

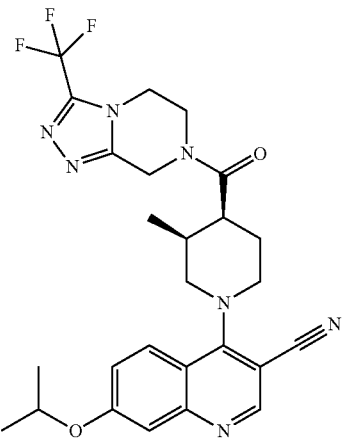 [SMILES: CC(C)Oc1ccc2c(N3CC[C@H](C(=O)N4CCn5c(nnc5C(F)(F)F)C4)[C@H](C)C3)c(C#N)cnc2c1]

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(propan-2-yloxy)quinoline-3-carbonitrile 7-hydroxy-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (25 mg, 0.051 mmol), cesium carbonate (25 mg, 0.077 mmol), 2-iodopropane (7.72 µl, 0.077 mmol), and DMF (0.52 mL) were combined in a sealed tube. The reaction was heated to 40° C. for 4 h. The reaction mixture was cooled to room temperature, diluted with EtOAc and washed with water (3×). The organic layers were dried with magnesium sulfate, filtered, concentrated and purified by silica gel chromatography (0-100% 3:1 EtOAc:EtOH in hexane. The combined fractions were concentrated to give the title compound. MS: 528 (M+1). Human CYP8B1 IC50 (nM) 0.30.

Example 65

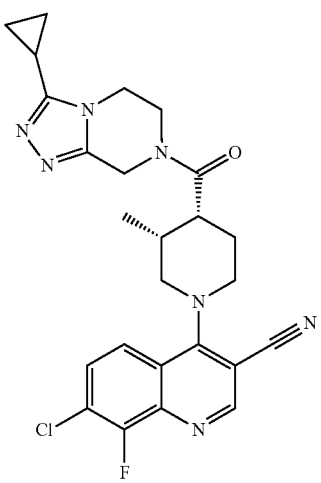 [SMILES: C[C@H]1CN(c2c(C#N)cnc3c(F)c(Cl)ccc23)CC[C@H]1C(=O)N1CCn2c(nnc2C2CC2)C1]

7-chloro-4-{(3R,4R)-4-[(3-cyclopropyl-5,6-dihydro[1,2,4]triazolo[4,3-a]pyrazin-7(8H)-yl)carbonyl]-3-methylpiperidin-1-yl}-8-fluoroquinoline-3-carbonitrile DIPEA (0.051 mL, 0.29 mmol) was added to a stirred solution of (3R,4R)-1-(7-chloro-3-cyano-8-fluoroquinolin-4-yl)-3-methylpiperidine-4-carboxylic acid trifluoroacetate (27 mg, 0.058 mmol), 3-cyclopropyl-5,6,7,8-tetrahydro-[1,2,4]triazolo[4,3-a]pyrazine oxalate (18 mg, 0.070 mmol), HATU (33 mg, 0.088 mmol) in DMF (0.59 mL). The reaction was stirred at room temperature for 15 h. The reaction was filtered and purified directly by reverse phase HPLC (10-100% MeCN/Water, with 0.05% TFA). The combined fractions were combined and neutralized with aqueous saturated sodium bicarbonate. The aqueous layer was extracted with EtOAc (2×). The combined organic layers were washed with water (1×). The organic layer was dried with magnesium sulfate, filtered, and concentrated to give the title compound. MS: 494 (M+1). Human CYP8B1 IC50 (nM) 318.

Example 66

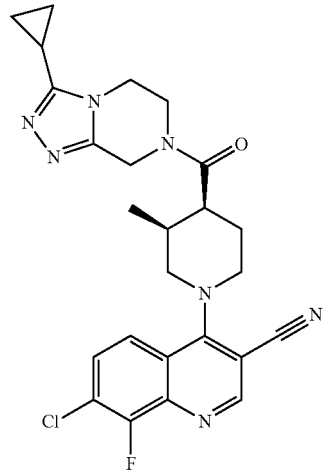 [SMILES: C[C@@H]1CN(c2c(C#N)cnc3c(F)c(Cl)ccc23)CC[C@@H]1C(=O)N1CCn2c(nnc2C2CC2)C1]

7-chloro-4-{(3S,4S)-4-[(3-cyclopropyl-5,6-dihydro[1,2,4]triazolo[4,3-a]pyrazin-7(8H)-yl)carbonyl]-3-methylpiperidin-1-yl}-8-fluoroquinoline-3-carbonitrile DIPEA (0.079 mL, 0.46 mmol) was added to a stirred solution of (3S,4S)-1-(7-chloro-3-cyano-8-fluoroquinolin-4-yl)-3-methylpiperidine-4-carboxylic acid trifluoroacetate (42 mg, 0.091 mmol), 3-cyclopropyl-5,6,7,8-tetrahydro-[1,2,4]triazolo[4,3-a]pyrazine oxalate (28 mg, 0.11 mmol), HATU (52 mg, 0.14 mmol) in DMF (0.91 mL). The reaction was stirred at room temperature for 15 h. The reaction was filtered and purified directly by reverse phase HPLC (10-100% MeCN/Water, with 0.05% TFA). The combined fractions were combined and neutralized with aqueous saturated sodium bicarbonate. The aqueous layer was extracted with EtOAc (2×). The combined organic layers were washed with water (1×). The organic layer was dried with magnesium sulfate, filtered, and concentrated to give the title compound. MS: 494 (M+1). Human CYP8B1 IC50 (nM) 0.51.

Example 67

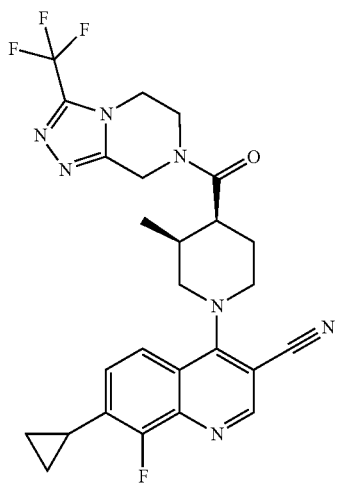 [SMILES: C[C@@H]1CN(c2c(C#N)cnc3c(F)c(C4CC4)ccc23)CC[C@@H]1C(=O)N1CCn2c(nnc2C(F)(F)F)C1]

7-cyclopropyl-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 7-bromo-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile (40 mg, 0.071 mmol), potassium cyclopropyltrifluoroborate (16 mg, 0.106 mmol), PdCl$_2$(dppf)-CH$_2$Cl$_2$Adduct (5.77 mg, 7.06 μmol) and potassium phosphate tribasic (1M in water, 0.212 mL, 0.212 mmol) were added to a sealed tube. Dioxane (1.41 mL) was added and the reaction was purged with nitrogen gas for 5 min. The reaction was heated to 60° C. After 4 h, the mixture was cooled to room temperature and potassium cyclopropyltrifluoroborate (16 mg, 0.106 mmol) and PdCl$_2$(dppf)-CH$_2$Cl$_2$Adduct (5.77 mg, 7.06 μmol) was added. The mixture was continually stirred at 60° C. for 15 h. The reaction mixture was diluted with water and washed with EtOAc 3×. The organic layers were dried with magnesium sulfate, filtered, concentrated and purified by silica gel chromatography (0-100% 3:1 EtOAc:EtOH in hexane). The combined fractions were concentrated to give the title compound. MS: 528 (M+1). Human CYP8B1 IC50 (nM) 0.89.

Example 68

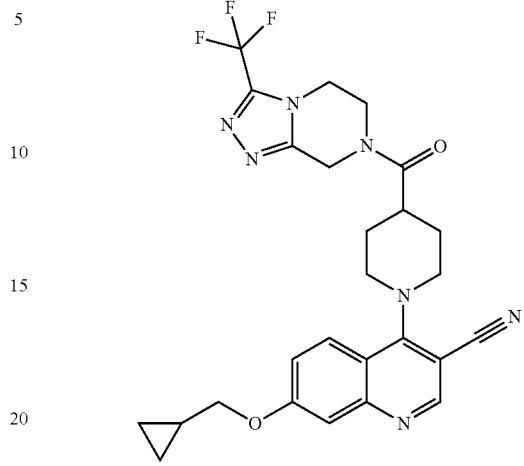

7-(cyclopropylmethoxy)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile 7-hydroxy-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile (40 mg, 0.085 mmol), cesium carbonate (41 mg, 0.13 mmol), (bromomethyl)cyclopropane (0.012 mL, 0.127 mmol), and DMF (0.42 mL) were combined in a sealed tube. The reaction was heated to 70° C. for 2 h. The reaction mixture was filtered and purified by reverse phase HPLC (10-100% MeCN/Water, with 0.05% TFA). The fractions were combined and neutralized with saturated sodium bicarbonate. The aqueous layer was extracted with EtOAc (2×). The organic layers were combined and washed with water (1×). The organic layers were dried with magnesium sulfate, filtered, and concentrated to give the title compound. MS: 526 (M+1). Human CYP8B1 IC50 (nM) 0.43.

The following compounds were made in a similar way to Example 68 substituting the appropriate reactants and reagents.

TABLE 8

| Example | Structure | Chemical Name | Exact Mass [M + H]+ | Human CYP8B1 IC50 (nM) |
|---|---|---|---|---|
| 69 | 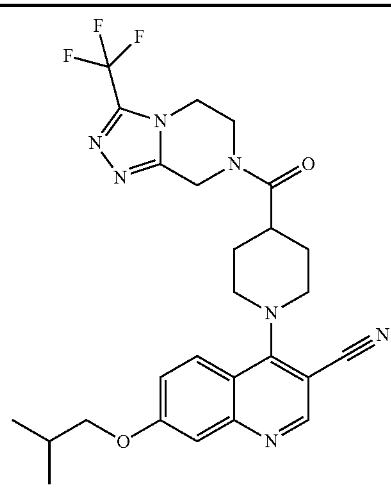 | 7-(2-methylpropoxy)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile | 528 | 0.42 |

Example 70

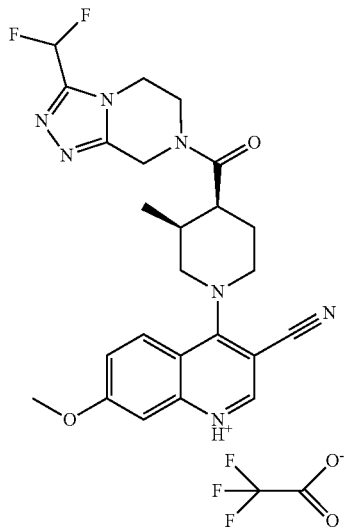 [SMILES: COc1ccc2c(N3CC[C@H](C(=O)N4CCn5c(nnc5C(F)F)C4)[C@H](C)C3)c(C#N)c[nH+]c2c1 ; O=C([O-])C(F)(F)F]

4-[(3S,4S)-4-{[3-(difluoromethyl)-5,6-dihydro[1,2,4]triazolo[4,3-a]pyrazin-7(8H)-yl]carbonyl}-3-methylpiperidin-1-yl]-7-methoxyquinoline-3-carbonitrile DIPEA (0.080 mL, 0.46 mmol) was added to a stirred solution of (3S,4S)-1-(3-cyano-7-methoxyquinolin-4-yl)-3-methylpiperidine-4-carboxylic acid (40 mg, 0.091 mmol), 3-(difluoromethyl)-5,6,7,8-tetrahydro-[1,2,4]triazolo[4,3-a]pyrazine (19 mg, 0.11 mmol), and HATU (52 mg, 0.14 mmol) in DMF (0.910 mL). The reaction was stirred at room temperature for 15 h. The reaction was filtered and purified directly by reverse phase HPLC (10-100% MeCN/Water, with 0.05% TFA). The combined fractions were combined and frozen and dried in the lyophilizer to give the title compound. MS: 482 (M+1). Human CYP8B1 IC50 (nM) 0.88.

Example 71

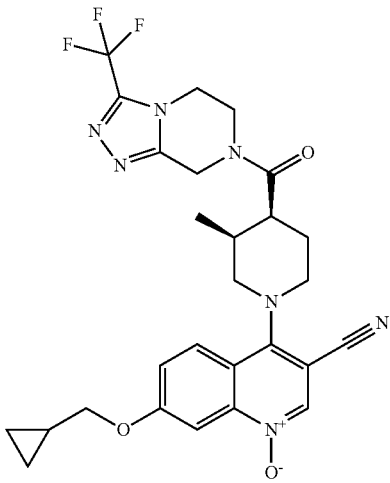 [SMILES: C[C@@H]1CN(c2c(C#N)c[n+]([O-])c3cc(OCC4CC4)ccc23)CC[C@@H]1C(=O)N1CCn2c(nnc2C(F)(F)F)C1]

7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 1-oxide 7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile hydrochloride (55 mg, 0.095 mmol) was free based by dissolving in DCM and neutralizing with saturated sodium bicarbonate. The organic layer was dried with magnesium sulfate, filtered and concentrated. To the residue was added DCM (1.91 mL) followed by mCPBA (25 mg, 0.143 mmol). The reaction was stirred at room temperature for 15 h. Additional mCPBA (25 mg, 0.143 mmol) was added and was stirred at room temperature for 15 h. Saturated sodium thiosulfate and the reaction stirred for 30 min. The aqueous layer was extracted 3× with EtOAc. The combined organic layers were dried with magnesium sulfate, filtered and concentrated. The residue was taken up in DMF and purified by reverse phase chromatography (10-100% MeCN/Water, with 0.05% TFA). The combined fractions were neutralized with saturated sodium bicarbonate and extracted 3× with EtOAc. The organic layers were washed with water (1×), dried with magnesium sulfate, filtered, and concentrated to give the title compound. MS: 556 (M+1). Human CYP8B1 IC50 (nM) 0.54.

Examples 72a and 72b

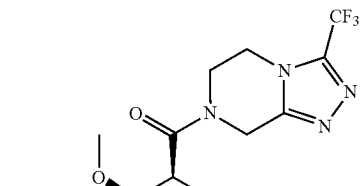

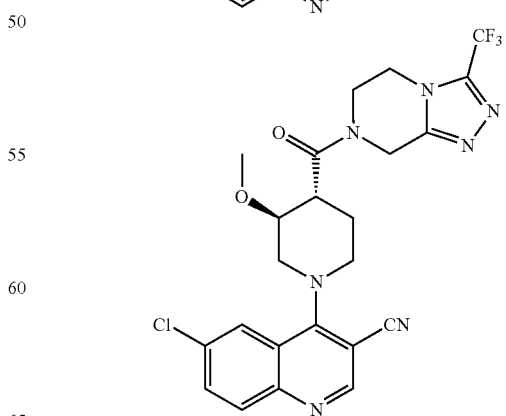

6-chloro-4-[(3S,4S)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile 6-chloro-4-[(3S,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile A mixture of (3S,4S)-1-(6-chloro-3-cyanoquinolin-4-yl)-3-methoxypiperidine-4-carboxylic acid (65 mg, 0.187 mmol), 3-(trifluoromethyl)-5,6,7,8-tetrahydro-[1,2,4]triazolo[4,3-a]pyrazine (40 mg, 0.206 mmol), HATU (142 mg, 0.375 mmol) and DIPEA (131 µL, 0.749 mmol) in DMF (3 mL) was stirred at 16° C. for 1.5 h. Water (20 mL) was added and the mixture was extracted with EtOAc (3×8 mL). The combined organic layers were dried with Na$_2$SO$_4$, filtered and concentrated. The residue was purified by prep-HPLC then dried by lyophilization to 6-chloro-4-[(3S,4S)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile (Human CYP8B1 IC50 (nM) 22) and 6-chloro-4-[(3S,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile (Human CYP8B1 IC50 (nM) 441). MS: 556 (M+1).

The following compounds were made in a similar way to Examples 73a and 73b substituting the appropriate reactants and reagents.

TABLE 9

| Example | Structure | Chemical Name | Exact Mass [M + H]+ | Human CYP8B1 IC50 (nM) |
|---|---|---|---|---|
| 72c | 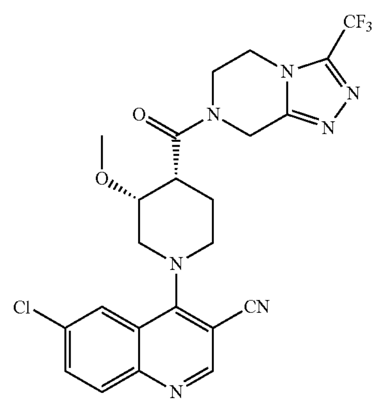 [SMILES: CO[C@H]1CN(c2c(C#N)cnc3ccc(Cl)cc23)CC[C@H]1C(=O)N1CCn2c(nnc2C(F)(F)F)C1] | 6-chloro-4-[(3R,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 556 | 2211 |
| 72d | 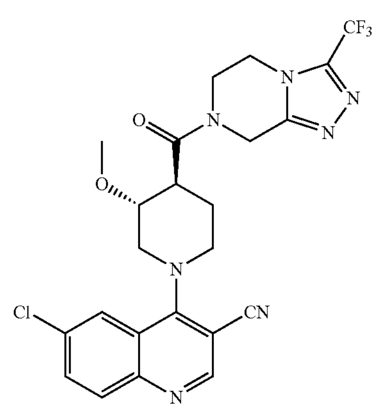 [SMILES: CO[C@H]1CN(c2c(C#N)cnc3ccc(Cl)cc23)CC[C@@H]1C(=O)N1CCn2c(nnc2C(F)(F)F)C1] | 6-chloro-4-[(3R,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 556 | 6140 |

Examples 73a and 73b

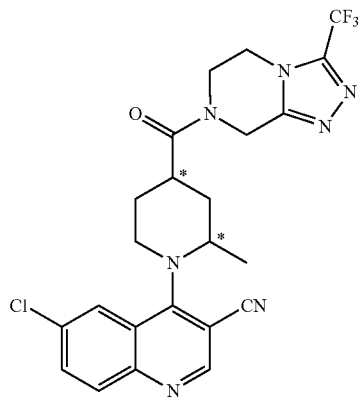 [SMILES: CC1CC(C(=O)N2CCn3c(nnc3C(F)(F)F)C2)CCN1c1c(C#N)cnc2ccc(Cl)cc12]

6-chloro-4-[(2R,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 6-chloro-4-[(2S,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile DIPEA (0.307 mL, 1.759 mmol) was added to a mixture of 3-(trifluoromethyl)-5,6,7,8-tetrahydro-[1,2,4]triazolo[4,3-a]pyrazine (127 mg, 0.660 mmol), cis-1-(6-chloro-3-cyanoquinolin-4-yl)-2-methylpiperidine-4-carboxylic acid (145 mg, 0.440 mmol), and HATU (334 mg, 0.879 mmol) in DMF (4 mL) and stirred at 18° C. for 3 h. The reaction was quenched with water (30 mL) and extracted with EtOAc (30 mL×4), the combined organic phases were washed with brine (30 mL), dried over $Na_2SO_4$, filtered. The filtrates were concentrated and purified by p-HPLC to give cis-6-chloro-4-(2-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile. MS: 504 (M+1). The product was resolved by SFC (Column: Chiralpak AD-3 Mobile phase: A: $CO_2$ B: methanol (0.05% DEA) Gradient: from 5% to 40% of B SFC separation gave peak 1 (70 mg, 0.135 mmol) MS: 504 (M+1); and peak 2 (R,R or S,S) MS: 504 (M+1).

TABLE 10

| Example | Structure | Chemical Name | Exact Mass [M + H]+ | Human CYP8B1 IC50 (nM) |
|---|---|---|---|---|
| 73a | 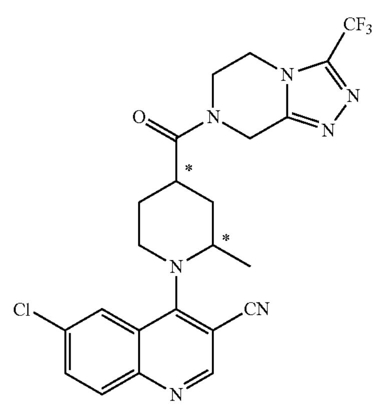 | Peak 1; 6-chloro-4-[(2R,4R) or (2S,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 504 | 6.4 |
| 73b | 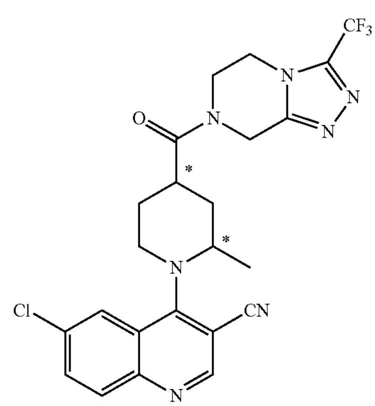 | Peak 2; 6-chloro-4-[(2R,4R) or (2S,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 504 | 15 |

Examples 73c and 73d

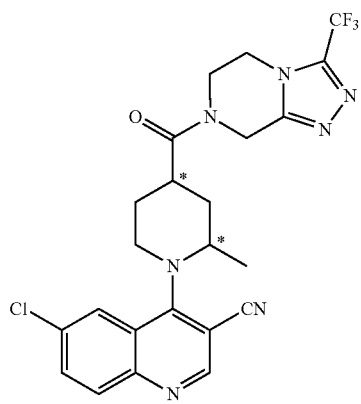 [SMILES: CC1CC(C(=O)N2CCn3c(nnc3C(F)(F)F)C2)CCN1c1c(C#N)cnc2ccc(Cl)cc12]

6-chloro-4-[(2R,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 6-chloro-4-[(2S,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile DIPEA (0.275 mL, 1.577 mmol) was added to a mixture of 3-(trifluoromethyl)-5,6,7,8-tetrahydro-[1,2,4]triazolo[4,3-a]pyrazine (114 mg, 0.591 mmol), trans-1-(6-chloro-3-cyanoquinolin-4-yl)-2-methylpiperidine-4-carboxylic acid (130 mg, 0.394 mmol), HATU (300 mg, 0.788 mmol) in DMF (3 mL) was stirred at 18° C. for 2 h. The reaction was quenched with water (20 mL) and extracted with EtOAc (30 mL×3), the combined organic phases were washed with brine (30 mL), dried over $Na_2SO_4$ and filtered. The filtrates were concentrated and purified by p-HPLC to give trans-6-chloro-4-(2-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile which was resolved by SFC. MS: 504 (M+1). The material was resolved by SFC (Column: Chiralcel OD-3 Mobile phase: A: $CO_2$ B: ethanol (0.05% DEA), Gradient: from 5% to 40% of). SFC separation gave peak 1 (R,S or R,S) (19.5 mg, 0.038 mmol) MS: 504 (M+1); and peak 2 (R,S or S,R) (25.3 mg, 0.050 mmol) MS: 504 (M+1).

TABLE 11

| Example | Structure | Chemical Name | Exact Mass [M + H]+ | Human CYP8B1 IC50 (nM) |
|---|---|---|---|---|
| 73c | 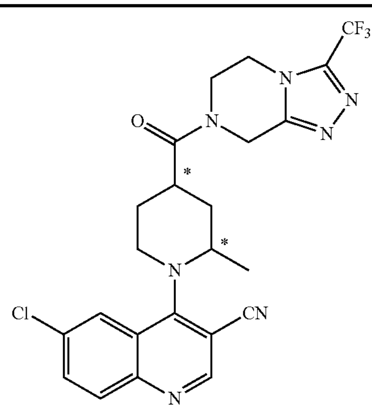 | Peak 1; 6-chloro-4-[(2R,4S) or (2S,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 504 | 16 |
| 73d | 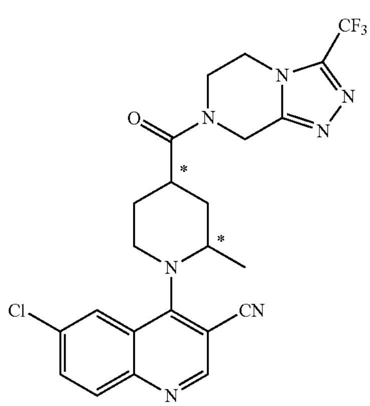 | Peak 2; 6-chloro-4-[(2R,4S) or (2S,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 504 | 636 |

Example 74a

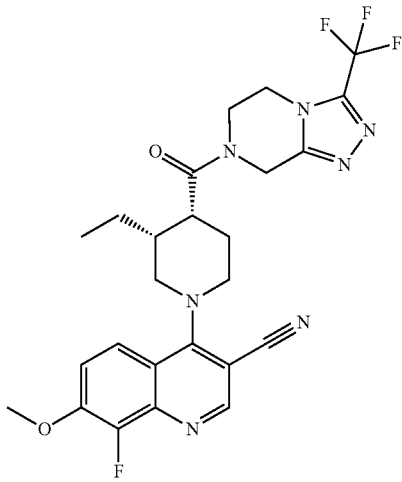 [SMILES: CC[C@H]1CN(c2c(C#N)cnc3c(F)c(OC)ccc23)CC[C@H]1C(=O)N1CCn2c(nnc2C(F)(F)F)C1]

4-[(3R,4R)-3-ethyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile DIPEA (0.055 mL, 0.317 mmol) was added to a mixture of 4-chloro-8-fluoro-7-methoxyquinoline-3-carbonitrile (15 mg, 0.063 mmol) and [(3R,4R)-3-ethylpiperidin-4-yl][3-(trifluoromethyl)-5,6-dihydro[1,2,4]triazolo[4,3-a]pyrazin-7(8H)-yl]methanone trifluoroacetate (27.2 mg, 0.063 mmol) in DMF (2 mL) and stirred at 25° C. for 44 h. The reaction was filtered and the filtrates was directly purified by p-HPLC to give 4-[(3R,4R)-3-ethyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile (Human CYP8B1 IC50 (nM) 343). MS: 532 (M+1).

The following compounds were made in a similar way to Example 73a substituting the appropriate reactants and reagents.

TABLE 12

| Example | Structure | Chemical Name | Exact Mass [M + H]+ | Human CYP8B1 IC50 (nM) |
|---|---|---|---|---|
| 75a | 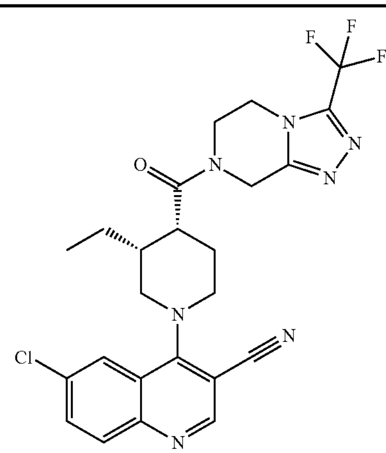 | 6-chloro-4-[(3R,4R)-3-ethyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 518 | 307 |

Example 74b

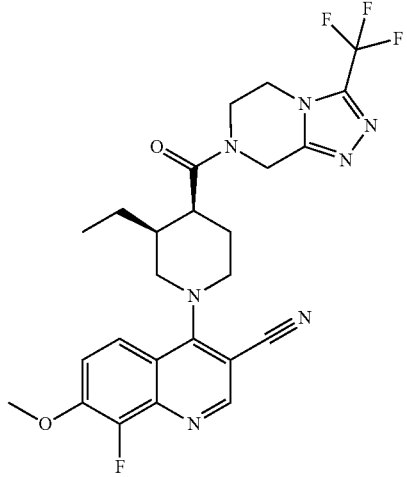

4-[(3S,4S)-3-ethyl-4-{[3-(trifluoromethyl)-5,6-di-hydro[1,2,4]triazolo[4,3-a]pyrazin-7(8H)-yl]carbonyl}piperidin-1-yl]-8-fluoro-7-methoxyquinoline-3-carbonitrile DIPEA (0.055 mL, 0.317 mmol) was added to a mixture of 4-chloro-8-fluoro-7-methoxyquinoline-3-carbonitrile (15 mg, 0.063 mmol) and [(3S,4S)-3-ethylpiperidin-4-yl][3-(trifluoromethyl)-5,6-dihydro[1,2,4]triazolo[4,3-a]pyrazin-7(8H)-yl]methanone trifluoroacetate (27.2 mg, 0.063 mmol) in DMF (2 mL) and stirred at 25° C. for 44 h. The reaction was filtered and the filtrates was directly purified by p-HPLC to give 4-[(3S,4S)-3-ethyl-4-{[3-(trifluoromethyl)-5,6-di-hydro[1,2,4]triazolo[4,3-a]pyrazin-7(8H)-yl]carbonyl}piperidin-1-yl]-8-fluoro-7-methoxyquinoline-3-carbonitrile (Human CYP8B1 IC50 (nM) 2.1). MS: 532 (M+1).

The following compounds was made in a similar way to Example 73b substituting the appropriate reactants and reagents.

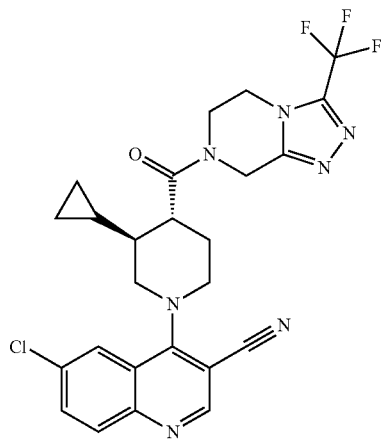

TABLE 13

| Example | Structure | Chemical Name | Exact Mass [M + H]+ | Human CYP8B1 IC50 (nM) |
|---------|-----------|---------------|---------------------|------------------------|
| 75b | 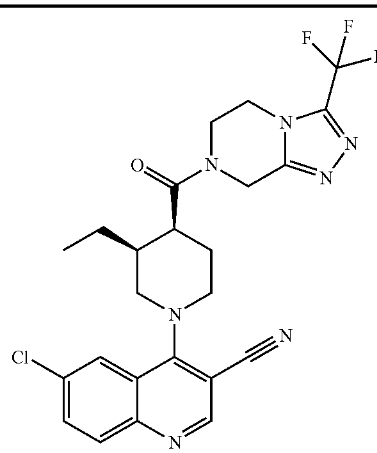 | 6-chloro-4-[(3S,4S)-3-ethyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 518 | 2.8 |

Example 76a and 76b

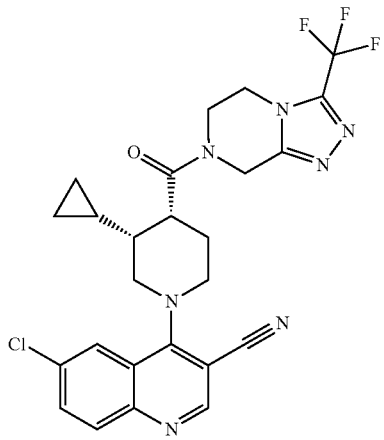 [SMILES: CC[C@H]1CN(c2c(C#N)cnc3ccc(Cl)cc23)CC[C@H]1C(=O)N1CCn2c(nnc2C(F)(F)F)C1]

6-chloro-4-[(3R,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 6-chloro-4-[(3S,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile

[(3R,4R)-3-cyclopropylpiperidin-4-yl][3-(trifluoromethyl)-5,6-dihydro[1,2,4]triazolo[4,3-a]pyrazin-7(8H)-yl]methanone trifluoroacetate (contaminated with ~15% of the trans isomer) (34.7 mg, 0.101 mmol) was added to a stirred mixture of 4,6-dichloroquinoline-3-carbonitrile (22.53 mg, 0.101 mmol) and DIEA (0.071 mL, 0.404 mmol) in DMF (1 mL) and the mixture was stirred at 30° C. for 16 h. The reaction was poured into 10 mL cold water and extracted with EtOAc (3×8 mL). The combined organic layers were dried over Na$_2$SO$_4$, filtered and concentrated. The residue was purified by prep-HPLC to give the (3R,4R) title compound (20 mg, 0.038 mmol) which was contaminated with 15% of the trans isomer. The material was purified with SFC (Chiralpak AD-3 150×4.6 mm I.D., 3 um, Mobile phase: A: $CO_2$ B: ethanol (0.05% DEA), Gradient: from 5% to 40% of). SFC yielded 6-chloro-4-[(3S,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile (Rt=5.04 min) Human CYP8B1 IC50 (nM) 221 and 6-chloro-4-[(3R,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile (Rt=5.44 min) Human CYP8B1 IC50 (nM) 1316. MS: 530 (M+1).

The following compounds were made in a similar way to Example 75a substituting the appropriate reactants and reagents.

TABLE 14

| Example | Structure | Chemical Name | Exact Mass [M + H]+ | Human CYP8B1 IC50 (nM) |
|---|---|---|---|---|
| 77a | 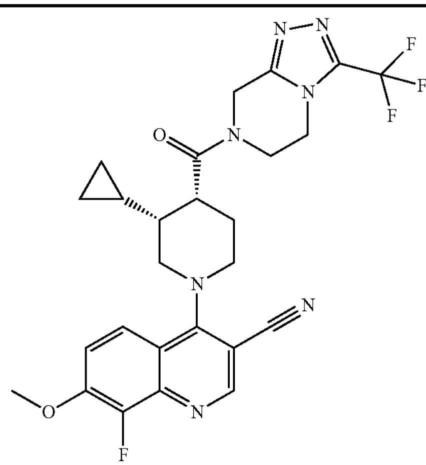 | 4-[(3R,4R)-3-cyclopropyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile | 544 | 231 |

Example 76c

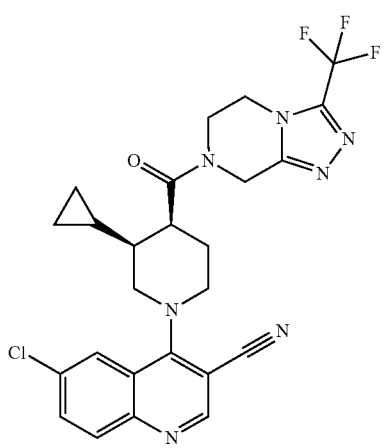 [SMILES: N#Cc1cnc2ccc(Cl)cc2c1N1CC[C@H](C(=O)N2CCn3c(nnc3C(F)(F)F)C2)[C@H](C2CC2)C1]

6-chloro-4-[(3S,4S)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile

[(3S,4S)-3-cyclopropylpiperidin-4-yl][3-(trifluoromethyl)-5,6-dihydro[1,2,4]triazolo[4,3-a]pyrazin-7(8H)-yl]methanone trifluoroacetate (25 mg, 0.073 mmol) was added to a stirred mixture of 4,6-dichloroquinoline-3-carbonitrile (16.24 mg, 0.073 mmol) and DIEA (0.051 mL, 0.291 mmol) in DMF (1 mL) and the mixture was stirred at 30° C. for 16 h. Poured the mixture was poured into 10 mL cold water and extracted with EtOAc (3×8 mL). The combined organic layers were dried over $Na_2SO_4$, filtered and concentrated. The residue was purified by prep-HPLC to give the title compound Human CYP8B1 IC50 (nM) 0.29. MS: 530 (M+1).

The following compounds were made in a similar way to Example 75c substituting the appropriate reactants and reagents.

TABLE 15

| Example | Structure | Chemical Name | Exact Mass [M + H]+ | Human CYP8B1 IC50 (nM) |
|---|---|---|---|---|
| 76d | 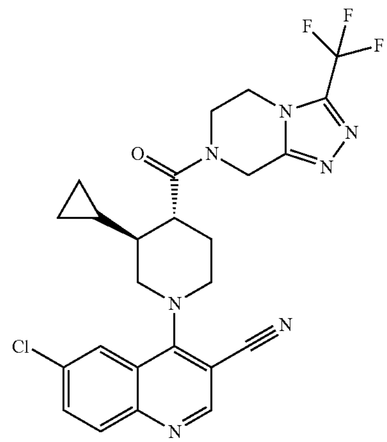 [SMILES: N#Cc1cnc2ccc(Cl)cc2c1N1CC[C@@H](C(=O)N2CCn3c(nnc3C(F)(F)F)C2)[C@H](C2CC2)C1] | 6-chloro-4-[(3S,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 530 | 2649 |
| 77b | 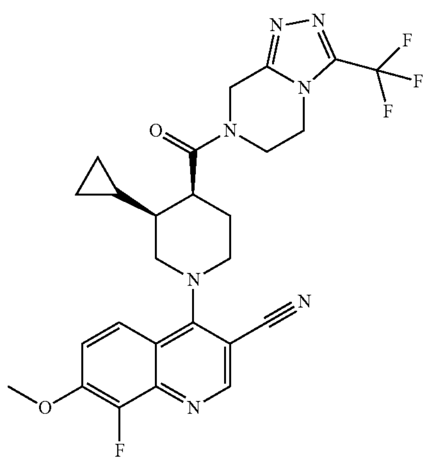 [SMILES: COc1ccc2c(N3CC[C@H](C(=O)N4CCn5c(nnc5C(F)(F)F)C4)[C@H](C4CC4)C3)c(C#N)cnc2c1F] | 4-[(3S,4S)-3-cyclopropyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile | 544 | 1.8 |

Example 78

7-(1,1-difluoroethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile

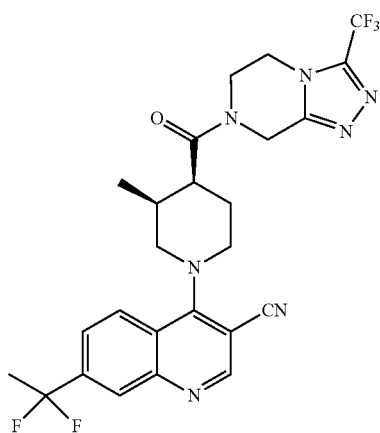 [SMILES: C[C@@H]1CN(c2c(C#N)cnc3cc(C(C)(F)F)ccc23)CC[C@@H]1C(=O)N1CCn2c(nnc2C(F)(F)F)C1]

A mixture of {(3S,4S)-1-[3-bromo-7-(1,1-difluoroethyl)quinolin-4-yl]-3-methylpiperidin-4-yl}[3-(trifluoromethyl)-5,6-dihydro[1,2,4]triazolo[4,3-a]pyrazin-7(8H)-yl]methanone (50 mg, 0.085 mmol) and coppercyanide (15.25 mg, 0.170 mmol) in NMP (0.5 mL) was stirred at 180° C. for 90 min in a sealed tube. The mixture was diluted with NH₄OH (10%, 30 mL) and extracted with EtOAc (15 Ml×3). The organic layer was washed with brine (15 mL), dried over Na₂SO₄, filtered and concentrated. The residue was purified by p-HPLC (water (10 mM NH₄HCO₃)-MeCN) to afford the title compound (Human CYP8B1 IC50 (nM) 1.0). MS: 534 (M+1).

Example 79

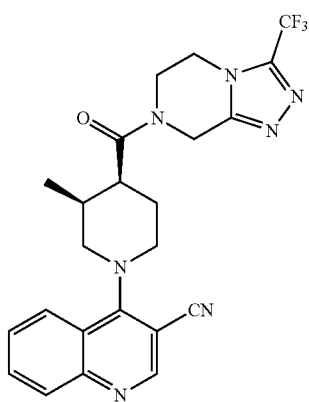 [SMILES: C[C@@H]1CN(c2c(C#N)cnc3ccccc23)CC[C@@H]1C(=O)N1CCn2c(nnc2C(F)(F)F)C1]

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile A mixture of 6-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (35 mg, 0.07 mmol), ammonium formate (6.6 mg, 0.1 mmol) and Pd—C (0.75 mg, 0.007 mmol) in ethyl acetate (0.1 mL) and MeOH (0.1 mL) was heated at 80° C. for 15 min. The mixture was filtered and washed with MeOH (20 mL). The filtrate was concentrated in vacuo. The residue was purified by p-HPLC (water (10 mM NH$_4$HCO$_3$)-MeCN) to give the title compound (Human CYP8B1 IC50 (nM) 1.6). MS: 470 (M+1).

Example 80

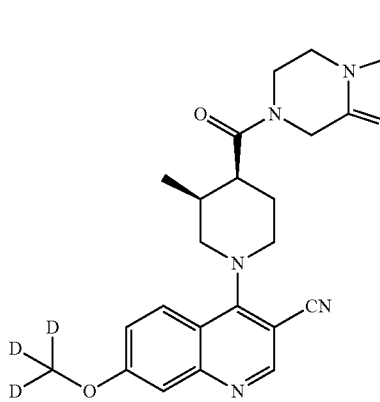

7-[($^2$H$_3$)methyloxy]-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile To a stirred solution of 7-hydroxy-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (50 mg, 0.103 mmol) and ($^2$H$_3$)methyl 4-methylbenzenesulfonate (21.44 mg, 0.113 mmol) in DMF (515 μL) was added Cs$_2$CO$_3$ (101 mg, 0.309 mmol), followed by the addition Bu$_4$N$^+$I$^-$ (3.80 mg, 10.30 μmol). After stirring at 40° C. for 3 h under nitrogen the mixture was partitioned between water (50 mL) and EtOAc (30 mL). The aqueous layer was extracted with EtOAc (30 mL*3). The combined extracts were dried over Na$_2$SO$_4$, filtered and concentrated in vacuo. The residue was purified by p-TLC (DCM:MeOH=10:1), then purified by p-HPLC (water (0.1% TFA)-MeCN) to give the title compound (Human CYP8B1 IC50 (nM) 0.35). MS: 503 (M+1).

Examples 81a and 81b

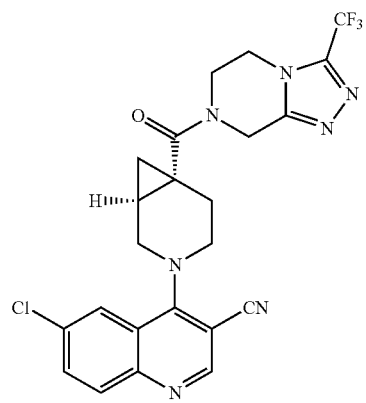

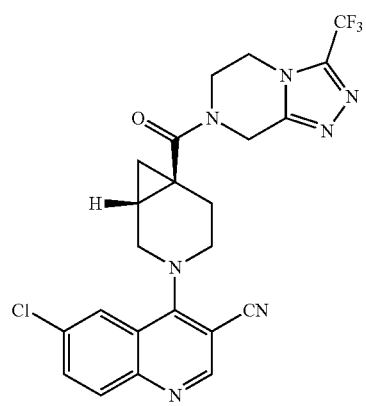

6-chloro-4-((1S,6R)-6-(3-(trifluoromethyl)-5,6,7,8-tetrahydro-[1,2,4]triazolo[4,3-a]pyrazine-7-carbonyl)-3-azabicyclo[4.1.0]heptan-3-yl)quinoline-3-carbonitrile 6-chloro-4-((1R,6S)-6-(3-(trifluoromethyl)-5,6,7,8-tetrahydro-[1,2,4]triazolo[4,3-a]pyrazine-7-carbonyl)-3-azabicyclo[4.1.0]heptan-3-yl)quinoline-3-carbonitrile HATU (490 mg, 1.3 mmol) followed by DIPEA (450 μl, 2.6 mmol) was added to a stirred solution of 3-(6-chloro-3- cyanoquinolin-4-yl)-3-azabicyclo[4.1.0]heptane-6-carboxylic acid (280 mg, 0.86 mmol) and 3-(trifluoromethyl)-5,6,7,8-tetrahydro-[1,2,4]triazolo[4,3-a]pyrazine hydrochloride (240 mg, 1.0 mmol) in DMF (4.3 mL) at room temperature. The resulting mixture was stirred at room temperature for 15 hours, then diluted with water and extracted with EtOAc (3×). The combined organic layers were washed with water (2×) and brine, then dried with $Na_2SO_4$, filtered and concentrated. The residue was purified by MPLC (24 g $SiO_2$; 0→100% [(3:1) EtOH:EtOAc]:hexanes) to provide racemic product. MS: 502 (M+1). The racemic product was further resolved by SFC (Column Whelk O(S,S) (2×25 cm) 45% (2:1) iPOH:MeCN (0.1% $NH_4OH)/CO_2$) to provide 6-chloro-4-((1S,6R)-6-(3-(trifluoromethyl)-5,6,7,8-tetrahydro-[1,2,4]triazolo[4,3-a]pyrazine-7-carbonyl)-3-azabicyclo[4.1.0]heptan-3-yl)quinoline-3-carbonitrile (peak 1, SFC $t_R$=4.38 min) (Human CYP8B1 IC50 (nM) 1288). MS: 502 (M+1) and 6-chloro-4-((1R,6S)-6-(3-(trifluoromethyl)-5,6,7,8-tetrahydro-[1,2,4]triazolo[4,3-a]pyrazine-7-carbonyl)-3-azabicyclo[4.1.0]heptan-3-yl)quinoline-3-carbonitrile (peak 2, SFC $t_R$=5.29 min) (Human CYP8B1 IC50 (nM) 1926). MS: 502 (M+1).

Example 82

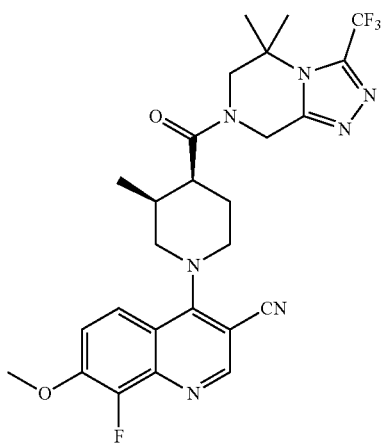 [SMILES: COc1ccc2c(N3CC[C@H](C(=O)N4Cc5nnc(C(F)(F)F)n5C(C)(C)C4)[C@H](C)C3)c(C#N)cnc2c1F]

4-((3S,4S)-4-(5,5-dimethyl-3-(trifluoromethyl)-5,6,7,8-tetrahydro-[1,2,4]triazolo[4,3-a]pyrazine-7-carbonyl)-3-methylpiperidin-1-yl)-8-fluoro-7-methoxyquinoline-3-carbonitrile HATU (22 mg, 0.057 mmol) and TEA (0.018 ml, 0.13 mmol) were added to (3S,4S)-1-(3-cyano-8-fluoro-7-methoxyquinolin-4-yl)-3-methylpiperidine-4-carboxylic acid (15 mg, 0.044 mmol) and 5,5-dimethyl-3-(trifluoromethyl)-5,6,7,8-tetrahydro-[1,2,4]triazolo[4,3-a]pyrazine (11 mg, 0.048 mmol) in THF (1 mL). The mixture was stirred at room temperature for 3 h, then concentrated and purified by MPLC (12 g SiO2; 0→100% hexanes: (3:1 EtOAc:EtOH)) to provide 4-((3S,4S)-4-(5,5-dimethyl-3-(trifluoromethyl)-5,6,7,8-tetrahydro-[1,2,4]triazolo[4,3-a]pyrazine-7-carbonyl)-3-methylpiperidin-1-yl)-8-fluoro-7-methoxyquinoline-3-carbonitrile. Human CYP8B1 IC50 (nM) 58. MS: 545 (M+1).

Example 83a

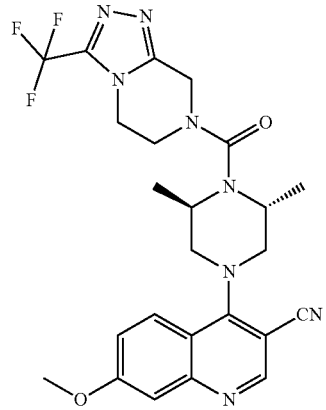 [SMILES: COc1ccc2c(N3C[C@@H](C)N(C(=O)N4CCn5c(nnc5C(F)(F)F)C4)[C@H](C)C3)c(C#N)cnc2c1]

4-((3R,5R)-3,5-dimethyl-4-(3-(trifluoromethyl)-5,6,7,8-tetrahydro-[1,2,4]triazolo[4,3-a]pyrazine-7-carbonyl)piperazin-1-yl)-7-methoxyquinoline-3-carbonitrile To a solution of 4-chloro-7-methoxyquinoline-3-carbonitrile (80 mg, 0.366 mmol) and (2R,6R)-2,6-dimethylpiperazine, HCl (71.7 mg, 0.476 mmol) in DMF (2 ml) was added $K_2CO_3$ (152 mg, 1.098 mmol). The mixture was heated to 70° C. and stirred overnight. The mixture was filtered through a pad of CELITE to remove the solids. After washing the CELITE pad with DCM, the combined filtrates were evaporated in vacuo to remove the volatiles. The residue was purified by column chromatography on silica gel, eluting with 0-5% MeOH in DCM to give 4-((3R,5R)-3,5-dimethylpiperazin-1-yl)-7-methoxyquinoline-3-carbonitrile (96 mg, 0.324 mmol).

Triphosgene (36.5 mg, 0.123 mmol) was added to a solution of 4-((3R,5R)-3,5-dimethylpiperazin-1-yl)-7-methoxyquinoline-3-carbonitrile (96 mg, 0.324 mmol) and Py (0.105 ml, 1.296 mmol) in DCM (3 ml) at 0° C. The mixture was stirred at 0° C. for 30 min, then warmed to room temperature and stirred for 1 h, followed by the addition of 3-(trifluoromethyl)-5,6,7,8-tetrahydro-[1,2,4]triazolo[4,3-a]pyrazine, HCl (104 mg, 0.453 mmol) and DIPEA (0.226 ml, 1.296 mmol). The mixture was heated to 40° C. and stirred for 2 h and concentrated in vacuo. The residue was purified by column chromatography on silica gel, eluting with 0-5% MeOH in DCM to give, as a solid, 4-((3R,5R)-3,5-dimethyl-4-(3-(trifluoromethyl)-5,6,7,8-tetrahydro-[1,2,4]triazolo[4,3-a]pyrazine-7-carbonyl)piperazin-1-yl)-7-methoxyquinoline-3-carbonitrile (Human CYP8B1 IC50 (nM) 11.3). MS: 515 (M+1)

Examples 82b was made using a similar synthesis to Example 81a substituting the appropriate reactants and reagents.

TABLE 16

| Example | Structure | Chemical Name | Exact Mass [M + H]+ | Human CYP8B1 IC50 (nM) |
|---|---|---|---|---|
| 83b | 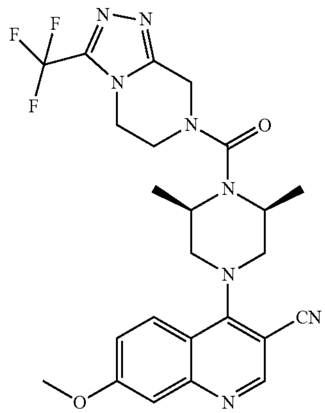 [SMILES: COc1ccc2c(N3C[C@@H](C)N(C(=O)N4CCn5c(nnc5C(F)(F)F)C4)[C@@H](C)C3)c(C#N)cnc2c1] | 4-((3S,5R)-3,5-dimethyl-4-(3-(trifluoromethyl)-5,6,7,8-tetrahydro-[1,2,4]triazolo[4,3-a]pyrazine-7-carbonyl)piperazin-1-yl)-7-methoxyquinoline-3-carbonitrile | 515 | 987 |

Example 84

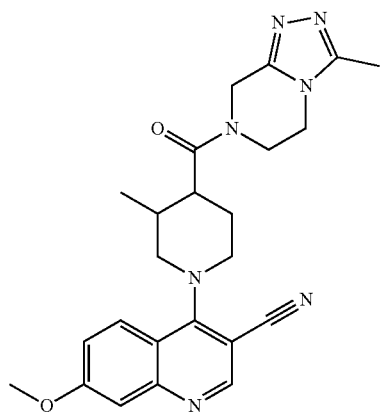

7-methoxy-4-{3-methyl-4-[(3-methyl-5,6-dihydro[1,2,4]triazolo[4,3-a]pyrazin-7(8H)-yl)carbonyl]piperidin-1-yl}quinoline-3-carbonitrile A microwave tube was charged with 4-chloro-7-methoxy-quinoline-3-carbonitrile (60 mg, 0.274 mmol), 3-methylpiperidine-4-carboxylic acid (51.1 mg, 0.357 mmol), DIPEA (0.240 ml, 1.372 mmol) and DMF (3 ml). The reaction was microwaved at 100° C. for 45 min and cooled to room temperature. 3-methyl-5,6,7,8-tetrahydro-[1,2,4]triazolo[4,3-a]pyrazine (60.7 mg, 0.439 mmol) and HATU (167 mg, 0.439 mmol) were added. The mixture was stirred at room temperature overnight. The residue was concentrated and was purified by column chromatography on silica gel, eluting with 0-5% MeOH in DCM to give the title compound (Human CYP8B1 IC50 (nM) 3.3). MS: 446 (M+1l).

Example 85

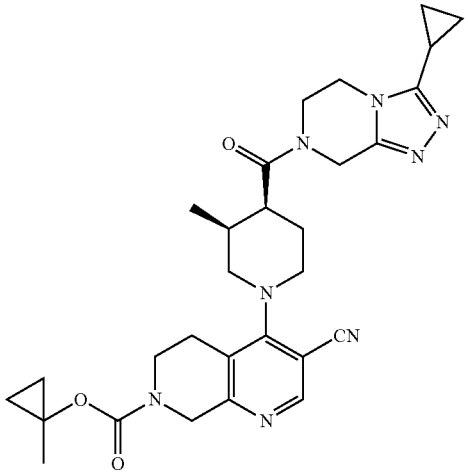 [SMILES: C[C@@H]1CN(c2c(C#N)cnc3c2CCN(C(=O)OC2(C)CC2)C3)CC[C@@H]1C(=O)N1CCn2c(nnc2C2CC2)C1]

1-methylcyclopropyl 3-cyano-4-((3S,4S)-4-(3-cyclopropyl-5,6,7,8-tetrahydro-[1,2,4]triazolo[4,3-a]pyrazine-7-carbonyl)-3-methylpiperidin-1-yl)-5,6-dihydro-1,7-naphthyridine-7(8H)-carboxylate Second generation RuPhos precatalyst (115 mg, 0.148 mmol) was added to a solution of (3S,4S)-tert-butyl 3-methylpiperidine-4-carboxylate, HCl (418 mg, 1.774 mmol), tert-butyl 4-bromo-3-cyano-5,6-dihydro-1,7-naphthyridine-7(8H)-carboxylate (500 mg, 1.478 mmol) and $Cs_2CO_3$ (1445 mg, 4.44 mmol) in 1,4-Dioxane (6 ml). The mixture was heated to 80° C. and stirred overnight and concentrated in vacuo. The residue was purified by column chromatography on silica gel, eluting with 0-5% MeOH in DCM to give, as a solid, tert-butyl 4-((3S,4S)-4-(tert-butoxycarbonyl)-3-methylpiperidin-1-yl)-3-cyano-5,6-dihydro-1,7-naphthyridine-7(8H)-carboxylate.

TFA (1 ml, 12.98 mmol) was added to a solution of tert-butyl 4-((3S,4S)-4-(tert-butoxycarbonyl)-3-methylpiperidin-1-yl)-3-cyano-5,6-dihydro-1,7-naphthyridine-7(8H)-carboxylate (88 mg, 0.193 mmol) in DCM (2 ml). The mixture was stirred at room temperature for 2 h and concentrated in vacuo. The residue was dissolved in THF (2 mL) and $Et_3N$ (0.107 ml, 0.771 mmol), followed by addition of 2,5-dioxopyrrolidin-1-yl (1-methylcyclopropyl) carbonate (61.6 mg, 0.289 mmol) and stirred at room temperature overnight and concentrated in vacuo. The residue was purified by preparative TLC, eluting with MeOH/Acetic Acid/DCM (4/1/95), to give, a solid, (3S,4S)-1-(3-cyano-7-((1-methylcyclopropoxy)carbonyl)-5,6,7,8-tetrahydro-1,7-naphthyridin-4-yl)-3-methylpiperidine-4-carboxylic acid. MS: 399 (M+11).

HATU (25.8 mg, 0.068 mmol) was added to a solution of (3S,4S)-1-(3-cyano-7-((1-methylcyclopropoxy)carbonyl)-5,6,7,8-tetrahydro-1,7-naphthyridin-4-yl)-3-methylpiperidine-4-carboxylic acid (18 mg, 0.045 mmol), 3-cyclopropyl-5,6,7,8-tetrahydro-[1,2,4]triazolo[4,3-a]pyrazine, Oxalic acid (17.23 mg, 0.068 mmol) and DIPEA (0.024 ml, 0.136 mmol) in tetrahydrofuran (2 ml). The mixture was heated to 50° C. and stirred for 2 h and concentrated in vacuo. The residue was purified by preparative TLC, eluting with 5% MeOH/DCM, to give 1-methylcyclopropyl 3-cyano-4-((3S,4S)-4-(3-cyclopropyl-5,6,7,8-tetrahydro-[1,2,4]triazolo[4,3-a]pyrazine-7-carbonyl)-3-methylpiperidin-1-yl)-5,6-dihydro-1,7-naphthyridine-7(8H)-carboxylate (Human CYP8B1 IC50 (nM) 2.0). MS: 545 (M+11).

Example 86

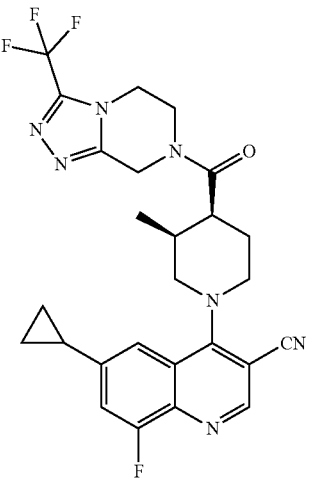 [SMILES: C[C@@H]1CN(c2c(C#N)cnc3c(F)cc(C4CC4)cc23)CC[C@@H]1C(=O)N1CCn2c(nnc2C(F)(F)F)C1]

6-cyclopropyl-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile DIPEA (0.367 ml, 2.102 mmol) was added to a solution of 6-bromo-4-chloro-8-fluoroquinoline-3-carbonitrile (200 mg, 0.701 mmol) and ((3S,4S)-3-methylpiperidin-4-yl)(3-(trifluoromethyl)-5,6-dihydro-[1,2,4]triazolo[4,3-a]pyrazin-7(8H)-yl)methanone, HCl (248 mg, 0.701 mmol) in DMF (3 ml). The mixture was heated to 80° C. and stirred for 3 h. The mixture was worked up with water, extracted with ethyl acetate, dried over Na₂SO₄, filtered and concentrated in vacuo. The residue was purified by column chromatography on silica gel, eluting with 0-5% MeOH/DCM to give 6-bromo-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile.

A microwave tube was charged with 6-bromo-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (30 mg, 0.053 mmol), cyclopropylzinc(II) bromide (0.318 ml, 0.159 mmol), THF (1 ml) and Ph₃P precat (6.06 mg, 10.59 µmol) and heated to 60° C. and stirred overnight. The mixture was worked up with saturated NH₄Cl, extracted with ethyl acetate, dried over Na₂SO₄, filtered and concentrated in vacuo. The residue was purified by preparative TLC, eluting with 4% MeOH/DCM, to give the free form product which was dissolved in 2 ml MeOH. 1 ml 1N HCl in ether was added and the mixture was stirred at room temperature for 20 min. The mixture was concentrated in vacuo to give the solid 6-cyclopropyl-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile, HCl (Human CYP8B1 IC50 (nM) 0.4). MS: 528 (M+11).

Example 86 was made using a similar synthesis to Example 85 substituting the appropriate reactants and reagents.

TABLE 17

| Example | Structure | Chemical Name | Exact Mass [M + H]+ | Human CYP8B1 IC50 (nM) |
|---|---|---|---|---|
| 87 | 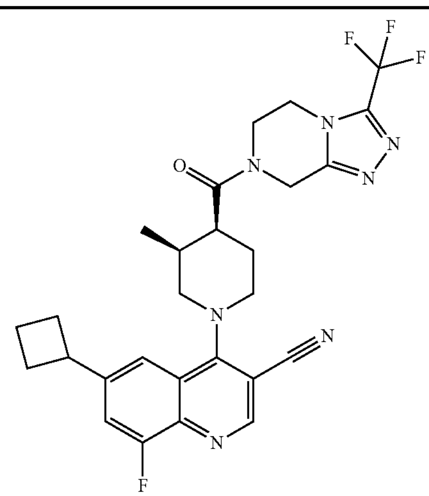 | 6-cyclobutyl-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile | 542 | 0.3 |

Example 88

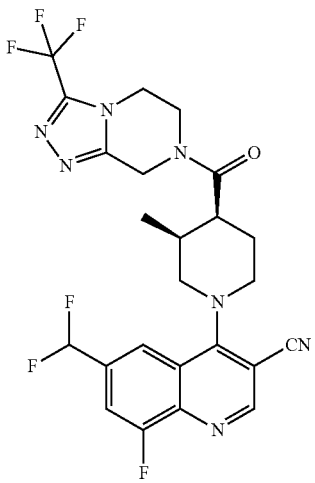 [SMILES: C[C@@H]1CN(c2c(C#N)cnc3c(F)cc(C(F)F)cc23)CC[C@@H]1C(=O)N1CCn2c(nnc2C(F)(F)F)C1]

6-(difluoromethyl)-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile A microwave tube was charged with 6-bromo-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (100 mg, 0.177 mmol), tributyl (vinyl)tin (0.077 ml, 0.265 mmol), Pd(Ph$_3$P)$_4$ (30.6 mg, 0.026 mmol) and 1,4-Dioxane (1.5 ml). The mixture was microwaved at 150° C. for 30 min. The mixture was filtrated through a pad of the CELITE to remove solids which were washed with ethyl acetate. The combined filtrate was concentrated in vacuo. The residue was purified by column chromatography on silica gel, eluting with 0-3% MeOH/DCM to give the solid 8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-6-vinylquinoline-3-carbonitrile.

Water (200 µL), osmium(VIII) oxide (2.5% in t-BuOH) (0.036 ml, 3.51 µmol), 2,6-dimethylpyridine (0.033 ml, 0.280 mmol) and sodium periodate (120 mg, 0.561 mmol) was sequentially added to a solution of 8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-6-vinylquinoline-3-carbonitrile (72 mg, 0.140 mmol) in 1,4-Dioxane (1 ml). The reaction mixture was stirred for 2 h at room temperature, quenched by adding H2O (20 mL), and extracted two times with DCM (2×20 mL). The combined organic layers were dried over MgSO, concentrated, and purified by silica gel chromatography (hexanes/EtOAc 100:0 to 50:50 gradient) to afford 8-fluoro-6-formyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile. MS: 516 (M+1).

DAST (0.037 ml, 0.283 mmol) was added to a solution of 8-fluoro-6-formyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (73 mg, 0.142 mmol) in DCM (1.5 ml). The mixture was stirred at room temperature overnight and concentrated in vacuo. The residue was purified by preparative TLC, eluting with 4% MeOH/DCM, to give solid 6-(difluoromethyl)-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (Human CYP8B1 IC50 (nM) 0.7). MS: 538 (M+1).

Example 89

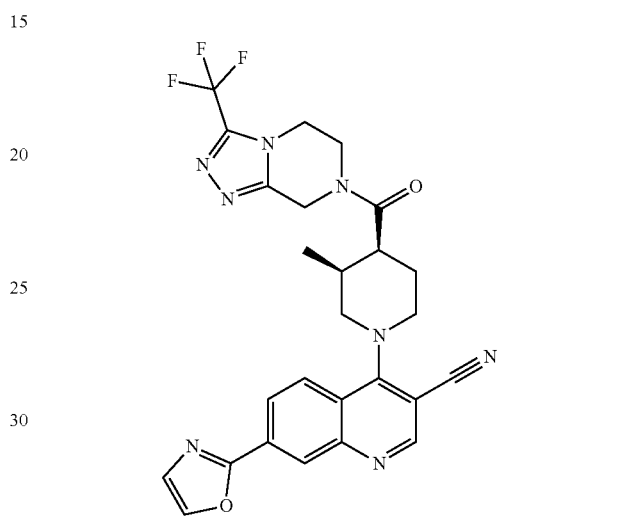

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-(oxazol-2-yl)quinoline-3-carbonitrile DIPEA (0.588 ml, 3.36 mmol) was added to a solution of 7-bromo-4-chloroquinoline-3-carbonitrile (300 mg, 1.121 mmol) in DMF (2 ml). ((3S,4S)-3-methylpiperidin-4-yl)(3-(trifluoromethyl)-5,6-dihydro-[1,2,4]triazolo[4,3-a]pyrazin-7(8H)-yl)methanone and HCl (417 mg, 1.178 mmol) were added to the mixture. The mixture was heated to 60° C. and stirred overnight. The mixture was then cooled to room temperature. Water (15 mL) was added and stirred for 5 min. The filtration collected a solid which was washed with extra water and dried over high vacuo to give 7-bromo-4-((3S, 4S)-3-methyl-4-(3-(trifluoromethyl)-5,6,7,8-tetrahydro-[1, 2,4]triazolo[4,3-a]pyrazine-7-carbonyl)piperidin-1-yl)quinoline-3-carbonitrile.

A solution of 7-bromo-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (40 mg, 0.073 mmol) and 2-(tributylstannyl)oxazole (0.023 ml, 0.109 mmol) in 1,4-Dioxane (1 ml) was microwaved at 150° C. for 20 min and concentrated in vacuo. The residue was purified by column chromatography on silica gel, eluting with 0-3% MeOH in DCM to give 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-(oxazol-2-yl)quinoline-3-carbonitrile (Human CYP8B1 IC50 (nM) 0.4). MS: 537 (M+1).

Example 90

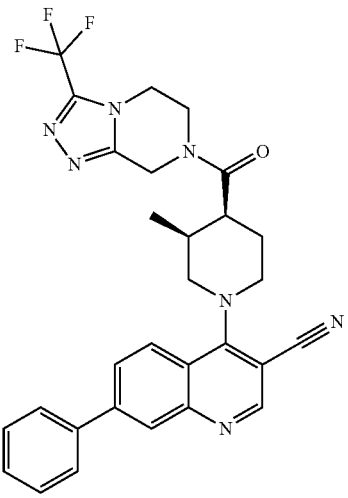 [SMILES: C[C@@H]1CN(c2c(C#N)cnc3cc(-c4ccccc4)ccc23)CC[C@@H]1C(=O)N1CCn2c(nnc2C(F)(F)F)C1]

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-phenylquinoline-3-carbonitrile To a microwave tube was charged with 7-bromo-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (40 mg, 0.073 mmol), phenylboronic acid pinacol ester (22.33 mg, 0.109 mmol), DTBPF $PdCl_2$ (7.13 mg, 10.94 µmol), $Cs_2CO_3$ (47.5 mg, 0.146 mmol), 1,4-dioxane (1.5 ml) and water (100 µL). The mixture was heated to 80° C., stirred overnight and concentrated in vacuo. The residue was purified by column chromatography on silica gel, eluting with 0-3% MeOH/DCM to give 4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-phenylquinoline-3-carbonitrile (Human CYP8B1 IC50 (nM) 0.2). MS: 546 (M+1)

Example 91

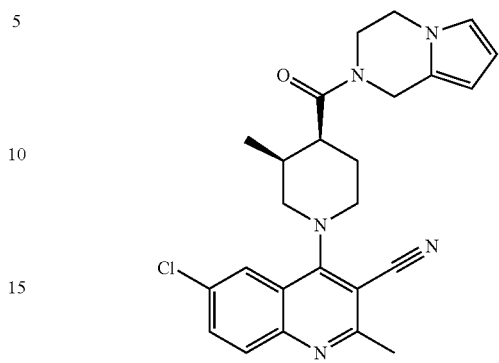

6-chloro-4-[(3S,4S)-4-(3,4-dihydropyrrolo[1,2-a]pyrazin-2(1H)-ylcarbonyl)-3-methylpiperidin-1-yl]-2-methylquinoline-3-carbonitrile (3S,4S)-1-(6-chloro-3-cyano-2-methylquinolin-4-yl)-3-methylpiperidine-4-carboxylic acid (8 mg, 0.023 mmol) in DMF (1 ml), followed by addition of $Et_3N$ (0.013 ml, 0.093 mmol) and HATU (17.70 mg, 0.047 mmol) in DMF (0.2 mL) was added to one drum vail containing 3-(trifluoromethyl)-4,5,6,7-tetrahydro-2H-pyrazolo[4,3-c]pyridine (0.070 mmol) and shaken at room temperature for 16 hours. Crude materials were filtered and purified by HPLC. [column: Waters XBridge C18, or Waters Sunfire C18, 5 µm, solvent: MeCN (with 5 mM Ammonium Ammonium Bicarbonate) in water (with 5 mM Ammonium Bicarbonate)] to afford 6-chloro-2-methyl-4-[(3S,4S)-3-methyl-4-{[3-(trifluoromethyl)-2,4,6,7-tetrahydro-5H-pyrazolo[4,3-c]pyridin-5-yl]carbonyl}piperidin-1-yl]quinoline-3-carbonitrile (Human CYP8B1 IC50 (nM) 5.8). MS: 448 (M+1).

Examples 91-98 was made using a similar synthesis to Example 90 substituting the appropriate reactants and reagents.

TABLE 18

| Examples | Structure | Chemical Name | Exact Mass [M + H]+ | Human CYP8B1 IC50 (nM) |
|---|---|---|---|---|
| 92 | 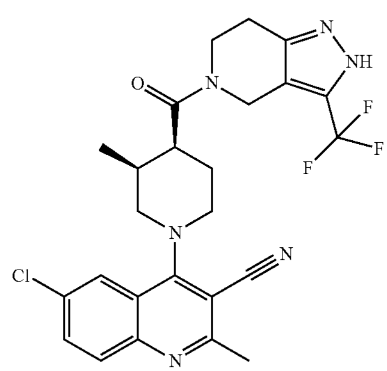 [SMILES: Cc1nc2ccc(Cl)cc2c(N2CC[C@H](C(=O)N3CCc4n[nH]c(C(F)(F)F)c4C3)[C@H](C)C2)c1C#N] | 6-chloro-2-methyl-4-[(3S,4S)-3-methyl-4-{[3-(trifluoromethyl)-2,4,6,7-tetrahydro-5H-pyrazolo[4,3-c]pyridin-5-yl]carbonyl}piperidin-1-yl]quinoline-3-carbonitrile | 517 | 35 |

TABLE 18-continued

| Examples | Structure | Chemical Name | Exact Mass [M + H]+ | Human CYP8B1 IC50 (nM) |
|---|---|---|---|---|
| 93 | 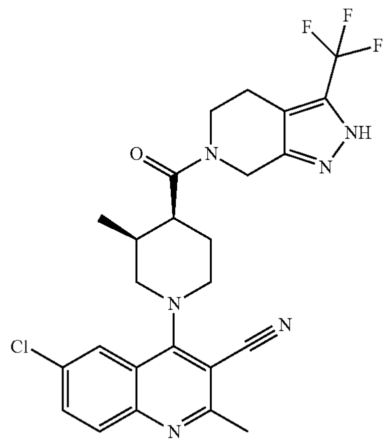 [SMILES: Cc1nc2ccc(Cl)cc2c(N2CC[C@H](C(=O)N3CCc4c(n[nH]c4C(F)(F)F)C3)[C@H](C)C2)c1C#N] | 6-chloro-2-methyl-4-[(3S,4S)-3-methyl-4-{[3-(trifluoromethyl)-2,4,5,7-tetrahydro-6H-pyrazolo[3,4-c]pyridin-6-yl]carbonyl}piperidin-1-yl]quinoline-3-carbonitrile | 517 | 28 |
| 94 | 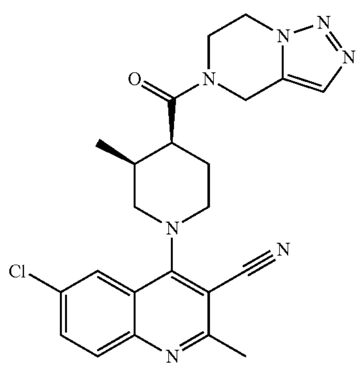 [SMILES: Cc1nc2ccc(Cl)cc2c(N2CC[C@H](C(=O)N3CCn4nncc4C3)[C@H](C)C2)c1C#N] | 6-chloro-4-[(3S,4S)-4-(6,7-dihydro[1,2,3]triazolo[1,5-a]pyrazin-5-(4H)-ylcarbonyl)-3-methylpiperidin-1-yl]-2-methylquinoline-3-carbonitrile | 504 | 4503 |
| 95 | 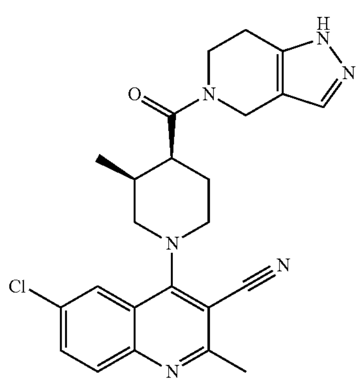 [SMILES: Cc1nc2ccc(Cl)cc2c(N2CC[C@H](C(=O)N3CCc4[nH]ncc4C3)[C@H](C)C2)c1C#N] | 6-chloro-2-methyl-4-[(3S,4S)-3-methyl-4-(1,4,6,7-tetrahydro-5H-pyrazolo[4,3-c]pyridin-5-ylcarbonyl)piperidin-1-yl]quinoline-3-carbonitrile | 449 | 17 |
| 96 | 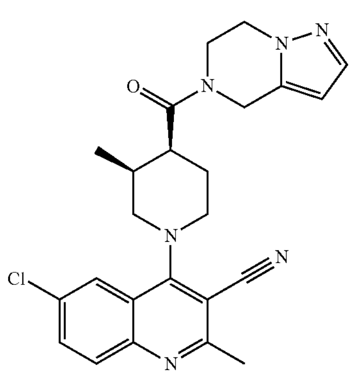 [SMILES: Cc1nc2ccc(Cl)cc2c(N2CC[C@H](C(=O)N3CCn4nccc4C3)[C@H](C)C2)c1C#N] | 6-chloro-4-[(3S,4S)-4-(6,7-dihydropyrazolo[1,5-a]pyrazin-5(4H)-ylcarbonyl)-3-methylpiperidin-1-yl]-2-methylquinoline-3-carbonitrile | 449 | 8.6 |

TABLE 18-continued

| Examples | Structure | Chemical Name | Exact Mass [M + H]+ | Human CYP8B1 IC50 (nM) |
|---|---|---|---|---|
| 97 | 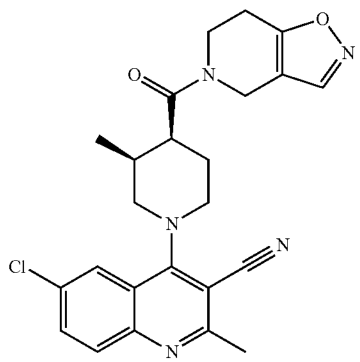 [SMILES: Cc1nc2ccc(Cl)cc2c(N2CC[C@H](C(=O)N3CCc4oncc4C3)[C@H](C)C2)c1C#N] | 6-chloro-4-[(3S,4S)-4-(6,7-dihydroisoxazolo[4,5-c]pyridin-5(4H)-ylcarbonyl)-3-methylpiperidin-1-yl]-2-methylquinoline-3-carbonitrile | 450 | 4.2 |
| 98 | 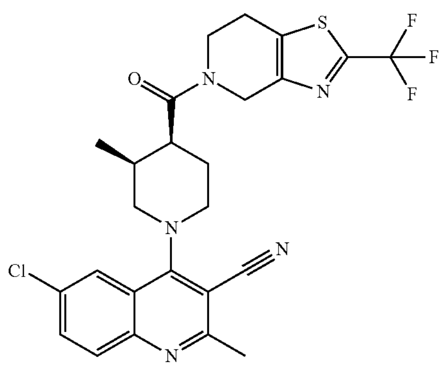 [SMILES: Cc1nc2ccc(Cl)cc2c(N2CC[C@H](C(=O)N3CCc4sc(C(F)(F)F)nc4C3)[C@H](C)C2)c1C#N] | 6-chloro-2-methyl-4-[(3S,4S)-3-methyl-4-{[2-(trifluoromethyl)-6,7-dihydro[1,3]thiazolo[4,5-c]pyridin-5(4H)-yl]carbonyl}piperidin-1-yl]quinoline-3-carbonitrile | 534 | 19 |
| 99 | 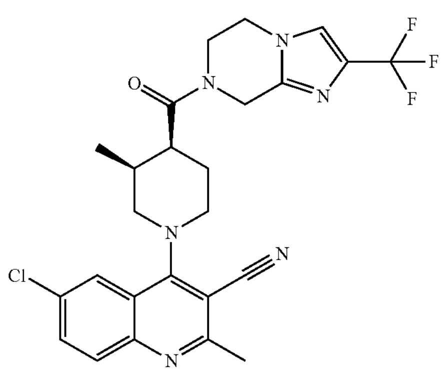 [SMILES: Cc1nc2ccc(Cl)cc2c(N2CC[C@H](C(=O)N3CCn4cc(C(F)(F)F)nc4C3)[C@H](C)C2)c1C#N] | 6-chloro-2-methyl-4-[(3S,4S)-3-methyl-4-{[2-(trifluoromethyl)-5,6-dihydroimidazo[1,2-a]pyrazin-7(8H)-yl]carbonyl}piperidin-1-yl]quinoline-3-carbonitrile | 517 | 52 |

Example 100

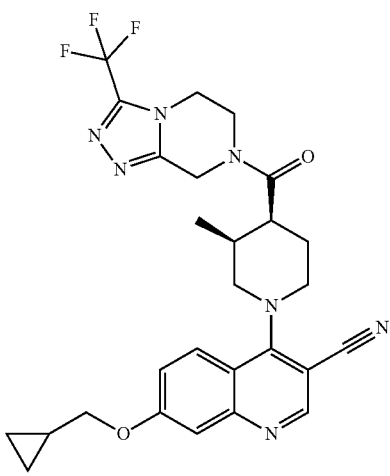 [SMILES: C[C@@H]1CN(c2c(C#N)cnc3cc(OCC4CC4)ccc23)CC[C@@H]1C(=O)N1CCn2c(nnc2C(F)(F)F)C1]

7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 7-hydroxy-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (650 mg, 1.34 mmol), cesium carbonate (654 mg, 2.01 mmol), (bromomethyl)cyclopropane (0.195 mL, 2.01 mmol), and DMF (6.7 mL) were combined in a sealed tube. The reaction was heated to 70° C. for 1 h. The reaction was cooled to room temperature, filtered and purified by reverse phase HPLC (10-100% MeCN in water, with 0.05% TFA). The combined fractions were neutralized with saturated sodium bicarbonate and extracted with EtOAc (2×). The combined organic layers were washed with water (1×). The organic layer was dried with magnesium sulfate, filtered and concentrated to give the title compound. MS: 540 (M+1). Human CYP8B1 IC50 (nM) 0.35.

The following compounds were made in a similar way to Example 100 substituting the appropriate reactants and reagents.

TABLE 19

| Example | Structure | Chemical Name | Exact Mass [M + H]+ | Human CYP8B1 IC50 (nM) |
|---|---|---|---|---|
| 101 | 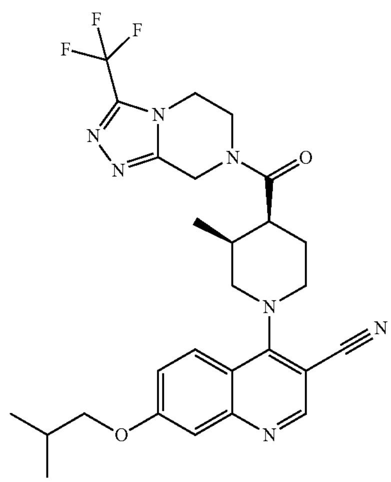 [SMILES: CC(C)COc1ccc2c(N3CC[C@H](C(=O)N4CCn5c(nnc5C(F)(F)F)C4)[C@H](C)C3)c(C#N)cnc2c1] | 7-(2-methylpropoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 542 | 0.33 |
| 102 | 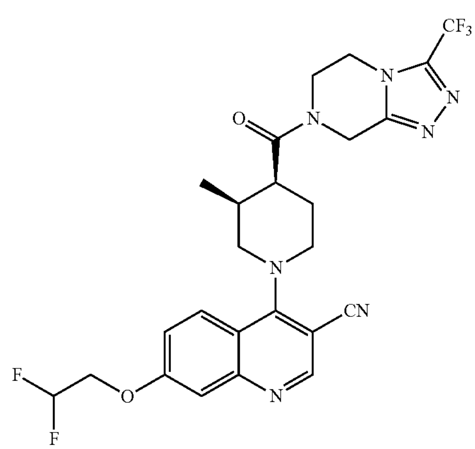 [SMILES: C[C@@H]1CN(c2c(C#N)cnc3cc(OCC(F)F)ccc23)CC[C@@H]1C(=O)N1CCn2c(nnc2C(F)(F)F)C1] | 7-(2,2-difluoroethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 550 | 0.33 |

Example 103

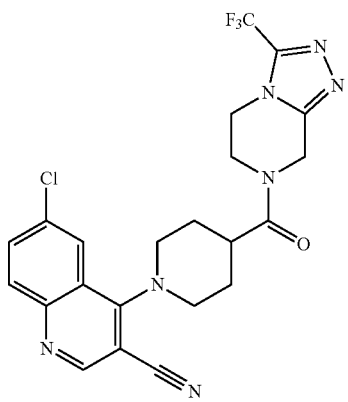 [SMILES: N#Cc1cnc2ccc(Cl)cc2c1N1CCC(C(=O)N2CCn3c(nnc3C(F)(F)F)C2)CC1]

6-chloro-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile Anhydrous DMF and N-ethyl-N-isopropylpropan-2-amine (20.88 mg, 0.162 mmol) were added to a mixture of HATU (28.7 mg, 0.075 mmol), HOAT (10.3 mg, 0.075 mmol), 1-(6-chloro-3-cyanoquinolin-4-yl)piperidine-4-carboxylic acid (17 mg, 0.054 mmol) and 3-(trifluoromethyl)-5,6,7,8-tetrahydro-[1,2,4]triazolo[4,3-a]pyrazine (12.3 mg, 0.054 mmol). The mixture was stirred at room temperature for 6 hours. The reaction mixture was poured into 10 ml NaHCO$_3$ aqueous solution, and the resulting suspension was stirred for 1 hour. The mixture was filtered and the filter cake was washed with water, and dried to afford the title compound.

MS: 490 (M+1). Human CYP8B1 IC$_{50}$ (nM) 23.2.

Examples 104-115 were made using a similar synthesis to Example 103 substituting the appropriate reactants and reagents.

TABLE 20

| Example | Structure | Chemical Name | Exact Mass [M + H]+ | Human CYP8B1 IC50 (nM) |
|---|---|---|---|---|
| 104 | 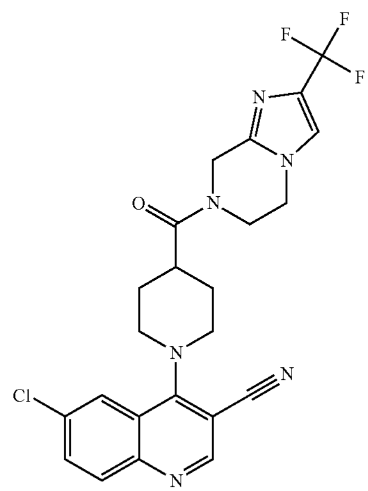 [SMILES: N#Cc1cnc2ccc(Cl)cc2c1N1CCC(C(=O)N2CCn3cc(C(F)(F)F)nc3C2)CC1] | 6-chloro-4-(4-{[2-(trifluoromethyl)-5,6-dihydroimidazo[1,2-a]pyrazin-7(8H)-yl]carbonyl}piperidin-1-yl)quinoline-3-carbonitrile | 489 | 863.2 |
| 105 | 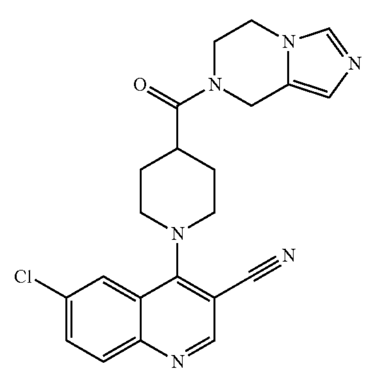 [SMILES: N#Cc1cnc2ccc(Cl)cc2c1N1CCC(C(=O)N2CCn3cncc3C2)CC1] | 6-chloro-4-[4-(5,6-dihydroimidazo[1,5-a]pyrazin-7(8H)-ylcarbonyl)piperidin-1-yl]quinoline-3-carbonitrile | 421 | 878.5 |

TABLE 20-continued

| Example | Structure | Chemical Name | Exact Mass [M + H]+ | Human CYP8B1 IC50 (nM) |
|---------|-----------|---------------|---------------------|------------------------|
| 106 | 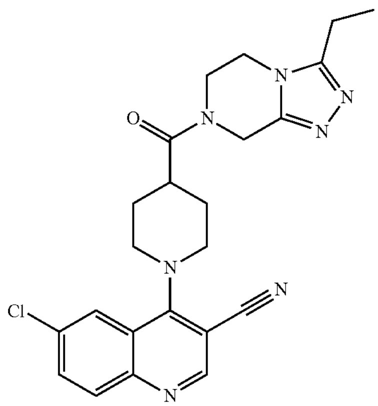 [SMILES: CCc1nnc2n1CCN(C(=O)C1CCN(c3c(C#N)cnc4ccc(Cl)cc34)CC1)C2] | 6-chloro-4-{4-[(3-ethyl-5,6-dihydro[1,2,4]triazolo[4,3-a]pyrazin-7(8H)-yl)carbonyl]piperidin-1-yl}quinoline-3-carbonitrile | 450 | 8.1 |
| 107 | 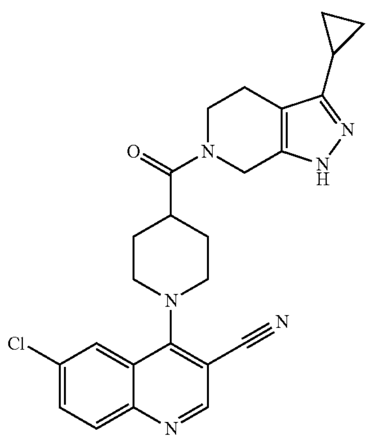 [SMILES: N#Cc1cnc2ccc(Cl)cc2c1N1CCC(C(=O)N2CCc3c(C4CC4)n[nH]c3C2)CC1] | 6-chloro-4-{4-[(3-cyclopropyl-1,4,5,7-tetrahydro-6H-pyrazolo[3,4-c]pyridin-6-yl)carbonyl]piperidin-1-yl}quinoline-3-carbonitrile | 461 | 5.6 |
| 108 | 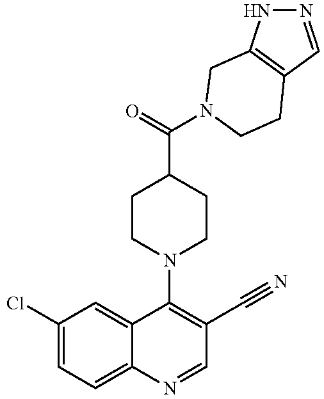 [SMILES: N#Cc1cnc2ccc(Cl)cc2c1N1CCC(C(=O)N2CCc3cn[nH]c3C2)CC1] | 6-chloro-4-[4-(1,4,5,7-tetrahydro-6H-pyrazolo[3,4-c]pyridin-6-ylcarbonyl)piperidin-1-yl]quinoline-3-carbonitrile | 421 | 141.7 |

TABLE 20-continued

| Example | Structure | Chemical Name | Exact Mass [M + H]+ | Human CYP8B1 IC50 (nM) |
|---|---|---|---|---|
| 109 | 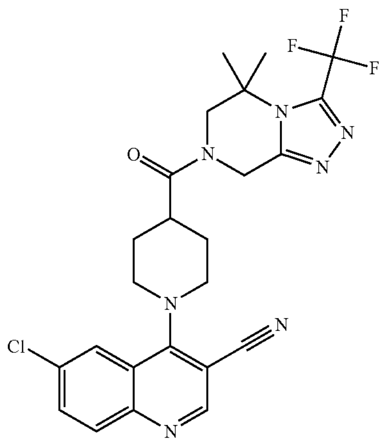 [SMILES: CC1(C)CN(C(=O)C2CCN(c3c(C#N)cnc4ccc(Cl)cc34)CC2)Cc2nnc(C(F)(F)F)n21] | 6-chloro-4-(4-{[5,5-dimethyl-3-(trifluoromethyl)-5,6-dihydro[1,2,4]triazolo[4,3-a]pyrazin-7(8H)-yl]carbonyl}piperidin-1-yl)quinoline-3-carbonitrile | 518 | 375.4 |
| 110 | 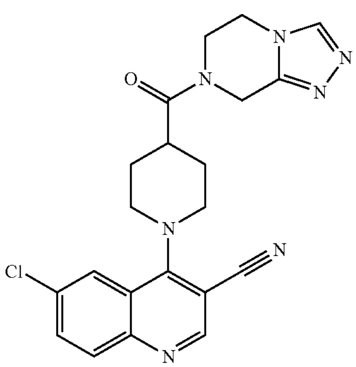 [SMILES: N#Cc1cnc2ccc(Cl)cc2c1N1CCC(C(=O)N2CCn3cnnc3C2)CC1] | 6-chloro-4-[4-(5,6-dihydro[1,2,4]triazolo[4,3-a]pyrazin-7(8H)-ylcarbonyl)piperidin-1-yl]quinoline-3-carbonitrile | 422 | 180.6 |
| 111 | 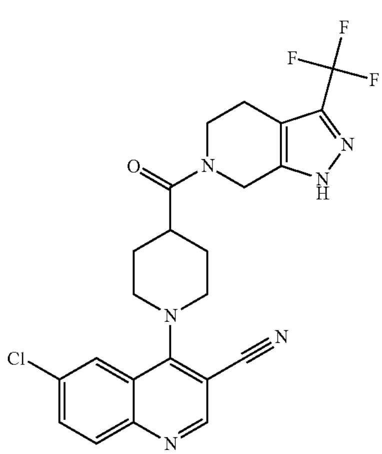 [SMILES: N#Cc1cnc2ccc(Cl)cc2c1N1CCC(C(=O)N2CCc3c(C(F)(F)F)n[nH]c3C2)CC1] | 6-chloro-4-(4-{[3-(trifluoromethyl)-1,4,5,7-tetrahydro-6H-pyrazolo[3,4-c]pyridin-6-yl]carbonyl}piperidin-1-yl)quinoline-3-carbonitrile | 489 | 90 |

TABLE 20-continued

| Example | Structure | Chemical Name | Exact Mass [M + H]+ | Human CYP8B1 IC50 (nM) |
|---|---|---|---|---|
| 112 | 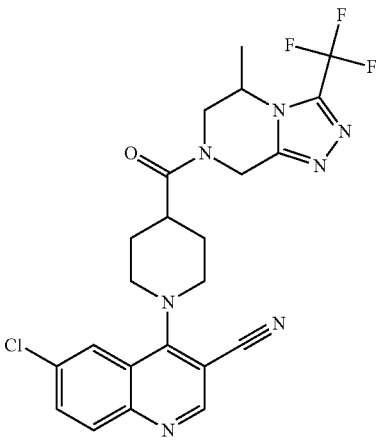 [SMILES: CC1CN(C(=O)C2CCN(c3c(C#N)cnc4ccc(Cl)cc34)CC2)Cc2nnc(C(F)(F)F)n21] | 6-chloro-4-(4-{[5-methyl-3-(trifluoromethyl)-5,6-dihydro[1,2,4]triazolo[4,3-a]pyrazin-7(8H)-yl]carbonyl}piperidin-1-yl)quinoline-3-carbonitrile | 504 | 69.7 |
| 113 | 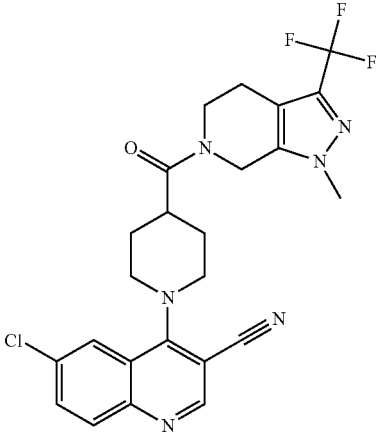 [SMILES: Cn1nc(C(F)(F)F)c2c1CN(C(=O)C1CCN(c3c(C#N)cnc4ccc(Cl)cc34)CC1)CC2] | 6-chloro-4-(4-{[1-methyl-3-(trifluoromethyl)-1,4,5,7-tetrahydro-6H-pyrazolo[3,4-c]pyridin-6-yl]carbonyl}piperidin-1-yl)quinoline-3-carbonitrile | 503 | 16.1 |
| 114 | 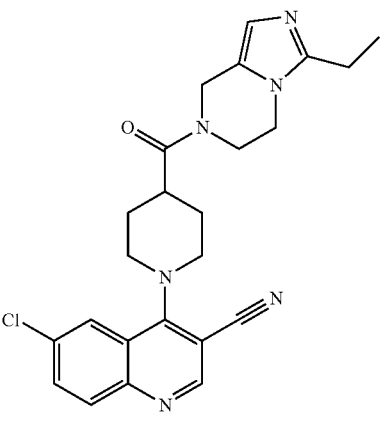 [SMILES: CCc1ncc2n1CCN(C(=O)C1CCN(c3c(C#N)cnc4ccc(Cl)cc34)CC1)C2] | 6-chloro-4-{4-[(3-ethyl-5,6-dihydroimidazo[1,5-a]pyrazin-7(8H)-yl)carbonyl]piperidin-1-yl}quinoline-3-carbonitrile | 449 | 1223 |

TABLE 20-continued

| Example | Structure | Chemical Name | Exact Mass [M + H]+ | Human CYP8B1 IC50 (nM) |
|---|---|---|---|---|
| 115 | 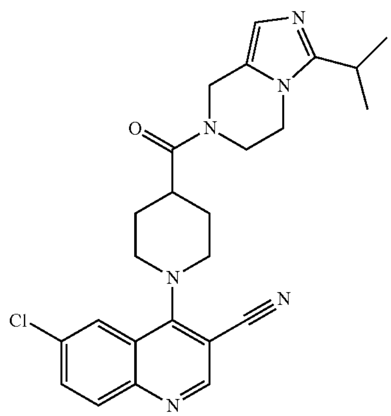 [SMILES: CC(C)c1ncc2n1CCN(C(=O)C1CCN(c3c(C#N)cnc4ccc(Cl)cc34)CC1)C2] | 6-chloro-4-(4-{[3-(propan-2-yl)-5,6-dihydroimidazo[1,5-a]pyrazin-7(8H)-yl]carbonyl}piperidin-1-yl)quinoline-3-carbonitrile | 463 | 1669 |

Example 116

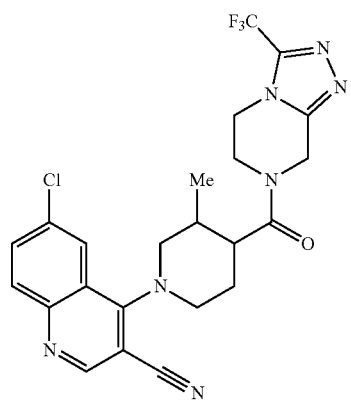 [SMILES: CC1CN(c2c(C#N)cnc3ccc(Cl)cc23)CCC1C(=O)N1CCn2c(nnc2C(F)(F)F)C1]

6-chloro-4-(3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile A mixture of HATU (150 mg, 0.394 mmol), HOAT (53.6 mg, 0.394 mmol), 3-(trifluoromethyl)-5,6,7,8-tetrahydro-[1,2,4]triazolo[4,3-a]pyrazine (HCl salt, 69.3 mg, 0.303 mmol), and 1-(6-chloro-3-cyanoquinolin-4-yl)-3-methylpiperidine-4-carboxylic acid (100 mg, 0.303 mmol) was flushed with $N_2$ three times. Anhydrous DMF (2 ml) was then added, followed by N-ethyl-N-isopropylpropan-2-amine (118 mg, 0.910 mmol). The mixture was stirred at room temperature for 6 hours. The reaction mixture was poured into 50 ml or a $NaHCO_3$ solution, and the resulting suspension was stirred for 1 hour. The mixture was filtered. The filter cake was washed with water and dried to afford the title compound as stereoisomers mixture. MS: 504 (M+1). Human CYP8B1 IC50 (1.4 nM).

Example 116a

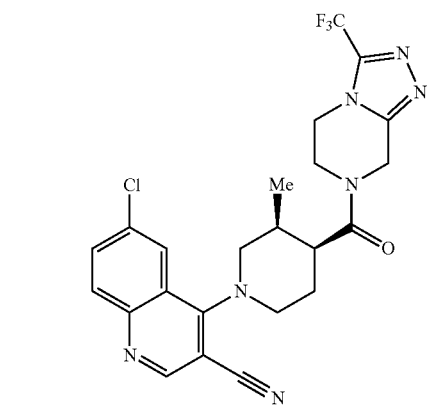 [SMILES: C[C@@H]1CN(c2c(C#N)cnc3ccc(Cl)cc23)CC[C@@H]1C(=O)N1CCn2c(nnc2C(F)(F)F)C1]

6-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile 6-chloro-4-(3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile was submitted for chiral SFC resolution. Preparative Method: ChiralPak (2×15 cm); 30% methanol (0.1% DEA)/$CO_2$, 100 bar; 70 mL/min, 220 nm; injection vol.: 1.0 mL, 6 mg/mL methanol. The SFC separation yielded peak 1 (faster eluting) (chemical purity >98%, ee >99%), and peak 2 as the title compound (slower eluting, chemical purity >96%, ee >97%, Human CYP8B1 IC50 (0.4 nM)).

1HNMR (500 MHz, CD3OD) δ 8.70 (s, 1H), 8.13 (d, J=1.9 Hz, 1H), 7.98 (d, J=8.8 Hz, 1H), 7.81 (dd, J=8.9, 2.1 Hz, 1H), 5.26-5.15 (m, 1H), 4.59 (s, 2H), 4.39-4.23 (m, 2H), 4.16-4.13 (m, 1H), 4.02-3.95 (m, 2H), 3.86-3.83 (m, 1H), 3.60-3.52 (m, 1H), 3.45-3.39 (m, 1H), 2.54-2.50 (m, 1H), 2.47-2.36 (m, 1H), 1.88-1.85 (m, 1H), 1.40-1.30 (m, 3H).

Examples 117-118 were made using a similar synthesis to Example 116 substituting the appropriate reactants and reagents.

TABLE 21

| Example | Structure | Chemical Name | Exact Mass [M + H]+ | Human CYP8B1 IC50 (nM) |
|---|---|---|---|---|
| 117 | 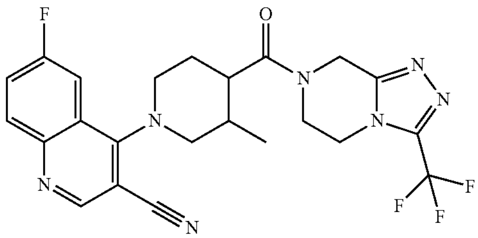 [SMILES: CC1CN(c2c(C#N)cnc3ccc(F)cc23)CCC1C(=O)N1CCn2c(nnc2C(F)(F)F)C1] | 6-fluoro-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile | 488 | 1.2 |
| 118 | 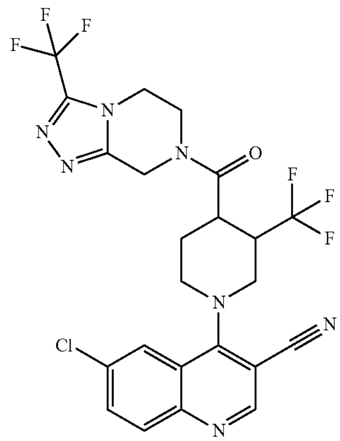 [SMILES: N#Cc1cnc2ccc(Cl)cc2c1N1CCC(C(=O)N2CCn3c(nnc3C(F)(F)F)C2)C(C(F)(F)F)C1] | 6-chloro-4-[3-(trifluoromethyl)-4-{[3-(trifluoromethyl)-5,6-dihydro[1,2,4]triazolo[4,3-a]pyrazin-7(8H)-yl]carbonyl}piperidin-1-yl]quinoline-3-carbonitrile | 558 | 2.1 |
| 119 | 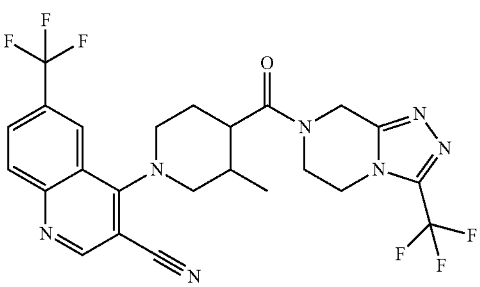 [SMILES: CC1CN(c2c(C#N)cnc3ccc(C(F)(F)F)cc23)CCC1C(=O)N1CCn2c(nnc2C(F)(F)F)C1] | 4-(3-methyl-4-{[3-(trifluoromethyl)-5,6-dihydro[1,2,4]triazolo[4,3-a]pyrazin-7(8H)-yl]carbonyl}piperidin-1-yl)-6-(trifluoromethyl)quinoline-3-carbonitrile | 538 | 1.2 |

Examples 119a and 119b

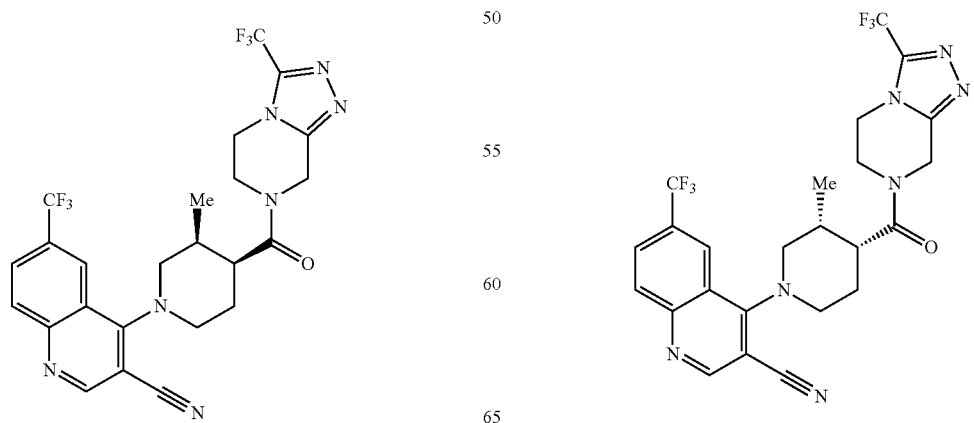

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-6-(trifluoromethyl)quinoline-3-carbonitrile

4-[(3R,4R)-3-methyl-4-{[3-(trifluoromethyl)-5,6-dihydro[1,2,4]triazolo[4,3-a]pyrazin-7(8H)-yl]carbonyl}piperidin-1-yl]-6-(trifluoromethyl)quinoline-3-carbonitrile The stereoisomers were submitted for chiral SFC resolution. Preparative Method: ChiralPak (2×15 cm); 13% methanol (0.1% DEA)/CO$_2$, 100 bar; 60 mL/min, 220 nm; injection vol.: 0.5 mL, 5 mg/mL 1:5 DCM:methanol. The SFC separation yielded Example 119a (faster eluting), MS: 538 (M+1), Human CYP8B1 IC50 (41.4 nM), and Example 119b (slower eluting), MS: 538 (M+1), Human CYP8B1 IC50 (0.3 nM).

Example 120

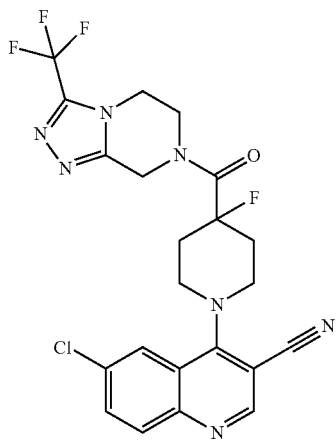 [SMILES: N#Cc1cnc2ccc(Cl)cc2c1N1CCC(F)(C(=O)N2CCn3c(nnc3C(F)(F)F)C2)CC1]

6-chloro-4-(4-fluoro-4-{[3-(trifluoromethyl)-5,6-dihydro[1,2,4]triazolo[4,3-a]pyrazin-7(8H)-yl]carbonyl}piperidin-1-yl)quinoline-3-carbonitrile 1-(6-chloro-3-cyanoquinolin-4-yl)-4-fluoropiperidine-4-carboxylic acid (40 mg, 0.120 mmol), HATU (63.8 mg, 0.168 mmol), 1-hydroxy-7-azabenzotriazole (22.84 mg, 0.168 mmol) and 3-(trifluoromethyl)-5,6,7,8-tetrahydro-[1,2,4]triazolo[4,3-a]pyrazine hydrochloride (30.1 mg, 0.132 mmol) were added to a vial. The mixture was placed under nitrogen atmosphere and DMF (1.2 mL) and DIEA (41.9 µl, 0.24 mmol) were added. The reaction was stirred for 1 hour at room temperature. The residue was purified by mass directed Gilson purification 20-80% MeCN/H2O (+0.05% TFA). The combined fractions were lyophilized to give the title compound. MS: 508 (M+1), Human CYP8B1 IC50 (169 nM).

Example 121

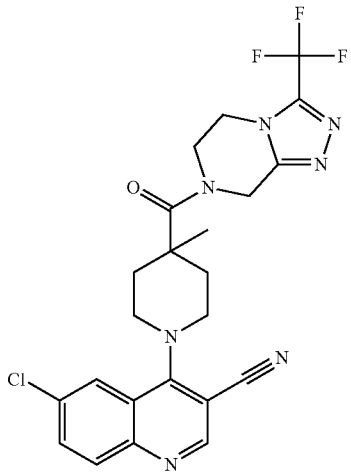 [SMILES: CC1(C(=O)N2CCn3c(nnc3C(F)(F)F)C2)CCN(c2c(C#N)cnc3ccc(Cl)cc23)CC1]

6-chloro-4-(4-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile 1-(6-chloro-3-cyanoquinolin-4-yl)-4-methylpiperidine-4-carboxylic acid (60 mg, 0.182 mmol), HATU (97 mg, 0.255 mmol), 1-hydroxy-7-azabenzotriazole (34.7 mg, 0.255 mmol) and 3-(trifluoromethyl)-5,6,7,8-tetrahydro-[1,2,4]triazolo[4,3-a]pyrazine hydrochloride (45.8 mg, 0.200 mmol) were added to a vial. The mixture was placed under a nitrogen atmosphere and DMF (1.8, l) and DIEA (63.6 µl, 0.364 mmol) were added. The reaction mixture was stirred for 1 hour at room temperature then stirred at 50° C. for 15 hours. The residue was submitted for mass direction purification 15-55% MeCN/H2O (+0.05% TFA). The fractions were combined and lyophilized to give the title compound. MS: 504 (M+1). Human CYP8B1 IC50 (nM) 14.0.

Example 122

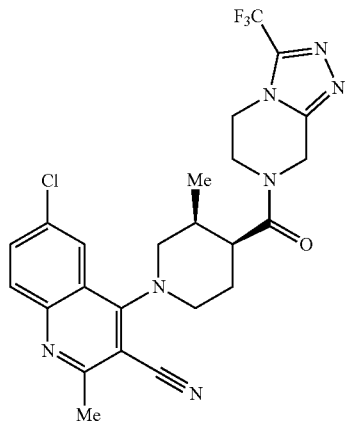 [SMILES: Cc1nc2ccc(Cl)cc2c(N2CC[C@H](C(=O)N3CCn4c(nnc4C(F)(F)F)C3)[C@H](C)C2)c1C#N]

6-chloro-2-methyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile TFA (0.540 mL, 8.97 mmol) and tert-butyl ethaneperoxoate (200 uL, 1.3525 mmol) was added to a stirred solution of 6-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (280 mg, 0.541 mmol) in anhydrous MeCN (4.86 mL), followed by [Ir(ppy)2(dtbpy)](PF6) (6.51 mg, 0.00541 mmol) precatalyst. The reaction mixture was irradiated with 450 nm light overnight. The crude reaction mixture was diluted with 10 mL of 20% MeCN—H$_2$O, filtered through a filter and purified using orthogonal HPLC [method 1: 30×100 mm RP C-18, MeCN-water containing 0.1 v % NH$_4$OH; method 2: 30×100 mm RP C-18, MeCN—H$_2$O containing 0.05% TFA]. The isolated product was evaporated to dryness and partitioned between CDCl$_3$ and saturated aqueous NaHCO$_3$. The organic phase was separated and dried over Na$_2$SO$_4$, filtered and evaporated to afford the title compound. MS: 518 (M+1). 1HNMR (500 MHz, CD3OD) δ 8.11 (d, J=2.1 Hz, 1H), 7.90 (d, J=9.0, 1H), 7.77 (dd, J=8.9, 2.0 Hz, 1H), 5.25-5.16 (m, 2H), 4.86 (s, 2H), 4.36-4.26 (m, 2H), 4.00-3.97 (m, 2H), 3.81-3.77 (m, 1H), 3.55-3.50 (m, 1H), 3.42-3.40 (m, 1H), 2.78 (s, 3H), 2.58-2.50 (m, 1H), 2.41-2.39 (m, 1H), 1.88-1.84 (m, 1H), 1.11-1.07 (m, 3H). Human CYP8B1 IC50 (0.5 nM).

Example 123

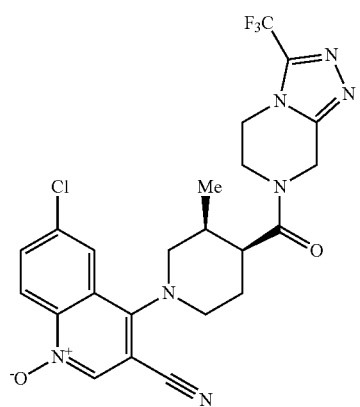

6-chloro-3-cyano-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline 1-oxide mCPBA (10.27 mg, 0.060 mmol) was added to a solution of 6-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (20 mg, 0.040 mmol) in DCM (0.397 mL). The reaction mixture was stirred overnight. Then mCPBA (10.27 mg, 0.060 mmol) was added again and the reaction mixture was stirred overnight. The reaction mixture was concentrated and dissolved in DMSO (1 mL). The DMSO solution was filtered and purified by reverse phase HPLC (ACN/water with 0.1% NH$_4$OH modifier) to afford the title compound. MS: 520 (M+1). Human CYP8B1 IC50 (1.9 nM).

Example 124

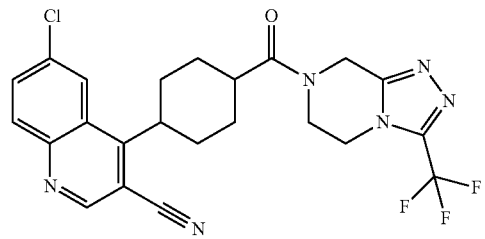 [SMILES: N#Cc1cnc2ccc(Cl)cc2c1C1CCC(C(=O)N2CCn3c(nnc3C(F)(F)F)C2)CC1]

6-chloro-4-(4-{[3-(trifluoromethyl)-5,6-dihydro[1,2,4]triazolo[4,3-a]pyrazin-7(8H)-yl]carbonyl}cyclohexyl)quinoline-3-carbonitrile A mixture of HATU (157 mg, 0.413 mmol), HOAT (56.2 mg, 0.413 mmol), 3-(trifluoromethyl)-5,6,7,8-tetrahydro-[1,2,4]triazolo[4,3-a]pyrazine hydrochloride (94 mg, 0.413 mmol) and 4-(6-chloro-3-cyanoquinolin-4-yl)cyclohexanecarboxylic acid (100 mg, 0.318 mmol) was flushed with N$^2$ three times. Anhydrous DMF (10 ml) was then added, followed by N-ethyl-N-isopropylpropan-2-amine (0.171 ml, 0.953 mmol). The mixture was stirred at room temperature for 4 hours. The reaction mixture was poured into 50 mL of saturated sodium bicarbonate solution, and the resulting suspension was stirred for 1 hour. The mixture was filtered and the filter cake was washed with water, and dried by air. The filter cake was purified by flash chromatography (Isco Combiflash Rf, RediSep Silica 80 g) eluting with hexane grading to acetone (15cv) to give a mixture of isomers. MS: 489 (M+1). Human CYP8B1 IC50 (110 nM).

Example 125

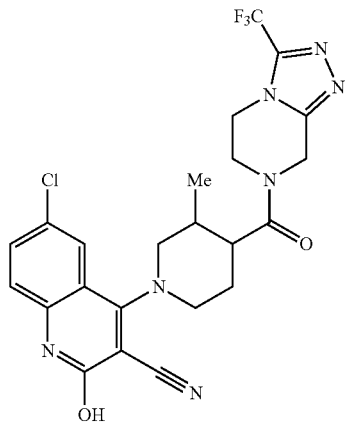 [SMILES: CC1CN(c2c(C#N)c(O)nc3ccc(Cl)cc23)CCC1C(=O)N1CCn2c(nnc2C(F)(F)F)C1]

6-chloro-2-hydroxy-4-(3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile N-ethyl-N-isopropylpropan-2-amine (1.09 mL, 6.27 mmol) was added to a mixture of 4,6-dichloro-2-hydroxyquinoline-3-carbonitrile (300 mg, 1.25 mmol), (3-methylpiperidin-4-yl)(3-(trifluoromethyl)-5,6-dihydro-[1,2,4]triazolo[4,3-a]pyrazin-7(8H)-yl)methanone (HCl salt, 488 mg, 1.38 mmol) in DMF (10 mL). The mixture was stirred at 100° C. for 10 minutes and then cooled to room temperature. The reaction mixture was poured into a mixture of EtOAc (45 mL) and water (150 mL). Then brine was added. The organic layer was dried over MgSO$_4$, filtered, concentrated. The residue was washed with MeOH, and dried to afford the title compound. MS: 520 (M+1). Human CYP8B1 IC50 (nM).

Example 126

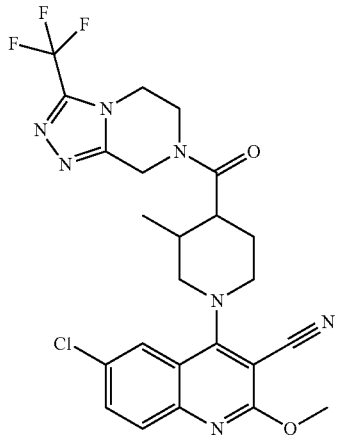 [SMILES: COc1nc2ccc(Cl)cc2c(N2CCC(C(=O)N3CCn4c(nnc4C(F)(F)F)C3)C(C)C2)c1C#N]

6-chloro-2-methoxy-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile Iodomethane (6.55 mg, 0.046 mmol) was added to a suspension of 6-chloro-2-hydroxy-4-(3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile (20 mg, 0.038 mmol), Cs$_2$CO$_3$ (25.07 mg, 0.077 mmol) in DMF (1 mL). The mixture was stirred at room temperature overnight. The reaction was then diluted with water (6 mL). The resulting mixture was filtered and dried to give the title compound. MS: 534 (M+1). Human CYP8B1 IC50 (210 nM).

Example 127

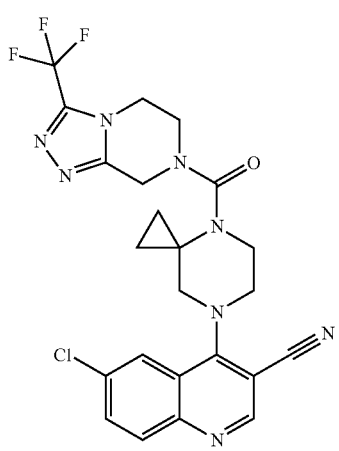 [SMILES: N#Cc1cnc2ccc(Cl)cc2c1N1CCN(C(=O)N2CCn3c(nnc3C(F)(F)F)C2)C2(CC2)C1]

6-chloro-4-(4-{[3-(trifluoromethyl)-5,6-dihydro[1,2,4]triazolo[4,3-a]pyrazin-7(8H)-yl]carbonyl}-4,7-diazaspiro[2.5]oct-7-yl)quinoline-3-carbonitrile N,N-diisopropylethylamine (0.117 ml, 0.669 mmol) and DCM (1.5 ml) were added to a vial containing 6-chloro-4-(4,7-diazaspiro[2.5]octan-7-yl)quinoline-3-carbonitrile (40 mg, 0.134 mmol). The reaction was cooled to 0° C. and then triphosgene (13.11 mg, 0.044 mmol) was added in DCM (0.2 mL). Upon addition of triphosgene a solution formed. It was stirred for 15 minutes at 0° C. allowing the bath to warm. After 15 minutes the bath was taken away and the reaction was stirred at room temperature over the weekend. 3-(trifluoromethyl)-5,6,7,8-tetrahydro-[1,2,4]triazolo[4,3-a]pyrazine hydrochloride (30.6 mg, 0.134 mmol) in DCM (0.2 mL) was added to the reaction. The reaction was stirred for 15 hours at room temperature. The reaction was concentrated and the residue loaded on to a 12 g silica gel column (eluting with 0-10% MeOH in DCM). The fractions were combined and concentrated to give the title compound. MS: 517 (M+1). Human CYP8B1 IC50 (98 nM).

Example 128

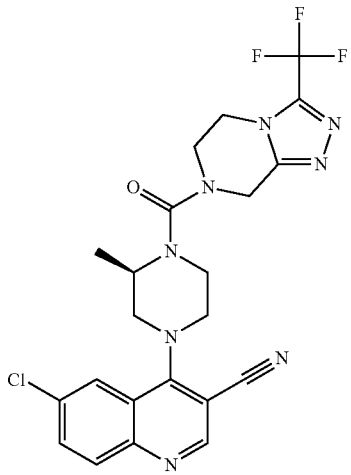 [SMILES: C[C@@H]1CN(c2c(C#N)cnc3ccc(Cl)cc23)CCN1C(=O)N1CCn2c(nnc2C(F)(F)F)C1]

6-chloro-4-[(3R)-3-methyl-4-{[3-(trifluoromethyl)-5,6-dihydro[1,2,4]triazolo[4,3-a]pyrazin-7(8H)-yl]carbonyl}piperazin-1-yl]quinoline-3-carbonitrile N,N-diisopropylethylamine (0.167 ml, 0.959 mmol) and DCM (2 mL) were added to a vial containing (R)-6-chloro-4-(3-methylpiperazin-1-yl)quinoline-3-carbonitrile (55 mg, 0.192 mmol). The reaction was cooled to 0° C. and then triphosgene (18.78 mg, 0.063 mmol) was added in DCM (0.2 mL). The reaction was stirred for 15 minutes at 0° C. allowing the bath to warm. After 15 minutes, the bath was taken away and the reaction was stirred at room temperature over the weekend. To the reaction, 3-(trifluoromethyl)-5,6,7,8-tetrahydro-[1,2,4]triazolo[4,3-a]pyrazine hydrochloride (43.8 mg, 0.192 mmol) in DCM (0.2 mL) was added. The reaction was stirred for 15 hours. The reaction was concentrated and the residue was loaded on to a silica gel column (eluting with 0-10% MeOH in DCM). The fractions were combined and concentrated to give the title compound. MS: 505 (M+1). Human CYP8B1 IC50 (2.9 nM).

Example 129

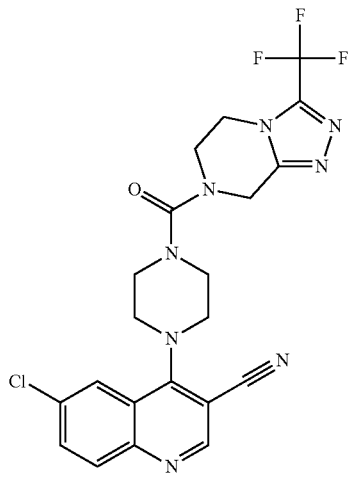 [SMILES: N#Cc1cnc2ccc(Cl)cc2c1N1CCN(C(=O)N2CCn3c(nnc3C(F)(F)F)C2)CC1]

6-chloro-4-(4-{[3-(trifluoromethyl)-5,6-dihydro[1,2,4]triazolo[4,3-a]pyrazin-7(8H)-yl]carbonyl}piperazin-1-yl)quinoline-3-carbonitrile Triphosgene (35.9 mg, 0.121 mmol) was added to a mixture of 6-chloro-4-(piperazin-1-yl)quinoline-3-carbonitrile (100 mg, 0.367 mmol) and Hunig's Base (0.192 mL, 1.100 mmol) in DCM (1 mL) at 0° C. The mixture was stirred at room temperature for 1 hour, then 3-(trifluoromethyl)-5,6,7,8-tetrahydro-[1,2,4]triazolo[4,3-a]pyrazine hydrochloride (84 mg, 0.367 mmol) was added. The reaction was left to stir at room temperature for 48 hours. The reaction mixture was treated with aqueous $NaHCO_3$ solution (20 mL) and DCM (50 mL). The organic layer was separated and dried over $Na_2SO_4$, filtered and and evaporated. The residue was purified by silica chromatography (0-100% acetone in hexanes) to afford the title compound. MS: 491 (M+1). Human CYP8B1 IC50 (nM) 386.3.

Human CYP8B1 Liver Microsome Assay

To a 384 well polypropylene plate (Corning 3656), 250 nl of inhibitor in 100% DMSO (1.25% final DMSO concentration) was pre-plated using an Echo liquid handler (Labcyte Inc.). Human liver microsomes (Xenotech) were diluted in of 0.1 M phosphate buffer, pH 7.4, at a concentration of 65 μg/ml and 15 μL was added to the 384 well plate. The plates were incubated at ambient room temperature for 30 minutes. After pre-incubation with inhibitor, the reaction was initiated by adding 5 μl of substrate solution (4.0 μM 7a-hydroxy-4-cholesten-3-one (Toronto Research Chemicals), 2 mM of NADPH (Sigma), 0.1 M phosphate buffer (pH 7.4). The reaction was carried out for 45 minutes at ambient room temperature and was quenched by the addition of 50 μl of acetonitrile+0.1% vol/vol formic acid (FA)+300 nM 7α-hydroxy-4-cholesten-3-one-d7 (Toronto Research Chemicals). The plates were sealed and centrifuged at 3000 rpm for 5 minutes. Plates were loaded onto the Agilent RapidFire RF300 HTMS system, wherein samples were sipped for 600 ms, and the sip sensor detection signals the diversion of sample from the loop onto a C4 solid phase extraction (SPE) cartridge, where salts were washed off for 2500 ms with a mobile phase of water with 0.1% vol/vol FA at a flow rate of 1.5 ml/min. The column path was switched, and the sample was eluted off the cartridge and flowed into the mass spectrometer for 3000 ms with a mobile phase of acetonitrile and 0.1% vol/vol FA at a flow rate of 1.25 ml/min. The aspirator tip was washed separately with water and acetonitrile between sample aspirations (each for 600 ms) to minimize carryover contamination. Mass spectrometry was carried out using a Sciex API4000 triple quadrupole mass spectrometer (Applied Biosystems, Concord, ON, Canada) equipped with electrospray ionization (ESI) operated in the positive-ion mode. The product 7α,12α-dihydroxy-4-cholesten-3-one and internal standard 7α-hydroxy-4-cholsten-3-one-d7 were detected using multiple reaction monitoring (MRM) with Q1/Q3 transitions at m/z 417.3 to 381.3 and m/z 408.3 to 390.3, respectively, with a dwell time of 100 ms and a collision energy of 24 V for each transition. The mass spectrometer used an ESI voltage of 5000 V and a source temperature of 650° C. Extracted ion chromatograms for each transition were integrated and processed using the RapidFire Integrator software. The data for each well were normalized by monitoring product conversion with the ratio of AUCproduct/(AUCinternal standard). The data was then fitted to a four parameter logistic fit using ActivityBase Software to calculate an IC50 of the inhibitor.

What is claimed is:
1. A compound of Formula I:

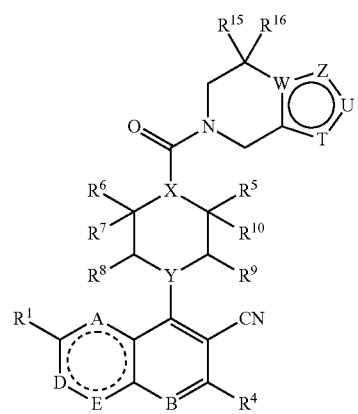

or a pharmaceutically acceptable salt thereof, wherein the dashed lines in Formula I indicate the possibility of aromaticity or no aromaticity in the ring depending on the substitution of the ring and wherein:

A is N or $CR^{17}$;
B is N or NO;
D is N, $NR^{12}$ or $CR^2$;
E is N or $CR^3$;
T is N, $NR^{12}$ or $CR^{12}$, wherein T is not $CR^{12}$ when W is C and Z is $CR^{14}$ and U is $CR^{13}$;
U is N, NH or $CR^{13}$, wherein U is not $CR^{13}$ when W is C and T is $CR^{12}$ and Z is $CR^{14}$;
Z is N, NH, S, O or $CR^{14}$, wherein Z is not $CR^{14}$ when W is C and T is $CR^{12}$ and U is $CR^{13}$;
W is N or C, wherein W is not C when T is $CR^{12}$ and U is $CR^{13}$ and Z is $CR^{14}$;
X is N or $CR^{11}$;
Y is N or CH;
$R^1$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, halo$C_1$-$C_6$alkyl, $C_3$-$C_6$cycloalkyl, $C_2$-$C_6$alkenyl, $COOC_1$-$C_6$alkyl, $COOC_1$-$C_6$alkyl$C_3$-$C_6$cycloalkyl, phenyl and oxazole;

$R^2$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, $COOC_1$-$C_6$alkyl, $COOC_1$-$C_6$alkyl$C_3$-$C_6$cycloalkyl, phenyl and oxazole;

$R^3$ is selected from the group consisting of hydrogen, halogen, CN, OH, $C_1$-$C_6$alkylOH, $C_1$-$C_6$alkoxy, $C_1$-$C_6$alkyl, $C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, $COOC_1$-$C_6$alkyl, $COOC_1$-$C_6$alkyl$C_3$-$C_6$cycloalkyl, phenyl and oxazole;

$R^4$ is selected from the group consisting of hydrogen, halogen, CN, OH, $C_1$-$C_6$alkylOH, $C_1$-$C_6$alkoxy, $C_1$-$C_6$alkyl$C_1$-$C_6$alkoxy, halo$C_1$-$C_6$alkoxy, $C_3$-$C_6$cycloalkyl$C_1$-$C_6$alkoxy, $C_1$-$C_6$alkyl, halo$C_1$-$C_6$alkyl, $C_3$-$C_6$cycloalkyl, $C_2$-$C_6$alkenyl, $COOC_1$-$C_6$alkyl, $COOC_1$-$C_6$alkyl$C_3$-$C_6$cycloalkyl, phenyl and oxazole;

$R^5$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^{10}$ forms a $C_3$-$C_6$cycloalkyl;

$R^6$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^7$ forms a $C_3$-$C_6$cycloalkyl, or when taken with $R^{11}$ forms a $C_3$-$C_6$cycloalkyl;

$R^7$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^6$ forms a $C_3$-$C_6$cycloalkyl;

$R^8$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl;

$R^9$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl;

$R^{10}$ is selected from the group consisting of hydrogen, halogen, $C_1$-$C_6$alkyl, $C_3$-$C_6$cycloalkyl, $C_1$-$C_6$alkoxy and halo$C_1$-$C_6$alkyl or when taken with $R^5$ forms a $C_3$-$C_6$cycloalkyl;

$R^{11}$ is selected from the group consisting of hydrogen, halogen, OH, $C_1$-$C_6$alkyl, and halo$C_1$-$C_6$alkyl or when taken with $R^6$ forms a $C_3$-$C_6$cycloalkyl;

$R^{12}$ is selected from the group consisting of hydrogen, halogen, OH, $C_1$-$C_6$alkyl, $C_3$-$C_6$cycloalkyl, $COOC_1$-$C_6$alkyl$C_3$-$C_6$cycloalkyl, and halo$C_1$-$C_6$alkyl;

$R^{13}$ is selected from the group consisting of hydrogen, halogen, OH, $C_1$-$C_6$alkyl, $C_3$-$C_6$cycloalkyl and halo$C_1$-$C_6$alkyl;

$R^{14}$ is selected from the group consisting of hydrogen, halogen, OH, $C_1$-$C_6$alkyl, $C_3$-$C_6$cycloalkyl and halo$C_1$-$C_6$alkyl;

$R^{15}$ is selected from the group consisting of hydrogen, halogen, OH, $C_1$-$C_6$alkyl, and halo$C_1$-$C_6$alkyl;

$R^{16}$ is selected from the group consisting of hydrogen, halogen, OH, $C_1$-$C_6$alkyl, and halo$C_1$-$C_6$alkyl; and $R^{17}$ is selected from the group consisting of hydrogen, halogen, $C_1$-$C_6$alkyl, $C_1$-$C_6$alkoxy, and halo$C_1$-$C_6$alkyl.

2. The compound of claim 1, or a pharmaceutically acceptable salt thereof, wherein Y is N.

3. The compound of claim 1, or a pharmaceutically acceptable salt thereof, wherein B is N.

4. The compound of claim 1, or a pharmaceutically acceptable salt thereof, wherein X is $CR^{11}$, wherein $R^{11}$ is hydrogen.

5. The compound of claim 1, or a pharmaceutically acceptable salt thereof, wherein Z is $CR^{14}$, wherein $R^{14}$ is trifluoromethyl.

6. The compound of claim 1, or a pharmaceutically acceptable salt thereof, wherein T is N.

7. The compound of claim 1, or a pharmaceutically acceptable salt thereof, wherein W is N.

8. The compound of claim 1, or a pharmaceutically acceptable salt thereof, wherein U is N.

9. The compound of claim 1, or a pharmaceutically acceptable salt thereof, wherein A is $CR^{17}$, wherein $R^{17}$ is hydrogen.

10. The compound of claim 1, or a pharmaceutically acceptable salt thereof, wherein E is $CR^3$, wherein $R^3$ is hydrogen.

11. The compound of claim 1, or a pharmaceutically acceptable salt thereof, wherein D is $CR^2$.

12. The compound of claim 11, or a pharmaceutically acceptable salt thereof, wherein $R^2$ is selected from the group consisting of halogen and halo$C_1$-$C_6$alkyl.

13. The compound of claim 11, or a pharmaceutically acceptable salt thereof, wherein $R^2$ is halo$C_1$-$C_6$alkyl.

14. The compound of claim 1, or a pharmaceutically acceptable salt thereof, wherein $R^6$ is methyl and $R^5$, $R^7$, $R^8$, $R^9$, $R^{10}$, $R^{15}$ and $R^{16}$ are hydrogen.

15. A compound, or pharmaceutically acceptable salt thereof, selected from the group consisting of:
  7-chloro-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  8-fluoro-7-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  6-chloro-8-(difluoromethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  7-bromo-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  7-hydroxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  7-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  6,7,8-trifluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  7,8-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  6-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;
  6,8-difluoro-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-chloro-7-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-chloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-chloro-6,8-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)quinoline-3-carbonitrile;

8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)quinoline-3-carbonitrile;

6-chloro-8-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-methoxy-8-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-bromo-7-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethyl)-1,8-naphthyridine-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(trifluoromethoxy)quinoline-3-carbonitrile;

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-(trifluoromethyl)quinoline-3-carbonitrile;

6,7-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6,8-difluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-chloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-methoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-fluoro-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-bromo-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-1,8-naphthyridine-3-carbonitrile;

6-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-1,7-naphthyridine-3-carbonitrile 6-methoxy-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-1,5-naphthyridine-3-carbonitrile;

7-methoxy-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

5-methoxy-2-methyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-(difluoromethoxy)-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(propan-2-yloxy)quinoline-3-carbonitrile;

7-(cyclopropyloxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-ethoxy-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-bromo-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

7-chloro-8-fluoro-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

8-fluoro-7-methoxy-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

7-(trifluoromethyl)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

7-methoxy-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-fluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-methoxy-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-methoxy-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-bromo-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6,8-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6,7-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

5,6-difluoro-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

2,6-dimethyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-cyclopropyl-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

2-methyl-4-(4-(3-(trifluoromethyl)-5,6,7,8-tetrahydro-[1,2,4]triazolo[4,3-a]pyrazine-7-carbonyl)piperidin-1-yl)-6-vinylquinoline-3-carbonitrile;

6-(difluoromethyl)-2-methyl-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

2,6-dichloro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-2-(difluoromethyl)-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-2-(difluoromethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-2-(difluoromethyl)-4-[(3R,4R)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-8-(difluoromethyl)-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

methyl 6-chloro-3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2-carboxylate;

dimethyl 3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2,6-dicarboxylate;

methyl 6-chloro-3-cyano-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-2-carboxylate;

7-(difluoromethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-cyclopropyl-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-7-(propan-2-yloxy)quinoline-3-carbonitrile;

7-chloro-4-{(3R,4S)-4-[(3-cyclopropyl-5,6-dihydro[1,2,4]triazolo[4,3-a]pyrazin-7(8H)-yl)carbonyl]-3-methylpiperidin-1-yl}-8-fluoroquinoline-3-carbonitrile;

7-chloro-4-{(3S,4S)-4-[(3-cyclopropyl-5,6-dihydro[1,2,4]triazolo[4,3-a]pyrazin-7(8H)-yl)carbonyl]-3-methylpiperidin-1-yl}-8-fluoroquinoline-3-carbonitrile;

7-cyclopropyl-8-fluoro-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-(cyclopropylmethoxy)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

7-(2-methylpropoxy)-4-(4-{[3-(trifluoromethyl)-5,6-dihydro[1,2,4]triazolo[4,3-a]pyrazin-7(8H)-yl]carbonyl}piperidin-1-yl)quinoline-3-carbonitrile;

4-[(3S,4S)-4-{[3-(difluoromethyl)-5,6-dihydro[1,2,4]triazolo[4,3-a]pyrazin-7(8H)-yl]carbonyl}-3-methylpiperidin-1-yl]-7-methoxyquinoline-3-carbonitrile;

7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 1-oxide;

6-chloro-4-[(3S,4S)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3 S,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3R,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3R,4R)-3-methoxy-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2R,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile 6-chloro-4-[(2S,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2R,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2S,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2R,4S)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(2S,4R)-2-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3R,4R)-3-ethyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile;

6-chloro-4-[(3R,4R)-3-ethyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-ethyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile;

6-chloro-4-[(3S,4S)-3-ethyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3R,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3S,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3R,4R)-3-cyclopropyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile;

6-chloro-4-[(3S,4S)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-[(3S,4R)-3-cyclopropyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-cyclopropyl-4-{[3-(trifluoromethyl)-5,6-dihydro[1,2,4]triazolo[4,3-a]pyrazin-7(8H)-yl]carbonyl}piperidin-1-yl]-8-fluoro-7-methoxyquinoline-3-carbonitrile;

7-(1,1-difluoroethyl)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-[($^2H_3$)methyl oxy]-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-((1S,6R)-6-(3-(trifluoromethyl)-5,6,7,8-tetrahydro-[1,2,4]triazolo[4,3-a]pyrazine-7-carbonyl)-3-azabicyclo[4.0.0]heptan-3-yl)quinoline-3-carbonitrile;

6-chloro-4-((1R,6S)-6-(3-(trifluoromethyl)-5,6,7,8-tetrahydro-[1,2,4]triazolo[4,3-a]pyrazine-7-carbonyl)-3-azabicyclo[4.0.0]heptan-3-yl)quinoline-3-carbonitrile;

4-((3S,4S)-4-(5,5-dimethyl-3-(trifluoromethyl)-5,6,7,8-tetrahydro-[1,2,4]triazolo[4,3-a]pyrazine-7-carbonyl)-3-methylpiperidin-1-yl)-8-fluoro-7-methoxyquinoline-3-carbonitrile;

4-((3R,5R)-3,5-dimethyl-4-(3-(trifluoromethyl)-5,6,7,8-tetrahydro-[1,2,4]triazolo[4,3-a]pyrazine-7-carbonyl)piperazin-1-yl)-7-methoxyquinoline-3-carbonitrile;

4-((3S,5R)-3,5-dimethyl-4-(3-(trifluoromethyl)-5,6,7,8-tetrahydro-[1,2,4]triazolo[4,3-a]pyrazine-7-carbonyl)piperazin-1-yl)-7-methoxyquinoline-3-carbonitrile;

7-methoxy-4-{3-methyl-4-[(3-methyl-5,6-dihydro[1,2,4]triazolo[4,3-a]pyrazin-7(8H)-yl)carbonyl]piperidin-1-yl}quinoline-3-carbonitrile;

1-methylcyclopropyl 3-cyano-4-((3S,4S)-4-(3-cyclopropyl-5,6,7,8-tetrahydro-[1,2,4]triazolo[4,3-a]pyrazine-7-carbonyl)-3-methylpiperidin-1-yl)-5,6-dihydro-1,7-naphthyridine-7(8H)-carboxylate;

6-cyclopropyl-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-cyclobutyl-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-(difluoromethyl)-8-fluoro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-(oxazol-2-yl)quinoline-3-carbonitrile;

4-((3S,4S)-3-methyl-4-(3-(trifluoromethyl)-5,6,7,8-tetrahydro-[1,2,4]triazolo[4,3-a]pyrazine-7-carbonyl)piperidin-1-yl)-7-phenylquinoline-3-carbonitrile;

6-chloro-4-[(3S,4S)-4-(3,4-dihydropyrrolo[1,2-a]pyrazin-2(1H)-ylcarbonyl)-3-methylpiperidin-1-yl]-2-methylquinoline-3-carbonitrile;

6-chloro-2-methyl-4-[(3S,4S)-3-methyl-4-{[3-(trifluoromethyl)-2,4,6,7-tetrahydro-5H-pyrazolo[4,3-c]pyridin-5-yl]carbonyl}piperidin-1-yl]quinoline-3-carbonitrile;

6-chloro-2-methyl-4-[(3S,4S)-3-methyl-4-{[3-(trifluoromethyl)-2,4,5,7-tetrahydro-6H-pyrazolo[3,4-c]pyridin-6-yl]carbonyl}piperidin-1-yl]quinoline-3-carbonitrile;

6-chloro-4-[(3S,4S)-4-(6,7-dihydro[1,2,3]triazolo[1,5-a]pyrazin-5(4H)-ylcarbonyl)-3-methylpiperidin-1-yl]-2-methylquinoline-3-carbonitrile;

6-chloro-2-methyl-4-[(3S,4S)-3-methyl-4-(1,4,6,7-tetrahydro-5H-pyrazolo[4,3-c]pyridin-5-ylcarbonyl)piperidin-1-yl]quinoline-3-carbonitrile;

6-chloro-4-[(3S,4S)-4-(6,7-dihydropyrazolo[1,5-a]pyrazin-5(4H)-ylcarbonyl)-3-methylpiperidin-1-yl]-2-methylquinoline-3-carbonitrile;

6-chloro-4-[(3S,4S)-4-(6,7-dihydroisoxazolo[4,5-c]pyridin-5(4H)-ylcarbonyl)-3-methylpiperidin-1-yl]-2-methylquinoline-3-carbonitrile;

6-chloro-2-methyl-4-[(3S,4S)-3-methyl-4-{[2-(trifluoromethyl)-6,7-dihydro[1,3]thiazolo[4,5-c]pyridin-5(4H)-yl]carbonyl}piperidin-1-yl]quinoline-3-carbonitrile; and 6-chloro-2-methyl-4-[(3S,4S)-3-methyl-4-{[2-(trifluoromethyl)-5,6-dihydroimidazo[1,2-a]pyrazin-7(8H)-yl]carbonyl}piperidin-1-yl]quinoline-3-carbonitrile;

7-(cyclopropylmethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-(2-methylpropoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

7-(2,2-difluoroethoxy)-4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]quinoline-3-carbonitrile;

6-chloro-4-(4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-chloro-4-(4-{[2-(trifluoromethyl)-5,6-dihydroimidazo[1,2-a]pyrazin-7(8H)-yl]carbonyl}piperidin-1-yl)quinoline-3-carbonitrile;

6-chloro-4-[4-(5,6-dihydroimidazo[1,5-a]pyrazin-7(8H)-ylcarbonyl)piperidin-1-yl]quinoline-3-carbonitrile;

6-chloro-4-{4-[(3-ethyl-5,6-dihydro[1,2,4]triazolo[4,3-a]pyrazin-7(8H)-yl)carbonyl]piperidin-1-yl}quinoline-3-carbonitrile;

6-chloro-4-{4-[(3-cyclopropyl-1,4,5,7-tetrahydro-6H-pyrazolo[3,4-c]pyridin-6-yl)carbonyl]piperidin-1-yl}quinoline-3-carbonitrile;

6-chloro-4-[4-(1,4,5,7-tetrahydro-6H-pyrazolo[3,4-c]pyridin-6-ylcarbonyl)piperidin-1-yl]quinoline-3-carbonitrile;

6-chloro-4-(4-{[5,5-dimethyl-3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-[4-(5,6-dihydro[1,2,4]triazolo[4,3-a]pyrazin-7(8H)-ylcarbonyl)piperidin-1-yl]quinoline-3-carbonitrile;

6-chloro-4-(4-{[3-(trifluoromethyl)-5,7-tetrahydro-6H-pyrazolo[3,4-c]pyridin-6-yl]carbonyl}piperidin-1-yl)quinoline-3-carbonitrile;

6-chloro-4-(4-{[5-methyl-3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-(4-{[1-methyl-3-(trifluoromethyl)-1,4,5,7-tetrahydro-6H-pyrazolo[3,4-c]pyridin-6-yl]carbonyl}piperidin-1-yl)quinoline-3-carbonitrile;

6-chloro-4-{4-[(3-ethyl-5,6-dihydroimidazo[1,5-a]pyrazin-7(8H)-yl)carbonyl]piperidin-1-yl}quinoline-3-carbonitrile;

6-chloro-4-(4-{[3-(propan-2-yl)-5,6-dihydroimidazo[1,5-a]pyrazin-7(8H)-yl]carbonyl}piperidin-1-yl)quinoline-3-carbonitrile;

6-chloro-4-(3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-chloro-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-fluoro-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-[3-(trifluoromethyl)-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

4-(3-methyl-4-{[3-(trifluoromethyl)-5,6-dihydro[1,2,4]triazolo[4,3-a]pyrazin-7(8H)-yl]carbonyl}piperidin-1-yl)-6-(trifluoromethyl)quinoline-3-carbonitrile;

4-[(3S,4S)-3-methyl-4-{[3-(trifluoromethyl)-5,6-dihydro[1,2,4]triazolo[4,3-a]pyrazin-7(8H)-yl]carbonyl}piperidin-1-yl]-6-(trifluoromethyl)quinoline-3-carbonitrile;

4-[(3R,4R)-3-methyl-4-{[3-(trifluoromethyl)-5,6-dihydro[1,2,4]triazolo[4,3-a]pyrazin-7(8H)-yl]carbonyl}piperidin-1-yl]-6-(trifluoromethyl)quinoline-3-carbonitrile;

6-chloro-4-(4-fluoro-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-(4-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-2-methyl-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-chloro-3-cyano-4-((3S,4S)-3-methyl-4-(3-(trifluoromethyl)-5,6,7,8-tetrahydro-[1,2,4]triazolo[4,3-a]pyrazine-7-carbonyl)piperidin-1-yl)quinolone 1-oxide;

6-chloro-4-(4-{[3-(trifluoromethyl)-5,6-dihydro[1,2,4]triazolo[4,3-a]pyrazin-7(8H)-yl]carbonyl}cyclohexyl)quinoline-3-carbonitrile;

6-chloro-2-hydroxy-4-(3-methyl-4-(3-(trifluoromethyl)-5,6,7,8-tetrahydro-[1,2,4]triazolo[4,3-a]pyrazine-7-carbonyl)piperidin-1-yl)quinoline-3-carbonitrile;

6-chloro-2-methoxy-4-(3-methyl-4-{[3-(trifluoromethyl)-5,6-dihydro[1,2,4]triazolo[4,3-a]pyrazin-7(8H)-yl]carbonyl}piperidin-1-yl)quinoline-3-carbonitrile;

6-chloro-4-(4-{[3-(trifluoromethyl)-5,6-dihydro[1,2,4]triazolo[4,3-a]pyrazin-7(8H)-yl]carbonyl}-4,7-diazaspiro[2.5]oct-7-yl)quinoline-3-carbonitrile;

6-chloro-4-[(3R)-3-methyl-4-[3-(trifluoromethyl)-5,6-dihydro[1,2,4]triazolo[4,3-a]pyrazin-7(8H)-yl]carbonyl}piperazin-1-yl]quinoline-3-carbonitrile;

6-chloro-4-(4-{[3-(trifluoromethyl)-5,6-dihydro[1,2,4]triazolo[4,3-a]pyrazin-7(8H)-yl]carbonyl}piperazin-1-yl)quinoline-3-carbonitrile;

or a pharmaceutically acceptable salt thereof.

16. A method of treating diabetes comprising administering to a patient in need thereof a compound, or pharmaceutically acceptable salt thereof, of claim 1.

17. A pharmaceutical composition comprising a compound of claim 1, or a pharmaceutically acceptable salt thereof and a pharmaceutically acceptable carrier.

18. A pharmaceutical composition comprising a compound of claim 1 and a pharmaceutically acceptable carrier.

* * * * *